US010316305B2

(12) United States Patent
Los et al.

(10) Patent No.: US 10,316,305 B2
(45) Date of Patent: *Jun. 11, 2019

(54) CARBOHYDRATE DEGRADING POLYPEPTIDE AND USES THEREOF

(71) Applicant: DSM IP ASSETS B.V., Heerlen (NL)

(72) Inventors: Alrik Pieter Los, Echt (NL); Rene Marcel De Jong, Echt (NL); Maaike Appeldoorn, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/962,058

(22) Filed: Apr. 25, 2018

(65) Prior Publication Data

US 2018/0245059 A1    Aug. 30, 2018

Related U.S. Application Data

(63) Continuation of application No. 14/763,263, filed as application No. PCT/EP2014/051998 on Feb. 3, 2014, now Pat. No. 9,988,615.

(30) Foreign Application Priority Data

| Feb. 4, 2013 | (EP) | 13153821 |
| Feb. 4, 2013 | (EP) | 13153823 |
| Feb. 4, 2013 | (EP) | 13153824 |
| Feb. 4, 2013 | (EP) | 13153825 |
| Feb. 4, 2013 | (EP) | 13153828 |
| Feb. 4, 2013 | (EP) | 13153829 |
| Feb. 4, 2013 | (EP) | 13153831 |
| Feb. 4, 2013 | (EP) | 13153833 |
| Feb. 4, 2013 | (EP) | 13153834 |
| Feb. 4, 2013 | (EP) | 13153835 |
| Feb. 4, 2013 | (EP) | 13153836 |
| Feb. 4, 2013 | (EP) | 13153837 |
| Feb. 4, 2013 | (EP) | 13153839 |
| Feb. 4, 2013 | (EP) | 13153840 |
| Feb. 4, 2013 | (EP) | 13153841 |
| Feb. 26, 2013 | (EP) | 13156678 |
| Feb. 26, 2013 | (EP) | 13156679 |
| Feb. 26, 2013 | (EP) | 13156682 |
| Feb. 26, 2013 | (EP) | 13156684 |
| Feb. 26, 2013 | (EP) | 13156685 |
| Feb. 26, 2013 | (EP) | 13156688 |
| Feb. 26, 2013 | (EP) | 13156690 |
| Feb. 26, 2013 | (EP) | 13156692 |
| Feb. 26, 2013 | (EP) | 13156693 |
| Feb. 26, 2013 | (EP) | 13156694 |
| Feb. 26, 2013 | (EP) | 13156696 |
| Feb. 26, 2013 | (EP) | 13156698 |
| Feb. 26, 2013 | (EP) | 13156701 |
| Feb. 26, 2013 | (EP) | 13156702 |
| Feb. 26, 2013 | (EP) | 13156703 |

(51) Int. Cl.
| C12N 9/24 | (2006.01) |
| C12P 19/02 | (2006.01) |
| C12P 19/12 | (2006.01) |
| C12P 19/14 | (2006.01) |

(52) U.S. Cl.
CPC ............ C12N 9/2402 (2013.01); C12P 19/02 (2013.01); C12P 19/12 (2013.01); C12P 19/14 (2013.01); C12Y 302/01 (2013.01)

(58) Field of Classification Search
CPC ........ C12N 9/2437; C12N 15/81; C12P 19/02
See application file for complete search history.

(56) References Cited

FOREIGN PATENT DOCUMENTS

| CN | 102119219 A | 7/2011 |
| CN | 102439145 A | 5/2012 |
| WO | 2007/091231 A1 | 8/2007 |
| WO | 2010/113020 A1 | 10/2010 |
| WO | 2011/098577 A1 | 8/2011 |
| WO | 2012000892 A1 | 1/2012 |
| WO | 2012/018691 A2 | 2/2012 |
| WO | 2012/125925 A2 | 9/2012 |

OTHER PUBLICATIONS

International Search Report from corresponding PCT/EP2014/051998, dated Jul. 28, 2014.
Reen et al., "Molecular Characterisation and expression analysis of the first hemicellulase gene (bxll) encoding beta-kylosidase from the thermophilic fungus *Talaromyces emersonii*", Biochemical and Biophysical Research Communications, Academic Press Inc., Orlando, FL, US, vol. 305, No. 3, Jun. 6, 2003 (Jun. 6, 2003), pp. 579-585, XP002685776.
Heneghan et al., "Cloning, characterisation and expression analysis of alpha-glucuronidase from the thermophilic fungus *Talaromyces emersonii*", Enzyme and Microbial Technology, Stoneham, MA, US, vol . 41, No. 6-7, Sep. 5, 2007 (Sep. 5, 2007), pp. 677-682, XP022231120.

(Continued)

*Primary Examiner* — Kagnew H Gebreyesus
(74) *Attorney, Agent, or Firm* — McBee Moore Woodward & Vanik IP, LLC; Susan McBee; Chester Moore

(57) ABSTRACT

The invention relates to a polypeptide having hemicellulase activity. The invention features the full length coding sequence of the novel gene as well as the amino acid sequence of the full-length functional protein and functional equivalents of the gene or the amino acid sequence. The invention also relates to methods for using the polypeptide in industrial processes. Also included in the invention are cells transformed with a polynucleotide according to the invention suitable for producing these proteins.

17 Claims, 5 Drawing Sheets

Specification includes a Sequence Listing.

(56) References Cited

OTHER PUBLICATIONS

Tuohy et al., "Production of Thermostable Xylan-Degrading Enzymes by Talaromyces-Emersonii", Bioresource Technology, Elsevier BV, GB, vol. 39, No. 2, Jan. 1, 1992 (Jan. 1, 1992) pp. 131-138, XP002330765.
Houbraken et al., "Rasamsonia, a new genus comprising thermotolerant and thermophilic *Talaromyces* and *Geosmithia* species", Antonie Van Leeuwenhoek, Kluwer Academic Publishers, DO, vol. 101, No. 2, Oct. 2, 2011 (Oct. 2, 2011), pp. 403-421, XP035003862.
Knob et al., "B-Xylosidases from filamentous fungi: an overview", World Journal of Microbiology and Biotechnology, Kluwer Academic Publishers, DO, vol . 26, No. 3, Oct. 3, 2009 (Oct. 3, 2009), pp. 389-407, XP019796224.
Tuohy et al., "Characteri Zation of the Individual Components of the Xylanolytic Enzym E System of Talaromyces Emersonii", Bioresource Technology, Elsevier BV, GB, vol. 50, No. I, Jan. 1, 1994 (Jan. 1, 1994), pp. 37-42, XP000876865.
Van Zyl, WH et al., "*Aspergillus fumigatus* Af293 derived protein sequence," Nov. 25, 2010, AYK18226, XP-002769992.
Visser, J. et al., "Myceliophthora thermophilia CI carbohydrase Agu2 coding sequence, SEQ 17," Mar. 29, 2012, AZT28334, XP-002769993.
Database EMBL [Online] Mar. 13, 2012, "TSA: Sclerotinia homoeocarpa SHT_3237 mRNA sequence", retrieved from EBI accession No. EM_TSA:JU093104 Database accession No. JU093104.
Mitchinson, C. et al., "Biomass saccharification related enzyme-encoding DNA, SEQ 80", Database [Online] Nov. 8, 2012, EBI accession GSN BAA07940.

SEQUENCE LISTING

<160> NUMBER OF SEQ ID NOS: 82

<210> SEQ ID NO 1
<211> LENGTH: 2286
<212> TYPE: DNA
<213> ORGANISM: Rasamsonia emersonii
<220> FEATURE:
<221> NAME/KEY: source
<222> LOCATION: (1)..(2286)
<223> OTHER INFORMATION: /organism="Rasamsonia emersonii"
      /mol_type="unassigned DNA"

<400> SEQUENCE: 1

```
atggtccttg gtgtctccct ggtccttctg gccactgctg tctccgccac cttccccgac      60
tgctctcagc ctcctctcaa ggacaacgcc gtctgcgaca ccagccttga ccctgtctcc     120
cgcgctgctg ccctcgttgc tgctttcacc ctggaggaga agatcaacaa cactcagaac     180
ggctcccccg gtgttccccg tctgggtctg cctccctacc agtggtggtc tgagggtctg     240
cacggtgttg ccatctcccc cggcgtcaac ttctctgctc acggtgactt ctcctacgcc     300
accagcttcc ctcagcccat cctgatgtcc gctgccttcg atgatgacct catccgccag     360
gtcggctccg tcgtcagcac tgaggctcgt gctttctcca cgccaaccg cgctggtctg     420 gactactgga ctcccaacat caacccctcc aaggaccctc gctggggtcg tggccaggag     480
actcccggtg aagatgcctt ccacatccag cgctacgtgt actctttgat tgatggcctc     540
cagaacggca ttggacctgc caaccccaag atcatggcca cctgcaagca cttcgctgcc     600
tacgacctcg aggactggca cggcaacgag cgctacggtt tcaacgccgt tgtgagcact     660
caggacctgg cggaatacta ccttcctccc ttcaagtcct gcgctcgtga tgccaaggtc     720
gatgccctca tgtgctcgta caacgctgtc aacggtgtgc cctcttgcgc ggactcctac     780
ctcttggaag atatcctccg tgaccactgg ggctggaaca ccaccggtca ctgggtgacc     840
tccgactgcg atgccgtcca gaacatctac gccaaccacc actacacttc caccgctccc     900
caggctgctg ccgatgcctt gggtgctggt actgatcttg actgcggtac cacctacccc     960
gacaaccttg gtgccgccta cacccagggt ctgttccaga accagacctt ggacaccgct    1020
```

```
ctgatccgtc tgtactcttc tctggtcaag cttggatact tcgaccctcc cgagaaccag    1080
ccctaccgca gcattggctg gtcagatgtc agcactcctg ctgctcagca gcttgcccgc    1140
actgctgctg ctgagggcat tgtcctcctc aagaacgatg agaagaaggt cctcccctc     1200 agccgtgagg tcagaccct cgccgtcatc ggtcccttcg ccaacgccac cacccagctg    1260
cagggtaact accagggtgt tgctccttac atctggactg ttgttgctgc tgcggagcag    1320
ctgggctaca aggtcaacta cgccgacggt actgccatca acgctaccaa caccactggc    1380
ttcgccgagg ccgttgctgc cgccaagtcc tccgatgttg tcatctacgc tggtggtatc    1440
gacaacagca ttgaggctga aggccacgac cgtgacacca ttgtgtggcc cggcaaccag    1500
ctccagctca tctccgagct ggcgcagacc ggcaagcctc tggttgtcat ccagttcggt    1560
ggtggtcagg ttgatgactc ctccctcctt gccaacgact ccggtgtcaa cgccctcctc    1620
tgggctggct accccctccca ggctggtggt gctgccatct tcgagatcct gaccggtgcc    1680 actgccccg ccggtcgtct gcctaccacc cagtaccctg tcagtacgt ggatgaggtt     1740 cccatgaccg acatgaccct ccgcccctct gccaccaacc ccggtcgcac ctacagatgg    1800
tacgacaagg ccgtcatccc cttcggttc ggcttgcact acaccacctt cgatgtcacc     1860
tggagcaagg cccagcttgg accttacgaa attggctctc ttgtcaagaa cgcgtcgtcg    1920
tcggatgctc ctgccgacac cgccccctt gacaccttca ccatccacgt ccgcaacact    1980
ggcaagacca cctcggacta cgtggctctc tcttcctct ccacccgcaa cgccggtcct     2040
gctccctacc ccctcaagac cctagttgga tacactcgtg cccgtgccat ccagcccggt    2100
gagactcgtg ccgtcgacat tgccgtcacc gttggcagcg ttgcccgtac cgacgagcgt    2160
ggtgacctcg tcctctaccc cggcacctac accctcgagg ttgacgtcaa cggccagtac    2220
cccactgctg gcttcgaagt caccggtgag gctgctgtcc tggatgagtt ccccagccc    2280 ccggcg                                                                2286
```

<210> SEQ ID NO 2  
<211> LENGTH: 746  
<212> TYPE: PRT  
<213> ORGANISM: Rasamsonia emersonii

<400> SEQUENCE: 2

```
Thr Phe Pro Asp Cys Ser Gln Pro Pro Leu Lys Asp Asn Ala Val Cys
1               5                   10                  15

Asp Thr Ser Leu Asp Pro Val Ser Arg Ala Ala Leu Val Ala Ala
            20                  25                  30

Phe Thr Leu Glu Glu Lys Ile Asn Asn Thr Gln Asn Gly Ser Pro Gly
        35                  40                  45

Val Pro Arg Leu Gly Leu Pro Pro Tyr Gln Trp Trp Ser Glu Gly Leu
    50                  55                  60

His Gly Val Ala Ile Ser Pro Gly Val Asn Phe Ser Ala His Gly Asp
65                  70                  75                  80

Phe Ser Tyr Ala Thr Ser Phe Pro Gln Pro Ile Leu Met Ser Ala Ala
                85                  90                  95

Phe Asp Asp Asp Leu Ile Arg Gln Val Gly Ser Val Val Ser Thr Glu
            100                 105                 110

Ala Arg Ala Phe Ser Asn Ala Asn Arg Ala Gly Leu Asp Tyr Trp Thr
        115                 120                 125

Pro Asn Ile Asn Pro Phe Lys Asp Pro Arg Trp Gly Arg Gly Gln Glu
    130                 135                 140
```

```
Thr Pro Gly Glu Asp Ala Phe His Ile Gln Arg Tyr Val Tyr Ser Leu
145                 150                 155                 160

Ile Asp Gly Leu Gln Asn Gly Ile Gly Pro Ala Asn Pro Lys Ile Met
            165                 170                 175

Ala Thr Cys Lys His Phe Ala Ala Tyr Asp Leu Glu Asp Trp His Gly
        180                 185                 190

Asn Glu Arg Tyr Gly Phe Asn Ala Val Val Ser Thr Gln Asp Leu Ala
    195                 200                 205

Glu Tyr Tyr Leu Pro Pro Phe Lys Ser Cys Ala Arg Asp Ala Lys Val
210                 215                 220

Asp Ala Leu Met Cys Ser Tyr Asn Ala Val Asn Gly Val Pro Ser Cys
225                 230                 235                 240

Ala Asp Ser Tyr Leu Leu Glu Asp Ile Leu Arg Asp His Trp Gly Trp
            245                 250                 255

Asn Thr Thr Gly His Trp Val Thr Ser Asp Cys Asp Ala Val Gln Asn
            260                 265                 270

Ile Tyr Ala Asn His His Tyr Thr Ser Thr Ala Pro Gln Ala Ala Ala
            275                 280                 285

Asp Ala Leu Gly Ala Gly Thr Asp Leu Asp Cys Gly Thr Thr Tyr Pro
290                 295                 300

Asp Asn Leu Gly Ala Ala Tyr Thr Gln Gly Leu Phe Gln Asn Gln Thr
305                 310                 315                 320

Leu Asp Thr Ala Leu Ile Arg Leu Tyr Ser Ser Leu Val Lys Leu Gly
            325                 330                 335

Tyr Phe Asp Pro Pro Glu Asn Gln Pro Tyr Arg Ser Ile Gly Trp Ser
            340                 345                 350

Asp Val Ser Thr Pro Ala Ala Gln Gln Leu Ala Arg Thr Ala Ala Ala
            355                 360                 365

Glu Gly Ile Val Leu Leu Lys Asn Asp Glu Lys Lys Val Leu Pro Leu
370                 375                 380

Ser Arg Glu Gly Gln Thr Leu Ala Val Ile Gly Pro Phe Ala Asn Ala
385                 390                 395                 400

Thr Thr Gln Leu Gln Gly Asn Tyr Gln Gly Val Ala Pro Tyr Ile Trp
            405                 410                 415

Thr Val Ala Ala Ala Glu Gln Leu Gly Tyr Lys Val Asn Tyr Ala
            420                 425                 430

Asp Gly Thr Ala Ile Asn Ala Thr Asn Thr Thr Gly Phe Ala Glu Ala
            435                 440                 445

Val Ala Ala Lys Ser Ser Asp Val Val Ile Tyr Ala Gly Gly Ile
450                 455                 460

Asp Asn Ser Ile Glu Ala Glu Gly His Asp Arg Asp Thr Ile Val Trp
465                 470                 475                 480

Pro Gly Asn Gln Leu Gln Leu Ile Ser Glu Leu Ala Gln Thr Gly Lys
            485                 490                 495

Pro Leu Val Val Ile Gln Phe Gly Gly Gly Gln Val Asp Ser Ser
            500                 505                 510

Leu Leu Ala Asn Asp Ser Gly Val Asn Ala Leu Leu Trp Ala Gly Tyr
            515                 520                 525

Pro Ser Gln Ala Gly Gly Ala Ile Phe Glu Ile Leu Thr Gly Ala
            530                 535                 540

Thr Ala Pro Ala Gly Arg Leu Pro Thr Thr Gln Tyr Pro Ala Gln Tyr
545                 550                 555                 560

Val Asp Glu Val Pro Met Thr Asp Met Thr Leu Arg Pro Ser Ala Thr
```

```
                        565                 570                 575
Asn Pro Gly Arg Thr Tyr Arg Trp Tyr Asp Lys Ala Val Ile Pro Phe
            580                 585                 590

Gly Phe Gly Leu His Tyr Thr Thr Phe Asp Val Thr Trp Ser Lys Ala
        595                 600                 605

Gln Leu Gly Pro Tyr Glu Ile Gly Ser Leu Val Lys Asn Ala Ser Ser
    610                 615                 620

Ser Asp Ala Pro Ala Asp Thr Ala Pro Phe Asp Thr Phe Thr Ile His
625                 630                 635                 640

Val Arg Asn Thr Gly Lys Thr Thr Ser Asp Tyr Val Ala Leu Leu Phe
                645                 650                 655

Leu Ser Thr Arg Asn Ala Gly Pro Ala Pro Tyr Pro Leu Lys Thr Leu
            660                 665                 670

Val Gly Tyr Thr Arg Ala Arg Ala Ile Gln Pro Gly Glu Thr Arg Ala
        675                 680                 685

Val Asp Ile Ala Val Thr Val Gly Ser Val Ala Arg Thr Asp Glu Arg
    690                 695                 700

Gly Asp Leu Val Leu Tyr Pro Gly Thr Tyr Thr Leu Glu Val Asp Val
705                 710                 715                 720

Asn Gly Gln Tyr Pro Thr Ala Gly Phe Glu Val Thr Gly Glu Ala Ala
                725                 730                 735

Val Leu Asp Glu Phe Pro Gln Pro Pro Ala
            740                 745

<210> SEQ ID NO 3
<211> LENGTH: 16
<212> TYPE: PRT
<213> ORGANISM: Rasamsonia emersonii

<400> SEQUENCE: 3

Met Val Leu Gly Val Ser Leu Val Leu Leu Ala Thr Ala Val Ser Ala
1               5                   10                  15

<210> SEQ ID NO 4
<211> LENGTH: 2289
<212> TYPE: DNA
<213> ORGANISM: Rasamsonia emersonii
<220> FEATURE:
<221> NAME/KEY: source
<222> LOCATION: (1)..(2289)
<223> OTHER INFORMATION: /organism="Rasamsonia emersonii"
      /mol_type="unassigned DNA"

<400> SEQUENCE: 4
atggttctgg gtgtcagtct cgtcctcctg gcgacggccg tctctgccac gttccccgac      60
tgcagccagc ctccgctgaa ggacaacgcc gtgtgcgata cctcgctgga ccccgtatcg     120
cgtgctgctg cgctcgtcgc ggccttcacg ctcgaggaga agatcaacaa cacgcagaat     180
ggatcgcctg gcgtgccccg gctgggcctg ccgccgtatc aatggtggag cgaaggcctg     240
cacggcgtgg ccatctcgcc gggcgtcaac ttctccgcgc acggcgactt cagctacgca     300
acctccttcc cccagcccat cctcatgagc gccgcctttg acgacgacct catcaggcag     360
gtcggcagtg tggtcagcac cgaggcgcgc gccttcagca acgccaaccg cgctggcctc     420
gactactgga cgcccaacat caaccccttc aaggacccgc gctggggtcg cgggcaggag     480
acgcccggcg aagacgcatt ccacatccag cgctacgtct acagcctcat cgacggcctg     540
caaaacggca ttgggccggc caaccccaag atcatggcca cctgcaagca cttcgccgcc     600
```

| | |
|---|---|
| tacgacctcg aggactggca cggcaacgag cgctatggct tcaacgccgt cgtgtccacg | 660 |
| caggacctgg ccgagtacta cctgccgccc ttcaagagct gcgcccgcga cgccaaagtc | 720 |
| gacgcgctca tgtgcagcta caacgccgtc aacggggtgc cctcgtgcgc cgactcgtat | 780 |
| ctgctggagg acatcctgcg cgaccactgg ggctggaaca cgaccggcca ctgggtgacg | 840 |
| tccgactgcg atgccgtgca gaacatctac gccaaccatc actacacgtc gactgcgccc | 900 |
| caggcggccg cggacgccct gggcgccggc accgatctcg actgcggcac cacttatccc | 960 |
| gacaatctgg gcgctgccta cacgcagggg ctcttccaga accagaccct cgacacggcg | 1020 |
| ctcatccgcc tgtactcgtc gctcgtcaag ctgggctact tgatccgcc ggagaaccag | 1080 |
| ccctaccggt cgataggctg gagtgatgtg tccacgccgg ccgcgcagca gctggcccgc | 1140 |
| acggcggcgg cggaggggat cgttcttctc aagaacgacg agaagaaagt cctgccgctg | 1200 |
| tcgcgcgagg acagacgct cgccgtgatc gggcccttcg ccaacgcgac gacccagctg | 1260 |
| cagggcaatt accaaggcgt ggcgccgtac atctggacgg tggtcgcggc agcagagcag | 1320 |
| ctgggataca aggtcaacta cgcggatggc acggctatca cgcgaccaa cacgactggc | 1380 |
| tttgcagagg cagtggccgc agccaagtcg tccgacgtcg tcatctatgc gggcggcatc | 1440 |
| gacaactcga tcgaagcgga gggccacgac cgcgacacga tcgtctggcc gggcaaccag | 1500 |
| ctgcagctga tcagcgagct agcgcagact ggcaaaccgc tggtcgtcat ccaattcggc | 1560 |
| ggcgggcaag tggacgactc gtccctgctg caaacgaca gcggcgtcaa cgccctgctg | 1620 |
| tgggcgggct atcccagcca ggctgggggc gccgccatct tcgaaatcct gacgggagcg | 1680 |
| acagcgccgg caggccgtct cccgacgacg cagtacccgg cgcagtacgt cgacgaggtg | 1740 |
| ccgatgacgg acatgacgct gcggccgagc gcgacgaacc cgggacggac gtaccggtgg | 1800 |
| tacgacaagg cggtgatccc gttcggattc gggctgcact acacgacgtt tgacgtgacg | 1860 |
| tggagcaagg cgcagctggg accgtacgag atcggctctc tcgtgaaaaa cgcctcttct | 1920 |
| tccgatgcgc ctgccgacac ggctccgttc gacaccttca ccatccacgt ccgaaacacg | 1980 |
| ggcaagacga cctcagacta cgtcgcgctg ctcttcctct cgacgcgcaa cgcgggacca | 2040 |
| gcaccgtatc cgctcaagac gctggtgggc tacacgcggg cgcgggcgat ccagccgggc | 2100 |
| gagacgcgcg cggtcgacat cgcggtgacg gtgggatcgg tggcgcggac agacgagcgc | 2160 |
| ggggatctgg tactgtatcc ggggacgtac acgctggagg tggatgtgaa cgggcagtat | 2220 |
| ccaactgcag ggtttgaggt gaccggggag gcggcggttc tggatgagtt tccgcagccg | 2280 |
| ccggcataa | 2289 |

<210> SEQ ID NO 5
<211> LENGTH: 2289
<212> TYPE: DNA
<213> ORGANISM: Rasamsonia emersonii
<220> FEATURE:
<221> NAME/KEY: source
<222> LOCATION: (1)..(2289)
<223> OTHER INFORMATION: /organism="Rasamsonia emersonii"
    /mol_type="unassigned DNA"

<400> SEQUENCE: 5

| | |
|---|---|
| atggttctgg gtgtcagtct cgtcctcctg gcgacggccg tctctgccac gttccccgac | 60 |
| tgcagccagc ctccgctgaa ggacaacgcc gtgtgcgata cctcgctgga ccccgtatcg | 120 |
| cgtgctgctg cgctcgtcgc ggccttcacg ctcgaggaga agatcaacaa cacgcagaat | 180 |
| ggatcgcctg gcgtgccccg gctgggcctg ccgccgtatc aatggtggag cgaaggcctg | 240 |

-continued

```
cacggcgtgg ccatctcgcc gggcgtcaac ttctccgcgc acggcgactt cagctacgca    300
acctccttcc cccagcccat cctcatgagc gccgcctttg acgacgacct catcaggcag    360
gtcggcagtg tggtcagcac cgaggcgcgc gccttcagca acgccaaccg cgctggcctc    420
gactactgga cgcccaacat caacccttc aaggacccgc gctggggtcg cgggcaggag    480
acgcccggcg aagacgcatt ccacatccag cgctacgtct acagcctcat cgacggcctg    540
caaaacggca ttgggccggc caaccccaag atcatggcca cctgcaagca cttcgccgcc    600
tacgacctcg aggactggca cggcaacgag cgctatggct caacgccgt cgtgtccacg    660 caggacctgg ccgagtacta cctgccgccc ttcaagagct cgcccgcga cgccaaagtc    720 gacgcgctca tgtgcagcta caacgccgtc aacggggtgc cctcgtgcgc cgactcgtat    780
ctgctggagg acatcctgcg cgaccactgg ggctggaaca cgaccggcca ctgggtgacg    840
tccgactgcg atgccgtgca gaacatctac gccaaccatc actacacgtc gactgcgccc    900
caggcggccg cggacgccct gggcgccggc accgatctcg actgcggcac cacttatccc    960
gacaatctgg gcgctgccta cacgcagggg ctcttccaga accagaccct cgacacggcg    1020
ctcatccgcc tgtactcgtc gctcgtcaag ctgggctact tgatccgcc ggagaaccag    1080 ccctaccggt cgataggctg gagtgatgtg tccacgccgg ccgcgcagca gctggcccgc    1140
acggcggcgg cggaggggat cgttcttctc aagaacgacg agaagaaagt cctgccgctg    1200
tcgcgcgagg acagacgct cgccgtgatc gggcccttcg ccaacgcgac gacccagctg    1260
cagggcaatt accaaggcgt ggcgccgtac atctggacgg tggtcgcggc agcagagcag    1320
ctgggataca aggtcaacta cgcggatggc acggctatca acgcgaccaa cacgactggc    1380
tttgcagagg cagtggccgc agccaagtcg tccgacgtcg tcatctatgc gggcggcatc    1440
gacaactcga tcgaagcgga gggccacgac cgcgacacga tcgtctggcc gggcaaccag    1500
ctgcagctga tcagcgagct agcgcagact ggcaaaccgc tggtcgtcat ccaattcggc    1560
ggcgggcaag tggacgactc gtccctgctg gcaaacgaca gcggcgtcaa cgccctgctg    1620
tgggcgggct atcccagcca ggctgggggc gccgccatct tcgaaatcct gacgggagcg    1680
acagcgccgg caggccgtct cccgacgacg cagtacccgg cgcagtacgt cgacgaggtg    1740
ccgatgacgg acatgacgct gcggccgagc gcgacgaacc cgggacggac gtaccggtgg    1800
tacgacaagg cggtgatccc gttcggattc gggctgcact acacgacgtt tgacgtgacg    1860
tggagcaagg cgcagctggg accgtacgag atcggctctc tcgtgaaaaa cgcctcttct    1920
tccgatgcgc ctgccgacac ggctccgttc gacaccttca ccatccacgt ccgaaacacg    1980
ggcaagacga cctcagacta cgtcgcgctg ctcttcctct cgacgcgcaa cgcgggacca    2040
gcaccgtatc cgctcaagac gctggtgggc tacacgcggg cgcgggcgat ccagccgggc    2100
gagacgcgcg cggtcgacat cgcggtgacg gtgggatcgg tggcgcggac agacgagcgc    2160
ggggatctgg tactgtatcc ggggacgtac acgctggagg tggatgtgaa cgggcagtat    2220
ccaactgcag ggtttgaggt gaccggggag gcggcggttc tggatgagtt tccgcagccg    2280
ccggcataa                                                           2289
```

<210> SEQ ID NO 6
<211> LENGTH: 2388
<212> TYPE: DNA
<213> ORGANISM: Rasamsonia emersonii
<220> FEATURE:
<221> NAME/KEY: source
<222> LOCATION: (1)..(2388)
<223> OTHER INFORMATION: /organism="Rasamsonia emersonii"

/mol_type="unassigned DNA"

<400> SEQUENCE: 6

```
atggtgaccc gtgctgccat tttgactgct gttgctgctc tcctcccac tgccacctgg      60
gcgcaggaca accagaccta cgccaactac tcttcccaga gccagcccga cctcttcccc     120
cgcaccgttg ccaccatcga tctttctttc cctgactgcg agaacggacc tctgagcacc     180
aacctcgtct gcaacaagtc ggcggacccc tgggctcgtg ctgaggctct gatctccctc     240
ttcactttgg aggagctcat caacaacacc cagaacactg ctcccggtgt tcctcgtctg     300
ggcctccccc agtaccaggt ctggaacgag gccttgcacg tcttgaccg tgccaacttc      360
tctcactccg gtgaatactc ttgggccacc agcttcccca tgccatcct gagcatggcc      420
tccttcaacc gcaccctcat caaccagatt gcctccatca ttgccactca ggcccgtgct     480
ttcaacaacg ctggccgcta cggcttggat tcctacgctc ccaacatcaa cggtttccgc     540
tctcctctct ggggtcgtgg tcaggaaacc cccggtgagg atgccttctt cctgagctca     600
acatacgcct acgaatacat caccggcttg cagggtggtg ttgaccctga gcacgtcaag     660
atcgtcgcca ctgccaagca cttcgctgga tacgaccttg agaactgggg taacgtgtct     720
cgcttgggtt tcaacgccat catcacccag caggatcttt ctgaatacta cactccccag     780
ttcctggcct ccgctcgcta cgccaagacc cgcagcatca tgtgctccta caacgccgtc     840
aacggtgttc cctcctgcgc gaactcgttc ttcctgcaga ctctcctccg cgagaacttc     900
gacttcgtcg acgatggata cgtgagctcc gactgcgatg ccgtctacaa cgtgttcaac     960
ccccacggat acgctctcaa ccagtctggt gctgctgccg actctcttct ggctggtacc    1020
gacatcgact gcggtcagac cctcccctgg cacctgaacg agagcttcgt ggaaggatat    1080
gtctcccgtg gtgacattga agtccctc accgtctgt actccaacct ggtccgccta    1140
ggatacttcg atggaaacaa cagcgaatac cgcaacctca actggaacga cgttgtcacc    1200
accgatgcct ggaacatctc ctacgaagcc gccgttgagg gtatcaccct gctcaagaac    1260
gatggcaccc ttcctctttc caagaaggtc cgctccatcg ccttgattgg accttgggcc    1320
aacgccactg tccagatgca gggcaactac tacggcactc ctccctacct catctccct    1380
ctggaggctg ccaaggcctc cggcttcacc gtcaactacg ctttcggcac caacatctcc    1440
accgacagca cccagtggtt cgctgaggcc atcgctgctg ccaagaagtc ggatgtcatc    1500
atctacgctg gtggcattga caacaccatt gaggctgagg ccaggaccg taccgacttg    1560
aaatggcccg gcaaccagct cgacctcatt gagcagctgt cccaggtcgg caagcctctg    1620
gtcgtcctcc agatgggtgg tggccaggtc gactcttcct ccctcaaggc caacaagaac    1680
gtcaacgccc ttgtctgggg tggatacct ggccagtccg gcggtgctgc tcttttcgac    1740
atcctgaccg gcaagcgtgc tcctgctggt cgtcttgtct ccacccagta ccccgctgaa    1800
tacgccaccc agttccccgc caacgacatg aacctgcgcc caacggctc caaccccggc    1860
cagacttaca tctggtacac cggtactccc gtctacgagt tcggccacgg tctgttctac    1920
actgagttcc aggagtccgc tgctgctggt accaacaaga ccagcacttt tgacatcctg    1980
gatctgttct ccactcctca ccctggttac gagtacatcg agcaggttcc cttcatcaac    2040
gtcaccgttg atgtcaagaa cgttggccac accccttctc cctacaccgg cctcctcttc    2100
gccaacacca ctgctggtcc caagccctac cccaacaagt ggctggtcgg tttcgaccgt    2160
ctgcccacca ttcaaccagg cgaaaccgcc aagctcacca tccccgttcc tcttggtgcc    2220
attgcccgtg ccgatgagaa cggcaacaag gttgtgttcc ccggtaacta cgagcttgct    2280
```

```
ctcaacaacg agcgctccgt tgttgtctct ttcaccctca ccggtgatgc tgccaccctc    2340
gagaagtggc ccctctggga gcaggctgtt cccggtgtca ctcagcag                 2388
```

<210> SEQ ID NO 7
<211> LENGTH: 775
<212> TYPE: PRT
<213> ORGANISM: Rasamsonia emersonii

<400> SEQUENCE: 7

```
Gln Asp Asn Gln Thr Tyr Ala Asn Tyr Ser Ser Gln Ser Gln Pro Asp
1               5                   10                  15

Leu Phe Pro Arg Thr Val Ala Thr Ile Asp Leu Ser Phe Pro Asp Cys
            20                  25                  30

Glu Asn Gly Pro Leu Ser Thr Asn Leu Val Cys Asn Lys Ser Ala Asp
        35                  40                  45

Pro Trp Ala Arg Ala Glu Ala Leu Ile Ser Leu Phe Thr Leu Glu Glu
    50                  55                  60

Leu Ile Asn Asn Thr Gln Asn Thr Ala Pro Gly Val Pro Arg Leu Gly
65                  70                  75                  80

Leu Pro Gln Tyr Gln Val Trp Asn Glu Ala Leu His Gly Leu Asp Arg
                85                  90                  95

Ala Asn Phe Ser His Ser Gly Glu Tyr Ser Trp Ala Thr Ser Phe Pro
            100                 105                 110

Met Pro Ile Leu Ser Met Ala Ser Phe Asn Arg Thr Leu Ile Asn Gln
        115                 120                 125

Ile Ala Ser Ile Ile Ala Thr Gln Ala Arg Ala Phe Asn Asn Ala Gly
    130                 135                 140

Arg Tyr Gly Leu Asp Ser Tyr Ala Pro Asn Ile Asn Gly Phe Arg Ser
145                 150                 155                 160

Pro Leu Trp Gly Arg Gly Gln Glu Thr Pro Gly Glu Asp Ala Phe Phe
                165                 170                 175

Leu Ser Ser Thr Tyr Ala Tyr Glu Tyr Ile Thr Gly Leu Gln Gly Gly
            180                 185                 190

Val Asp Pro Glu His Val Lys Ile Val Ala Thr Ala Lys His Phe Ala
        195                 200                 205

Gly Tyr Asp Leu Glu Asn Trp Gly Asn Val Ser Arg Leu Gly Phe Asn
    210                 215                 220

Ala Ile Ile Thr Gln Gln Asp Leu Ser Glu Tyr Tyr Thr Pro Gln Phe
225                 230                 235                 240

Leu Ala Ser Ala Arg Tyr Ala Lys Thr Arg Ser Ile Met Cys Ser Tyr
                245                 250                 255

Asn Ala Val Asn Gly Val Pro Ser Cys Ala Asn Ser Phe Phe Leu Gln
            260                 265                 270

Thr Leu Leu Arg Glu Asn Phe Asp Phe Val Asp Asp Gly Tyr Val Ser
        275                 280                 285

Ser Asp Cys Asp Ala Val Tyr Asn Val Phe Asn Pro His Gly Tyr Ala
    290                 295                 300

Leu Asn Gln Ser Gly Ala Ala Ala Asp Ser Leu Leu Ala Gly Thr Asp
305                 310                 315                 320

Ile Asp Cys Gly Gln Thr Leu Pro Trp His Leu Asn Glu Ser Phe Val
                325                 330                 335

Glu Gly Tyr Val Ser Arg Gly Asp Ile Glu Lys Ser Leu Thr Arg Leu
            340                 345                 350
```

```
Tyr Ser Asn Leu Val Arg Leu Gly Tyr Phe Asp Gly Asn Asn Ser Glu
        355                 360                 365

Tyr Arg Asn Leu Asn Trp Asn Asp Val Thr Thr Asp Ala Trp Asn
    370                 375                 380

Ile Ser Tyr Glu Ala Ala Val Glu Gly Ile Thr Leu Leu Lys Asn Asp
385                 390                 395                 400

Gly Thr Leu Pro Leu Ser Lys Lys Val Arg Ser Ile Ala Leu Ile Gly
                405                 410                 415

Pro Trp Ala Asn Ala Thr Val Gln Met Gln Gly Asn Tyr Tyr Gly Thr
                420                 425                 430

Pro Pro Tyr Leu Ile Ser Pro Leu Glu Ala Ala Lys Ala Ser Gly Phe
            435                 440                 445

Thr Val Asn Tyr Ala Phe Gly Thr Asn Ile Ser Thr Asp Ser Thr Gln
        450                 455                 460

Trp Phe Ala Glu Ala Ile Ala Ala Ala Lys Lys Ser Asp Val Ile Ile
465                 470                 475                 480

Tyr Ala Gly Gly Ile Asp Asn Thr Ile Glu Ala Glu Gly Gln Asp Arg
                485                 490                 495

Thr Asp Leu Lys Trp Pro Gly Asn Gln Leu Asp Leu Ile Glu Gln Leu
                500                 505                 510

Ser Gln Val Gly Lys Pro Leu Val Leu Gln Met Gly Gly Gly Gln
                515                 520                 525

Val Asp Ser Ser Ser Leu Lys Ala Asn Lys Asn Val Asn Ala Leu Val
    530                 535                 540

Trp Gly Gly Tyr Pro Gly Gln Ser Gly Gly Ala Ala Leu Phe Asp Ile
545                 550                 555                 560

Leu Thr Gly Lys Arg Ala Pro Ala Gly Arg Leu Val Ser Thr Gln Tyr
                565                 570                 575

Pro Ala Glu Tyr Ala Thr Gln Phe Pro Ala Asn Asp Met Asn Leu Arg
                580                 585                 590

Pro Asn Gly Ser Asn Pro Gly Gln Thr Tyr Ile Trp Tyr Thr Gly Thr
            595                 600                 605

Pro Val Tyr Glu Phe Gly His Gly Leu Phe Tyr Thr Glu Phe Gln Glu
    610                 615                 620

Ser Ala Ala Ala Gly Thr Asn Lys Thr Ser Thr Phe Asp Ile Leu Asp
625                 630                 635                 640

Leu Phe Ser Thr Pro His Pro Gly Tyr Glu Tyr Ile Glu Gln Val Pro
                645                 650                 655

Phe Ile Asn Val Thr Val Asp Val Lys Asn Val Gly His Thr Pro Ser
                660                 665                 670

Pro Tyr Thr Gly Leu Leu Phe Ala Asn Thr Thr Ala Gly Pro Lys Pro
            675                 680                 685

Tyr Pro Asn Lys Trp Leu Val Gly Phe Asp Arg Leu Pro Thr Ile Gln
    690                 695                 700

Pro Gly Glu Thr Ala Lys Leu Thr Ile Pro Val Pro Leu Gly Ala Ile
705                 710                 715                 720

Ala Arg Ala Asp Glu Asn Gly Asn Lys Val Val Phe Pro Gly Asn Tyr
                725                 730                 735

Glu Leu Ala Leu Asn Asn Glu Arg Ser Val Val Ser Phe Thr Leu
                740                 745                 750

Thr Gly Asp Ala Ala Thr Leu Glu Lys Trp Pro Leu Trp Glu Gln Ala
        755                 760                 765

Val Pro Gly Val Thr Gln Gln
```

<210> SEQ ID NO 8
<211> LENGTH: 21
<212> TYPE: PRT
<213> ORGANISM: Rasamsonia emersonii

<400> SEQUENCE: 8

Met Val Thr Arg Ala Ala Ile Leu Thr Ala Val Ala Ala Leu Leu Pro
1               5                   10                  15

Thr Ala Thr Trp Ala
            20

<210> SEQ ID NO 9
<211> LENGTH: 2391
<212> TYPE: DNA
<213> ORGANISM: Rasamsonia emersonii
<220> FEATURE:
<221> NAME/KEY: source
<222> LOCATION: (1)..(2391)
<223> OTHER INFORMATION: /organism="Rasamsonia emersonii"
    /mol_type="unassigned DNA"

<400> SEQUENCE: 9

| | | | |
|---|---|---|---|
| atggtgactc | gcgcggcgat | tctcaccgca | gtggcggcgc tcctgcccac cgcgacatgg | 60 |
| gcacaggata | accaaaccta | tgccaattac | tcgtcgcagt ctcagccgga cctgtttccc | 120 |
| cggaccgtcg | cgaccatcga | cctgtccttc | cccgactgtg agaatggccc gctcagcacg | 180 |
| aacctggtgt | gcaacaaatc | ggccgatccc | tgggcccgag ctgaggccct catctcgctc | 240 |
| tttaccctcg | aagagctgat | taacaacacc | cagaacaccg ctcctggcgt gccccgtttg | 300 |
| ggtctgcccc | agtatcaggt | gtggaatgaa | gctctgcacg gactggaccg cgccaatttc | 360 |
| tcccattcgg | gcgaatacag | ctgggccacg | tccttcccca tgcccatcct gtcgatggcg | 420 |
| tccttcaacc | ggaccctcat | caaccagatt | gcctccatca ttgcaacgca agcccgtgcc | 480 |
| ttcaacaacg | ccggccgtta | cggccttgac | agctatgcgc ccaacatcaa tggcttccgc | 540 |
| agtcccctct | ggggccgtgg | acaggagacg | cctggtgagg atgcgttctt cttgagttcc | 600 |
| acctatgcgt | acgagtacat | cacaggcctg | cagggcggtg tcgacccaga gcatgtcaag | 660 |
| atcgtcgcga | cggcgaagca | cttcgccggc | tatgatctgg agaactgggg caacgtctct | 720 |
| cggctggggt | tcaatgctat | catcacgcag | caggatctct ccgagtacta cacccctcag | 780 |
| ttcctggcgt | ctgctcgata | cgccaagacg | cgcagcatca tgtgctccta caatgcagtg | 840 |
| aatggagtcc | aagctgtgc | caactccttc | ttcctccaga cgcttctccg agaaaacttt | 900 |
| gacttcgttg | acgacgggta | cgtctcgtcg | gattgcgacg ccgtctacaa cgtcttcaac | 960 |
| ccacacggtt | acgcccttaa | ccagtcggga | gccgctgcgg actcgctcct agcaggtacc | 1020 |
| gatatcgact | gtggtcagac | cttgccgtgg | cacctgaatg agtccttcgt agaaggatac | 1080 |
| gtctcccgcg | gtgatatcga | gaatccctc | accgtctct actcaaacct ggtgcgtctc | 1140 |
| ggctactttg | acggcaacaa | cagcgagtac | cgcaacctca actggaacga cgtcgtgact | 1200 |
| acggacgcct | ggaacatctc | gtacgaggcc | gcggtggaag gtatcaccct gctcaagaac | 1260 |
| gacggaacgc | tgccgctgtc | caagaaggtc | cgcagcattg cgctcatcgg tccttgggcc | 1320 |
| aatgccacgg | tgcagatgca | gggtaactac | tatgaacgc accgtatctc gatcagtccg | 1380 |
| ctggaagccg | ccaaggccag | tgggttcacg | gtcaactatg cattcggtac caacatctcg | 1440 |
| accgattcta | cccagtggtt | cgcggaagcc | atcgcggcgg cgaagaagtc ggacgtgatc | 1500 |

| atctacgccg gtggtattga caacacgatc gaggcagagg acaggaccg cacggatctc | 1560 |
| aagtggccgg ggaaccagct ggatctgatc gagcagctca gccaggtggg caagcccttg | 1620 |
| gtcgtcctgc agatgggcgg tggccaggtg gattcgtcgt cactcaaggc caacaagaat | 1680 |
| gtcaacgctc tggtgtgggg tggctatccc ggacagtcgg gtggtgcggc cctgtttgac | 1740 |
| atccttacgg gcaagcgtgc gccggccggt cgtctggtga gcacgcagta cccggccgag | 1800 |
| tatgcgacgc agttcccggc caacgacatg aacctgcgtc cgaacggcag caacccggga | 1860 |
| cagacataca tctggtacac gggcacgccc gtgtatgagt tcggccacgg tctgttctac | 1920 |
| acggagttcc aggagtcggc tgcggcgggc acgaacaaga cgtcgacttt cgacattctg | 1980 |
| gacctttct ccaccccctca tccgggatac gagtacatcg agcaggttcc gttcatcaac | 2040 |
| gtgactgtgg acgtgaagaa cgtcggccac acgccatcgc cgtacacggg tctgttgttc | 2100 |
| gcgaacacga cagccgggcc caagccgtac ccgaacaaat ggctcgtcgg gttcgaccgg | 2160 |
| ctgccgacga tccagccggg cgagactgcc aagttgacga tcccggtgcc gttgggcgcg | 2220 |
| attgcgcggg cggacgagaa cggcaacaag gtggtcttcc cgggcaacta cgaattggca | 2280 |
| ctgaacaatg agcgatcggt agtggtgtcg ttcacgctga cgggcgatgc ggcgactcta | 2340 |
| gagaaatggc ctttgtggga gcaggcggtg ccggggggtga cccagcagta g | 2391 |

<210> SEQ ID NO 10
<211> LENGTH: 2391
<212> TYPE: DNA
<213> ORGANISM: Rasamsonia emersonii
<220> FEATURE:
<221> NAME/KEY: source
<222> LOCATION: (1)..(2391)
<223> OTHER INFORMATION: /organism="Rasamsonia emersonii"
/mol_type="unassigned DNA"

<400> SEQUENCE: 10

| atggtgactc gcgcggcgat tctcaccgca gtggcggcgc tcctgcccac cgcgacatgg | 60 |
| gcacaggata accaaaccta tgccaattac tcgtcgcagt ctcagccgga cctgtttccc | 120 |
| cggaccgtcg cgaccatcga cctgtccttc cccgactgtg agaatggccc gctcagcacg | 180 |
| aacctggtgt gcaacaaatc ggccgatccc tgggcccgag ctgaggccct catctcgctc | 240 |
| tttaccctcg aagagctgat taacaacacc cagaacaccg ctcctggcgt gccccgtttg | 300 |
| ggtctgcccc agtatcaggt gtggaatgaa gctctgcacg gactggaccg cgccaatttc | 360 |
| tcccattcgg gcgaatacag ctgggccacg tccttcccca tgcccatcct gtcgatggcg | 420 |
| tccttcaacc ggaccctcat caaccagatt gcctccatca ttgcaacgca agcccgtgcc | 480 |
| ttcaacaacg ccggccgtta cggccttgac agctatgcgc ccaacatcaa tggcttccgc | 540 |
| agtcccctct ggggccgtgg acaggagacg cctggtgagg atgcgttctt cttgagttcc | 600 |
| acctatgcgt acgagtacat cacaggcctg cagggcggtg tcgacccaga gcatgtcaag | 660 |
| atcgtcgcga cggcgaagca cttcgccggc tatgatctgg agaactgggg caacgtctct | 720 |
| cggctggggt tcaatgctat catcacgcag caggatctct ccgagtacta cacccctcag | 780 |
| ttcctggcgt ctgctcgata cgccaagacg cgcagcatca tgtgctccta caatgcagtg | 840 |
| aatggagtcc caagctgtgc caactccttc ttcctccaga cgcttctccg agaaaacttt | 900 |
| gacttcgttg acgacgggta cgtctcgtcg gattgcgacg ccgtctacaa cgtcttcaac | 960 |
| ccacacggtt acgcccttaa ccagtcggga gccgctgcgg actcgctcct agcaggtacc | 1020 |
| gatatcgact gtggtcagac cttgccgtgg cacctgaatg agtccttcgt agaaggatac | 1080 |

```
gtctcccgcg gtgatatcga gaaatccctc acccgtctct actcaaacct ggtgcgtctc    1140
ggctactttg acggcaacaa cagcgagtac cgcaacctca actggaacga cgtcgtgact    1200
acggacgcct ggaacatctc gtacgaggcc gcggtggaag gtatcaccct gctcaagaac    1260 gacgaacgc tgccgctgtc caagaaggtc cgcagcattg cgctcatcgg tccttgggcc     1320
aatgccacgg tgcagatgca gggtaactac tatggaacgc caccgtatct gatcagtccg    1380
ctggaagccg ccaaggccag tgggttcacg gtcaactatg cattcggtac caacatctcg    1440
accgattcta cccagtggtt cgcggaagcc atcgcggcgg cgaagaagtc ggacgtgatc    1500
atctacgccg tggtattga caacacgatc gaggcagagg acaggaccg cacgatctc      1560 aagtggccgg ggaaccagct ggatctgatc gagcagctca gccaggtggg caagcccttg    1620
gtcgtcctgc agatgggcgg tggccaggtg gattcgtcgt cactcaaggc caacaagaat    1680
gtcaacgctc tggtgtgggg tggctatccc ggacagtcgg gtggtgcggc cctgtttgac    1740
atccttacgg gcaagcgtgc gccggccggt cgtctggtga gcacgcagta cccggccgag    1800
tatgcgacgc agttcccggc caacgacatg aacctgcgtc cgaacggcag caacccggga    1860
cagacataca tctggtacac gggcacgccc gtgtatgagt tcggccacgg tctgttctac    1920
acggagttcc aggagtcggc tgcggcgggc acgaacaaga cgtcgacttt cgacattctg    1980
gaccttttct ccacccctca tccgggatac gagtacatcg agcaggttcc gttcatcaac    2040
gtgactgtgg acgtgaagaa cgtcggccac acgccatcgc cgtacacggg tctgttgttc    2100
gcgaacacga cagccgggcc caagccgtac ccgaacaaat ggctcgtcgg gttcgaccgg    2160
ctgccgacga tccagccggg cgagactgcc aagttgacga tcccggtgcc gttgggcgcg    2220
attgcgcggg cggacgagaa cggcaacaag gtggtcttcc cgggcaacta cgaattggca    2280
ctgaacaatg agcgatcggt agtggtgtcg ttcacgctga cgggcgatgc ggcgactcta    2340
gagaaatggc ctttgtggga gcaggcggtg ccggggggtga cccagcagta g            2391
```

<210> SEQ ID NO 11
<211> LENGTH: 1473
<212> TYPE: DNA
<213> ORGANISM: Rasamsonia emersonii
<220> FEATURE:
<221> NAME/KEY: source
<222> LOCATION: (1)..(1473)
<223> OTHER INFORMATION: /organism="Rasamsonia emersonii"
    /mol_type="unassigned DNA"

<400> SEQUENCE: 11

```
atgggtcgcc gcattgccac tgctgctctg ctcctgttcg gtctgaacgc cctcaagggt     60
gttgttgctc tcgacaacgg tcttgccatc actccccaga tgggctggaa cacctggaac    120
tcgttcggct gctcgctgaa cgaaaccgtc atcctggatg ctgctgagaa gcttgtgtcg    180
ctaggattca aggacctagg atacgagtac gtggtgctgg atgactgctg gtccgctggc    240
cgtaacgcct ctggctacct ggttcctgac cctgccaagt tccccaacgg cattgatggt    300
cttgccgaga agatccacgc tcttggcctc aagatcggta tctactcttc tgctggtacc    360
atgacctgcg ctcgttacgc tggctctctt ggatacgagg agaaggatgc cgccctctgg    420
gcctcctggg gtatcgacta cctcaagtac gacaactgct acaaccaggg tcaagagggt    480
actcccaagc tcagctacga ccgctacaac gccatgggcc aggctctgaa caagaccggc    540
cgtcccattc tctactccct ctgcaactgg ggtgttgacg ccccctggaa cttcgcctcc    600
accattgcca acagctggcg cacctccggt gacctgctca cacctgggga ccgtgatgat    660
```

```
gccaactgcc cctgctctga gctcgaaggc ttggactgca agaccccggg ctacaagtgc    720
tcgatcctga acgtcatcaa caaggccgtc tactacccct ccaaggcctt ccctggtgcc    780
tggaacgacc ttgacatgct ccaggtcggc aacggtggat tgaccgacga tgaggccgtt    840
gctcacatga gcctctgggc tgctttcaag tctcctctcc tcatgaccaa cgtcctcagc    900
aacattgacc ctcccaccct gtccatcctg cagaaccccg ccgttctagc ggtgtctcag    960
gaccccgtcg ctcctccgt caaccgtatc tggcgctact acgtggatga tgtcgacgcc   1020
aacggatacg gcgagatcca gctgttctcc ggtggtcttg ctggtggtga ccagctcgtc   1080
ctccttctga acgctggcag caaggaccgt accatgaacg ccaccctgga ggacatcttc   1140
tgggaagatg gacctggtgg tactgcctcc caggtccagc agtcctggga tgtctacgat   1200
ctctgggcca accgcatgag caacgagact gctgctgcca tcatcaacgc cgccaacagc   1260
actggaagcg ctgctcctgc tgctcccatc aacatgactg ctcttggtgg tgccaagcac   1320
gtctactctc aggttcctcc ctccgactcc aaggctctga tgggtaccaa ggtcggctcc   1380
gtccagccct ccggcaccgt caaggctttc gtcaaggccc acggtgttgc catgctccgc   1440
ctccgtcagc agtcccagaa gaaggacgaa cta                                1473
```

<210> SEQ ID NO 12
<211> LENGTH: 468
<212> TYPE: PRT
<213> ORGANISM: Rasamsonia emersonii

<400> SEQUENCE: 12

```
Leu Asp Asn Gly Leu Ala Ile Thr Pro Gln Met Gly Trp Asn Thr Trp
1               5                   10                  15

Asn Ser Phe Gly Cys Ser Leu Asn Glu Thr Val Ile Leu Asp Ala Ala
            20                  25                  30

Glu Lys Leu Val Ser Leu Gly Phe Lys Asp Leu Gly Tyr Glu Tyr Val
        35                  40                  45

Val Leu Asp Asp Cys Trp Ser Ala Gly Arg Asn Ala Ser Gly Tyr Leu
    50                  55                  60

Val Pro Asp Pro Ala Lys Phe Pro Asn Gly Ile Asp Gly Leu Ala Glu
65                  70                  75                  80

Lys Ile His Ala Leu Gly Leu Lys Ile Gly Ile Tyr Ser Ser Ala Gly
                85                  90                  95

Thr Met Thr Cys Ala Arg Tyr Ala Gly Ser Leu Gly Tyr Glu Glu Lys
            100                 105                 110

Asp Ala Ala Leu Trp Ala Ser Trp Gly Ile Asp Tyr Leu Lys Tyr Asp
        115                 120                 125

Asn Cys Tyr Asn Gln Gly Gln Glu Gly Thr Pro Lys Leu Ser Tyr Asp
    130                 135                 140

Arg Tyr Asn Ala Met Gly Gln Ala Leu Asn Lys Thr Gly Arg Pro Ile
145                 150                 155                 160

Leu Tyr Ser Leu Cys Asn Trp Gly Val Asp Gly Pro Trp Asn Phe Ala
                165                 170                 175

Ser Thr Ile Ala Asn Ser Trp Arg Thr Ser Gly Asp Leu Leu Asn Thr
            180                 185                 190

Trp Asp Arg Asp Asp Ala Asn Cys Pro Cys Ser Glu Leu Glu Gly Leu
        195                 200                 205

Asp Cys Lys Thr Pro Gly Tyr Lys Cys Ser Ile Leu Asn Val Ile Asn
    210                 215                 220

Lys Ala Val Tyr Tyr Pro Ser Lys Ala Phe Pro Gly Ala Trp Asn Asp
```

```
                225                 230                 235                 240
Leu Asp Met Leu Gln Val Gly Asn Gly Gly Leu Thr Asp Asp Glu Ala
                245                 250                 255

Val Ala His Met Ser Leu Trp Ala Ala Phe Lys Ser Pro Leu Leu Met
            260                 265                 270

Thr Asn Val Leu Ser Asn Ile Asp Pro Pro Thr Leu Ser Ile Leu Gln
        275                 280                 285

Asn Pro Ala Val Leu Ala Val Ser Gln Asp Pro Val Gly Ser Ser Val
    290                 295                 300

Asn Arg Ile Trp Arg Tyr Tyr Val Asp Asp Val Asp Ala Asn Gly Tyr
305                 310                 315                 320

Gly Glu Ile Gln Leu Phe Ser Gly Gly Leu Ala Gly Gly Asp Gln Leu
                325                 330                 335

Val Leu Leu Leu Asn Ala Gly Ser Lys Asp Arg Thr Met Asn Ala Thr
            340                 345                 350

Leu Glu Asp Ile Phe Trp Glu Asp Gly Pro Gly Gly Thr Ala Ser Gln
        355                 360                 365

Val Gln Gln Ser Trp Asp Val Tyr Asp Leu Trp Ala Asn Arg Met Ser
    370                 375                 380

Asn Glu Thr Ala Ala Ala Ile Ile Asn Ala Ala Asn Ser Thr Gly Ser
385                 390                 395                 400

Ala Ala Pro Ala Ala Pro Ile Asn Met Thr Ala Leu Gly Gly Ala Lys
                405                 410                 415

His Val Tyr Ser Gln Val Pro Pro Ser Asp Ser Lys Ala Leu Met Gly
            420                 425                 430

Thr Lys Val Gly Ser Val Gln Pro Ser Gly Thr Val Lys Ala Phe Val
        435                 440                 445

Lys Ala His Gly Val Ala Met Leu Arg Leu Arg Gln Gln Ser Gln Lys
    450                 455                 460

Lys Asp Glu Leu
465

<210> SEQ ID NO 13
<211> LENGTH: 23
<212> TYPE: PRT
<213> ORGANISM: Rasamsonia emersonii

<400> SEQUENCE: 13

Met Gly Arg Arg Ile Ala Thr Ala Ala Leu Leu Leu Phe Gly Leu Asn
1               5                   10                  15

Ala Leu Lys Gly Val Val Ala
            20

<210> SEQ ID NO 14
<211> LENGTH: 1670
<212> TYPE: DNA
<213> ORGANISM: Rasamsonia emersonii
<220> FEATURE:
<221> NAME/KEY: source
<222> LOCATION: (1)..(1670)
<223> OTHER INFORMATION: /organism="Rasamsonia emersonii"
      /mol_type="unassigned DNA"

<400> SEQUENCE: 14
atggggagaa gaattgctac tgctgcactt ctcttgttcg ggctcaatgc cttgaaagga      60
gtggtggcgc tggacaatgg cctggccatc actccgcaga tgggatgggt aagaatatat    120
ccaattgaat ggccaaactt gaaagttgca attggaattt gataatcct gctcatgcat     180
```

```
aagtcaacag aacacatgga actccttcgg atgctcgcta aacgagaccg tcatcctaga    240
cgcggccgaa aagctcgtct cgctcggatt caaggatctc ggctatgagt acgtcgtcct    300
ggacgactgc tggtctgccg gccggaacgc gtctggctat ctggtgccgg atccagccaa    360
gtttcccaat ggcatcgatg gcctggcgga gaagatccat gcgctgggct tgaagattgg    420
catttattcc agtgcgggaa ccatgacttg cgcccgctat gctgggtcgt tgggatatga    480
agagaaggat gcagcgcttt gggctagttg ggggtaagt acgcctaaag gcataaaac     540
ctgcaaagaa aatacttaaa aaaaaacgta aatagatcga ctacctcaaa tacgacaact    600
gctacaacca aggccaagaa ggcacgccca agctctcgta cgaccgctac aacgccatgg    660
gccaagccct caacaagaca ggccgcccga ttctctactc gctctgcaac tggggcgtcg    720
acggccgtg gaactttgcc tcgaccatcc caactcgtg gcgcacgtcg ggcgatctgc     780
tcaacacgtg ggaccgcgac gacgcaaact gtccgtgcag tgagctcgag ggcctcgact    840
gcaagactcc cggtacaag tgttcgatcc tgaacgtcat caacaaggcg gtgtattatc     900
cgtctaaggc gttccctggg gcgtggaatg acctggacat gctacgtatg tctccatcta    960
tctatcattc tattacatga tctaacacgc ctgcagaggt tggcaacgga ggcctcaccg   1020
acgacgaagc cgtcgcccac atgagtctct gggcagcctt caagtccccg ctgctgatga   1080
ccaacgtcct gagcaacatc gaccctccta cgctgtccat cctgcagaac ccggccgtgc   1140
tggccgtctc gcaggaccg gtcggctcca gcgtcaaccg catctggcgg tactacgtcg    1200
acgacgtgga cgccaacggg tacgcgaga tccagctgtt cagcggcggc ctggcaggag    1260
gcgaccagct ggtgctgctg ctgaacgcgg ggtcgaagga ccgcaccatg aacgcgacgc   1320
tggaggacat cttctgggaa gacgggcccg gtggcacggc cagccaggta cagcagagct   1380
gggacgtgta cgacctgtgg gcgaaccgga tgagcaacga gacggcggcg gcgatcatca   1440
acgccgccaa ctcgaccggt tctgctgcgc ctgctgcgcc gatcaacatg accgccctcg   1500
ggggtgccaa gcacgtgtac tcgcaggtgc cgccgtccga ctcgaaggcg ttgatgggca   1560
ccaaggttgg gagcgtccag ccgagtggga cggtcaaggc gtttgtcaag gcgcacggcg   1620
tggcgatgtt gcggctgcgc cagcagtcgc agaagaagga tgagttgtaa               1670
```

<210> SEQ ID NO 15
<211> LENGTH: 1476
<212> TYPE: DNA
<213> ORGANISM: Rasamsonia emersonii
<220> FEATURE:
<221> NAME/KEY: source
<222> LOCATION: (1)..(1476)
<223> OTHER INFORMATION: /organism="Rasamsonia emersonii"
    /mol_type="unassigned DNA"

<400> SEQUENCE: 15

```
atggggagaa gaattgctac tgctgcactt ctcttgttcg ggctcaatgc cttgaaagga     60
gtggtggcgc tggacaatgg cctggccatc actccgcaga tggatgaa cacatggaac     120
tccttcggat gctcgctaaa cgagaccgtc atcctagacg cggccgaaaa gctcgtctcg    180
ctcggattca aggatctcgg ctatgagtac gtcgtcctgg acgactgctg gtctgccggc    240
cggaacgcgt ctggctatct ggtgccggat ccagccaagt ttcccaatgg catcgatggc    300
ctggcgaga gatccatgc gctgggcttg aagattggca tttattccag tgcgggaacc     360
atgacttgcg cccgctatgc tgggtcgttg ggatatgaag agaaggatgc agcgctttgg    420
gctagttggg ggatcgacta cctcaaatac gacaactgct acaaccaagg ccaagaaggc    480
```

```
acgcccaagc tctcgtacga ccgctacaac gccatgggcc aagccctcaa caagacaggc    540
cgcccgattc tctactcgct ctgcaactgg ggcgtcgacg gcccgtggaa ctttgcctcg    600
accatcgcca actcgtggcg cacgtcgggc gatctgctca cacgtggga ccgcgacgac     660 gcaaactgtc cgtgcagtga gctcgagggc ctcgactgca agactcccgg gtacaagtgt    720
tcgatcctga acgtcatcaa caaggcggtg tattatccgt ctaaggcgtt ccctggggcg    780
tggaatgacc tggacatgct acaggttggc aacggaggcc tcaccgacga cgaagccgtc    840
gcccacatga gtctctgggc agccttcaag tccccgctgc tgatgaccaa cgtcctgagc    900
aacatcgacc ctcctacgct gtccatcctg cagaacccgg ccgtgctggc cgtctcgcag    960
gacccggtcg gctccagcgt caaccgcatc tggcggtact acgtcgacga cgtggacgcc   1020
aacgggtacg gcgagatcca gctgttcagc ggcggcctgg caggaggcga ccagctggtg   1080
ctgctgctga acgcggggtc gaaggaccgc accatgaacg cgacgctgga ggacatcttc   1140
tgggaagacg ggcccggtgg cacggccagc caggtacagc agagctggga cgtgtacgac   1200
ctgtgggcga accggatgag caacgagacg gcggcggcga tcatcaacgc cgccaactcg   1260
accggttctg ctgcgcctgc tgcgccgatc aacatgaccg ccctcggggg tgccaagcac   1320
gtgtactcgc aggtgccgcc gtccgactcg aaggcgttga tgggcaccaa ggttgggagc   1380
gtccagccga gtgggacggt caaggcgttt gtcaaggcgc acggcgtggc gatgttgcgg   1440
ctgcgccagc agtcgcagaa gaaggatgag ttgtaa                             1476

<210> SEQ ID NO 16
<211> LENGTH: 2046
<212> TYPE: DNA
<213> ORGANISM: Rasamsonia emersonii
<220> FEATURE:
<221> NAME/KEY: source
<222> LOCATION: (1)..(2046)
<223> OTHER INFORMATION: /organism="Rasamsonia emersonii"
      /mol_type="unassigned DNA"

<400> SEQUENCE: 16
atgactcgct acccctccct ctcctactac gctctcagca gctaccttct cttcacctcc     60
tgcggtgctc ttgccagcac tcgtctggag ccccgtctgg acaacggatt ggccatcact    120
cctcccatgg gctggaactc ctacaaccac tactcttgct ccccccaacga gtccatcatc    180 cagtccaacg ccaaggcctt ggttgacttc ggtctggaca cctaggata ccgctacgtc     240 accaccgact gcggctggac tgtccccta cgtctgccca cggctccct cacctggaac    300 gagactctct tccccctcgg tttccctgct cttggccagt acatccacga ccttggactc    360
ctcttcggtg tctaccagga tgctggtatc aagacctgcg gtggtccccc tgaccaggtc    420
ggttccctgt tccacgagca gcaggatgcc gagactttcg ctgcctggaa ggccgatgcc    480
ctcaagtacg acaactgcta ctcggatgct gctgctggct accccgatgc cgactacact    540
cctagcacct ccccagcttt ccgttacgcc aacatgacca aggcccttgc ctccgttgac    600
cgcaagatcc tcttccagat ctgcgactgg ggtgttgact tccccgccct ctgggctcct    660
tctctgggaa acacctggcg catctccaac gacattattc ctgcctggcg caccatcttc    720
cgtatcctga accaggcggt gcctcagact tctttcgctg gtcccggtca ctggcccgac    780
ctcgacatgc ttgaggttgg caacaacgtg ttcaccatcc ccgaggagca gacccacttc    840
tctctgtggg ccattctcaa gtcgcctctg accattggtg ctgccctcaa cgacaccctg    900
accaccatcc gcgatgcctc cctccagatc ctcaagcaga aggatgtcat cagctacaac    960
```

```
caggacccct tgggtgtctc tgcctccctg aagcgtcgtt ggaccgaaga aggattcgag    1020
gtctggagcg gtcccatctc cggtggcaag accgttgctg ctctcatcaa ctgggcggac    1080
gagtcccgca acctgaccct ggatcttcct gttgttggcc tccagcacgc tcagaccctc    1140
cgcaacatct gggatgagtc tgctgccacc aacgtccgca cctcctacac tgccaacgtc    1200
gctgctcacg gcaccatgtt ggttgagctt gctggtacca ctgaggctgg aaagtacccc    1260
gccgacatct cgccacctc ggatggccac tccaccactt cgagaacat ctacgctgag    1320 actacttctt cccagtacca gctcaccatt gctttcgctc ccggttcttc tcactcttcc    1380
gagatcacca tccgtacctc gctaggcggc ttcaagacct cggccaaggt ccagcccact    1440
gagagccaga tctccgtcaa catctccctg tctgctggca gctccaacac catcaccatc    1500
tctcccagcc ccatcatctc ctacatcaac gtcacctcgc ctagcggtac ctactacccc    1560
tgcacctcgt tcactcctgt cggttccgcc aagcccgaga cttgcgatgc tggtttctgc    1620
ctgcccgtcg gctccaagat tggttacatc tcccccaccg gcaacgccag catcaccatt    1680
cccgccaccg tcgtcagcgg ctccggtgac aacaccactg ccgccaccac caccgctggc    1740
aagtacctcg aaattgatta catcaacaac gacatcgctt tctccacctc ctggaccact    1800
ggcagcaact ctcgcaacct caccatttcc gtcaacggtg gtcctcctac ccgtattgag    1860
gttcctcttt ctggcaagca cagcgaactc ttcggtcctg gtcgtggctg gtgggattct    1920
gccaccttcg gtgtgcttgt tgacggctgg cgcaacggtg agaacactgt tgtcattggc    1980
aaccagggtg gtgacgaggg tgtgcagccc tacggtgccg acttcgtcgg tctgcgtctg    2040
tacgac                                                              2046
```

<210> SEQ ID NO 17
<211> LENGTH: 657
<212> TYPE: PRT
<213> ORGANISM: Rasamsonia emersonii

<400> SEQUENCE: 17

Ser Thr Arg Leu Glu Pro Arg Leu Asp Asn Gly Leu Ala Ile Thr Pro
1               5                   10                  15

Pro Met Gly Trp Asn Ser Tyr Asn His Tyr Ser Cys Ser Pro Asn Glu
            20                  25                  30

Ser Ile Ile Gln Ser Asn Ala Lys Ala Leu Val Asp Phe Gly Leu Asp
        35                  40                  45

Thr Leu Gly Tyr Arg Tyr Val Thr Thr Asp Cys Gly Trp Thr Val Pro
    50                  55                  60

Tyr Arg Leu Pro Asn Gly Ser Leu Thr Trp Asn Glu Thr Leu Phe Pro
65                  70                  75                  80

Ser Gly Phe Pro Ala Leu Gly Gln Tyr Ile His Asp Leu Gly Leu Leu
                85                  90                  95

Phe Gly Val Tyr Gln Asp Ala Gly Ile Lys Thr Cys Gly Gly Pro Pro
            100                 105                 110

Asp Gln Val Gly Ser Leu Phe His Glu Gln Gln Asp Ala Glu Thr Phe
        115                 120                 125

Ala Ala Trp Lys Ala Asp Ala Leu Lys Tyr Asp Asn Cys Tyr Ser Asp
    130                 135                 140

Ala Ala Ala Gly Tyr Pro Asp Ala Asp Tyr Thr Pro Ser Thr Ser Pro
145                 150                 155                 160

Ser Phe Arg Tyr Ala Asn Met Thr Lys Ala Leu Ala Ser Val Asp Arg
                165                 170                 175

```
Lys Ile Leu Phe Gln Ile Cys Asp Trp Gly Val Asp Phe Pro Ala Leu
                180                 185                 190

Trp Ala Pro Ser Leu Gly Asn Thr Trp Arg Ile Ser Asn Asp Ile Ile
            195                 200                 205

Pro Ala Trp Arg Thr Ile Phe Arg Ile Leu Asn Gln Ala Val Pro Gln
        210                 215                 220

Thr Ser Phe Ala Gly Pro Gly His Trp Pro Asp Leu Asp Met Leu Glu
225                 230                 235                 240

Val Gly Asn Asn Val Phe Thr Ile Pro Glu Glu Gln Thr His Phe Ser
                245                 250                 255

Leu Trp Ala Ile Leu Lys Ser Pro Leu Thr Ile Gly Ala Ala Leu Asn
            260                 265                 270

Asp Thr Leu Thr Thr Ile Arg Asp Ala Ser Leu Gln Ile Leu Lys Gln
        275                 280                 285

Lys Asp Val Ile Ser Tyr Asn Gln Asp Pro Leu Gly Val Ser Ala Ser
    290                 295                 300

Leu Lys Arg Arg Trp Thr Glu Glu Gly Phe Glu Val Trp Ser Gly Pro
305                 310                 315                 320

Ile Ser Gly Gly Lys Thr Val Ala Ala Leu Ile Asn Trp Ala Asp Glu
                325                 330                 335

Ser Arg Asn Leu Thr Leu Asp Leu Pro Val Val Gly Leu Gln His Ala
            340                 345                 350

Gln Thr Leu Arg Asn Ile Trp Asp Glu Ser Ala Ala Thr Asn Val Arg
        355                 360                 365

Thr Ser Tyr Thr Ala Asn Val Ala Ala His Gly Thr Met Leu Val Glu
    370                 375                 380

Leu Ala Gly Thr Thr Glu Ala Gly Lys Tyr Pro Ala Asp Ile Phe Ala
385                 390                 395                 400

Thr Ser Asp Gly His Ser Thr Thr Phe Glu Asn Ile Tyr Ala Glu Thr
                405                 410                 415

Thr Ser Ser Gln Tyr Gln Leu Thr Ile Ala Phe Ala Pro Gly Ser Ser
            420                 425                 430

His Ser Ser Glu Ile Thr Ile Arg Thr Ser Leu Gly Gly Phe Lys Thr
        435                 440                 445

Ser Ala Lys Val Gln Pro Thr Glu Ser Gln Ile Ser Val Asn Ile Ser
450                 455                 460

Leu Ser Ala Gly Ser Ser Asn Thr Ile Thr Ile Ser Pro Ser Pro Ile
465                 470                 475                 480

Ile Ser Tyr Ile Asn Val Thr Ser Pro Ser Gly Thr Tyr Tyr Pro Cys
                485                 490                 495

Thr Ser Phe Thr Pro Val Gly Ser Ala Lys Pro Glu Thr Cys Asp Ala
            500                 505                 510

Gly Phe Cys Leu Pro Val Gly Ser Lys Ile Gly Tyr Ile Ser Pro Thr
        515                 520                 525

Gly Asn Ala Ser Ile Thr Ile Pro Ala Thr Val Val Ser Gly Ser Gly
    530                 535                 540

Asp Asn Thr Thr Ala Ala Thr Thr Thr Ala Gly Lys Tyr Leu Glu Ile
545                 550                 555                 560

Asp Tyr Ile Asn Asn Asp Ile Ala Phe Ser Thr Ser Trp Thr Thr Gly
                565                 570                 575

Ser Asn Ser Arg Asn Leu Thr Ile Ser Val Asn Gly Gly Pro Pro Thr
            580                 585                 590
```

```
Arg Ile Glu Val Pro Leu Ser Gly Lys His Ser Glu Leu Phe Gly Pro
            595                 600                 605

Gly Arg Gly Trp Trp Asp Ser Ala Thr Phe Gly Val Leu Val Asp Gly
        610                 615                 620

Trp Arg Asn Gly Glu Asn Thr Val Val Ile Gly Asn Gln Gly Gly Asp
625                 630                 635                 640

Glu Gly Val Gln Pro Tyr Gly Ala Asp Phe Val Gly Leu Arg Leu Tyr
            645                 650                 655

Asp

<210> SEQ ID NO 18
<211> LENGTH: 25
<212> TYPE: PRT
<213> ORGANISM: Rasamsonia emersonii

<400> SEQUENCE: 18

Met Thr Arg Tyr Pro Ser Leu Ser Tyr Tyr Ala Leu Ser Ser Tyr Leu
1               5                  10                  15

Leu Phe Thr Ser Cys Gly Ala Leu Ala
            20                  25

<210> SEQ ID NO 19
<211> LENGTH: 2315
<212> TYPE: DNA
<213> ORGANISM: Rasamsonia emersonii
<220> FEATURE:
<221> NAME/KEY: source
<222> LOCATION: (1)..(2315)
<223> OTHER INFORMATION: /organism="Rasamsonia emersonii"
      /mol_type="unassigned DNA"

<400> SEQUENCE: 19
atgacaagat atcctagtct tagctactat gcactctctt catatttact atttaccagc      60
tgtggtgcac tggcatccac aaggttggaa cctaggttag acaatggact ggcaatcaca    120
cctccaatgg ggtaagtctc gtcttgtgaa gagttattat tattattatt ctagctagat    180
acagcttggc tcattcatat atgaaccgtg aagatgaaac tcctacaacc actactcatg    240
ctccccgaac gaatcgatca tccagtcaaa cgcgaaggct ctcgtggact ttggccttga    300
tacccttggc tatcgatatg tcacaactga ttgcggctgg acggtcccct accgactccc    360
caatgggtcc ttgacctgga atgaaacgct gtttccgagt ggattccgg cactagggca    420 gtacattcac gatctggggc ttctcttggg cgtctatcaa gatgcgggga ttaagacttg    480
tggaggaccc cctgatcaag taggaagttt atgtaagggc tttgactccc ccggatgtg    540 cattggccgg cgtggttaat tcgaatcaag tccatgaaca acaggacgca gagacgttcg    600
ctgcctggaa agcggatgcg ttgaaatgta cgtgctgttg tgtctcttct tgcgccgtc    660 gcattgattg atactgatct tccttccaga cgacaactgc tattctgatg cagccgctgg    720
gtatccagat gcggattata caccgagcac ctcgccatcg ttccgctacg cgaacatgac    780
aaaggcgctg gccagtgtgg atcggaaaat ccttttccaa atctgtgact ggggcgtcga    840
tttccccgcg ctctgggctc cctctctggg caacacctgg cgaatttcca acgacataat    900
ccccgcgtgg cggacgatct tcaggatcct caaccaggcc gtgccgcaga cttcttttgc    960
cggacctggc cactggccag acctcgatat gctcgaggtg gggaacaatg tgtttacgat   1020
cccggaagag cagacgcact ttcccttttg ggcgatcctg aaaagccccc tgaccatcgg   1080
tgccgcgttg aatgatacct tgacgacgat cagagatgcc tcgctccaga tcttgaaaca   1140
```

```
gaaggatgtc atcagctaca accaagaccc gcttggtgtg agtgccagtc tgaagaggag    1200
atggaccgaa gagggctttg aagtgtggag cgggcccata tcgggtggga agacagtggc    1260
tgcattgatc aactgggcgg atgaatcgag gaacttgacg ctggatctcc ctgtcgtagg    1320
cctacaacac gcgcagacgc tgcggaacat ctgggacgaa agcgcagcca cgaacgtccg    1380
tacgtcgtac actgcgaacg tggcagctca tggaacgatg ttggtagaac tggccgggac    1440
aacagaagca gggaagtatc ctgctgatat ttttgcaact tcagatgggt cagtcctaac    1500
ccctcttccc ttgacaggaa aaaaaaata agggacgctg accgcttagc aggcactcga    1560
caacttttga aaacatctat gccgagacca ctagcagcca gtaccagttg acaatcgcgt    1620
ttgctcccgg atcatctcac tcgagcgaaa taacgatccg aacgagcctc ggggattca    1680 agacgtctgc caaggtgcaa ccgactgaga gccaaatctc ggtcaacatc tcgctgtcag    1740
caggttcatc gaacacgatc acgatttcgc cgtctccaat tatcagttac ataaacgtca    1800
cctccccatc ggggacatac tatccctgta catcgtttac acctgtggga tccgccaaac    1860
ccgagacttg cgatgcggga ttctgcctgc ctgtcgggtc caaaatcggc tatatcagcc    1920
cgacaggtaa tgcaagcatc actatccctg ccacggtggt gtctggcagt ggcgataata    1980
ctactgctgc tactacgact gcagggaaat acctcgagat cgactacatc aacaacgaca    2040
ttgccttttc aacctcgtgg accacgggct ccaattctcg gaatctgaca atctcggtca    2100
acggcggacc accgacgagg atcgaggtgc ctctttctgg gaagcacagc gagctcttcg    2160
gaccaggccg tggctggtgg gatagcgcga cctttggcgt tttggttgat gggtggagga    2220
atggagaaaa cacggtggtg ataggggaacc agggaggtga cgagggagta cagccgtatg    2280
gtgcggactt tgtgggcttg cgactgtatg attga                               2315
```

<210> SEQ ID NO 20
<211> LENGTH: 2049
<212> TYPE: DNA
<213> ORGANISM: Rasamsonia emersonii
<220> FEATURE:
<221> NAME/KEY: source
<222> LOCATION: (1)..(2049)
<223> OTHER INFORMATION: /organism="Rasamsonii emersonii"
      /mol_type="unassigned DNA"

<400> SEQUENCE: 20

```
atgacaagat atcctagtct tagctactat gcactctctt catatttact atttaccagc     60
tgtggtgcac tggcatccac aaggttggaa cctaggttag acaatggact ggcaatcaca    120
cctccaatgg gatggaactc ctacaaccac tactcatgct ccccgaacga atcgatcatc    180
cagtcaaacg cgaaggctct cgtggacttt ggccttgata cccttggcta tcgatatgtc    240
acaactgatt gcggctggac ggtcccctac cgactcccca tgggtccctt gacctggaat    300
gaaacgctgt ttccgagtgg attcccggca ctagggcagt acattcacga tctggggctt    360
ctctttggcg tctatcaaga tgcggggatt aagacttgtg gaggaccccc tgatcaagta    420
ggaagtttat tccatgaaca acaggacgca gagacgttcg ctgcctggaa agcggatgcg    480
ttgaaatacg acaactgcta ttctgatgca gccgctgggt atccagatgc ggattataca    540
ccgagcacct cgccatcgtt ccgctacgcg aacatgacaa aggcgctggc cagtgtggat    600
cggaaaatcc ttttccaaat ctgtgactgg ggcgtcgatt tccccgcgct ctgggctccc    660
tctctgggca cacctggcg aatttccaac gacataatcc ccgcgtggcg gacgatcttc    720
aggatcctca accaggccgt gccgcagact tcttttgccg gacctggcca ctggccagac    780
```

| | |
|---|---|
| ctcgatatgc tcgaggtggg gaacaatgtg tttacgatcc cggaagagca gacgcacttt | 840 |
| tcccttggg cgatcctgaa aagcccctg accatcggtg ccgcgttgaa tgataccttg | 900 |
| acgacgatca gagatgcctc gctccagatc ttgaaacaga aggatgtcat cagctacaac | 960 |
| caagacccgc ttggtgtgag tgccagtctg aagaggagat ggaccgaaga gggctttgaa | 1020 |
| gtgtggagcg ggcccatatc gggtgggaag acagtggctg cattgatcaa ctgggcggat | 1080 |
| gaatcgagga acttgacgct ggatctccct gtcgtaggcc tacaacacgc gcagacgctg | 1140 |
| cggaacatct gggacgaaag cgcagccacg aacgtccgta cgtcgtacac tgcgaacgtg | 1200 |
| gcagctcatg gaacgatgtt ggtagaactg gccgggacaa cagaagcagg gaagtatcct | 1260 |
| gctgatattt ttgcaacttc agatgggcac tcgacaactt ttgaaaacat ctatgccgag | 1320 |
| accactagca gccagtacca gttgacaatc gcgtttgctc ccggatcatc tcactcgagc | 1380 |
| gaaataacga tccgaacgag cctcggggga ttcaagacgt ctgccaaggt gcaaccgact | 1440 |
| gagagccaaa tctcggtcaa catctcgctg tcagcaggtt catcgaacac gatcacgatt | 1500 |
| tcgccgtctc caattatcag ttacataaac gtcacctccc catcggggac atactatccc | 1560 |
| tgtacatcgt ttacacctgt gggatccgcc aaacccgaga cttgcgatgc gggattctgc | 1620 |
| ctgcctgtcg ggtccaaaat cggctatatc agcccgacag gtaatgcaag catcactatc | 1680 |
| cctgccacgg tggtgtctgg cagtggcgat aatactactg ctgctactac gactgcaggg | 1740 |
| aaatacctcg agatcgacta catcaacaac gacattgcct tttcaacctc gtggaccacg | 1800 |
| ggctccaatt ctcggaatct gacaatctcg gtcaacggcg gaccaccgac gaggatcgag | 1860 |
| gtgcctcttt ctgggaagca cagcgagctc ttcggaccag gccgtggctg gtgggatagc | 1920 |
| gcgacctttg gcgttttggt tgatgggtgg aggaatggag aaaacacggt ggtgataggg | 1980 |
| aaccagggag gtgacgaggg agtacagccg tatggtgcgg actttgtggg cttgcgactg | 2040 |
| tatgattga | 2049 |

```
<210> SEQ ID NO 21
<211> LENGTH: 1821
<212> TYPE: DNA
<213> ORGANISM: Rasamsonia emersonii
<220> FEATURE:
<221> NAME/KEY: source
<222> LOCATION: (1)..(1821)
<223> OTHER INFORMATION: /organism="Rasamsonia emersonii"
      /mol_type="unassigned DNA"

<400> SEQUENCE: 21
```

| | |
|---|---|
| atgatctccg ctgctgttct ggtgtctttg ctactcacca ccatccagcc cggtgcctac | 60 |
| gcccagtggc agtgcggtgg ttccacctac actcccggct ccgtcaactt caccgaggag | 120 |
| tgctaccagc tgctcaggga ctgcgttgct cagttcggtg cgaacgcctc tctggtcaac | 180 |
| tgccaggatg ctgctggtaa cctcttcatg cagcagcagt ccaaccaggg caagaacaac | 240 |
| gactacttga ttgcctacca ggatatcctg gacttctgct tgctcgatgg attcaccact | 300 |
| ggtacctggt acgatgactc tcagtggtac tggatggctg ctgagcctgg ctgctactct | 360 |
| cccaacggct ccatcggtac caccggtccc ggtttctgcg tgcagaaccg cgatgacacc | 420 |
| gtcctcaacg gctgctaccc ccagcccag tccggtgctg tcctctcca ggtcctccgc | 480 |
| actgctcgca ctgccaacgg cttcacctcg tctgcccgtg gctggaacag ctggggaatc | 540 |
| caggctctgg agaaccccag caccatcccc ggctggactg tgttcaacca gactgctgtc | 600 |
| aagcagcagt gctccgtcct tgctcgctcc gacttcaagg ctgctggcta cgacctttgc | 660 |

```
tctcttgatg ctggctggtc gacctcttcc gaggttgatg agtacggccg tatcctgtac    720
aacagcaccc tcttcgacct tcctgagctg gccgactacc tccacggtca gggtctgaag    780
ctcggtgtct acgtcatccc cggtgttcct tgcgttgccg ccaacaagac cattgagggt    840
accaacatcc gcattggtga tgtcctgaac ggcaacaacg acgagctctc ctactgcgac    900
tgggacttct ccaaggatgg tgtccagcag tggcacgact cgctgatcaa cctctgggcc    960
agctggggtg ttgacatgat caagctcgac ttcgtcactc ctggaagccc tcagaacggt   1020
gccaacttgg tgtgcaacaa ctctgctgcc gttgaggcct accacaaggc cattgccaac   1080
tctggccgtc agatccgtct ggacctcagc tggaagctct gccgtaacga aacctacctg   1140
cccgtctggt ccagccttgc cgactccatc cgcactgacc aggacattga taactacggc   1200
tacaacacct tcgtcgcctg gcaggtcgtc cagcgtgcca tcgagaacta ccgtcagtac   1260
atcctgctgc agaagcagcg caacgttccc atcaccctgt accccgacat ggacaacctg   1320
ttcgtcggca acgccgccaa cctcaccggt gtctccgatg cccagcgtat caccatcatg   1380
aaccactggc ttggtgctgc tgccaacctg atcattggct ccgacctcaa ccagctcgat   1440
gaccttggta ccaagctcct cacctccaac gagtccatcc aggctgccga cttcttcgct   1500
cagtacccca tgcagccccg caaccctggt actggtgaca cgtcccccca gcagctccag   1560
gcctggattg ctggccccct cgacaacaac gaagcctacg tgcttgttgt caactacggc   1620
cctgaccagg ccacggtgg tttcggtacc agcttgactg gtgtgcagaa cgtcaccgtt   1680
tctcttgccg atcttggtat cgctggcaag agctgggaat ctccgatgt ctggaacgga   1740 aactcctcca ccgtcagcac ctcgttcact gcctacctgg atgagggtga gtcccagctc   1800
ctgcacctca ccgttgcgca g                                              1821
```

<210> SEQ ID NO 22
<211> LENGTH: 586
<212> TYPE: PRT
<213> ORGANISM: Rasamsonia emersonii

<400> SEQUENCE: 22

Gln Trp Gln Cys Gly Gly Ser Thr Tyr Thr Pro Gly Ser Val Asn Phe
1               5                   10                  15

Thr Glu Glu Cys Tyr Gln Ala Ala Gln Asp Cys Val Ala Gln Phe Gly
            20                  25                  30

Ala Asn Ala Ser Leu Val Asn Cys Gln Asp Ala Ala Gly Asn Leu Phe
        35                  40                  45

Met Gln Gln Ser Asn Gln Gly Lys Asn Asn Asp Tyr Leu Ile Ala
    50                  55                  60

Tyr Gln Asp Ile Leu Asp Phe Cys Leu Leu Asp Gly Phe Thr Thr Gly
65                  70                  75                  80

Thr Trp Tyr Asp Asp Ser Gln Trp Tyr Trp Met Ala Ala Glu Pro Gly
                85                  90                  95

Cys Tyr Ser Pro Asn Gly Ser Ile Gly Thr Thr Gly Pro Gly Phe Cys
            100                 105                 110

Val Gln Asn Arg Asp Asp Thr Val Leu Asn Gly Cys Tyr Pro Gln Pro
        115                 120                 125

Gln Ser Gly Ala Gly Pro Leu Gln Val Leu Arg Thr Ala Arg Thr Ala
    130                 135                 140

Asn Gly Phe Thr Ser Ser Ala Arg Gly Trp Asn Ser Trp Gly Ile Gln
145                 150                 155                 160

Ala Leu Glu Asn Pro Ser Thr Ile Pro Gly Trp Thr Val Phe Asn Gln

```
                165                 170                 175
Thr Ala Val Lys Gln Gln Cys Ser Val Leu Ala Arg Ser Asp Phe Lys
            180                 185                 190
Ala Ala Gly Tyr Asp Leu Cys Ser Leu Asp Ala Gly Trp Ser Thr Ser
            195                 200                 205
Ser Glu Val Asp Glu Tyr Gly Arg Ile Leu Tyr Asn Ser Thr Leu Phe
    210                 215                 220
Asp Leu Pro Glu Leu Ala Asp Tyr Leu His Gly Gln Gly Leu Lys Leu
225                 230                 235                 240
Gly Val Tyr Val Ile Pro Gly Val Pro Cys Val Ala Ala Asn Lys Thr
                245                 250                 255
Ile Glu Gly Thr Asn Ile Arg Ile Gly Asp Val Leu Asn Gly Asn Asn
            260                 265                 270
Asp Glu Leu Ser Tyr Cys Asp Trp Asp Phe Ser Lys Asp Gly Val Gln
            275                 280                 285
Gln Trp His Asp Ser Leu Ile Asn Leu Trp Ala Ser Trp Gly Val Asp
        290                 295                 300
Met Ile Lys Leu Asp Phe Val Thr Pro Gly Ser Pro Gln Asn Gly Ala
305                 310                 315                 320
Asn Leu Val Cys Asn Asn Ser Ala Ala Val Glu Ala Tyr His Lys Ala
                325                 330                 335
Ile Ala Asn Ser Gly Arg Gln Ile Arg Leu Asp Leu Ser Trp Lys Leu
            340                 345                 350
Cys Arg Asn Glu Thr Tyr Leu Pro Val Trp Ser Ser Leu Ala Asp Ser
            355                 360                 365
Ile Arg Thr Asp Gln Asp Ile Asp Asn Tyr Gly Tyr Asn Thr Phe Val
    370                 375                 380
Ala Trp Gln Val Val Gln Arg Ala Ile Glu Asn Tyr Arg Gln Tyr Ile
385                 390                 395                 400
Leu Leu Gln Lys Gln Arg Asn Val Pro Ile Thr Leu Tyr Pro Asp Met
                405                 410                 415
Asp Asn Leu Phe Val Gly Asn Ala Ala Asn Leu Thr Gly Val Ser Asp
                420                 425                 430
Ala Gln Arg Ile Thr Ile Met Asn His Trp Leu Gly Ala Ala Ala Asn
            435                 440                 445
Leu Ile Ile Gly Ser Asp Leu Asn Gln Leu Asp Asp Leu Gly Thr Lys
    450                 455                 460
Leu Leu Thr Ser Asn Glu Ser Ile Gln Ala Ala Asp Phe Phe Ala Gln
465                 470                 475                 480
Tyr Pro Met Gln Pro Arg Asn Pro Gly Thr Gly Asp Asn Val Pro Gln
                485                 490                 495
Gln Leu Gln Ala Trp Ile Ala Gly Pro Ser Asp Asn Asn Glu Ala Tyr
            500                 505                 510
Val Leu Val Val Asn Tyr Gly Pro Asp Gln Gly His Gly Gly Phe Gly
            515                 520                 525
Thr Ser Leu Thr Gly Val Gln Asn Val Thr Val Ser Leu Ala Asp Leu
    530                 535                 540
Gly Ile Ala Gly Lys Ser Trp Glu Phe Ser Asp Val Trp Asn Gly Asn
545                 550                 555                 560
Ser Ser Thr Val Ser Thr Ser Phe Thr Ala Tyr Leu Asp Glu Gly Glu
                565                 570                 575
Ser Gln Leu Leu His Leu Thr Val Ala Gln
            580                 585
```

<210> SEQ ID NO 23
<211> LENGTH: 21
<212> TYPE: PRT
<213> ORGANISM: Rasamsonia emersonii

<400> SEQUENCE: 23

Met Ile Ser Ala Ala Val Leu Val Ser Leu Leu Leu Thr Thr Ile Gln
1               5                   10                  15

Pro Gly Ala Tyr Ala
            20

<210> SEQ ID NO 24
<211> LENGTH: 1824
<212> TYPE: DNA
<213> ORGANISM: Rasamsonia emersonii
<220> FEATURE:
<221> NAME/KEY: source
<222> LOCATION: (1)..(1824)
<223> OTHER INFORMATION: /organism="Rasamsonia emersonii"
      /mol_type="unassigned DNA"

<400> SEQUENCE: 24

| | | | | | | |
|---|---|---|---|---|---|---|
| atgatctccg | ccgcagtcct | ggtctccctg | cttctgacca | ccatccagcc | cggggcttac | 60 |
| gcccagtggc | aatgtggcgg | atcaacgtac | acgccaggct | cggtgaactt | caccgaagag | 120 |
| tgctaccagg | ctgctcagga | ttgcgtcgcg | caattcggcg | ctaatgccag | cctggtcaac | 180 |
| tgtcaagacg | ccgcaggcaa | tctgttcatg | cagcagcaat | ccaaccaggg | gaagaacaac | 240 |
| gactacctga | ttgcctacca | ggacatcctt | gacttctgcc | tgctcgatgg | cttcacgaca | 300 |
| gggacgtggt | acgacgacag | ccagtggtac | tggatggccg | ctgaaccggg | ctgctactct | 360 |
| ccaaacggca | gcattggcac | cactgggccc | ggtttctgcg | tccagaaccg | cgacgacacc | 420 |
| gtcctcaatg | gttgctatcc | ccagccccag | tctggtgcag | gcccctgca | ggtattgcga | 480 |
| accgcccgca | cagccaacgg | gtttacttcg | tctgcgcgag | gatggaattc | ctggggaatt | 540 |
| caggcgcttg | agaatccgag | cacgattccc | ggctggacgg | tattcaacca | gacagccgtg | 600 |
| aaacagcaat | gctcagtgct | ggctcgctcg | gatttcaagg | cagcaggcta | cgatctctgc | 660 |
| agcctggacg | ccggttggtc | cacgagcagc | gaagtcgacg | aatacgggcg | aatcctctac | 720 |
| aacagcacct | tgttcgacct | ccccgagctg | gcagattacc | tgcacggaca | aggcctcaag | 780 |
| ctgggtgtgt | atgtgatccc | gggcgtgccc | tgcgttgcgg | caaataagac | gatcgaaggg | 840 |
| accaacattc | gcatcgggga | cgtcctcaat | ggcaacaacg | atgaactgtc | gtactgcgac | 900 |
| tgggacttct | ccaaggacgg | cgtgcagcaa | tggcacgatt | cacttatcaa | cctgtgggcc | 960 |
| tcctggggcg | tggacatgat | caagctggac | tttgtcacgc | caggcagtcc | gcaaaacggc | 1020 |
| gcgaatctcg | tctgcaacaa | cagcgccgca | gtggaggcgt | accacaaggc | aatcgccaat | 1080 |
| tcggggcgcc | agatccgact | ggatctgtcg | tggaaactgt | gccgcaatga | aacctacctg | 1140 |
| ccggtctgga | gcagtctggc | ggattcgatc | cgaacgacc | aggacatcga | caattatgga | 1200 |
| tacaacacgt | tcgtcgcatg | gcaggtcgtg | cagcgggcga | tcgagaatta | ccgccagtat | 1260 |
| atcctgttgc | agaagcagcg | caacgtgccc | atcacgctgt | acccggacat | ggacaatctc | 1320 |
| tttgtgggca | atgcagcgaa | cctgacgggg | gtcagcgacg | cgcaacgcat | caccatcatg | 1380 |
| aaccactggc | tcgggggcgg | agcgaatctg | atcataggct | cggatttgaa | ccagctcgac | 1440 |
| gatctgggca | cgaagctgct | gacgagcaat | gagtccatcc | aggctgccga | tttctttgcg | 1500 |
| cagtatccga | tgcaaccgcg | caacccgggc | acgggcgata | acgtcccgca | acagctgcaa | 1560 |

```
gcgtggatcg ccggaccgtc cgacaacaac gaagcgtatg tcctcgtcgt caactacgga    1620
ccggatcagg ggcacggcgg gtttgggacg tcgttgactg gcgtccagaa tgtgaccgtg    1680
tcgctggcgg atctgggcat cgcaggcaag agctgggagt tctctgatgt ctggaatggg    1740
aactcgagca cggtgtcgac ttcttttaca gcctatctag atgaagggga gtcgcagctc    1800
ctgcatttga ccgtggcaca ataa                                           1824
```

```
<210> SEQ ID NO 25
<211> LENGTH: 1824
<212> TYPE: DNA
<213> ORGANISM: Rasamsonia emersonii
<220> FEATURE:
<221> NAME/KEY: source
<222> LOCATION: (1)..(1824)
<223> OTHER INFORMATION: /organism="Rasamsonia emersonii"
      /mol_type="unassigned DNA"

<400> SEQUENCE: 25
```

```
atgatctccg ccgcagtcct ggtctccctg cttctgacca ccatccagcc cggggcttac      60
gcccagtggc aatgtggcgg atcaacgtac acgccaggct cggtgaactt caccgaagag     120
tgctaccagg ctgctcagga ttgcgtcgcg caattcggcg ctaatgccag cctggtcaac     180
tgtcaagacg ccgcaggcaa tctgttcatg cagcagcaat ccaaccaggg gaagaacaac     240
gactacctga ttgcctacca ggacatcctt gacttctgcc tgctcgatgg cttcacgaca     300
gggacgtggt acgacgacag ccagtggtac tggatggccg ctgaaccggg ctgctactct     360
ccaaacggca gcattggcac cactgggccc ggtttctgcg tccagaaccg cgacgacacc     420
gtcctcaatg gttgctatcc ccagccccag tctggtgcag gcccctgca ggtattgcga     480 accgcccgca cagccaacgg gtttacttcg tctgcgcgag gatggaattc ctggggaatt     540
caggcgcttg agaatccgag cacgattccc ggctggacgg tattcaacca gacagccgtg     600
aaacagcaat gctcagtgct ggctcgctcg gatttcaagg cagcaggcta cgatctctgc     660
agcctggacg ccggttggtc cacgagcagc gaagtcgacg aatacgggcg aatcctctac     720
aacagcacct tgttcgacct ccccgagctg gcagattacc tgcacggaca aggcctcaag     780
ctgggtgtgt atgtgatccc gggcgtgccc tgcgttgcgg caaataagac gatcgaaggg     840
accaacattc gcatcgggga cgtcctcaat ggcaacaacg atgaactgtc gtactgcgac     900
tgggacttct ccaaggacgg cgtgcagcaa tggcacgatt cacttatcaa cctgtgggcc     960
tcctggggcg tggacatgat caagctggac tttgtcacgc caggcagtcc gcaaaacggc    1020
gcgaatctcg tctgcaacaa cagcgccgca gtggaggcgt accacaaggc aatcgccaat    1080
tcggggcgcc agatccgact ggatctgtcg tggaaactgt gccgcaatga acctacctg     1140 ccggtctgga gcagtctggc ggattcgatc cgaacggacc aggacatcga caattatgga    1200
tacaacacgt tcgtcgcatg gcaggtcgtg cagcgggcga tcgagaatta ccgccagtat    1260
atcctgttgc agaagcagcg caacgtgccc atcacgctgt acccggacat ggacaatctc    1320
tttgtgggca atgcagcgaa cctgacgggg gtcagcgacg cgcaacgcat caccatcatg    1380
aaccactggc tcggggcggc agcgaatctg atcataggct cggatttgaa ccagctcgac    1440
gatctgggca cgaagctgct gacgagcaat gagtccatcc aggctgccga tttctttgcg    1500
cagtatccga tgcaaccgcg caacccgggc acgggcgata acgtcccgca acagctgcaa    1560
gcgtggatcg ccggaccgtc cgacaacaac gaagcgtatg tcctcgtcgt caactacgga    1620
ccggatcagg ggcacggcgg gtttgggacg tcgttgactg gcgtccagaa tgtgaccgtg    1680
```

-continued

```
tcgctggcgg atctgggcat cgcaggcaag agctgggagt tctctgatgt ctggaatggg    1740
aactcgagca cggtgtcgac ttcttttaca gcctatctag atgaagggga gtcgcagctc    1800
ctgcatttga ccgtggcaca ataa                                           1824
```

<210> SEQ ID NO 26
<211> LENGTH: 756
<212> TYPE: DNA
<213> ORGANISM: Rasamsonia emersonii
<220> FEATURE:
<221> NAME/KEY: source
<222> LOCATION: (1)..(756)
<223> OTHER INFORMATION: /organism="Rasamsonia emersonii"
     /mol_type="unassigned DNA"

<400> SEQUENCE: 26

```
atgaagtcgt tcctggctgt gaccctcagc ctttctcttg cctccctgac cactgctgct     60
cctactccca ccaagaccct ggagaagcgt gccgacttct gcggccagtg ggattcgacc    120
gtcactggca gctacaccgt ttacaacaac ctctggggtg agagctctgc ctcctccggc    180
agccagtgca ccggtgttga ctcgctgaac ggcaacaccc tggcctggca caccagctgg    240
acctgggagg gtggtgcctc ttccgtcaag tcgttcgcca acgctgccta cgcttttcact    300 gccactcagc tctcccagat ctcctccatc ccaccaccct ggcagtggag ctacactggt    360
acctccatcg atgccgatgt tgcctacgac ctcttcacct cctcctcccc cagcggcagc    420
aacgaatacg aagtcatgat ctggctagct gctcttggtg gtgctttccc tatatcttcc    480
accggtacca cccccattgc cactcctacc attggtggta tctcctggaa cctgtactct    540
ggccccaacg gtgccaccac cgtctactct ttcgtcgcct cccgcgagca gaccgacttc    600
tccggtgaca tcaacgactt cctgacctac ctccagcaga acgagggtct ttcttcttcc    660
cagtacctcc tctccatcca ggctggcacc gagcccttca ctggtgagaa cgctgagctc    720
aagaccactg cctactctgt ctccgtcagc acttca                              756
```

<210> SEQ ID NO 27
<211> LENGTH: 233
<212> TYPE: PRT
<213> ORGANISM: Rasamsonia emersonii

<400> SEQUENCE: 27

```
Ala Pro Thr Pro Thr Lys Thr Leu Glu Lys Arg Ala Asp Phe Cys Gly
1               5                   10                  15

Gln Trp Asp Ser Thr Val Thr Gly Ser Tyr Thr Val Tyr Asn Asn Leu
            20                  25                  30

Trp Gly Glu Ser Ser Ala Ser Ser Gly Ser Gln Cys Thr Gly Val Asp
        35                  40                  45

Ser Leu Asn Gly Asn Thr Leu Ala Trp His Thr Ser Trp Thr Trp Glu
    50                  55                  60

Gly Gly Ala Ser Ser Val Lys Ser Phe Ala Asn Ala Ala Tyr Ala Phe
65                  70                  75                  80

Thr Ala Thr Gln Leu Ser Gln Ile Ser Ser Ile Pro Thr Thr Trp Gln
                85                  90                  95

Trp Ser Tyr Thr Gly Thr Ser Ile Asp Ala Asp Val Ala Tyr Asp Leu
            100                 105                 110

Phe Thr Ser Ser Pro Ser Gly Ser Asn Glu Tyr Glu Val Met Ile
        115                 120                 125

Trp Leu Ala Ala Leu Gly Gly Ala Phe Pro Ile Ser Ser Thr Gly Thr
```

```
                130                 135                 140
Thr Pro Ile Ala Thr Pro Thr Ile Gly Gly Ile Ser Trp Asn Leu Tyr
145                 150                 155                 160

Ser Gly Pro Asn Gly Ala Thr Thr Val Tyr Ser Phe Val Ala Ser Arg
                165                 170                 175

Glu Gln Thr Asp Phe Ser Gly Asp Ile Asn Asp Phe Leu Thr Tyr Leu
            180                 185                 190

Gln Gln Asn Glu Gly Leu Ser Ser Gln Tyr Leu Leu Ser Ile Gln
        195                 200                 205

Ala Gly Thr Glu Pro Phe Thr Gly Glu Asn Ala Glu Leu Lys Thr Thr
        210                 215                 220

Ala Tyr Ser Val Ser Val Ser Thr Ser
225                 230

<210> SEQ ID NO 28
<211> LENGTH: 19
<212> TYPE: PRT
<213> ORGANISM: Rasamsonia emersonii

<400> SEQUENCE: 28

Met Lys Ser Phe Leu Ala Val Thr Leu Ser Leu Ser Leu Ala Ser Leu
1               5                   10                  15

Thr Thr Ala

<210> SEQ ID NO 29
<211> LENGTH: 819
<212> TYPE: DNA
<213> ORGANISM: Rasamsonia emersonii
<220> FEATURE:
<221> NAME/KEY: source
<222> LOCATION: (1)..(819)
<223> OTHER INFORMATION: /organism="Rasamsonia emersonii"
      /mol_type="unassigned DNA"

<400> SEQUENCE: 29
atgaagtcct tcctcgccgt aactctgtcc ctatccctcg caagcctcac caccgccgcc      60
ccaaccccaa ccaaaaccct cgaaaagcgg gccgacttct gcggacaatg ggactcgacc     120
gtcacaggca gctacaccgt ctacaacaac ctctgggggg aatccagcgc gtcgtccgga     180
tcgcagtgca cgggcgtcga ctcgctcaac gggaacacgc tcgcctggca cacctcgtgg     240
acctgggagg gcgggcgtc cagtgtcaag agcttcgcca atgccgcgta tgcgttcacg      300
gcgacgcagc tgagccagat tagcagtatt ccgacgacgt ggcagtggag gtatgaatga     360
cacttccttt tctgcctctc tgtctatgta cttgctgctg acacgtacag ctacaccggc     420
acctccatcg acgccgacgt cgcgtacgac ctattcacga gttccagccc cagcggcagc     480
aacgagtacg aggttatgat ctggctggcc gcgctcgggg gcgcattccc catctcgtcg     540
acgggcacga cgcccatcgc gacgcccacc atcggcggca tctcatggaa tctgtacagc     600
gggcccaacg gcgcgacgac ggtgtacagc ttcgtagcgt cgagagagca gacggacttt     660
tcgggcgaca tcaacgattt tctgacctat ctccagcaga acgagggcct cagctcgagc     720 cagtaccctgc tgtccatcca ggcgggcacg gagccgttta cgggggagaa tgcggagctg     780
aagacgacgg cgtatagtgt cagtgtatca acctcgtga                            819

<210> SEQ ID NO 30
<211> LENGTH: 759
<212> TYPE: DNA
<213> ORGANISM: Rasamsonia emersonii
```

```
<220> FEATURE:
<221> NAME/KEY: source
<222> LOCATION: (1)..(759)
<223> OTHER INFORMATION: /organism="Rasamsonia emersonii"
      /mol_type="unassigned DNA"

<400> SEQUENCE: 30
atgaagtcct tcctcgccgt aactctgtcc ctatccctcg caagcctcac caccgccgcc      60
ccaaccccaa ccaaaaccct cgaaaagcgg gccgacttct gcggacaatg ggactcgacc     120
gtcacaggca gctacaccgt ctacaacaac ctctgggggg aatccagcgc gtcgtccgga     180
tcgcagtgca cgggcgtcga ctcgctcaac gggaacacgc tcgcctggca cacctcgtgg     240
acctgggagg gcgggcgtc cagtgtcaag agcttcgcca atgccgcgta tgcgttcacg      300
gcgacgcagc tgagccagat tagcagtatt ccgacgacgt ggcagtggag ctacaccggc     360
acctccatcg acgccgacgt cgcgtacgac ctattcacga gttccagccc cagcggcagc     420
aacgagtacg aggttatgat ctggctggcg gcgctcgggg gcgcattccc catctcgtcg     480
acgggcacga cgcccatcgc gacgcccacc atcggcggca tctcatggaa tctgtacagc     540
gggcccaacg cgcgacgac ggtgtacagc ttcgtagcgt cgagagagca gacggacttt      600
tcgggcgaca tcaacgattt tctgacctat ctccagcaga acgagggcct cagctcgagc     660
cagtacctgc tgtccatcca ggcgggcacg gagccgttta cggggagaa tgcggagctg      720 aagacgacgg cgtatagtgt cagtgtatca acctcgtga                           759

<210> SEQ ID NO 31
<211> LENGTH: 1923
<212> TYPE: DNA
<213> ORGANISM: Rasamsonia emersonii
<220> FEATURE:
<221> NAME/KEY: source
<222> LOCATION: (1)..(1923)
<223> OTHER INFORMATION: /organism="Rasamsonia emersonii"
      /mol_type="unassigned DNA"

<400> SEQUENCE: 31
atgtccctcg ccagcaagaa cctgcttgct tgcggcctct tcctggctgt tgctcagctt      60
gctcagcccg ttactggctt ggaattgact gtcagcacct ccggtggcaa caagtcctcc     120
cccatcctct acggcttcat gttcgaagat atcaaccact ccggtgatgg tggtatccac     180
tcccagctcc tccagaacaa cggattccag ggtgccaacc ccggtctgac tgcctacgcc     240
cccatcggta acgtttccct cgccgttgac actgagaacc ctctctcctc tgccatcacc     300
cgctcgctga aggtcaccgt tcctcccaac gcctctggca aggtcggttt ctccaactcc     360
ggctactggg ggatacccgt caacgaggcc aactacacca actcgttcta catcaagggt     420
gactacaacg tgatgtcac cctccgcctc gccggtgcct cctccggctc tctgtacgcc     480
tcccagacca tctccgtcaa gtccaacagc agcagctaca cctacgtcga gactcagtac     540
cccgtcaagc aggctcctga cggcaacaac atctgggagc tcaccttcga tgcctccaag     600
gttgctggca agtccctcaa cttcgacctc atccagctgt accctcctac cttccacgac     660
cgtcccaacg gtctgaagcc cgagattgcc aacgtccttg ttgacatgaa gggctctttc     720
ctccgtttcc ccggtggtaa caacctcgag ggtctgaccc ccgccacccg ttggaagtgg     780
aacgagacta ttggaccctct gacctcccgt cctggtcgcc agggtaactg gggctacccc     840
aacaccgatg ctcttggtct gaacgaatac ttcctctgga tccaggacat gggcttgact     900
gctgtcctgg gtgtctggga tggcttgacc attggtggtc cttctcccca ggtcatcacc     960
```

-continued

```
ggtgatgctc tcaagcccta cattgatgat gttctcaacg agctggaata catcctgggt  1020
gacaaggaca ccacctacgg caagctccgt gcctctcacg gattccccga cccttggccc  1080
ctccagtacg tggagattgg caacgaggac aacctgaacg tggtggacc tagctacgct    1140
gagcgcttca ctgctttcca cgacgccatc aaggccaagt accccccacct gaccatcatc  1200
tccagcactg accagtacct tcccaacccc aagcccaagg gtatctggat ggactggcac   1260
acctactctc ctgctggtga attggtgagc atgtttaaca agttcgacaa cgtcgaccgc   1320
gctttcccct acttcgtcgg tgaatacgcc tgcatttctc ttgacaacgg cactgagctt   1380
gcccagccca tcatgcaggg ctctgttgct gaggctgtgt tcatgatcgg tatggagcgc   1440
aactcggatg ttgtcaagat ggccgcctac gctcccttgc tccagcagta cggcggctac   1500
acctggaacg accacgtccc caacctgatc atgttcaaca caacccccaa cggcattgtc   1560
cgctccacct cgtactacgt gcagcagatg ttctccgtga accgtggaag caccatcctt   1620
cctgttgagt ccgacggctc tttcggtcct gtctactacg tggcctccaa gacctccgac   1680
aacaagacct actacgtcaa gttcgccaac tacggtccta ctccccagcc cgtcaccgtc   1740
aacatcccca agaccgagac tggtcgtctg accaccctct ctggtgctgc cactgctgcc   1800
aacacctggt ccagccccaa cgccgtcact cctaagacct cgaacgtcag ctccgccgat   1860
ggtgctcctg gcaagttcac catcacccctc cccgcctggt ccgttgctgt ccttgctgtc   1920
gag                                                                  1923
```

<210> SEQ ID NO 32
<211> LENGTH: 615
<212> TYPE: PRT
<213> ORGANISM: Rasamsonia emersonii

<400> SEQUENCE: 32

```
Leu Glu Leu Thr Val Ser Thr Ser Gly Gly Asn Lys Ser Ser Pro Ile
1               5                   10                  15

Leu Tyr Gly Phe Met Phe Glu Asp Ile Asn His Ser Gly Asp Gly Gly
            20                  25                  30

Ile His Ser Gln Leu Leu Gln Asn Asn Gly Phe Gln Gly Ala Asn Pro
        35                  40                  45

Gly Leu Thr Ala Tyr Ala Pro Ile Gly Asn Val Ser Leu Ala Val Asp
    50                  55                  60

Thr Glu Asn Pro Leu Ser Ser Ala Ile Thr Arg Ser Leu Lys Val Thr
65                  70                  75                  80

Val Pro Pro Asn Ala Ser Gly Lys Val Gly Phe Ser Asn Ser Gly Tyr
                85                  90                  95

Trp Gly Ile Pro Val Asn Glu Ala Asn Tyr Thr Asn Ser Phe Tyr Ile
            100                 105                 110

Lys Gly Asp Tyr Asn Gly Asp Val Thr Leu Arg Leu Ala Gly Ala Ser
        115                 120                 125

Ser Gly Ser Leu Tyr Ala Ser Gln Thr Ile Ser Val Lys Ser Asn Ser
    130                 135                 140

Ser Ser Tyr Thr Tyr Val Glu Thr Gln Tyr Pro Val Lys Gln Ala Pro
145                 150                 155                 160

Asp Gly Asn Asn Ile Trp Glu Leu Thr Phe Asp Ala Ser Lys Val Ala
                165                 170                 175

Gly Lys Ser Leu Asn Phe Asp Leu Ile Gln Leu Tyr Pro Pro Thr Phe
            180                 185                 190

His Asp Arg Pro Asn Gly Leu Lys Pro Glu Ile Ala Asn Val Leu Val
```

```
            195                 200                 205
Asp Met Lys Gly Ser Phe Leu Arg Phe Pro Gly Gly Asn Asn Leu Glu
    210                 215                 220
Gly Leu Thr Pro Ala Thr Arg Trp Lys Trp Asn Glu Thr Ile Gly Pro
225                 230                 235                 240
Leu Thr Ser Arg Pro Gly Arg Gln Gly Asn Trp Gly Tyr Pro Asn Thr
                245                 250                 255
Asp Ala Leu Gly Leu Asn Glu Tyr Phe Leu Trp Ile Gln Asp Met Gly
                260                 265                 270
Leu Thr Ala Val Leu Gly Val Trp Asp Gly Leu Thr Ile Gly Gly Pro
            275                 280                 285
Ser Pro Gln Val Ile Thr Gly Asp Ala Leu Lys Pro Tyr Ile Asp Asp
        290                 295                 300
Val Leu Asn Glu Leu Glu Tyr Ile Leu Gly Asp Lys Asp Thr Thr Tyr
305                 310                 315                 320
Gly Lys Leu Arg Ala Ser His Gly Phe Pro Asp Pro Trp Pro Leu Gln
                325                 330                 335
Tyr Val Glu Ile Gly Asn Glu Asp Asn Leu Asn Gly Gly Gly Pro Ser
                340                 345                 350
Tyr Ala Glu Arg Phe Thr Ala Phe His Asp Ala Ile Lys Ala Lys Tyr
            355                 360                 365
Pro His Leu Thr Ile Ile Ser Ser Thr Asp Gln Tyr Leu Pro Asn Pro
        370                 375                 380
Lys Pro Lys Gly Ile Trp Met Asp Trp His Thr Tyr Ser Pro Ala Gly
385                 390                 395                 400
Glu Leu Val Ser Met Phe Asn Lys Phe Asp Asn Val Asp Arg Ala Phe
                405                 410                 415
Pro Tyr Phe Val Gly Glu Tyr Ala Cys Ile Ser Leu Asp Asn Gly Thr
                420                 425                 430
Glu Leu Ala Gln Pro Ile Met Gln Gly Ser Val Ala Glu Ala Val Phe
            435                 440                 445
Met Ile Gly Met Glu Arg Asn Ser Asp Val Val Lys Met Ala Ala Tyr
        450                 455                 460
Ala Pro Leu Leu Gln Gln Tyr Gly Gly Tyr Thr Trp Asn Asp His Val
465                 470                 475                 480
Pro Asn Leu Ile Met Phe Asn Asn Pro Asn Gly Ile Val Arg Ser
                485                 490                 495
Thr Ser Tyr Tyr Val Gln Gln Met Phe Ser Val Asn Arg Gly Ser Thr
                500                 505                 510
Ile Leu Pro Val Glu Ser Asp Gly Ser Phe Gly Pro Val Tyr Tyr Val
            515                 520                 525
Ala Ser Lys Thr Ser Asp Asn Lys Thr Tyr Tyr Val Lys Phe Ala Asn
        530                 535                 540
Tyr Gly Pro Thr Pro Gln Pro Val Thr Val Asn Ile Pro Lys Thr Glu
545                 550                 555                 560
Thr Gly Arg Leu Thr Thr Leu Ser Gly Ala Ala Thr Ala Ala Asn Thr
                565                 570                 575
Trp Ser Ser Pro Asn Ala Val Thr Pro Lys Thr Ser Asn Val Ser Ser
                580                 585                 590
Ala Asp Gly Ala Pro Gly Lys Phe Thr Ile Thr Leu Pro Ala Trp Ser
            595                 600                 605
Val Ala Val Leu Ala Val Glu
        610                 615
```

<210> SEQ ID NO 33
<211> LENGTH: 26
<212> TYPE: PRT
<213> ORGANISM: Rasamsonia emersonii

<400> SEQUENCE: 33

Met Ser Leu Ala Ser Lys Asn Leu Leu Ala Cys Gly Leu Phe Leu Ala
1               5                   10                  15

Val Ala Gln Leu Ala Gln Pro Val Thr Gly
            20                  25

<210> SEQ ID NO 34
<211> LENGTH: 2381
<212> TYPE: DNA
<213> ORGANISM: Rasamsonia emersonii
<220> FEATURE:
<221> NAME/KEY: source
<222> LOCATION: (1)..(2381)
<223> OTHER INFORMATION: /organism="Rasamsonia emersonii"
    /mol_type="unassigned DNA"

<400> SEQUENCE: 34

| | | | | |
|---|---|---|---|---|
| atgtcgttgg | cttcgaagaa | tctcctggcc | tgcgggcttt | tcttagcagt cgcccagctt | 60 |
| gcacagccag | tgactggttt | agaacttacg | gtgtcgacgt | ctggcggcaa taaatccagc | 120 |
| cctatcttgt | atgggttcat | gttcgaggtg | agttttttgcc | aagctggctg tgaaaccgcc | 180 |
| tgctggtgga | gagttacgat | aaccatgtcc | acgctcacta | tagcgtgatt gattatgtgc | 240 |
| tgacacctgc | aggatatcaa | ccactctggt | gatggaggga | tccacagtca gcttctgcag | 300 |
| aacaacggct | tccagggtgc | aaaccccggc | ttgactgcat | acgctccaat cgggaatgtg | 360 |
| tcgttggccg | tggatacgga | aaaccctctc | tcgagcgcga | taacgcggtc tctgaaggtc | 420 |
| actgtcccgc | caacgcctc | cggaaaggtt | ggcttctcga | attcgggtta ctggggtatt | 480 |
| cccgtgaacg | aggccaacta | caccaacagc | ttctacatca | aggagactaa taatggcgac | 540 |
| gtcacgcttc | gccttgcggg | ggccagcagc | ggcagtctgt | atgcatcgca aacgatcagc | 600 |
| gtcaagagca | actcgtccag | ctacacctat | gtcgagacgc | aatatccagt gaagcaggct | 660 |
| cctgacggca | caacatctg | ggaactgacc | tttgacgcgt | ccaaggtggc gggaaagtca | 720 |
| ttgaattttg | acctgatcca | gctctaccca | ccaacattcc | acgacaggtg cgattgcttg | 780 |
| tattcctcca | ggattgtgtc | gctgatgctg | acctatttta | tagacctaat ggcctcaaac | 840 |
| cggaaattgc | aaatgttttg | gttgacatga | agggttcttt | cctgcgcttt cccggaggaa | 900 |
| acaatctgtg | agttgcttcg | gtctgtatct | ggcgatcctt | gctgacttt ggccagcgaa | 960 |
| ggattaactc | cggcaacgcg | ctggaagtgg | aatgagacca | ttgggcctct gacgagccgt | 1020 |
| cctgggcggc | aaggtaactg | ggggtatccc | aacacagatg | cacttggtag gctttattta | 1080 |
| aaagtgatct | gtgtatgaag | cattgctaaa | tgcgatgaca | ggtctgaatg aatatttctt | 1140 |
| gtggatccag | gacatgggtt | tgacggcagt | tctcggtgtc | tgggatggac tgactatcgg | 1200 |
| agggccgagc | cctcaagtta | tcactgggga | cgctttgaag | ccctacatcg acgacgtttt | 1260 |
| gaacgagctt | gaggtaagtg | cctctggatg | atctttttgt | tcggtttcgc taacaattgc | 1320 |
| agtatatcct | tggagacaag | gataccacgt | acggcaagct | tcgtgcttct catggcttcc | 1380 |
| ctgacccctg | gccactccaa | tacgtggaaa | tcggcaacga | ggacaacctc aatggaggcg | 1440 |
| ggccctcata | tgcagagcgc | ttcacggcct | tccacgacgc | aatcaaggcc aagtacccgc | 1500 |
| atctgaccat | cattagcagc | acggaccagt | acctcccaaa | tcccaagcca aaaggaatct | 1560 |

```
ggatggactg gcacacgtac tcgccggcgg gggagcttgt gagcatgttc aacaagttcg   1620
acaacgtgga ccgggctttc ccgtactttg tcggcgaata tgcctgcatc tccctcgata   1680
acgggaccga gctcgcgcag ccgatcatgc aggggtctgt ggcggaagct gtctttatga   1740
ttggcatgga aaggaacagc gatgttgtca agatggctgc ctatgcaccg ctgctgcagc   1800
aatacggcgg gtacacatgg aatgtgagat gcgcaaacga aaaatcaaga agactgatat   1860
atgcagactg actgactgac atcaggacca cgtgccaaac ctgattatgt caacaacaa   1920 cccaaacggc attgtccgga gcaccagcta ctacgtacag cagatgttct cagtgaaccg   1980
gggcagcacc attctgccag tggaatcaga cgggtcattt ggaccaggta cgtacagacc   2040
aacaaacacc agccacagcc agggcagcag gtccgcctcg acttactaat ttcaatgaca   2100
atgcagtcta ctacgtcgcc tccaaaacct cagacaacaa gacatactac gtcaagttcg   2160
ccaactacgg ccctaccccg cagcccgtca ccgtcaacat ccccaagaca gaaaccgggc   2220
gactgacgac gctgtccggc gccgctactg cagccaacac ctggagcagc cctaatgctg   2280
tcacacccaa gaccagcaat gtcagctctg ctgatggtgc gccaggaaag tttactatta   2340
ctctgcctgc gtggagtgtt gctgtgttgg ctgtggagtg a                       2381
```

<210> SEQ ID NO 35
<211> LENGTH: 1926
<212> TYPE: DNA
<213> ORGANISM: Rasamsonia emersonii
<220> FEATURE:
<221> NAME/KEY: source
<222> LOCATION: (1)..(1926)
<223> OTHER INFORMATION: /organism="Rasamsonia emersonii"
      /mol_type="unassigned DNA"

<400> SEQUENCE: 35

```
atgtcgttgg cttcgaagaa tctcctggcc tgcgggcttt tcttagcagt cgcccagctt     60
gcacagccag tgactggttt agaacttacg gtgtcgacgt ctggcggcaa taaatccagc    120
cctatcttgt atgggttcat gttcgaggat atcaaccact ctggtgatgg agggatccac    180
agtcagcttc tgcagaacaa cggcttccag ggtgcaaacc ccggcttgac tgcatacgct    240
ccaatcggga atgtgtcgtt ggccgtggat acggaaaacc ctctctcgag cgcgataacg    300
cggtctctga aggtcactgt cccgcccaac gcctccggaa aggttggctt ctcgaattcg    360
ggttactggg gtattcccgt gaacgaggcc aactacacca acagcttcta catcaaggga    420
gactataatg gcgacgtcac gcttcgcctt gcggggggcca gcagcggcag tctgtatgca    480
tcgcaaacga tcagcgtcaa gagcaactcg tccagctaca cctatgtcga gacgcaatat    540
ccagtgaagc aggctcctga cggcaacaac atctgggaac tgacctttga cgcgtccaag    600
gtggcgggaa agtcattgaa ttttgacctg atccagctct acccaccaac attccacgac    660
agacctaatg gcctcaaacc ggaaattgca aatgttttgg ttgacatgaa gggttctttc    720
ctgcgctttc ccgaggaaaa caatctcgaa ggattaactc cggcaacgcg ctggaagtgg    780
aatgagacca ttgggcctct gacgagccgt cctgggcggc aaggtaactg ggggtatccc    840
aacacagatg cacttggtct gaatgaatat ttcttgtgga tccaggacat gggtttgacg    900
gcagttctcg gtgtctggga tggactgact atcggagggc cgagccctca agttatcact    960
ggggacgctt tgaagcccta catcgacgac gttttgaacg agcttgagta tatccttgga   1020
gacaaggata ccacgtacgg caagcttcgt gcttctcatg gcttccctga cccctggcca   1080
ctccaatacg tggaaatcgg caacgaggac aacctcaatg gaggcgggcc ctcatatgca   1140
```

| | |
|---|---|
| gagcgcttca cggccttcca cgacgcaatc aaggccaagt acccgcatct gaccatcatt | 1200 |
| agcagcacgg accagtacct cccaaatccc aagccaaaag gaatctggat ggactggcac | 1260 |
| acgtactcgc cggcggggga gcttgtgagc atgttcaaca agttcgacaa cgtggaccgg | 1320 |
| gctttcccgt actttgtcgg cgaatatgcc tgcatctccc tcgataacgg gaccgagctc | 1380 |
| gcgcagccga tcatgcaggg gtctgtggcg gaagctgtct ttatgattgg catggaaagg | 1440 |
| aacagcgatg ttgtcaagat ggctgcctat gcaccgctgc tgcagcaata cggcgggtac | 1500 |
| acatggaatg accacgtgcc aaacctgatt atgttcaaca caacccaaa cggcattgtc | 1560 |
| cggagcacca gctactacgt acagcagatg ttctcagtga accggggcag caccattctg | 1620 |
| ccagtggaat cagacgggtc atttggacca gtctactacg tcgcctccaa aacctcagac | 1680 |
| aacaagacat actacgtcaa gttcgccaac tacggcccta ccccgcagcc cgtcaccgtc | 1740 |
| aacatcccca agacagaaac cgggcgactg acgacgctgt ccggcgccgc tactgcagcc | 1800 |
| aacacctgga gcagccctaa tgctgtcaca cccaagacca gcaatgtcag ctctgctgat | 1860 |
| ggtgcgccag gaaagtttac tattactctg cctgcgtgga gtgttgctgt gttggctgtg | 1920 |
| gagtga | 1926 |

<210> SEQ ID NO 36
<211> LENGTH: 2235
<212> TYPE: DNA
<213> ORGANISM: Rasamsonia emersonii
<220> FEATURE:
<221> NAME/KEY: source
<222> LOCATION: (1)..(2235)
<223> OTHER INFORMATION: /organism="Rasamsonia emersonii"
      /mol_type="unassigned DNA"

<400> SEQUENCE: 36

| | |
|---|---|
| atgatcctcc gctcgctacc catccacgcc gccgccattg ctgctgcttt gacttctctt | 60 |
| gttgacgcca agcccctccg ccacgacatc cgtcaggttg ctgagactca ccgtatcaac | 120 |
| agcactcact acaacgacac ttctgctgtt gtcctggatg tgtctctgaa ggacgccgcc | 180 |
| ggtcgtaaca acacttctcc tctcctgtac ggctggatgt tcgaggacat ctcccactct | 240 |
| ggcgatggcg gtatctacgc tgagctgatc aagaaccgtg cttttccaggg cagcacttct | 300 |
| actgtcaagc aggctcctgg tatctccggt gactccgttg ttgctgctca gaaccccatt | 360 |
| gtgcccttcg gtcctgtcct cgatggctgg cgccctatag gagatgccaa gctgtctctt | 420 |
| gatgtcctgc accctctgtc ggatgccctc cccgtcgtcc tccagatcga tatccccctgg | 480 |
| aacgccactg gcgaggttgg tttcctcaac gaaggctggt ggggtattga tgtccgccct | 540 |
| cagacctaca cgcctccctt ctacatgctt gccaacgctc ctcgctacaa caagaccttg | 600 |
| acctccatca acctgtcgct acgcagcaac ctcaccgacg atgtctgggc caccaccacc | 660 |
| atccacgttg accccgacaa ggttcctacc ttcgactacg agcagtacca ggcctccatt | 720 |
| gtgaacaccg tcaaggcccc caactccaac aacaccttcg ccatcacctt caacgccgac | 780 |
| gaggttgctg gaagcacctt ctacttcggc ttggtgtctc tgttccctga aaccttcaac | 840 |
| aaccgcccca acgcctacg caaggacctt gctcagggta tcaaggacat gggtgccaag | 900 |
| ttcctgcgtt tccctggtgg aaacaacctc gagggttact ccatcttcca gcgttggaag | 960 |
| tggaacgaaa ccattggtcc cctccgttac cgcaagggtc gtgtcggtaa ctgggaatac | 1020 |
| tacaacacca acggtcttgg tcttttggaa ttcctggaat ggactgagga ccttggcatg | 1080 |
| gagcccgtcc ttgctgtcta cgctggcttc tctctggaca tctgggcca ggaaggcacc | 1140 |

-continued

```
tcctacccccg aggaccgcat ggatgagatc gtccaggaca tcctgaacga gcttgagtac    1200
tgcatgggtg atgtcaacac ccactacggt gctctccgtg cccagcacgg ccaccccgag    1260
cccttcgaca tcaagtacat tgagatcggt aacgaggact ggttctccag cacctacccc    1320
taccgtttcc ccatcatcta caaggccatc aagtccgcct accccaacat taccctcatc    1380
tccactgcct acaacgagaa cgccaactac accatcgaca tccctgctgg tggtatgtgg    1440
gatacccacc actacgaaac ccctccttc ttcctggaga acttcaacta cttcgacaac    1500
tggcaggctg ccactaacaa caccgatgtc aagatcttcg tcggtgaata ctccgtctac    1560
cagatcgaca cccccgatgg ctacgtcaac ttctccaacc ccgagggtat ccacatgttc    1620
ttccccgagc ttgtatctgc tattgctgag gctgtctacc tccttggtgc tgagcgtaac    1680
cccaacactg tcaccatgac ctcctacgct cccagcttcc agaacctgaa ctggtacaac    1740
tggtccccca acctggttgc tttcactgcc aaccctgacg agactgtgtt cagcaccagc    1800
tactacatgc agaagatgtt cgccaaccac cgtggcaccc agaccctccc tgtcaagaac    1860
agcaagggtg acttcaaccc tctctggtgg gttgccacca ttgacgaggg tgctggtgtt    1920
gtctacttca agatcgtcaa ctccggcaac tcctccatcc ccctcaccat taacctggac    1980
caggcgtaca agggtgtcaa cggcaccatc ctcgtccgcc gccgtatctg cctccagctc    2040
cacatctaca ccgtccccga tgagctcacc attgctttcc tccagaccca ccccaacctc    2100
tacggattca actacctgaa caaccagact gccattgtcc ccgtgcctgc caacatcacc    2160
tcccccagca gtcccagaa ccgcttcgac tgggatgttc caagtactc cgtcaccgtt    2220 ctccagttcg acatc                                                     2235
```

<210> SEQ ID NO 37
<211> LENGTH: 722
<212> TYPE: PRT
<213> ORGANISM: Rasamsonia emersonii

<400> SEQUENCE: 37

```
Lys Pro Leu Arg His Asp Ile Arg Gln Val Ala Glu Thr His Arg Ile
1               5                   10                  15

Asn Ser Thr His Tyr Asn Asp Thr Ser Ala Val Leu Asp Val Ser
            20                  25                  30

Leu Lys Asp Ala Ala Gly Arg Asn Asn Thr Ser Pro Leu Leu Tyr Gly
        35                  40                  45

Trp Met Phe Glu Asp Ile Ser His Ser Gly Asp Gly Ile Tyr Ala
    50                  55                  60

Glu Leu Ile Lys Asn Arg Ala Phe Gln Gly Ser Thr Ser Thr Val Lys
65                  70                  75                  80

Gln Ala Pro Gly Ile Ser Gly Asp Ser Val Val Ala Ala Gln Asn Pro
                85                  90                  95

Ile Val Pro Phe Gly Pro Val Leu Asp Gly Trp Arg Pro Ile Gly Asp
            100                 105                 110

Ala Lys Leu Ser Leu Asp Val Leu His Pro Leu Ser Asp Ala Leu Pro
        115                 120                 125

Val Val Leu Gln Ile Asp Ile Pro Trp Asn Ala Thr Gly Glu Val Gly
    130                 135                 140

Phe Leu Asn Glu Gly Trp Trp Gly Ile Asp Val Arg Pro Gln Thr Tyr
145                 150                 155                 160

Asn Ala Ser Phe Tyr Met Leu Ala Asn Ala Pro Arg Tyr Asn Lys Thr
                165                 170                 175
```

```
Leu Thr Ser Ile Asn Leu Ser Leu Arg Ser Asn Leu Thr Asp Asp Val
            180                 185                 190

Trp Ala Thr Thr Thr Ile His Val Asp Pro Asp Lys Val Pro Thr Phe
            195                 200                 205

Asp Tyr Glu Gln Tyr Gln Ala Ser Ile Val Asn Thr Val Lys Ala Pro
            210                 215                 220

Asn Ser Asn Asn Thr Phe Ala Ile Thr Phe Asn Ala Asp Glu Val Ala
225                 230                 235                 240

Gly Ser Thr Phe Tyr Phe Gly Leu Val Ser Leu Phe Pro Glu Thr Phe
                245                 250                 255

Asn Asn Arg Pro Asn Gly Leu Arg Lys Asp Leu Ala Gln Gly Ile Lys
            260                 265                 270

Asp Met Gly Ala Lys Phe Leu Arg Phe Pro Gly Gly Asn Asn Leu Glu
            275                 280                 285

Gly Tyr Ser Ile Phe Gln Arg Trp Lys Trp Asn Glu Thr Ile Gly Pro
            290                 295                 300

Leu Arg Tyr Arg Lys Gly Arg Val Gly Asn Trp Glu Tyr Tyr Asn Thr
305                 310                 315                 320

Asn Gly Leu Gly Leu Leu Glu Phe Leu Glu Trp Thr Glu Asp Leu Gly
                325                 330                 335

Met Glu Pro Val Leu Ala Val Tyr Ala Gly Phe Ser Leu Asp Ile Trp
            340                 345                 350

Gly Gln Glu Gly Thr Ser Tyr Pro Glu Asp Arg Met Asp Glu Ile Val
            355                 360                 365

Gln Asp Ile Leu Asn Glu Leu Glu Tyr Cys Met Gly Asp Val Asn Thr
            370                 375                 380

His Tyr Gly Ala Leu Arg Ala Gln His Gly His Pro Glu Pro Phe Asp
385                 390                 395                 400

Ile Lys Tyr Ile Glu Ile Gly Asn Glu Asp Trp Phe Ser Ser Thr Tyr
                405                 410                 415

Pro Tyr Arg Phe Pro Ile Ile Tyr Lys Ala Ile Lys Ser Ala Tyr Pro
            420                 425                 430

Asn Ile Thr Leu Ile Ser Thr Ala Tyr Asn Glu Asn Ala Asn Tyr Thr
            435                 440                 445

Ile Asp Ile Pro Ala Gly Gly Met Trp Asp Thr His His Tyr Glu Thr
            450                 455                 460

Pro Ser Phe Phe Leu Glu Asn Phe Asn Tyr Phe Asp Asn Trp Gln Ala
465                 470                 475                 480

Ala Thr Asn Asn Thr Asp Val Lys Ile Phe Val Gly Glu Tyr Ser Val
                485                 490                 495

Tyr Gln Ile Asp Thr Pro Asp Gly Tyr Val Asn Phe Ser Asn Pro Glu
            500                 505                 510

Gly Ile His Met Phe Phe Pro Glu Leu Val Ser Ala Ile Ala Glu Ala
            515                 520                 525

Val Tyr Leu Leu Gly Ala Glu Arg Asn Pro Asn Thr Val Thr Met Thr
            530                 535                 540

Ser Tyr Ala Pro Ser Phe Gln Asn Leu Asn Trp Tyr Asn Trp Ser Pro
545                 550                 555                 560

Asn Leu Val Ala Phe Thr Ala Asn Pro Asp Glu Thr Val Phe Ser Thr
                565                 570                 575

Ser Tyr Tyr Met Gln Lys Met Phe Ala Asn His Arg Gly Thr Gln Thr
            580                 585                 590
```

```
Leu Pro Val Lys Asn Ser Lys Gly Asp Phe Asn Pro Leu Trp Trp Val
            595                 600                 605

Ala Thr Ile Asp Glu Gly Ala Gly Val Val Tyr Phe Lys Ile Val Asn
    610                 615                 620

Ser Gly Asn Ser Ser Ile Pro Leu Thr Ile Asn Leu Asp Gln Ala Tyr
625                 630                 635                 640

Lys Gly Val Asn Gly Thr Ile Leu Val Arg Arg Ile Cys Leu Gln
                645                 650                 655

Leu His Ile Tyr Thr Val Pro Asp Glu Leu Thr Ile Ala Phe Leu Gln
            660                 665                 670

Thr His Pro Asn Leu Tyr Gly Phe Asn Tyr Leu Asn Asn Gln Thr Ala
        675                 680                 685

Ile Val Pro Val Pro Ala Asn Ile Thr Ser Pro Ser Lys Ser Gln Asn
    690                 695                 700

Arg Phe Asp Trp Asp Val Pro Lys Tyr Ser Val Thr Val Leu Gln Phe
705                 710                 715                 720

Asp Ile

<210> SEQ ID NO 38
<211> LENGTH: 23
<212> TYPE: PRT
<213> ORGANISM: Rasamsonia emersonii

<400> SEQUENCE: 38

Met Ile Leu Arg Ser Leu Pro Ile His Ala Ala Ala Ile Ala Ala Ala
1               5                   10                  15

Leu Thr Ser Leu Val Asp Ala
            20

<210> SEQ ID NO 39
<211> LENGTH: 2483
<212> TYPE: DNA
<213> ORGANISM: Rasamsonia emersonii
<220> FEATURE:
<221> NAME/KEY: source
<222> LOCATION: (1)..(2483)
<223> OTHER INFORMATION: /organism="Rasamsonia emersonii"
      /mol_type="unassigned DNA"

<400> SEQUENCE: 39
atgatcctcc gatccctccc tatccatgct gcggccattg cagcagcctt aacttccctc      60
gtcgacgcaa aaccctgcg acatgacatc aggcaggtgg cagaaacgca tcggatcaat      120
agcacgcact acaacgacac ctctgccgtc gtgctggatg tgtcgttgaa ggacgcggcc      180
gggaggaaca atacgtcgcc gctgctgtat gggtggatgt ttgaggatat tagtgtaatt      240
acctccattt gttgacccct tgactattac cgttctcaaga tgcgttgttt gttttgtact      300
ggtgtcattt tatattactg tgcttcagac gaagatggtt tttttttcct atttcctcaa      360
gctaagcctt cttgcagcac tccggcgacg gcggtatata cgcggaattg atcaagaacc      420
gggctttcca gggtgagaac taccttgact ttctttctct tcgtcgttct gacgacctgc      480
caggctcgac atccaccgtc aaacaagcac ccggcatttc aggcgacagc gtggttgctg      540
cacagaaccc catcgtcccg tttggcccg tcctcgacgg atggcgaccc attggcgatg      600
caaaactctc tctcgacgtg cttcacccc tgtccgatgc ccttccggtc gtcctgcaga      660
tcgacatccc ctggaacgcc accggcgaag ttggcttcct gaatgaaggc tggtggggca      720
tcgacgtccg gccgcagaca tacaacgcct cgttctacat gctggccaac gccccgcgat      780
```

| | |
|---|---|
| acaacaagac gctgaccagc atcaacctgt cgctgcggtc gaacctgacg gacgacgtct | 840 |
| gggccacgac gacgatccac gtcgacccgg acaaggtccc cacgttcgac tacgagcagt | 900 |
| accaggccag catcgtcaac acggtcaagg cgcccaactc gaacaacacc tttgccatca | 960 |
| ccttcaatgc ggacgaggtg gctggctcga cattctactt tggcctcgtc agtctgttcc | 1020 |
| ctgagacgtt caacaaccgt cccaacggtc tgcgcaagga cctcgcccag ggcatcaagg | 1080 |
| acatgggcgc gaaattcctc cgcttcccag gcggcaacaa cctcgaggga tactccatct | 1140 |
| tccagcggtg gaagtggaac gagaccatcg gcccgttgcg ataccgcaag ggacgcgtcg | 1200 |
| gcaactggga atactacaac accaacgggc tgggtctgct ggagttcctg gagtggacgg | 1260 |
| aggacctcgg catggagccc gttctggccg tgtacgccgg attctcgctc gacatatggg | 1320 |
| gccaggaggg cacgtcctac cccgaagacc gcatggacga gattgtgcag gacatcctga | 1380 |
| acgagctgga gtactgcatg ggcgacgtca acacgcacta cggcgctctg cgcgcgcagc | 1440 |
| acggccaccc ggagccgttc gatatcaagt acatcgagat cggcaacgag gactggttct | 1500 |
| ccagcacgta tccctaccgg ttccccatca tctacaaggc catcaagtcc gcgtacccca | 1560 |
| acatcaccct catctcgacc gcctacaacg agaacgccaa ctacaccatc gacatccccg | 1620 |
| cgggcggcat gtgggacacg catcactacg agacgccgtc cttcttcctc gagaacttca | 1680 |
| actacttcga caactggcag gcggcgacga caacaccga cgtcaagatc ttcgtcggcg | 1740 |
| agtactccgt ctaccagatc gacacaccgg acggctacgt caacttcagc aacccggagg | 1800 |
| gcatccacat gttcttcccg gagctcgtgt cggcgatcgc agaggcagtc tatctgctcg | 1860 |
| gcgcagagcg caatccgaac acggtcacca tgacctcgta cgcgcccagc ttccagaacc | 1920 |
| tgaactggta caactggtcg cccaacctgg tggcctttac tgccaatccc gacgagacgg | 1980 |
| tcttcagcac cagctactac atgcagaaga tgtttgccaa tcaccggggc acgcagacgc | 2040 |
| tgccagtgaa gaattccaag ggagacttta acccgctgtg gtgggttgca acgattgacg | 2100 |
| aggggggctgg tgttgtttac ttcaaggtat tatccattat aacattgctc gttcctgttg | 2160 |
| tcactaacaa caagcagatc gtcaactcgg gaaactcctc catcccgttg acaatcaacc | 2220 |
| tcgaccaggc atacaaggga gtcaatggga cgatactggt gcgtcgcaga atctgccttc | 2280 |
| agctacatat atataccgtt cctgacgaac tgacaattgc ctttctacag acacaccca | 2340 |
| acctctacgg attcaactac ctgaacaacc agactgccat cgtgcctgtt ccggcgaaca | 2400 |
| tcacttctcc ctcgaagagt cagaaccgct tcgattggga tgtcccgaag tattcggtca | 2460 |
| cggtgttgca gtttgatatt taa | 2483 |

<210> SEQ ID NO 40
<211> LENGTH: 2238
<212> TYPE: DNA
<213> ORGANISM: Rasamsonia emersonii
<220> FEATURE:
<221> NAME/KEY: source
<222> LOCATION: (1)..(2238)
<223> OTHER INFORMATION: /organism="Rasamsonia emersonii"
      /mol_type="unassigned DNA"

<400> SEQUENCE: 40

| | |
|---|---|
| atgatcctcc gatccctccc tatccatgct gcggccattg cagcagcctt aacttccctc | 60 |
| gtcgacgcaa aaccccctgcg acatgacatc aggcaggtgg cagaaacgca tcggatcaat | 120 |
| agcacgcact acaacgacac ctctgccgtc gtgctggatg tgtcgttgaa ggacgcggcc | 180 |
| gggaggaaca atacgtcgcc gctgctgtat gggtggatgt ttgaggatat tagtcactcc | 240 |

```
ggcgacggcg gtatatacgc ggaattgatc aagaaccggg ctttccaggg ctcgacatcc      300
accgtcaaac aagcacccgg catttcaggc gacagcgtgg ttgctgcaca gaaccccatc      360
gtcccgtttg gccccgtcct cgacggatgg cgacccattg gcgatgcaaa actctctctc      420
gacgtgcttc accccctgtc cgatgccctt ccggtcgtcc tgcagatcga catcccctgg      480
aacgccaccg gcgaagttgg cttcctgaat gaaggctggt ggggcatcga cgtccggccg      540
cagacataca acgcctcgtt ctacatgctg gccaacgccc cgcgatacaa caagacgctg      600
accagcatca acctgtcgct gcggtcgaac ctgacggacg acgtctgggc cacgacgacg      660
atccacgtcg acccggacaa ggtccccacg ttcgactacg agcagtacca ggccagcatc      720
gtcaacacgg tcaaggcgcc caactcgaac aacacctttg ccatcacctt caatgcggac      780
gaggtggctg gctcgacatt ctactttggc ctcgtcagtc tgttccctga cgttcaac       840 aaccgtccca acggtctgcg caaggacctc gcccagggca tcaaggacat gggcgcgaaa      900
ttcctccgct tcccaggcgg caacaacctc gagggatact ccatcttcca gcggtggaag      960
tggaacgaga ccatcggccc gttgcgatac cgcaaggac gcgtcggcaa ctgggaatac      1020
tacaacacca cgggctgggt ctgctggag ttcctggagt ggacggagga cctcggcatg      1080
gagcccgttc tggccgtgta cgccggattc tcgctcgaca tatggggcca ggagggcacg      1140
tcctaccccg aagaccgcat ggacgagatt gtgcaggaca tcctgaacga gctggagtac      1200
tgcatgggcg acgtcaacac gcactacggc gctctgcgcg cgcagcacgg ccacccggag      1260
ccgttcgata tcaagtacat cgagatcggc aacgaggact ggttctccag cacgtatccc      1320
taccggttcc ccatcatcta caaggccatc aagtccgcgt accccaacat caccctcatc      1380
tcgaccgcct acaacgagaa cgccaactac accatcgaca tccccgcggg cggcatgtgg      1440
gacacgcatc actacgagac gccgtccttc ttcctcgaga acttcaacta cttcgacaac      1500
tggcaggcgg cgacgaacaa caccgacgtc aagatcttcg tcggcgagta ctccgtctac      1560
cagatcgaca caccggacgg ctacgtcaac ttcagcaacc cggagggcat ccacatgttc      1620
ttcccggagc tcgtgtcggc gatcgcagag gcagtctatc tgctcggcgc agagcgcaat      1680
ccgaacacgg tcaccatgac ctcgtacgcg cccagcttcc agaacctgaa ctggtacaac      1740
tggtcgccca acctggtggc ctttactgcc aatcccgacg agacggtctt cagcaccagc      1800
tactacatgc agaagatgtt tgccaatcac cggggcacgc agacgctgcc agtgaagaat      1860
tccaagggag actttaaccc gctgtggtgg gttgcaacga ttgacgaggg ggctggtgtt      1920
gtttacttca agatcgtcaa ctcgggaaac tcctccatcc cgttgacaat caacctcgac      1980
caggcataca agggagtcaa tgggacgata ctggtgcgtc gcagaatctg ccttcagcta      2040
catatatata ccgttcctga cgaactgaca attgccttc tacagacaca ccccaacctc      2100
tacggattca actacctgaa caaccagact gccatcgtgc ctgttccggc gaacatcact      2160
tctccctcga agagtcagaa ccgcttcgat tgggatgtcc cgaagtattc ggtcacggtg      2220
ttgcagtttg atatttaa                                                    2238
```

<210> SEQ ID NO 41
<211> LENGTH: 1518
<212> TYPE: DNA
<213> ORGANISM: Rasamsonia emersonii
<220> FEATURE:
<221> NAME/KEY: source
<222> LOCATION: (1)..(1518)
<223> OTHER INFORMATION: /organism="Rasamsonia emersonii"
    /mol_type="unassigned DNA"

<400> SEQUENCE: 41

```
atgaccacct tcaccaagct cagcgacgag gagactccta ccatctccgt ccacgcttct      60
cgccgcctct ccaagatcaa ccccaacatc tactctggct tcactgagca catgggccgc    120
tgcatctacg gtggtatcta cgaccccggc aaccctctct ccgacgagaa cggattccgc    180
aaggatgttc tcgaagcgtt gaaggagctc aacatccccg tcgtccgtta ccccggtggc    240
aacttcactg ccacctacca ctggttggat ggtgttggtc ccaaggacca cgcccccgcc    300
cgtcccgagc tggcctggct aggaaccgaa accaaccagt tcggtaccga cgagttcctc    360
aagtggtgcg agatgcttgg tgctgagccc tacctctgcc tgaacttcgg tactggtacc    420
ctcgacgagg ccatggcctg ggttgaatac tgcaacggca ccggcaacac ctactacgcc    480
aacctccgtc gcaagaacgg ccgtgagaag ccctacaacg tcaagtactg gctcttggc    540
aacgaaacct ggggtccctg gcagatcgag cagatgacca aggaagccta cgctcacaag    600
gcctaccagt gggccaaggc tctcaagctc ctggatccca acatcatcct gatcctctgc    660
ggtcaggatg gaactgccag ctgggactac tacaccctca gcactgcttt gcagcccacc    720
aaggccaccc tcaactccaa ccccgttcct ctgattgaca tgcactccat ccacatgtac    780
actgcttctt ccaagcacct gcccaacgcc actgcgcctc ttgctgctga gcgtgccatt    840
gagatcacca gcagcttgat tgaccttgct cgcattgaga acggcatctc ccccgatgag    900
cctcgtccca ccatctgctt cgacgaatgg aacgtctggg accctgtccg tgctgagggc    960
tccaagggtg ctgaggagag ctacactctg tcggatgccc ttgctgttgg tgtgttcctc   1020
aacgtgttcg tccgcaagtc caaggacctt ggaatggcct gcattgccca gtccgtcaac   1080
gtcatctccc ctctgatgac cactcgtgac ggtatcgtca agcagaccac ctggtggcct   1140
ctctggctgt tctcccgctt catgcgtggc tggaccattg tgctcacgt ttcctgcggt   1200
gcctacgagg gtgagacttc tcctgcctgg ctgcgtggtg tcaaggacac tccttggctg   1260
gatgtctctg ccgctcttgg tgatgacggc ttcgtcaacg ttgttgttgt caacatccac   1320
gaaaccaagg acttcaagac caacgtgaag ggtgtctccg gtggtcccgt gaccgtctac   1380
accgtcactg gtgctgatgt gtctgccacc aacatgaagg gcaagcagga agtcggtgtc   1440
caggagtcca cctgggatgg caagggcagc tacgtgttcc ccaagcactc gctgaccctg   1500
ctccgctgga aggccgag                                                 1518
```

<210> SEQ ID NO 42
<211> LENGTH: 506
<212> TYPE: PRT
<213> ORGANISM: Rasamsonia emersonii

<400> SEQUENCE: 42

```
Met Thr Thr Phe Thr Lys Leu Ser Asp Glu Glu Thr Pro Thr Ile Ser
1               5                   10                  15

Val His Ala Ser Arg Arg Leu Ser Lys Ile Asn Pro Asn Ile Tyr Ser
            20                  25                  30

Gly Phe Thr Glu His Met Gly Arg Cys Ile Tyr Gly Gly Ile Tyr Asp
        35                  40                  45

Pro Gly Asn Pro Leu Ser Asp Glu Asn Gly Phe Arg Lys Asp Val Leu
    50                  55                  60

Glu Ala Leu Lys Glu Leu Asn Ile Pro Val Val Arg Tyr Pro Gly Gly
65                  70                  75                  80

Asn Phe Thr Ala Thr Tyr His Trp Leu Asp Gly Val Gly Pro Lys Asp
                85                  90                  95
```

-continued

Gln Arg Pro Ala Arg Pro Glu Leu Ala Trp Leu Gly Thr Glu Thr Asn
            100                 105                 110

Gln Phe Gly Thr Asp Glu Phe Leu Lys Trp Cys Glu Met Leu Gly Ala
        115                 120                 125

Glu Pro Tyr Leu Cys Leu Asn Phe Gly Thr Gly Thr Leu Asp Glu Ala
    130                 135                 140

Met Ala Trp Val Glu Tyr Cys Asn Gly Thr Gly Asn Thr Tyr Tyr Ala
145                 150                 155                 160

Asn Leu Arg Arg Lys Asn Gly Arg Glu Lys Pro Tyr Asn Val Lys Tyr
                165                 170                 175

Trp Ala Leu Gly Asn Glu Thr Trp Gly Pro Trp Gln Ile Glu Gln Met
            180                 185                 190

Thr Lys Glu Ala Tyr Ala His Lys Ala Tyr Gln Trp Ala Lys Ala Leu
        195                 200                 205

Lys Leu Leu Asp Pro Asn Ile Ile Leu Ile Leu Cys Gly Gln Asp Gly
    210                 215                 220

Thr Ala Ser Trp Asp Tyr Tyr Thr Leu Lys His Cys Leu Gln Pro Thr
225                 230                 235                 240

Lys Ala Thr Leu Asn Ser Asn Pro Val Pro Leu Ile Asp Met His Ser
                245                 250                 255

Ile His Met Tyr Thr Ala Ser Ser Lys His Leu Pro Asn Ala Thr Ala
            260                 265                 270

Pro Leu Ala Ala Glu Arg Ala Ile Glu Ile Thr Ser Ser Leu Ile Asp
        275                 280                 285

Leu Ala Arg Ile Glu Asn Gly Ile Ser Pro Asp Glu Pro Arg Pro Thr
    290                 295                 300

Ile Cys Phe Asp Glu Trp Asn Val Trp Asp Pro Val Arg Ala Glu Gly
305                 310                 315                 320

Ser Lys Gly Ala Glu Glu Ser Tyr Thr Leu Ser Asp Ala Leu Ala Val
                325                 330                 335

Gly Val Phe Leu Asn Val Phe Val Arg Lys Ser Lys Asp Leu Gly Met
            340                 345                 350

Ala Cys Ile Ala Gln Ser Val Asn Val Ile Ser Pro Leu Met Thr Thr
        355                 360                 365

Arg Asp Gly Ile Val Lys Gln Thr Thr Trp Trp Pro Leu Trp Leu Phe
    370                 375                 380

Ser Arg Phe Met Arg Gly Trp Thr Ile Gly Ala His Val Ser Cys Gly
385                 390                 395                 400

Ala Tyr Glu Gly Glu Thr Ser Pro Ala Trp Leu Arg Gly Val Lys Asp
                405                 410                 415

Thr Pro Trp Leu Asp Val Ser Ala Ala Leu Gly Asp Asp Gly Phe Val
            420                 425                 430

Asn Val Val Val Asn Ile His Glu Thr Lys Asp Phe Lys Thr Asn
        435                 440                 445

Val Lys Gly Val Ser Gly Gly Pro Val Thr Val Tyr Thr Val Thr Gly
    450                 455                 460

Ala Asp Val Ser Ala Thr Asn Met Lys Gly Lys Gln Glu Val Gly Val
465                 470                 475                 480

Gln Glu Ser Thr Trp Asp Gly Lys Gly Ser Tyr Val Phe Pro Lys His
                485                 490                 495

Ser Leu Thr Leu Leu Arg Trp Lys Ala Glu
            500                 505

<210> SEQ ID NO 43
<211> LENGTH: 4
<212> TYPE: PRT
<213> ORGANISM: Artificial Sequence
<220> FEATURE:
<223> OTHER INFORMATION: no signal peptide predicted

<400> SEQUENCE: 43

Met Met Met Met
1

<210> SEQ ID NO 44
<211> LENGTH: 2005
<212> TYPE: DNA
<213> ORGANISM: Rasamsonia emersonii
<220> FEATURE:
<221> NAME/KEY: source
<222> LOCATION: (1)..(2005)
<223> OTHER INFORMATION: /organism="Rasamsonia emersonii"
    /mol_type="unassigned DNA"

<400> SEQUENCE: 44

| | | | | | |
|---|---|---|---|---|---|
| atgacgacat | tcaccaagct | cagcgacgag | gagacgccca | ccatctctgt | ccatgcgtcc | 60 |
| aggcgtctgt | ccaaaatcaa | ccccaacatc | tactcggggt | tcacagagta | gggagccgac | 120 |
| agacgtgtct | accggtttta | gttcgctagt | gagaccctgc | tgactgatag | ctttcgttac | 180 |
| caggcatatg | ggacgatgca | tctacggagg | catatatgat | cccggaaatc | ctctgtcgga | 240 |
| cgagaatggc | tttcgaaagg | atgttctgga | ggctctgaag | gagctcaata | tccctgtggt | 300 |
| tcgctatccc | ggcggaaact | ttaccgccac | gtatcactgg | ttagacggtg | ttggcccgaa | 360 |
| ggatcaacga | cccgcgaggt | attcaatgac | ttcttctctt | ggatttcatt | tctttcgttt | 420 |
| gactgtctgt | gttttaccat | ggttctgttt | taataccatg | aactatttga | gagactttag | 480 |
| ctggtttcca | tataattttt | ttaccatacg | cggcacctgt | catgctaaca | aagggaaaca | 540 |
| atttgaacag | accggagctc | gcctggctgg | ggactgagac | caatcagttc | ggcactgatg | 600 |
| agttcttaaa | atggtgtgag | atgctcggcg | cggagccgta | cctctgcttg | aactttggaa | 660 |
| caggtgcggc | gtgccgatat | cctgacccct | gtacctgaga | caaacaaac | taattggatt | 720 |
| gatttaggca | ctcttgatga | aggtgagcat | ccttcaattc | ctgtcctata | atgccagcac | 780 |
| aagatgatgt | tgacacttct | cagcaatggc | atgggtcgag | tactgcaatg | ggacgggaaa | 840 |
| tacctactat | gccaacctgc | ggaggaagaa | tggtcgggag | aagccctaca | atgtacgatc | 900 |
| cagtcactga | ttggacattc | tgttttttaa | atactaatac | cagagtttca | ggttaaatac | 960 |
| tgggctctgg | gtaacgagac | atggggtccg | tggcaaattg | aacaaatgac | caaggaagcc | 1020 |
| tatgctcaca | aggcgtatca | atgggccaaa | ggtacgttga | caatttatat | atctatttat | 1080 |
| ctatacctct | aacatacgta | cagctctcaa | gctgctcgat | ccgaatataa | ttctcattct | 1140 |
| ttgcggtcag | gacggcactg | catcgtggga | ctactacacc | ctcaaacact | gtctgcagcc | 1200 |
| aacaaaggct | actctaaaca | gcaacccggt | tccccttatt | gacatgcaca | gcattcacat | 1260 |
| gtacacggcg | tcgtccaagc | atttgccaaa | cgccaccgca | cccttggctg | cggagcgtgc | 1320 |
| gattgagatt | acatcctccc | tgatcgacct | ggctcggatc | gaaaacggga | tatcccggga | 1380 |
| tgagccgcgc | ccgacgatct | gctttgacga | gtggaacgtc | tgggatcccg | tgcgtgccga | 1440 |
| gggcagcaag | ggagccgagg | agagctacac | cctgtccgac | gcgttggcgg | tgggagtttt | 1500 |
| cctcaacgtg | ttcgtccgga | agagcaagga | cctgggaatg | gcgtgcatcg | cgcaaagcgt | 1560 |
| caatgtcatt | tcgccgctca | tgacgaccag | agacggcatt | gtgaagcaaa | cgacgtggtg | 1620 |

```
gccgctgtgg cttttctccc gattcatgcg gggctggacc atcggtgcgc atgtttcctg    1680
tggcgcctac gagggcgaaa cctcacccgc gtggctgcgc ggcgtcaagg acactccctg    1740
gctggacgtc agcgcggcct tgggtgacga tggctttgtc aacgtagttg tcgtcaacat    1800
ccatgaaact aaggacttta agaccaacgt caagggcgtc agtggaggtc ctgtcactgt    1860
ctacacggtc accggagccg atgtgtctgc tactaacatg aaggggaagc aagaggtggg    1920
agttcaggag agtacatggg acggcaaagg cagttatgtg ttcccgaagc attctctgac    1980
gctgctgaga tggaaggcag agtga                                          2005
```

<210> SEQ ID NO 45
<211> LENGTH: 1521
<212> TYPE: DNA
<213> ORGANISM: Rasamsonia emersonii
<220> FEATURE:
<221> NAME/KEY: source
<222> LOCATION: (1)..(1521)
<223> OTHER INFORMATION: /organism="Rasamsonia emersonii"
      /mol_type="unassigned DNA"

<400> SEQUENCE: 45

```
atgacgacat tcaccaagct cagcgacgag gagacgccca ccatctctgt ccatgcgtcc      60
aggcgtctgt ccaaaatcaa ccccaacatc tactcggggt tcacagagca tatgggacga    120
tgcatctacg gaggcatata tgatcccgga atcctctgt cggacgagaa tggctttcga    180
aaggatgttc tggaggctct gaaggagctc aatatccctg tggttcgcta tcccggcgga    240
aactttaccg ccacgtatca ctggttagac ggtgttggcc cgaaggatca acgaccgcg    300 agaccggagc tcgcctggct ggggactgag accaatcagt tcggcactga tgagttctta    360
aaatggtgtg agatgctcgg cgcggagccg tacctctgct tgaactttgg aacaggcact    420
cttgatgaag caatggcatg ggtcgagtac tgcaatggga cgggaaatac ctactatgcc    480
aacctgcgga ggaagaatgg tcgggagaag ccctacaatg ttaaatactg ggctctgggt    540
aacgagacat ggggtccgtg gcaaattgaa caaatgacca aggaagccta tgctcacaag    600
gcgtatcaat gggccaaagc tctcaagctg ctcgatccga atataattct cattctttgc    660
ggtcaggacg gcactgcatc gtgggactac tacaccctca acactgtctt gcagccaaca    720
aaggctactc taaacagcaa cccggttccc cttattgaca tgcacagcat tcacatgtac    780
acggcgtcgt ccaagcattt gccaaacgcc accgcaccct tggctgcgga gcgtgcgatt    840
gagattacat cctccctgat cgacctggct cggatcgaaa acgggatatc cccggatgag    900
ccgcgcccga cgatctgctt tgacgagtgg aacgtctggg atcccgtgcg tgccgagggc    960
agcaagggag ccgaggagag ctacacccctg tccgacgcgt tggcggtggg agttttcctc   1020
aacgtgttcg tccggaagag caaggacctg ggaatggcgt gcatcgcgca aagcgtcaat   1080
gtcatttcgc cgctcatgac gaccagagac ggcattgtga agcaaacgac gtggtggccg   1140
ctgtggcttt tctcccgatt catgcggggc tggaccatcg gtgcgcatgt tcctgtggc   1200 gcctacgagg gcgaaacctc acccgcgtgg ctgcgcggcg tcaaggacac tccctggctg   1260
gacgtcagcg cggccttggg tgacgatggc tttgtcaacg tagttgtcgt caacatccat   1320
gaaactaagg actttaagac caacgtcaag ggcgtcagtg gaggtcctgt cactgtctac   1380
acggtcaccg gagccgatgt gtctgctact aacatgaagg ggaagcaaga ggtgggagtt   1440
caggagagta catgggacgg caaaggcagt tatgtgttcc cgaagcattc tctgacgctg   1500
ctgagatgga aggcagagtg a                                             1521
```

<210> SEQ ID NO 46
<211> LENGTH: 966
<212> TYPE: DNA
<213> ORGANISM: Rasamsonia emersonii
<220> FEATURE:
<221> NAME/KEY: source
<222> LOCATION: (1)..(966)
<223> OTHER INFORMATION: /organism="Rasamsonia emersonii"
     /mol_type="unassigned DNA"

<400> SEQUENCE: 46

```
atgcgcccca gcttcctccg ctacgtgtct cttgctcctc tgctctggtc tgctgctgcc        60
tccgctgagc ctgtccgtgt tctcgacacc gacttccctg acccttgctt gatctccacc       120
aacggcaagt actacgcttt cgccaccact ggcaacggtg tcaacgtcca gattgcccag       180
tcggatgact tcgtcacctg ggagcgtctt gctggtactg atgcccttcc tggtcccttc       240
cccagctggg ttgcctcctc ccccactgtc tgggctcccg atgtcatcca gcgtctggac       300
ggtacctacg tcatgtacta ctctgctctt cttccaccg accccagcaa gcactgcttc       360
ggtgctgcca cctcgacctc catcaccggt ccctacaagc ccgaggacaa ctacattgcc       420
tgccccctcg accagggtgg tgccatcgac cccgatggat tcatcgatga tgacggcacc       480
atgtacgtgg tctacaaggt tgacggcagc aacctggatg gagatggcac catccacccc       540
actcccatca tgctccaggc tctggagcct gacggcatca ccccactgg tgaccccatc       600
aagctcctcg accgtgatgc ctccgacggc atcttgattg aggctcccctc cctcgtccgc       660
tccgttgttt ccggcaccta cttcctgagc tactcttctc actactacgc ctccctgcac       720
tacgacgttg atacgccac tggccctgcc gtcaagggtc ccttcaccaa ggcccaggct       780
cctcttctcg tcaccggtga caacaccacc aacgccggtc tctgggtgg tcccggtggt       840
gccgacttct ccgtcgacgg cactcgtatc gtgttccacg cttcgagaa cggccgcaac       900
ctgaccaacg ccgtgctctc tacaccagc ggtatcgtcc tcgagggtga tgtcattcgc       960
ctagtt                                                                 966
```

<210> SEQ ID NO 47
<211> LENGTH: 300
<212> TYPE: PRT
<213> ORGANISM: Rasamsonia emersonii

<400> SEQUENCE: 47

```
Glu Pro Val Arg Val Leu Asp Thr Asp Phe Pro Asp Pro Cys Leu Ile
1               5                   10                  15

Ser Thr Asn Gly Lys Tyr Tyr Ala Phe Ala Thr Thr Gly Asn Gly Val
            20                  25                  30

Asn Val Gln Ile Ala Gln Ser Asp Asp Phe Val Thr Trp Glu Arg Leu
        35                  40                  45

Ala Gly Thr Asp Ala Leu Pro Gly Pro Phe Pro Ser Trp Val Ala Ser
    50                  55                  60

Ser Pro Thr Val Trp Ala Pro Asp Val Ile Gln Arg Leu Asp Gly Thr
65                  70                  75                  80

Tyr Val Met Tyr Tyr Ser Ala Leu Ser Ser Thr Asp Pro Ser Lys His
            85                  90                  95

Cys Phe Gly Ala Ala Thr Ser Thr Ser Ile Thr Gly Pro Tyr Lys Pro
            100                 105                 110

Glu Asp Asn Tyr Ile Ala Cys Pro Leu Asp Gln Gly Gly Ala Ile Asp
        115                 120                 125
```

Pro Asp Gly Phe Ile Asp Asp Gly Thr Met Tyr Val Val Tyr Lys
            130                 135                 140

Val Asp Gly Ser Asn Leu Asp Gly Asp Gly Thr Ile His Pro Thr Pro
145                 150                 155                 160

Ile Met Leu Gln Ala Leu Glu Pro Asp Gly Ile Thr Pro Thr Gly Asp
                165                 170                 175

Pro Ile Lys Leu Leu Asp Arg Asp Ala Ser Asp Gly Ile Leu Ile Glu
            180                 185                 190

Ala Pro Ser Leu Val Arg Ser Val Ser Gly Thr Tyr Phe Leu Ser
        195                 200                 205

Tyr Ser Ser His Tyr Tyr Ala Ser Leu His Tyr Asp Val Gly Tyr Ala
210                 215                 220

Thr Gly Pro Ala Val Lys Gly Pro Phe Thr Lys Ala Gln Ala Pro Leu
225                 230                 235                 240

Leu Val Thr Gly Asp Asn Thr Thr Asn Ala Gly Pro Leu Gly Gly Pro
                245                 250                 255

Gly Gly Ala Asp Phe Ser Val Asp Gly Thr Arg Ile Val Phe His Ala
            260                 265                 270

Phe Glu Asn Gly Arg Asn Leu Thr Asn Gly Arg Ala Leu Tyr Thr Ser
            275                 280                 285

Gly Ile Val Leu Glu Gly Asp Val Ile Arg Leu Val
        290                 295                 300

<210> SEQ ID NO 48
<211> LENGTH: 22
<212> TYPE: PRT
<213> ORGANISM: Rasamsonia emersonii

<400> SEQUENCE: 48

Met Arg Pro Ser Phe Leu Arg Tyr Val Ser Leu Ala Pro Leu Leu Trp
1               5                   10                  15

Ser Ala Ala Ser Ala
            20

<210> SEQ ID NO 49
<211> LENGTH: 1026
<212> TYPE: DNA
<213> ORGANISM: Rasamsonia emersonii
<220> FEATURE:
<221> NAME/KEY: source
<222> LOCATION: (1)..(1026)
<223> OTHER INFORMATION: /organism="Rasamsonia emersonii"
      /mol_type="unassigned DNA"

<400> SEQUENCE: 49
atgcgaccat ctttccttcg atacgtctct ctagcacccc tcctgtggag cgcagcagca      60
tctgctgagc ccgtccgagt gctggacacc gacttcccag acccctgcct gatctccacc     120
aacggcaagt actatgcctt tgcgacgacg ggcaatggcg tcaacgtgca atcgcccag      180 tcggacgact tcgtcacctg ggagcgtctg gctggcactg atgccctgcc gggaccgttt     240
ccctcgtggg tggcgtcttc gccgactgta tgggcgccgg acgtgattca acgggtgcgt     300
ttaaactata cataggattt ttcatcgtca tatctaacga ggtgcatcta gctcgatggc     360
acgtacgtga tgtactactc cgccctctcg agcacggacc cgtccaagca ctgctttggc     420
gccgccacct cgacctccat cacaggccct acaagcccg aagacaacta catcgcctgt     480
ccgctggacc agggcggcgc catcgaccca gacggcttca tcgacgacga cggcaccatg     540

-continued

```
tacgtcgtct acaaggtcga cgggagcaac ctggacggcg acggcacgat ccatccgacg      600
cccatcatgc tgcaggcgct ggagccggac ggcatcactc cgacagggga cccgatcaag      660
ctgctagacc gggacgcgtc ggacgggatc ctgattgagg cgcccagtct ggtcagaagc      720
gtcgtcagcg ggacgtactt cctctcgtac tcgtcgcact actacgccag tttgcactac      780
gacgtcggct acgcgacagg gccggctgtg aaggggccct tcaccaaggc gcaggccccg      840
ttgctggtga cgggcgacaa tactaccaat gctggtcctc tgggtggacc tggaggagca      900
gacttttccg tcgacgggac gaggattgtc tttcatgcgt ttgagaatgg aaggaatctt      960
actaatggca gggcgctgta tacgtcgggg attgtccttg aggggacgt catacggttg      1020 gtgtag                                                                 1026
```

<210> SEQ ID NO 50
<211> LENGTH: 969
<212> TYPE: DNA
<213> ORGANISM: Rasamsonia emersonii
<220> FEATURE:
<221> NAME/KEY: source
<222> LOCATION: (1)..(969)
<223> OTHER INFORMATION: /organism="Rasamsonia emersonii"
    /mol_type="unassigned DNA"

<400> SEQUENCE: 50

```
atgcgaccat ctttccttcg atacgtctct ctagcacccc tcctgtggag cgcagcagca       60
tctgctgagc ccgtccgagt gctggacacc gacttcccag acccctgcct gatctccacc      120
aacggcaagt actatgcctt tgcgacgacg ggcaatggcg tcaacgtgca aatcgcccag      180
tcggacgact tcgtcacctg ggagcgtctg gctggcactg atgccctgcc gggaccgttt      240
ccctcgtggg tggcgtcttc gccgactgta tgggcgccgg acgtgattca acggctcgat      300
ggcacgtacg tgatgtacta ctccgccctc tcgagcacgg accgtccaa gcactgcttt      360 ggcgccgcca cctcgacctc catcacaggc cctacaagc ccgaagacaa ctacatcgcc      420
tgtccgctgg accagggcgg cgccatcgac ccagacggct catcgacga cgacggcacc      480 atgtacgtcg tctacaaggt cgacgggagc aacctggacg gcgacggcac gatccatccg      540
acgcccatca tgctgcaggc gctggagccg gacggcatca ctccgacagg ggacccgatc      600
aagctgctag accgggacgc gtcggacggg atcctgattg aggcgcccag tctggtcaga      660
agcgtcgtca gcgggacgta cttcctctcg tactcgtcgc actactacgc cagtttgcac      720
tacgacgtcg gctacgcgac agggccggct gtgaaggggc ccttcaccaa ggcgcaggcc      780
ccgttgctgt tgacgggcga caatactacc aatgctggtc ctctgggtgg acctggagga      840
gcagactttt ccgtcgacgg gacgaggatt gtctttcatg cgtttgagaa tggaaggaat      900
cttactaatg gcagggcgct gtatacgtcg gggattgtcc ttgagggga cgtcatacgg      960 ttggtgtag                                                              969
```

<210> SEQ ID NO 51
<211> LENGTH: 1998
<212> TYPE: DNA
<213> ORGANISM: Rasamsonia emersonii
<220> FEATURE:
<221> NAME/KEY: source
<222> LOCATION: (1)..(1998)
<223> OTHER INFORMATION: /organism="Rasamsonia emersonii"
    /mol_type="unassigned DNA"

<400> SEQUENCE: 51

```
atgctttctg ctttcctctt ctcctccccc actctcagct ctcctcagtc tgcttccaag       60
```

```
accgagaaca gcactgccaa cactcctggt atccgcttga tcaacggcca cgaacacgtc      120
ctgatccagc cctggggtgc cgatggcttc cgcgttcgtg ccactctcaa ccgcttcccc      180
gacaactccg tccagcgtca ccaccgctct ccttccggcc gtcccgccga tcttcccatt      240
ggtaccagct actccaccat caacgccact cagactgcca ccgtcaccaa cggacacgcc      300
tccgtcgtcg tcgacaaggg tcagctgtcg ttctaccgtg tcaacggcaa caactccaag      360
accctcgtcc tccaggagct ctggctccag accccggtt ccctgctcg ctggtaccag        420 aagcgtgatg ctcgccgtgg attccgtgct cagttctcct tcgtcgctcc tgactccccc      480
accgagcgtc tgttcggtac cggccaggat ttgactggc tctgatcaa gaagaaccag        540 accatcgatc ttgtcaagtt caacaccctc aaccccatcc caccattgt ctccgaccgt       600 ggatacctct tcttctggaa cgttcccctcc ctcggtcaga tggagctttc tcctacccgc     660
acctcgttcc tgtccgacca cacctccgtt gtggactact acattgccat ccgtcccgag      720
gccgactacg acggtctgct ccagcgttac acttccgtca ccggccgcag ccccatgatc      780
cctgacttcg gtactggata ctggcagtgc aagctccgtt acgccaccca ggaagaattg      840
ctcaacgtca ccatgggttt cgctgagcgc aagatccccg tcagcatgtt catcatcaac      900
tacctgagct ggtcccacga gggtgactgg gctctcaacg cctccgcctg cctgacccc       960 gccaagatgg ctgctgaggc tgagctgatg gccctccgtct ggccctccat tgaggatgcc     1020
agccccaact gggctgagat gcagtctctt ggattcgctg cccagacttt cgaccctctt      1080
gacattgctg gctactggca gaacaagtac cagaacggta tccgcaactt ctggctagat      1140
gaggatgagg gtggccaggt tgctctcgat gtctaccccct ggactgacta ctaccttgga    1200
cctggtgacc agtacgccat gcttttcccc tacttccacc agatgggtgt tttcgagggc     1260
cagatgaaaa ctgttggcag caacaacgtt tctgctgtct ctctgtcccg ctcgtctgcc     1320
aactgggaca gcatgaagat gatgatctcc gctggccagt ccatggccat gtccggccag     1380
ggatggtgga ccctcgacat tggtggtttc aagactgatg ccagtcgaa ctcggccaac      1440 atctcggacc ccgagtacca ggagctgttc gtccgctggc tgcagtgggg taccttcctc     1500
cccatcatgc gcaaccacgg tatgcgtacc tgcctgccct ccgctcagga aggcttcctg     1560 acctgccccct ccgagccctg gagctacggt cctgacaacc tgcccatcat tgtcagctac    1620
atcaacctcc gttacaagct gcagcccttac atcaaggccc tcttccgcat gctgagcgaa    1680
tctggccgtg ccatgatgcg ccctctgttc atggacttct ccctctccga ccctacacc      1740 ctggaggcca ctgaggacct caagctccag tacatgttcg gtcctcgctt gcttgtctct    1800
cctgtcacca cctaccgtgc caccaacgcc accgtctacc ttcccaagct tccttcggat     1860
gctcccgata ccagtggac ctactggtgg accaacgagt ctttcgatgg tggtcagtgg      1920
gtgaccgttc ctgccaacaa gtccatcatc cccttgttcc gtctgggcag cgaagcggac    1980
atcctcaccc gcaacatt                                                   1998
```

<210> SEQ ID NO 52
<211> LENGTH: 647
<212> TYPE: PRT
<213> ORGANISM: Rasamsonia emersonii

<400> SEQUENCE: 52

Lys Thr Glu Asn Ser Thr Ala Asn Thr Pro Gly Ile Arg Leu Ile Asn
1               5                   10                  15

Gly His Glu His Val Leu Ile Gln Pro Trp Gly Ala Asp Gly Phe Arg

-continued

```
                 20                  25                  30
Val Arg Ala Thr Leu Asn Arg Phe Pro Asp Asn Ser Val Gln Arg His
             35                  40                  45
His Arg Ser Pro Ser Gly Arg Pro Ala Asp Leu Pro Ile Gly Thr Ser
 50                  55                  60
Tyr Ser Thr Ile Asn Ala Thr Gln Thr Ala Thr Val Thr Asn Gly His
 65                  70                  75                  80
Ala Ser Val Val Val Asp Lys Gly Gln Leu Ser Phe Tyr Arg Val Asn
                 85                  90                  95
Gly Asn Asn Ser Lys Thr Leu Val Leu Gln Glu Leu Trp Leu Gln Thr
            100                 105                 110
Pro Gly Phe Pro Ala Arg Trp Tyr Gln Lys Arg Asp Ala Arg Arg Gly
            115                 120                 125
Phe Arg Ala Gln Phe Ser Phe Val Ala Pro Asp Ser Pro Thr Glu Arg
            130                 135                 140
Leu Phe Gly Thr Gly Gln Asp Leu Thr Gly Ser Leu Ile Lys Lys Asn
145                 150                 155                 160
Gln Thr Ile Asp Leu Val Lys Phe Asn Thr Leu Asn Pro Ile Pro Thr
            165                 170                 175
Ile Val Ser Asp Arg Gly Tyr Leu Phe Phe Trp Asn Val Pro Ser Leu
            180                 185                 190
Gly Gln Met Glu Leu Ser Pro Thr Arg Thr Ser Phe Leu Ser Asp His
            195                 200                 205
Thr Ser Val Val Asp Tyr Tyr Ile Ala Ile Arg Pro Glu Ala Asp Tyr
210                 215                 220
Asp Gly Leu Leu Gln Arg Tyr Thr Ser Val Thr Gly Arg Ser Pro Met
225                 230                 235                 240
Ile Pro Asp Phe Gly Thr Gly Tyr Trp Gln Cys Lys Leu Arg Tyr Ala
            245                 250                 255
Thr Gln Glu Glu Leu Leu Asn Val Thr Met Gly Phe Ala Glu Arg Lys
            260                 265                 270
Ile Pro Val Ser Met Phe Ile Ile Asn Tyr Leu Ser Trp Ser His Glu
            275                 280                 285
Gly Asp Trp Ala Leu Asn Ala Ser Ala Trp Pro Asp Pro Ala Lys Met
            290                 295                 300
Ala Ala Glu Ala Glu Leu Met Ala Ser Val Trp Pro Ser Ile Glu Asp
305                 310                 315                 320
Ala Ser Pro Asn Trp Ala Glu Met Gln Ser Leu Gly Phe Ala Ala Gln
            325                 330                 335
Thr Phe Asp Pro Leu Asp Ile Ala Gly Tyr Trp Gln Asn Lys Tyr Gln
            340                 345                 350
Asn Gly Ile Arg Asn Phe Trp Leu Asp Glu Asp Gly Gly Gln Val
            355                 360                 365
Ala Leu Asp Val Tyr Pro Trp Thr Asp Tyr Tyr Leu Gly Pro Gly Asp
            370                 375                 380
Gln Tyr Ala Met Leu Phe Pro Tyr Phe His Gln Met Gly Val Phe Glu
385                 390                 395                 400
Gly Gln Met Lys Thr Val Gly Ser Asn Val Ser Ala Val Ser Leu
            405                 410                 415
Ser Arg Ser Ser Ala Asn Trp Asp Ser Met Lys Met Ile Ser Ala
            420                 425                 430
Gly Gln Ser Met Ala Met Ser Gly Gln Gly Trp Trp Thr Leu Asp Ile
            435                 440                 445
```

```
Gly Gly Phe Lys Thr Asp Gly Gln Ser Asn Ser Ala Asn Ile Ser Asp
    450                 455                 460
Pro Glu Tyr Gln Glu Leu Phe Val Arg Trp Leu Gln Trp Gly Thr Phe
465                 470                 475                 480
Leu Pro Ile Met Arg Asn His Gly Met Arg Thr Cys Leu Pro Ser Ala
                485                 490                 495
Gln Glu Gly Phe Leu Thr Cys Pro Ser Glu Pro Trp Ser Tyr Gly Pro
            500                 505                 510
Asp Asn Leu Pro Ile Ile Val Ser Tyr Ile Asn Leu Arg Tyr Lys Leu
        515                 520                 525
Gln Pro Tyr Ile Lys Ala Leu Phe Arg Met Leu Ser Glu Ser Gly Arg
    530                 535                 540
Ala Met Met Arg Pro Leu Phe Met Asp Phe Ser Leu Ser Asp Pro Tyr
545                 550                 555                 560
Thr Leu Glu Ala Thr Glu Asp Leu Lys Leu Gln Tyr Met Phe Gly Pro
                565                 570                 575
Arg Leu Leu Val Ser Pro Val Thr Thr Tyr Arg Ala Thr Asn Ala Thr
            580                 585                 590
Val Tyr Leu Pro Lys Leu Pro Ser Asp Ala Pro Asp Thr Lys Trp Thr
        595                 600                 605
Tyr Trp Trp Thr Asn Glu Ser Phe Asp Gly Gly Gln Trp Val Thr Val
    610                 615                 620
Pro Ala Asn Lys Ser Ile Ile Pro Leu Phe Arg Leu Gly Ser Glu Ala
625                 630                 635                 640
Asp Ile Leu Thr Arg Asn Ile
                645

<210> SEQ ID NO 53
<211> LENGTH: 19
<212> TYPE: PRT
<213> ORGANISM: Rasamsonia emersonii

<400> SEQUENCE: 53

Met Leu Ser Ala Phe Leu Phe Ser Ser Pro Thr Leu Ser Ser Pro Gln
1               5                   10                  15
Ser Ala Ser

<210> SEQ ID NO 54
<211> LENGTH: 2684
<212> TYPE: DNA
<213> ORGANISM: Rasamsonia emersonii
<220> FEATURE:
<221> NAME/KEY: source
<222> LOCATION: (1)..(2684)
<223> OTHER INFORMATION: /organism="Rasamsonia emersonii"
     /mol_type="unassigned DNA"

<400> SEQUENCE: 54
atgctttccg cttttctttt ctcttcacca acgctgtcct caccacaaag cgcgtccaaa      60
acagagaaca gcacagcaaa taccagggg attcgtctga tcaacggcca tgaacacgtt     120
ctgattcagc cttggggagc agatgggttc cgtgtccggg ccactctgaa cagatttcct     180
gacagtgcgt agccacggaa aacgcatctt gttcatctga ctaatttctt acctgctgat     240
tgacactctg tagatgaagc gtacagcgtc atcatagatc ccctctggga cggcccgcag     300
acctccccat cggcaccagc tacagcacca tcaatgcgac acaaaccgcc accgtgacca     360
acggccatgc ctcggtggtc gtcgacaagg gccagctgag tttctatcgc gtaaatggca     420
```

```
acaacagtaa aacactcgtc ttgcaggagc tgtggctaca gacaccggga ttcccagcgc    480
gatggtatca aaagagagat gcaagacggg gctttcgagc gcagttcagc ttcgtcgcgc    540
ccgacagtcc cacggagcgg ctgtttggga cgggccagga tctgacgggc tctctcatca    600
agaagaatca gaccatcgac ttggtcaagt tcaacacgct gaatccgatt ccgacaatcg    660
tgtccgatcg agggtatctg tttttctgga acgtgccttc gcttgggcag atggagttgt    720
ctccaacgag gtatgcatca gcaaaatttg aggaacagga tcatttctaa tgtcaatatt    780
agaaccagtt tcctgagcga tcacacttca gtggtggact attacattgc cattcgcccc    840
gaagccgact atgacggcct gctgcagcgg tacaccagtg tcactgggag atcgcccatg    900
attcctgatt ttggcaccgg atactggcag tgcaagctcc gttatgcgac tcaggaggag    960
ctcctcaatg tgactatggg atttgcagag gtcagaccct ttggaaatga taagactgtt   1020
tctgctgact tgtttgcagc gaaaaatacc tgtttcgatg ttcatcatca actatctcag   1080
ctggtctcac gagggtgact gggctctgaa cgcatcggcg tggccagatc cggcgaagat   1140
ggccgcagag ggtgagaaga gtcatttcta ccaaggtgtt gtagtctgac tggagccgaa   1200
ctgatggcat ccgtctggcc cagtatcgag gacgccagtc ccaactgggc tgaaatgcag   1260
agcttgggtt ttgccgcgca gacattcgat cctctcgata ttgctggcta ctggcagaac   1320
aaatacgtgc atatgatcga tcctaccaat gcagcagcca gggacttcct ctggagtaac   1380 cttaccggc attactagca gaacgggatc cgaaacttct ggctcgacga agacgaggga   1440
ggccaggtcg cgctcgacgt ctacccgtgg acggactatt acctgggtcc ggggatcag   1500 tatgccatgc tgttccccta ctttcatcag atgggggttt ttgaaggaca gatgaagaca   1560
gtggggtcga ataatgtttc cgctgtgtcc ctgtcgcggt cctcgtgggt gggctcccag   1620 cgttttgcc ggcgcagtgt ggagtggaga tattttgtat gtgttgcaca cttttcaata   1680
atgtaacctg ctgattctgg tcaacagcgc caactgggat tccatgaaga tgatgatatc   1740
cgcaggacag agcatggcca tgtcagggca gggttggtgg actttggaca ttggaggctt   1800
caagacagac gggcagtcca actcggcgaa tattagcgac ccggagtacc aggaattgtt   1860
tgtacggtgg ctgcagtggt aagcatttga atactccatt tcctgtattg ataagtaata   1920
cgtacagggg aaccttctta ccggtgcgta aatgaatgcc ctgttggcaa ttcaccaact   1980
gaacttgacg tagattatgc gcaaccacgg aatgagaacc tgtctccctt cagcacagga   2040
aggcttcctg acctgtccta gcggtacaga cccgtgccat attttataa cccaaataag   2100 tatctactga cactgtcaaa cttctagaac cctggagcta cggccccgac aacctcccca   2160
tcatcgtgtc ctacatcaac ctccgataca aactgcagcc ctacatcaag gcgctcttcc   2220
ggatgctctc cgagagtgga cgggcaatga tgcggcccct gtttatggat ttctctctca   2280
gcgatcctta cactttggag gcgacggaag atctgaaatt gcagtacatg tttgggccgc   2340
gcttgctcgt cagtcccgtc acaacgtatc gcgcgacgaa tgcgaccgtc tacctgccaa   2400
aattgccgtc ggatgctccc gatacgaaat ggacgtactg gtggacgaac gagagttttg   2460
acggtggtca atgggtgagt tgtctctctc ttttttgata gccagttgac tgacattaat   2520
ttctcaggtc accgttcctg cgaacaaaag catgtaagta ttcaaatcac gtacacatgc   2580
agcttcgaat tgaaatattc ctgtctgacc tgagctgatc tgcatgcaga attccgctct   2640
tccgactcgg cagcgaagca gacatcttga cgaggaacat ctaa                    2684
```

<210> SEQ ID NO 55

```
<211> LENGTH: 2001
<212> TYPE: DNA
<213> ORGANISM: Rasamsonia emersonii
<220> FEATURE:
<221> NAME/KEY: source
<222> LOCATION: (1)..(2001)
<223> OTHER INFORMATION: /organism="Rasamsonia emersonii"
      /mol_type="unassigned DNA"

<400> SEQUENCE: 55
```

| | | | | | |
|---|---|---|---|---|---|
| atgctttccg | cttttctttt | ctcttcacca | acgctgtcct | caccacaaag | cgcgtccaaa | 60 |
| acagagaaca | gcacagcaaa | tacaccaggg | attcgtctga | tcaacggcca | tgaacacgtt | 120 |
| ctgattcagc | cttggggagc | agatgggttc | cgtgtccggg | ccactctgaa | cagatttcct | 180 |
| gacaatagcg | tacagcgtca | tcatagatcc | ccctctggac | ggcccgcaga | cctccccatc | 240 |
| ggcaccagct | acagcaccat | caatgcgaca | caaaccgcca | ccgtgaccaa | cggccatgcc | 300 |
| tcggtggtcg | tcgacaaggg | ccagctgagt | ttctatcgcg | taaatggcaa | caacagtaaa | 360 |
| acactcgtct | gcaggagct | gtggctacag | acaccgggat | tcccagcgcg | atggtatcaa | 420 |
| aagagagatg | caagacgggg | ctttcgagcg | cagttcagct | tcgtcgcgcc | cgacagtccc | 480 |
| acggagcggc | tgtttgggac | gggccaggat | ctgacgggc | ctctcatcaa | gaagaatcag | 540 |
| accatcgact | tggtcaagtt | caacacgctg | aatccgattc | cgacaatcgt | gtccgatcga | 600 |
| gggtatctgt | ttttctggaa | cgtgccttcg | cttgggcaga | tggagttgtc | tccaacgaga | 660 |
| accagtttcc | tgagcgatca | cacttcagtg | gtggactatt | acattgccat | tcgccccgaa | 720 |
| gccgactatg | acggcctgct | gcagcggtac | accagtgtca | ctgggagatc | gcccatgatt | 780 |
| cctgattttg | gcaccggata | ctggcagtgc | aagctccgtt | atgcgactca | ggaggagctc | 840 |
| ctcaatgtga | ctatgggatt | tgcagagcga | aaaatacctg | tttcgatgtt | catcatcaac | 900 |
| tatctcagct | ggtctcacga | gggtgactgg | gctctgaacg | catcggcgtg | ccagatccg | 960 |
| gcgaagatgg | ccgcagaggc | cgaactgatg | gcatccgtct | ggcccagtat | cgaggacgcc | 1020 |
| agtcccaact | gggctgaaat | gcagagcttg | ggttttgccg | cgcagacatt | cgatcctctc | 1080 |
| gatattgctg | gctactggca | gaacaaatac | cagaacggga | tccgaaactt | ctggctcgac | 1140 |
| gaagacgagg | gaggccaggt | cgcgctcgac | gtctacccgt | ggacggacta | ttacctgggt | 1200 |
| ccggggggatc | agtatgccat | gctgttcccc | tactttcatc | agatggggt | ttttgaagga | 1260 |
| cagatgaaga | cagtggggtc | gaataatgtt | tccgctgtgt | ccctgtcgcg | gtcctccgcc | 1320 |
| aactgggatt | ccatgaagat | gatgatatcc | gcaggacaga | gcatggccat | gtcagggcag | 1380 |
| ggttggtgga | ctttggacat | tggaggcttc | aagacagacg | ggcagtccaa | ctcggcgaat | 1440 |
| attagcgacc | cggagtacca | ggaattgttt | gtacggtggc | tgcagtgggg | aaccttctta | 1500 |
| ccgattatgc | gcaaccacgg | aatgagaacc | tgtctcccct | cagcacagga | aggcttcctg | 1560 |
| acctgtccta | gcgaacccctg | gagctacggc | cccgacaacc | tccccatcat | cgtgtcctac | 1620 |
| atcaacctcc | gatacaaact | gcagcccctac | atcaaggcgc | tcttccggat | gctctccgag | 1680 |
| agtggacggg | caatgatgcg | gccccctgttt | atggatttct | ctctcagcga | tccttacact | 1740 |
| ttggaggcga | cggaagatct | gaaattgcag | tacatgtttg | ggccgcgctt | gctcgtcagt | 1800 |
| cccgtcacaa | cgtatcgcgc | gacgaatgcg | accgtctacc | tgccaaaatt | gccgtcggat | 1860 |
| gctcccgata | cgaaatggac | gtactggtgg | acgaacgaga | gttttgacgg | tggtcaatgg | 1920 |
| gtcaccgttc | ctgcgaacaa | aagcataatt | ccgctcttcc | gactcggcag | cgaagcagac | 1980 |
| atcttgacga | ggaacatcta | a | | | 2001 |

<210> SEQ ID NO 56
<211> LENGTH: 840
<212> TYPE: DNA
<213> ORGANISM: Rasamsonia emersonii
<220> FEATURE:
<221> NAME/KEY: source
<222> LOCATION: (1)..(840)
<223> OTHER INFORMATION: /organism="Rasamsonia emersonii"
      /mol_type="unassigned DNA"

<400> SEQUENCE: 56

```
atgcagatgc tcctcttgtt gctcctcctc cttcctccca gcctttgcgc tatcatcaag      60
ggtatctccg ctcctctcct tgcccgtctg acccagatgg ccaccctctg catgagcacc     120
tacctgaacg acctttgcat tgttcccggt ggtatgacca agatctccga catcaccaac     180
tccaccactg atgtccacgg ctggatcctg cgtgatgatg gtgcccgtga gatcctggcg     240
gtgttccgtg gtaccgagtc cctccagaac tacgccaccg acaccaacta caccctggct     300
cccttcgaca tcttccccca gtgcgaaggc tgcgaggtcc acggtggata ctaccttgcc     360
tgggtgtcga ttgtcgagca ggtccaggct cgcctgcagg agcagaaggc cctcttcccc     420
gactacggtg ttgtcttgac tggccactcc ctcggtggct ccctggctgc tcttgctgct     480
gcccagttct ctcctctctt cgacaacatc accgtctaca ccatgggtga gcctcgcact     540
ggcaacgccg cctccgcctc cttcattgac cagcgttaca gcacttcttc tcccgagact     600
acccgcttct accgctgcac ccacgccgat gacggtatcc caacgctcc tcccacctcc     660
gacggctacg tccaccacgg tctggaatac tggaacctcg accccacttc tgctgagaac     720
acctacgtgt gcactgagga tggtgccgtc cagtgctgcg aagcgcagaa cggcagcggt     780
atcaacgctg cccacctggt ctacttcggc cgccccgttg ttgttggtgg ccagtgtctg     840
```

<210> SEQ ID NO 57
<211> LENGTH: 233
<212> TYPE: PRT
<213> ORGANISM: Rasamsonia emersonii

<400> SEQUENCE: 57

```
Ala Ile Ile Lys Gly Ile Ser Ala Pro Leu Leu Ala Arg Leu Thr Gln
1               5                   10                  15

Met Ala Thr Leu Cys Met Ser Thr Tyr Leu Asn Asp Leu Cys Ile Val
            20                  25                  30

Pro Gly Gly Met Thr Lys Ile Ser Asp Ile Thr Asn Ser Thr Thr Asp
        35                  40                  45

Val His Gly Trp Ile Leu Arg Asp Asp Gly Ala Arg Glu Ile Leu Ala
    50                  55                  60

Val Phe Arg Gly Thr Glu Ser Leu Gln Asn Tyr Ala Thr Asp Thr Asn
65                  70                  75                  80

Tyr Thr Leu Ala Pro Phe Asp Ile Phe Pro Gln Cys Glu Gly Cys Glu
                85                  90                  95

Val His Gly Gly Tyr Tyr Leu Ala Trp Val Ser Ile Val Glu Gln Val
            100                 105                 110

Gln Ala Arg Leu Gln Glu Gln Lys Ala Leu Phe Pro Asp Tyr Gly Val
        115                 120                 125

Val Leu Thr Gly His Ser Leu Gly Gly Ser Leu Ala Ala Leu Ala Ala
    130                 135                 140

Ala Gln Phe Ser Pro Leu Phe Asp Asn Ile Thr Val Tyr Thr Met Gly
145                 150                 155                 160
```

```
Glu Pro Arg Thr Gly Asn Ala Ala Phe Ala Ser Phe Ile Asp Gln Arg
                165                 170                 175

Tyr Ser Thr Ser Ser Pro Glu Thr Thr Arg Phe Tyr Arg Cys Thr His
            180                 185                 190

Ala Asp Asp Gly Ile Pro Asn Ala Pro Pro Thr Ser Asp Gly Tyr Val
        195                 200                 205

His His Gly Leu Glu Tyr Trp Asn Leu Asp Pro Thr Ser Ala Glu Asn
    210                 215                 220

Thr Phe Pro Met Asn Gly Gln Leu Ser
225                 230

<210> SEQ ID NO 58
<211> LENGTH: 20
<212> TYPE: PRT
<213> ORGANISM: Rasamsonia emersonii

<400> SEQUENCE: 58

Met Gln Met Leu Leu Leu Leu Leu Leu Leu Pro Pro Ser Leu Cys
1               5                   10                  15

Ala Ile Ile Lys
            20

<210> SEQ ID NO 59
<211> LENGTH: 1100
<212> TYPE: DNA
<213> ORGANISM: Rasamsonia emersonii
<220> FEATURE:
<221> NAME/KEY: source
<222> LOCATION: (1)..(1100)
<223> OTHER INFORMATION: /organism="Rasamsonia emersonii"
      /mol_type="unassigned DNA"

<400> SEQUENCE: 59
atgcaaacgc aaatgcaaat gctcctacta ctcctgctgc tactaccacc ctccctctgc      60
gccatcatca aaggcatctc cgccccccctc ctagcccgcc taacccagat ggccacgctc    120
tgcatgtcca cctacctcaa cgacctgtgc atcgtgcccg gggggatgac caagatcagc    180
gacatcacca acagcacaac cgacgtgcac ggctggatcc tgcgcgacga cggcgcgcgc    240
gagatcctcg ccgtgttccg cggcaccgag tcgctgcaga actacgcgac ggatacgaac    300
tacacgcttg cgccgttcga cattttcccg cagtgtgagg gctgtgaggt ccatggcggg    360
tactatctcg cctgggtatc gattgtcgag caggtgcagg ctcgtctgca ggagcagaag    420
gcgctgtttc cggattatgg ggttgttttg acggggcata ggtatgcata cccaccta     480 acctaggtat aaatatactg tctgtgtata gatactgact tgatatatag tcttggaggc    540
tccctcgccg cgctggccgc agcacagttc tctcccctct tcgacaacat caccgtgtac    600
acaatgggcg agcctcgcac cggcaacgcc gccttcgcgt ccttcatcga ccagcgctac    660
agcacgtcct cgcccgagac gacgcggttc taccggtgca cgcacgcgga cgacggcatc    720
cccaatgcgc cgccgacgtc ggacgggtat gtgcaccacg gctggagta  ctggaacttg   780 gacccgacga gtgcggagaa tacgtatgtc tgtacggagg acggggcggt gcagtgctgc    840
gaggcgcaga atgggtcggg tatcaatgct gctcatctgg tgtatttgg tcggccggtt     900 gtggtggggg ggcagtgtct ttaaatagta ttgagaaggg gaatcaacag gctggatggg   960
atcagatttg gatattcacg aggactaaca ttagctgatg ggtgtacata caggacattt   1020
atataaatga ccgcagatcg aaatcaatca actaataact acagacgtgt aggtttccta   1080
tgaacggtca actatcttag                                                1100
```

<210> SEQ ID NO 60
<211> LENGTH: 843
<212> TYPE: DNA
<213> ORGANISM: Rasamsonia emersonii
<220> FEATURE:
<221> NAME/KEY: source
<222> LOCATION: (1)..(843)
<223> OTHER INFORMATION: /organism="Rasamsonia emersonii"
     /mol_type="unassigned DNA"

<400> SEQUENCE: 60

| | | | | | | |
|---|---|---|---|---|---|---|
| atgcaaatgc | tcctactact | cctgctgcta | ctaccaccct | ccctctgcgc | catcatcaaa | 60 |
| ggcatctccg | ccccctcct | agcccgccta | acccagatgg | ccacgctctg | catgtccacc | 120 |
| tacctcaacg | acctgtgcat | cgtgcccggg | gggatgacca | agatcagcga | catcaccaac | 180 |
| agcacaaccg | acgtgcacgg | ctggatcctg | cgcgacgacg | gcgcgcgcga | gatcctcgcc | 240 |
| gtgttccgcg | gcaccgagtc | gctgcagaac | tacgcgacgg | atacgaacta | cacgcttgcg | 300 |
| ccgttcgaca | ttttcccgca | gtgtgagggc | tgtgaggtcc | atggcgggta | ctatctcgcc | 360 |
| tgggtatcga | ttgtcgagca | ggtgcaggct | cgtctgcagg | agcagaaggc | gctgtttccg | 420 |
| gattatgggg | ttgttttgac | ggggcatagt | cttggaggct | ccctcgccgc | gctggccgca | 480 |
| gcacagttct | ctcccctctt | cgacaacatc | accgtgtaca | aatgggcga | gcctcgcacc | 540 |
| ggcaacgccg | ccttcgcgtc | cttcatcgac | cagcgctaca | gcacgtcctc | gcccgagacg | 600 |
| acgcggttct | accggtgcac | gcacgcggac | gacggcatcc | ccaatgcgcc | gccgacgtcg | 660 |
| gacgggtatg | tgcaccacgg | gctggagtac | tggaacttgg | acccgacgag | tgcggagaat | 720 |
| acgtatgtct | gtacggagga | cggggcggtg | cagtgctgcg | aggcgcagaa | tgggtcgggt | 780 |
| atcaatgctg | ctcatctggt | gtattttggt | cggccggttg | tggtgggggg | gcagtgtctt | 840 |
| taa | | | | | | 843 |

<210> SEQ ID NO 61
<211> LENGTH: 1374
<212> TYPE: DNA
<213> ORGANISM: Rasamsonia emersonii
<220> FEATURE:
<221> NAME/KEY: source
<222> LOCATION: (1)..(1374)
<223> OTHER INFORMATION: /organism="Rasamsonia emersonii"
     /mol_type="unassigned DNA"

<400> SEQUENCE: 61

| | | | | | | |
|---|---|---|---|---|---|---|
| atgaagtcgc | tggtctacgc | tctttgcttc | gcctccgccg | ttgctgcctc | caacagcact | 60 |
| ggtactgcca | ctgttgacct | caacgtcaag | cgtggacctc | cctcccacct | tgcctccgga | 120 |
| ttcatctacg | gcattcctga | cacccccaac | caggttcctg | ctcactggta | caccgacatg | 180 |
| ggtttccgct | acggccgtgc | tggtggtgct | cagcttggtg | ctcctgctcg | tggctggatt | 240 |
| tggggtattg | atgaatacca | gggccgtctg | aactcgaccc | tcagcaacta | ccgcacctgc | 300 |
| cgtcagtacg | gtgccgactt | catcatcctc | ccccacgaca | tctgggtac | cgaccacgcc | 360 |
| aacgacagca | ccatctggcc | tggtgacaac | ggtgactgga | ctgactacga | caacttcatc | 420 |
| cgccgtctga | tggccgatct | caaggccaac | aacgccttgg | atggcctggt | ctgggatgtc | 480 |
| tggaacgagc | ctgacatctc | catcttctgg | actcgctctc | agcagcagtg | gattgatctc | 540 |
| tacatccgca | cccacaagct | cctccgccag | gatcctgact | cgaccgcgt | gcagatctct | 600 |
| ggccccaccc | tagcgttccg | tcccttcccc | aacaacacct | ggtggaccaa | ctggttggat | 660 |

```
cagattgctg gcaaccagac cattcccgat cagtacgcct accacctcga gggtgacccc    720 agcagcccg  atgatgacct gcagaacacc aacgcctccc tggctgccat gctgcagacc    780
taccgcctcc cctctcgcca gatcaacatc aacgagtacg ccaccttcgc tgagcagatc    840
cccgccggtg ctgcctggtg gatctcccgt cttgagcgct acgaggccta cggcctgcgt    900
ggcaactggc agtccggcac catgctccac gacctcttcg ccaacctcct caccaagaag    960 tccgaccct  ccaactacac tgccaccgac tacgtgtctg ctcctgaata ccccgtctac   1020
cgctactact accgcaacat gactggccag cgtgtgcaga ccactggatc cgaggaccgt   1080
ctgttggatg tctacgctac tgttgacaag gacaaggtcc gtatcctggc tggtgtccgt   1140
ctggccactg gtacctggca ggtcaccgtc aacagccttt ctgctgttgg attgccctcc   1200
gctggtaccc tcaacatcca gacctggggt ttcgatggtg actccgtctg gaagaggtt    1260 gaccgccccg aggatcttgg tgtcactgct cacacctact ctggcgactc cgtcaccttc   1320
cccatctacc agaccgacaa ccacaccgcc tgggcgttcg agttcgatgt agct          1374
```

<210> SEQ ID NO 62
<211> LENGTH: 442
<212> TYPE: PRT
<213> ORGANISM: Rasamsonia emersonii

<400> SEQUENCE: 62

```
Ser Asn Ser Thr Gly Thr Ala Thr Val Asp Leu Asn Val Lys Arg Gly
1               5                   10                  15

Pro Pro Ser His Leu Ala Ser Gly Phe Ile Tyr Gly Ile Pro Asp Thr
            20                  25                  30

Pro Asn Gln Val Pro Ala His Trp Tyr Thr Asp Met Gly Phe Arg Tyr
        35                  40                  45

Gly Arg Ala Gly Gly Ala Gln Leu Gly Ala Pro Ala Arg Gly Trp Ile
    50                  55                  60

Trp Gly Ile Asp Glu Tyr Gln Gly Arg Leu Asn Ser Thr Leu Ser Asn
65                  70                  75                  80

Tyr Arg Thr Cys Arg Gln Tyr Gly Ala Asp Phe Ile Ile Leu Pro His
                85                  90                  95

Asp Ile Trp Gly Thr Asp His Ala Asn Asp Ser Thr Ile Trp Pro Gly
            100                 105                 110

Asp Asn Gly Asp Trp Thr Asp Tyr Asp Asn Phe Ile Arg Arg Leu Met
        115                 120                 125

Ala Asp Leu Lys Ala Asn Asn Ala Leu Asp Gly Leu Val Trp Asp Val
    130                 135                 140

Trp Asn Glu Pro Asp Ile Ser Ile Phe Trp Thr Arg Ser Gln Gln Gln
145                 150                 155                 160

Trp Ile Asp Leu Tyr Ile Arg Thr His Lys Leu Leu Arg Gln Asp Pro
                165                 170                 175

Asp Phe Asp Arg Val Gln Ile Ser Gly Pro Thr Leu Ala Phe Arg Pro
            180                 185                 190

Phe Pro Asn Asn Thr Trp Trp Thr Asn Trp Leu Asp Gln Ile Ala Gly
        195                 200                 205

Asn Gln Thr Ile Pro Asp Gln Tyr Ala Tyr His Leu Glu Gly Asp Pro
    210                 215                 220

Ser Ser Pro Asp Asp Asp Leu Gln Asn Thr Asn Ala Ser Leu Ala Ala
225                 230                 235                 240

Met Leu Gln Thr Tyr Arg Leu Pro Ser Arg Gln Ile Asn Ile Asn Glu
                245                 250                 255
```

Tyr Ala Thr Phe Ala Glu Gln Ile Pro Ala Gly Ala Ala Trp Trp Ile
            260                 265                 270

Ser Arg Leu Glu Arg Tyr Glu Ala Tyr Gly Leu Arg Gly Asn Trp Gln
        275                 280                 285

Ser Gly Thr Met Leu His Asp Leu Phe Ala Asn Leu Leu Thr Lys Lys
    290                 295                 300

Ser Asp Pro Ser Asn Tyr Thr Ala Thr Asp Tyr Val Ser Ala Pro Glu
305                 310                 315                 320

Tyr Pro Val Tyr Arg Tyr Tyr Arg Asn Met Thr Gly Gln Arg Val
                325                 330                 335

Gln Thr Thr Gly Ser Glu Asp Arg Leu Leu Asp Val Tyr Ala Thr Val
                340                 345                 350

Asp Lys Asp Lys Val Arg Ile Leu Ala Gly Val Arg Leu Ala Thr Gly
                355                 360                 365

Thr Trp Gln Val Thr Val Asn Ser Leu Ser Ala Val Gly Leu Pro Ser
        370                 375                 380

Ala Gly Thr Leu Asn Ile Gln Thr Trp Gly Phe Asp Gly Asp Ser Val
385                 390                 395                 400

Trp Glu Glu Val Asp Arg Pro Glu Asp Leu Gly Val Thr Ala His Thr
                405                 410                 415

Tyr Ser Gly Asp Ser Val Thr Phe Pro Ile Tyr Gln Thr Asp Asn His
            420                 425                 430

Thr Ala Trp Ala Phe Glu Phe Asp Val Ala
        435                 440

<210> SEQ ID NO 63
<211> LENGTH: 16
<212> TYPE: PRT
<213> ORGANISM: Rasamsonia emersonii

<400> SEQUENCE: 63

Met Lys Ser Leu Val Tyr Ala Leu Cys Phe Ala Ser Ala Val Ala Ala
1               5                   10                  15

<210> SEQ ID NO 64
<211> LENGTH: 1377
<212> TYPE: DNA
<213> ORGANISM: Rasamsonia emersonii
<220> FEATURE:
<221> NAME/KEY: source
<222> LOCATION: (1)..(1377)
<223> OTHER INFORMATION: /organism="Rasamsonia emersonii"
      /mol_type="unassigned DNA"

<400> SEQUENCE: 64
atgaaaagtc tggtctatgc cctgtgcttc gccagcgctg ttgctgctag caacagcaca      60
ggcacggcga cagtcgacct caatgtcaag cgtggcccgc cctctcacct cgcttcaggc    120
ttcatctacg gcatcccga taccccaac caggtcccg cccactggta caccgacatg       180
ggcttccgat acggccgcgc aggcggtgcg cagctagggg ccccgcgcg aggctggatc     240 tggggcatcg acgagtacca gggccgtctc aactcgaccc tgtcgaatta ccgcacctgt    300
cgtcagtacg cgccgactt tatcatcttg ccgcacgaca tctggggcac cgaccacgcc     360
aacgactcaa caatctggcc cggcgacaac ggcgactgga ccgactacga caacttcatc    420
cgccgactga tggccgacct gaaggcgaac aacccctggg acggcctcgt ctgggatgtt    480
tggaacgagc ccgacatctc catcttctgg acgcgcagcc agcagcagtg gatcgatctg    540

| | |
|---|---|
| tacatccgca cgcacaagct tctccggcag gaccccgact ttgaccgtgt tcagatctca | 600 |
| ggtcccaccc tggccttccg tcccttcccc aacaatacct ggtggacgaa ctggctggac | 660 |
| cagattgcag gtaaccagac tatcccggac cagtacgcct atcatctgga gggcgatcca | 720 |
| tcctcgccgg atgatgacct ccagaacacc aacgcgtccc tggcggcgat gctgcagacg | 780 |
| taccggcttc cgtcgcggca gatcaacatc aacgagtacg cgacattcgc agagcagatt | 840 |
| cccgcaggcg cggcatggtg gatctcccgg ctcgagcgct atgaggcgta cgggctgcgc | 900 |
| gggaactggc agagcggaac catgctgcat gatcttttg ctaatctcct gaccaagaag | 960 |
| tcggacccct ccaactacac ggcgacagac tacgtatcgg cgccggagta cccggtgtac | 1020 |
| aggtactact accggaacat gacaggccag cgggtgcaga cgacgggctc cgaggatcgc | 1080 |
| ctgctggacg tgtatgccac tgtcgacaag gacaaggtgc gtatcttggc gggtgtgcgc | 1140 |
| ctggccactg gcacctggca agtcacggtc aattcactca gcgccgtggg cctacccagt | 1200 |
| gcggggacgt tgaacatcca gacctgggt tttgatggag actcggtgtg ggaggaggtc | 1260 |
| gaccgtccag aggatcttgg tgttaccgcg catacctaca gcggggattc ggtgacgttt | 1320 |
| ccaatctacc agacggacaa tcatacggcg tgggcatttg aattcgacgt tgcttga | 1377 |

<210> SEQ ID NO 65
<211> LENGTH: 1377
<212> TYPE: DNA
<213> ORGANISM: Rasamsonia emersonii
<220> FEATURE:
<221> NAME/KEY: source
<222> LOCATION: (1)..(1377)
<223> OTHER INFORMATION: /organism="Rasamsonia emersonii"
    /mol_type="unassigned DNA"

<400> SEQUENCE: 65

| | |
|---|---|
| atgaaaagtc tggtctatgc cctgtgcttc gccagcgctg ttgctgctag caacagcaca | 60 |
| ggcacggcga cagtcgacct caatgtcaag cgtggcccgc cctctcacct cgcttcaggc | 120 |
| ttcatctacg gcatccccga tacccccaac caggtccccg cccactggta caccgacatg | 180 |
| ggcttccgat acggccgcgc aggcggtgcg cagctagggg cccccgcgcg aggctggatc | 240 |
| tggggcatcg acgagtacca gggccgtctc aactcgaccc tgtcgaatta ccgcacctgt | 300 |
| cgtcagtacg gcgccgactt tatcatcttg ccgcacgaca tctggggcac cgaccacgcc | 360 |
| aacgactcaa caatctggcc cggcgacaac ggcgactgga ccgactacga caacttcatc | 420 |
| cgccgactga tggccgacct gaaggcgaac aacgccctgg acggcctcgt ctgggatgtt | 480 |
| tggaacgagc ccgacatctc catcttctgg acgcgcagcc agcagcagtg gatcgatctg | 540 |
| tacatccgca cgcacaagct tctccggcag gaccccgact ttgaccgtgt tcagatctca | 600 |
| ggtcccaccc tggccttccg tcccttcccc aacaatacct ggtggacgaa ctggctggac | 660 |
| cagattgcag gtaaccagac tatcccggac cagtacgcct atcatctgga gggcgatcca | 720 |
| tcctcgccgg atgatgacct ccagaacacc aacgcgtccc tggcggcgat gctgcagacg | 780 |
| taccggcttc cgtcgcggca gatcaacatc aacgagtacg cgacattcgc agagcagatt | 840 |
| cccgcaggcg cggcatggtg gatctcccgg ctcgagcgct atgaggcgta cgggctgcgc | 900 |
| gggaactggc agagcggaac catgctgcat gatcttttg ctaatctcct gaccaagaag | 960 |
| tcggacccct ccaactacac ggcgacagac tacgtatcgg cgccggagta cccggtgtac | 1020 |
| aggtactact accggaacat gacaggccag cgggtgcaga cgacgggctc cgaggatcgc | 1080 |
| ctgctggacg tgtatgccac tgtcgacaag gacaaggtgc gtatcttggc gggtgtgcgc | 1140 |

| | |
|---|---|
| ctggccactg gcacctggca agtcacggtc aattcactca gcgccgtggg cctacccagt | 1200 |
| gcggggacgt tgaacatcca gacctggggt tttgatggag actcggtgtg ggaggaggtc | 1260 |
| gaccgtccag aggatcttgg tgttaccgcg catacctaca gcggggattc ggtgacgttt | 1320 |
| ccaatctacc agacggacaa tcatacggcg tgggcatttg aattcgacgt tgcttga | 1377 |

<210> SEQ ID NO 66
<211> LENGTH: 1425
<212> TYPE: DNA
<213> ORGANISM: Rasamsonia emersonii
<220> FEATURE:
<221> NAME/KEY: source
<222> LOCATION: (1)..(1425)
<223> OTHER INFORMATION: /organism="Rasamsonia emersonii"
    /mol_type="unassigned DNA"

<400> SEQUENCE: 66

| | |
|---|---|
| atgatctccc tgctggccct tgctgctgtt cccatccccg tcctctctgc tccctcccgc | 60 |
| ccccacgctc acatctccgt caacacccag actcgcttcc agcaggttga cggcttcggt | 120 |
| ttcagcgaag cgttccagcg tgctgaggat atctacggca aggacggtct ttctcctgag | 180 |
| aaccgtaccc gtgtcctcga cctcctcttc tccgacaccc acggtgctgg tctgaccatt | 240 |
| gtccgcaacg gcattggcag cagcaacagc agcatcaagg acttcatgaa ctccattgag | 300 |
| cccttctccc ccggctcccc ctctgctcct cctcactacg tgtgggaccg caacgactct | 360 |
| ggccaggtct ggctatccca cgaagccgcc tcctacggtg tcaacacctt ctacgccgat | 420 |
| gcctggtccg ctcctggata catgaaaacc aacgatgatg actccaacgg tggataccctc | 480 |
| tgcggtgtca ccaacacttc ttgcgcttcc ggtgactgga gcaggccta cgccaactac | 540 |
| cttgttcagt acgtgcgctt ctaccagcag gtcggtatca aggtcaccca cctcggattc | 600 |
| ctgaacgagc cccaggaaga tgtcacctac gcctccatgc tctccgacgg cacccaggct | 660 |
| gccgacttca tcaaggtcct tgcccccacc gtcaaggccg ccggtctgga tgtcaagctc | 720 |
| acctgctgcg atggtgttgg ctgggaggag cagcgtgcca tgcttcctgg tctgcaggct | 780 |
| ggtggtcccg agcactccgc tgagagctac ctgtccgtca tcactgctca cggatacaac | 840 |
| agccctccca ccactcctct cgagacttct ctgcccgtgt ggatgactga atgggcggat | 900 |
| ctcaacggca actacactgc tgcctggtac gagaacggcg ctgctggtga aggcttgacc | 960 |
| tgggccaacc gtatccagga tgccttcacc cgctccaacg tgtctgcttt cctgcactgg | 1020 |
| attggtgctg agaacggcac cagcaactcg cctctgatca acctcaacgg tgacagctac | 1080 |
| gtggccacca agcgtctgtg ggcgttcggc cagttctccc gcttcgtccg tcccggtgcc | 1140 |
| gtccgtatcg atgccgtttc ctccgactct ttagtgaccg tttccgcttt ccagaacaag | 1200 |
| gacaacggtt tgttgccac tcaggccatc aacaacgccg acaccgacta cgaggttgag | 1260 |
| gttgagttga ctggctacgg tcctgtctcc gtcatccagc cctacctcac caacaacgag | 1320 |
| aacgacctcg aggcctccaa gcccatcatt gctctcgccg tcggtgctgc caccaagttc | 1380 |
| acctccatcg tccccgcccg ctctcttgtc tccttcgtat ctaag | 1425 |

<210> SEQ ID NO 67
<211> LENGTH: 459
<212> TYPE: PRT
<213> ORGANISM: Rasamsonia emersonii

<400> SEQUENCE: 67

Ala Pro Ser Arg Pro His Ala His Ile Ser Val Asn Thr Gln Thr Arg
1               5                   10                  15

```
Phe Gln Gln Val Asp Gly Phe Gly Phe Ser Glu Ala Phe Gln Arg Ala
                20                  25                  30

Glu Asp Ile Tyr Gly Lys Asp Gly Leu Ser Pro Glu Asn Arg Thr Arg
            35                  40                  45

Val Leu Asp Leu Leu Phe Ser Asp Thr His Gly Ala Gly Leu Thr Ile
 50                      55                  60

Val Arg Asn Gly Ile Gly Ser Ser Asn Ser Ile Lys Asp Phe Met
 65              70                  75                      80

Asn Ser Ile Glu Pro Phe Ser Pro Gly Ser Pro Ser Ala Pro Pro His
                85                  90                  95

Tyr Val Trp Asp Arg Asn Asp Ser Gly Gln Val Trp Leu Ser His Glu
            100                 105                 110

Ala Ala Ser Tyr Gly Val Asn Thr Phe Tyr Ala Asp Ala Trp Ser Ala
            115                 120                 125

Pro Gly Tyr Met Lys Thr Asn Asp Asp Ser Asn Gly Gly Tyr Leu
130                 135                 140

Cys Gly Val Thr Asn Thr Ser Cys Ala Ser Gly Asp Trp Lys Gln Ala
145                 150                 155                 160

Tyr Ala Asn Tyr Leu Val Gln Tyr Val Arg Phe Tyr Gln Gln Val Gly
                165                 170                 175

Ile Lys Val Thr His Leu Gly Phe Leu Asn Glu Pro Gln Glu Asp Val
            180                 185                 190

Thr Tyr Ala Ser Met Leu Ser Asp Gly Thr Gln Ala Ala Asp Phe Ile
            195                 200                 205

Lys Val Leu Ala Pro Thr Val Lys Ala Ala Gly Leu Asp Val Lys Leu
            210                 215                 220

Thr Cys Cys Asp Gly Val Gly Trp Glu Gln Arg Ala Met Leu Pro
225                 230                 235                 240

Gly Leu Gln Ala Gly Gly Pro Glu His Ser Ala Glu Ser Tyr Leu Ser
                245                 250                 255

Val Ile Thr Ala His Gly Tyr Asn Ser Pro Pro Thr Thr Pro Leu Glu
            260                 265                 270

Thr Ser Leu Pro Val Trp Met Thr Glu Trp Ala Asp Leu Asn Gly Asn
            275                 280                 285

Tyr Thr Ala Ala Trp Tyr Glu Asn Gly Ala Ala Gly Glu Gly Leu Thr
290                 295                 300

Trp Ala Asn Arg Ile Gln Asp Ala Phe Thr Arg Ser Asn Val Ser Ala
305                 310                 315                 320

Phe Leu His Trp Ile Gly Ala Glu Asn Gly Thr Ser Asn Ser Pro Leu
                325                 330                 335

Ile Asn Leu Asn Gly Asp Ser Tyr Val Ala Thr Lys Arg Leu Trp Ala
            340                 345                 350

Phe Gly Gln Phe Ser Arg Phe Val Arg Pro Gly Ala Val Arg Ile Asp
            355                 360                 365

Ala Val Ser Ser Asp Ser Leu Val Thr Val Ser Ala Phe Gln Asn Lys
            370                 375                 380

Asp Asn Gly Val Val Ala Thr Gln Ala Ile Asn Asn Ala Asp Thr Asp
385                 390                 395                 400

Tyr Glu Val Glu Val Glu Leu Thr Gly Tyr Gly Pro Val Ser Val Ile
                405                 410                 415

Gln Pro Tyr Leu Thr Asn Asn Glu Asn Asp Leu Glu Ala Ser Lys Pro
            420                 425                 430
```

```
Ile Ile Ala Leu Ala Val Gly Ala Ala Thr Lys Phe Thr Ser Ile Val
        435                 440                 445

Pro Ala Arg Ser Leu Val Ser Phe Val Ser Lys
    450                 455
```

<210> SEQ ID NO 68
<211> LENGTH: 16
<212> TYPE: PRT
<213> ORGANISM: Rasamsonia emersonii

<400> SEQUENCE: 68

```
Met Ile Ser Leu Leu Ala Leu Ala Ala Val Pro Ile Pro Val Leu Ser
1               5                   10                  15
```

<210> SEQ ID NO 69
<211> LENGTH: 1428
<212> TYPE: DNA
<213> ORGANISM: Rasamsonia emersonii
<220> FEATURE:
<221> NAME/KEY: source
<222> LOCATION: (1)..(1428)
<223> OTHER INFORMATION: /organism="Rasamsonia emersonii"
     /mol_type="unassigned DNA"

<400> SEQUENCE: 69

| | |
|---|---|
| atgatctctc tcctcgcgtt ggccgctgtg ccaattcctg tcctgtccgc cccgtctaga | 60 |
| cctcacgccc acatctccgt caatacacaa acccgcttcc agcaggtcga cggattcggc | 120 |
| ttctccgagg ccttccagcg cgcagaggac atctacggca aggatggctt gtcgcccgag | 180 |
| aaccgcacca gagtgctcga tctcctgttc agcgacaccc atggcgccgg cctgaccatc | 240 |
| gtccgcaatg gcatcggctc cagcaatagc tccatcaagg acttcatgaa ctccatcgag | 300 |
| cccttcagtc ccggctcgcc gtctgcgccg ccgcactacg tctgggaccg caacgacagc | 360 |
| ggccaggtgt ggctgtccca cgaagcggcc tcgtatggcg tcaacacgtt ctatgccgac | 420 |
| gcctggtctg ctcccggtta catgaagacc aacgacgacg actccaacgg cgggtacctg | 480 |
| tgcggcgtga ccaacacgtc ctgcgcctcc ggggactgga agcaggccta cgccaactac | 540 |
| ctcgtccagt acgtccggtt ctaccaacag gtcggcatca aggtcaccca cctgggtttc | 600 |
| ctgaacgagc cccaggaaga cgtcacctat gccagcatgc tgtcggacgg cacccaggcg | 660 |
| gccgacttca tcaaagttct agcacccacc gtcaaggcgg caggactcga cgtcaagctc | 720 |
| acctgctgcg acggcgtcgg gtgggaggag cagcgagcga tgctgccggg cctccaggct | 780 |
| ggaggtcccg agcacagcgc ggaaagctat ctgtctgtga tcaccgccca tggctacaac | 840 |
| tccccgccca caacgcctct tgagacctcg ttgccagtgt ggatgaccga gtgggccgat | 900 |
| ctgaatggga actatacggc cgcctggtac gagaacggcg ccgccggcga gggtctgacc | 960 |
| tgggcgaacc gcatccaaga cgccttcacg cggagcaacg tcagcgcctt tctgcactgg | 1020 |
| atcggagcgg agaatggcac gagcaacagc cctctcatca acctgaacgg cgattcgtat | 1080 |
| gtcgcgacca gcggctgtg gcgttcggc cagttcagtc gattcgtccg gccgggtgcc | 1140 |
| gtccgcatcg acgcggtcag ttcggactcc ttggtcacgg tgagcgcgtt ccagaacaag | 1200 |
| gataacggcg tggtggccac gcaggccatc aacaatgccg acacagacta tgaggtcgag | 1260 |
| gtggagttga cgggttatgg acccgtgtcc gttatccagc cgtatctgac gaacaatgaa | 1320 |
| aacgacctgg aagcctccaa gccgatcatc gcgcttgctg ttggggcagc aaccaagttc | 1380 |
| acgagtatcg ttccggcgag gtccttggtt agtttcgtaa gtaaatag | 1428 |

-continued

```
<210> SEQ ID NO 70
<211> LENGTH: 1428
<212> TYPE: DNA
<213> ORGANISM: Rasamsonia emersonii
<220> FEATURE:
<221> NAME/KEY: source
<222> LOCATION: (1)..(1428)
<223> OTHER INFORMATION: /organism="Rasamsonia emersonii"
      /mol_type="unassigned DNA"

<400> SEQUENCE: 70
atgatctctc tcctcgcgtt ggccgctgtg ccaattcctg tcctgtccgc cccgtctaga      60
cctcacgccc acatctccgt caatacacaa acccgcttcc agcaggtcga cggattcggc     120
ttctccgagg ccttccagcg cgcagaggac atctacggca aggatggctt gtcgcccgag     180
aaccgcacca gagtgctcga tctcctgttc agcgacaccc atggcgccgg cctgaccatc     240
gtccgcaatg gcatcggctc cagcaatagc tccatcaagg acttcatgaa ctccatcgag     300
cccttcagtc ccggctcgcc gtctgcgccg ccgcactacg tctgggaccg caacgacagc     360
ggccaggtgt ggctgtccca cgaagcggcc tcgtatggcg tcaacacgtt ctatgccgac     420
gcctggtctg ctcccggtta catgaagacc aacgacgacg actccaacgg cgggtacctg     480
tgcggcgtga ccaacacgtc ctgcgcctcc ggggactgga gcaggccta cgccaactac     540 ctcgtccagt acgtccggtt ctaccaacag gtcggcatca aggtcaccca cctgggtttc     600
ctgaacgagc cccaggaaga cgtcacctat gccagcatgc tgtcggacgg cacccaggcg     660
gccgacttca tcaaagttct agcacccacc gtcaaggcgg caggactcga cgtcaagctc     720
acctgctgcg acgcgtcgg gtgggaggag cagcgagcga tgctgccggg cctccaggct     780
ggaggtcccg agcacagcgc ggaaagctat ctgtctgtga tcaccgccca tggctacaac     840
tccccgccca caacgcctct tgagacctcg ttgccagtgt ggatgaccga gtgggccgat     900
ctgaatggga actatacggc cgcctggtac gagaacggcg ccgccggcga gggtctgacc     960
tgggcgaacc gcatccaaga cgccttcacg cggagcaacg tcagcgcctt tctgcactgg    1020
atcggagcgg agaatggcac gagcaacagc cctctcatca acctgaacgg cgattcgtat    1080
gtcgcgacca gcggctgtg gcgttcggc cagttcagtc gattcgtccg gccgggtgcc    1140
gtccgcatcg acgcggtcag ttcggactcc ttggtcacgg tgagcgcgtt ccagaacaag    1200
gataacggcg tggtggccac gcaggccatc aacaatgccg acacagacta tgaggtcgag    1260
gtggagttga cgggttatgg acccgtgtcc gttatccagc cgtatctgac gaacaatgaa    1320
aacgacctgg aagcctccaa gccgatcatc gcgcttgctg ttggggcagc aaccaagttc    1380
acgagtatcg ttccggcgag gtccttggtt agtttcgtaa gtaaatag                 1428

<210> SEQ ID NO 71
<211> LENGTH: 3036
<212> TYPE: DNA
<213> ORGANISM: Rasamsonia emersonii
<220> FEATURE:
<221> NAME/KEY: source
<222> LOCATION: (1)..(3036)
<223> OTHER INFORMATION: /organism="Rasamsonia emersonii"
      /mol_type="unassigned DNA"

<400> SEQUENCE: 71
atgatcctga gctctctcct cgtcggctgc gtatctctct ggggtgctgc ccacgccctt      60
ggccagcagc ccgttgttgc cttcacctcc tcccccggat acctcaagct ggctggcccc     120
ggtactcctc ccggtaccgt tgtcctcgac tctgccgact ggcccgctgt cctgcgtgct     180
```

```
gccggtgatc ttgctgtcga cttcggtcgt gtcaccggca ccaacctgac caagactgtc    240
atcaacggta ccaccaccag ctccggtctt gctgctgttt ccaacaaggg ccccgtcatc    300
attgctggta ccattggtaa cagcagcttg atcaacgccc ttgcccagtc cggcaagatc    360
gatgtctccg ccactgaggg ccgctgggag gctttccaga ccgagattgt ggacaacccc    420
ttcccaggga tatctcgtgc tctggtcgtt tccggctccg accgtcgtgg aactgtctac    480
ggcttgtacg acatctccga gcagatcggt gtctccccct ggtactggtt cgccgatgtt    540
cctcctgctc agcacgagga gatctacgcc ctggacacca agaagatcca gggttccccc    600
tccgtcaagt accgtggtct gttcatcaac gacgaggctc ccgccctcac caactggatc    660
aacgtcaact accctccttg caagtacggt cctggcttca cgccgactt ctacgcccac     720
gttttcgagc tcttgctgcg cctccgtgcc aactacctct ggcctgctga atggagcaac    780
atcttcgccc ttgacgaccc ccgcaacttc cctactgccg atctctacgg cattgtcatt    840
ggcacctccc acaccgagcc cttgatgcgc tggaccctgg aacaatcgct actactccag    900
ggcccttgga actggctgac caacgagaag aacatctacc agttcctcaa ggaaggtgtt    960
gagcgctcca agaactacga agtcatctac accatgggta tgcgtggtct tggtgacact    1020
gcctccccca ccatcaacgc caccactctg gctcagatcg tcgctgctga ggagcagatc    1080
ctctccgagg tgttcaacac caccaacatc tcctggatcc ccagatgtg gtgcctctac     1140
aaggaagtcg gtggttacta cgaggatggt ctgcgtgttg ccgatgacat cactctcctc    1200
tgggctgatg acaactgggg taacattgag agacttccca tcggtaacga gactgctcgc    1260
tccggtggtg ctggtgtcta ctaccacttc gactacgtcg gtgaccccca ggactacaag    1320
tggatcaaca ccatctccct ccagaaaacc tgggagcaga tgcacctggc ctacgagcgt    1380
caggctcgca catctggat tgtcaacgtt ggtgacctga aggcccttga gatccccacc    1440
aaccacttct tcgaccttgc ctacgacacc cccagctggt cagatcccga cagcacctcc    1500
cgctggctca gctctgggc tactcgtgag ttcggtgctg ctggtgccga caaggtcgcc    1560
gatatcgtca ccgctacgg ccagtacgct gcccgtcgca gttcgagat gatcaccccc     1620
tccacctcct ccatcatcaa ctacaacgag gccaacaacg tcgtgtctca gtgggaatct    1680
ctggtcaacg acgcccgtga tgtctaccgt ggcctgtccg aggctgctcg tcccgccttc    1740
ttcgagctgg tcctccagcc ctgcatggct ggtcacatca tcacccagat ccacgtcact    1800
gctgccaaga caacctgta cgcctcccag cgccgcactt ccgccaaggc catggccgat    1860
aaggccctga gcttttcaa ggaagatcac gacctcaccg tgagctacca caagattctt     1920
gacggcaagt ggaaccacat catggaccag acccacctgg gctacctcta ctggcagcag    1980
cccatgcgca cacccctccc tcccctccag tacacccagc tgttggaaga ttcgctagcg    2040
ggacctatgg gtgtttccgt tgagggcagc aacgcctccg ttcccggtga tgaccagtac    2100
cacgctctct ccagcaccac cttgactctt cctcccattg cccctacgg cccttctact     2160
cgttggattg agatctactc tcgctcgacc gagtccttcg agttccagat atctcccaat    2220
gtcagctggg tgaccgccac tcccagctct ggcactgtcc acgtttctgg caacggcacc    2280
accaccgatg ttcgcgttca gctctccgtt gactgggaca aggctcccat tggaagctct    2340
ctcgtcagca tcaacgtttc catccccact ggccacttcc ccaccggtga ttacggtaac    2400
tccgccatgc ccgtcgtcca gctccccgtc aacaagactg ttgttcctgc ttcttccac     2460
ggtttcgtgg aatcggatgg tgtcgttct atcgaagctc ctcacgccac ccgcaacacc     2520
agcactgcca acgtcagcta cgccgtcatc cccggctacg gccgcaccct gtccggtgtc    2580
```

```
accctcctgc ctgtcaacgc cccctcccag aaggctcctt cttcccctcg tctggagtac    2640
gacatgtacc tcttctctcc cgccgccaac ggatcgaccg tcaacatcac cctctacctc    2700
ggtccctccc tgaacgtcaa ccccgaccgc cctctccgtt acgctcttgc tttcgatgac    2760
gatgacaacc cccaggttgt ccagtacgtg cccagcaccg tcctcggcac ctacccacct    2820
gactggccct ctgctgtctc caacaatgtg tgggcctcca ccacctccta caccatcaag    2880
ggtttcaacg gcaactccac ttctgccact ggcaccggtt ccgctcacac tctcaagctg    2940
tgggctctgg agcccggtgt tgttttcgag aagatcgtca ttgaccttgg tggtcagcgt    3000
gacagctacc ttggtcctcc tgagtccagg atagta                              3036
```

<210> SEQ ID NO 72
<211> LENGTH: 991
<212> TYPE: PRT
<213> ORGANISM: Rasamsonia emersonii

<400> SEQUENCE: 72

```
Gln Gln Pro Val Val Ala Phe Thr Ser Ser Pro Gly Tyr Leu Lys Leu
1               5                   10                  15

Ala Gly Pro Gly Thr Pro Pro Gly Thr Val Val Leu Asp Ser Ala Asp
            20                  25                  30

Trp Pro Ala Val Leu Arg Ala Ala Gly Asp Leu Ala Val Asp Phe Gly
        35                  40                  45

Arg Val Thr Gly Thr Asn Leu Thr Lys Thr Val Ile Asn Gly Thr Thr
    50                  55                  60

Thr Ser Ser Gly Leu Ala Ala Val Ser Asn Lys Gly Pro Val Ile Ile
65                  70                  75                  80

Ala Gly Thr Ile Gly Asn Ser Ser Leu Ile Asn Ala Leu Ala Gln Ser
                85                  90                  95

Gly Lys Ile Asp Val Ser Ala Thr Glu Gly Arg Trp Glu Ala Phe Gln
            100                 105                 110

Thr Glu Ile Val Asp Asn Pro Phe Pro Gly Ile Ser Arg Ala Leu Val
        115                 120                 125

Val Ser Gly Ser Asp Arg Arg Gly Thr Val Tyr Gly Leu Tyr Asp Ile
    130                 135                 140

Ser Glu Gln Ile Gly Val Ser Pro Trp Tyr Trp Phe Ala Asp Val Pro
145                 150                 155                 160

Pro Ala Gln His Glu Glu Ile Tyr Ala Leu Asp Thr Lys Lys Ile Gln
                165                 170                 175

Gly Ser Pro Ser Val Lys Tyr Arg Gly Leu Phe Ile Asn Asp Glu Ala
            180                 185                 190

Pro Ala Leu Thr Asn Trp Ile Asn Val Asn Tyr Pro Pro Cys Lys Tyr
        195                 200                 205

Gly Pro Gly Phe Asn Ala Asp Phe Tyr Ala His Val Phe Glu Leu Leu
    210                 215                 220

Leu Arg Leu Arg Ala Asn Tyr Leu Trp Pro Ala Glu Trp Ser Asn Ile
225                 230                 235                 240

Phe Ala Leu Asp Asp Pro Arg Asn Phe Pro Thr Ala Asp Leu Tyr Gly
                245                 250                 255

Ile Val Ile Gly Thr Ser His Thr Glu Pro Leu Met Arg Trp Thr Leu
            260                 265                 270

Glu Gln Ser Leu Leu Leu Gln Gly Pro Trp Asn Trp Leu Thr Asn Glu
        275                 280                 285
```

```
Lys Asn Ile Tyr Gln Phe Leu Lys Glu Gly Val Glu Arg Ser Lys Asn
    290                 295                 300

Tyr Glu Val Ile Tyr Thr Met Gly Met Arg Gly Leu Gly Asp Thr Ala
305                 310                 315                 320

Ser Pro Thr Ile Asn Ala Thr Thr Leu Ala Gln Ile Val Ala Ala Glu
                325                 330                 335

Glu Gln Ile Leu Ser Glu Val Phe Asn Thr Thr Asn Ile Ser Trp Ile
                340                 345                 350

Pro Gln Met Trp Cys Leu Tyr Lys Glu Val Gly Tyr Tyr Glu Asp
                355                 360                 365

Gly Leu Arg Val Ala Asp Asp Ile Thr Leu Leu Trp Ala Asp Asp Asn
    370                 375                 380

Trp Gly Asn Ile Glu Arg Leu Pro Ile Gly Asn Glu Thr Ala Arg Ser
385                 390                 395                 400

Gly Gly Ala Gly Val Tyr Tyr His Phe Asp Tyr Val Gly Asp Pro Gln
                405                 410                 415

Asp Tyr Lys Trp Ile Asn Thr Ile Ser Leu Gln Lys Thr Trp Glu Gln
                420                 425                 430

Met His Leu Ala Tyr Glu Arg Gln Ala Arg Asn Ile Trp Ile Val Asn
        435                 440                 445

Val Gly Asp Leu Lys Ala Leu Glu Ile Pro Thr Asn His Phe Phe Asp
    450                 455                 460

Leu Ala Tyr Asp Thr Pro Ser Trp Ser Asp Pro Asp Ser Thr Ser Arg
465                 470                 475                 480

Trp Leu Lys Leu Trp Ala Thr Arg Glu Phe Gly Ala Ala Gly Ala Asp
                485                 490                 495

Lys Val Ala Asp Ile Val Asn Arg Tyr Gly Gln Tyr Ala Ala Arg Arg
                500                 505                 510

Lys Phe Glu Met Ile Thr Pro Ser Thr Phe Ser Ile Ile Asn Tyr Asn
                515                 520                 525

Glu Ala Asn Asn Val Val Ser Gln Trp Glu Ser Leu Val Asn Asp Ala
    530                 535                 540

Arg Asp Val Tyr Arg Gly Leu Ser Glu Ala Ala Arg Pro Ala Phe Phe
545                 550                 555                 560

Glu Leu Val Leu Gln Pro Cys Met Ala Gly His Ile Ile Thr Gln Ile
                565                 570                 575

His Val Thr Ala Ala Lys Asn Asn Leu Tyr Ala Ser Gln Arg Arg Thr
                580                 585                 590

Ser Ala Lys Ala Met Ala Asp Lys Ala Leu Lys Leu Phe Lys Glu Asp
            595                 600                 605

His Asp Leu Thr Val Ser Tyr His Lys Ile Leu Asp Gly Lys Trp Asn
    610                 615                 620

His Ile Met Asp Gln Thr His Leu Gly Tyr Leu Tyr Trp Gln Gln Pro
625                 630                 635                 640

Met Arg Asn Thr Leu Pro Pro Leu Gln Tyr Thr Gln Leu Leu Glu Asp
                645                 650                 655

Ser Leu Ala Gly Pro Met Gly Val Ser Val Glu Gly Ser Asn Ala Ser
                660                 665                 670

Val Pro Gly Asp Asp Gln Tyr His Ala Leu Ser Ser Thr Thr Leu Thr
            675                 680                 685

Leu Pro Pro Ile Asp Pro Tyr Gly Pro Ser Thr Arg Trp Ile Glu Ile
    690                 695                 700

Tyr Ser Arg Ser Thr Glu Ser Phe Glu Phe Gln Ile Ser Pro Asn Val
```

```
                705                 710                 715                 720
Ser Trp Val Thr Ala Thr Pro Ser Ser Gly Thr Val His Val Ser Gly
                    725                 730                 735

Asn Gly Thr Thr Thr Asp Val Arg Val Gln Leu Ser Val Asp Trp Asp
                    740                 745                 750

Lys Ala Pro Ile Gly Ser Ser Leu Val Ser Ile Asn Val Ser Ile Pro
                    755                 760                 765

Thr Gly His Phe Pro Thr Gly Asp Tyr Gly Asn Ser Ala Met Pro Val
                    770                 775                 780

Val Gln Leu Pro Val Asn Lys Thr Val Val Pro Ala Ser Phe His Gly
785                 790                 795                 800

Phe Val Glu Ser Asp Gly Val Val Ser Ile Glu Ala Pro His Ala Thr
                    805                 810                 815

Arg Asn Thr Ser Thr Ala Asn Val Ser Tyr Ala Val Ile Pro Gly Tyr
                    820                 825                 830

Gly Arg Thr Leu Ser Gly Val Thr Leu Leu Pro Val Asn Ala Pro Ser
                    835                 840                 845

Gln Lys Ala Pro Ser Ser Pro Arg Leu Glu Tyr Asp Met Tyr Leu Phe
                    850                 855                 860

Ser Pro Ala Ala Asn Gly Ser Thr Val Asn Ile Thr Leu Tyr Leu Gly
865                 870                 875                 880

Pro Ser Leu Asn Val Asn Pro Asp Arg Pro Leu Arg Tyr Ala Leu Ala
                    885                 890                 895

Phe Asp Asp Asp Asp Asn Pro Gln Val Val Gln Tyr Val Pro Ser Thr
                    900                 905                 910

Val Leu Gly Thr Tyr Pro Pro Asp Trp Pro Ser Ala Val Ser Asn Asn
                    915                 920                 925

Val Trp Ala Ser Thr Thr Ser Tyr Thr Ile Lys Gly Phe Asn Gly Asn
                    930                 935                 940

Ser Thr Ser Ala Thr Gly Thr Gly Ser Ala His Thr Leu Lys Leu Trp
945                 950                 955                 960

Ala Leu Glu Pro Gly Val Val Phe Glu Lys Ile Val Ile Asp Leu Gly
                    965                 970                 975

Gly Gln Arg Asp Ser Tyr Leu Gly Pro Pro Glu Ser Arg Ile Val
                    980                 985                 990

<210> SEQ ID NO 73
<211> LENGTH: 21
<212> TYPE: PRT
<213> ORGANISM: Rasamsonia emersonii

<400> SEQUENCE: 73

Met Ile Leu Ser Ser Leu Leu Val Gly Cys Val Ser Leu Trp Gly Ala
1               5                   10                  15

Ala His Ala Leu Gly
            20

<210> SEQ ID NO 74
<211> LENGTH: 3152
<212> TYPE: DNA
<213> ORGANISM: Rasamsonia emersonii
<220> FEATURE:
<221> NAME/KEY: source
<222> LOCATION: (1)..(3152)
<223> OTHER INFORMATION: /organism="Rasamsonia emersonii"
      /mol_type="unassigned DNA"

<400> SEQUENCE: 74
```

```
atgatcctct ccagtctcct tgtggggtgc gtctccctat ggggagcagc acatgccctt    60
ggacaacagc ctgtcgtcgc cttcacctcc agtccaggat atctgaagct tgcaggccca   120
ggaactcccc ctggaacggt tgttctcgat tcagccgact ggccggcagt cttgagagca   180
gccggtgacc ttgccgtgga ctttgggcgt gttactggaa cgaacctgac caaaacggtg   240
atcaatggca ccacaacgtc gtctgggcta gcagcagtat caaacaaggg ccccgtgatt   300
atcgccggca ccattggcaa ctccagtctc atcaatgctt tggcgcagtc cggcaagatc   360
gacgtctccg cgacagaggg cagatgggag gccttccaga ccgaaatcgt ggacaatcct   420
ttcccgggga tatcgcgggc gttggtcgtc agtggcagcg acaggcgtgg cactgtctac   480
gggctgtacg acatctcaga gcagatcggg gtctcgccgt ggtactggtt cgccgacgtg   540
ccgcccgctc agcacgagga gatatacgct ttggacacga agaaaatcca gggctcgccg   600
tcggtcaaat accgcggatt gttcatcaac gacgaggcac ctgccttgac aaactggatc   660
aatgtgaact ccacccctg caagtatggg cctgggttca cgccgacttc ctacgcacac   720
gtgttcgaac tcctcctgag gctgagagcc aactacctgt ggccggcaga atggagcaac   780
atcttcgctc tggacgatcc gcgcaatttc cccacagcag acctgtacgg gattgtgatt   840
ggaaccagcc acacagagcc cctgatgcga tggactctgg agcagagctt gcttctccag   900
ggcccgtgga attggcttac gaacgagaaa aacatctacc agttcctgaa gaaggcgtc   960 gagaggtcca agaattacga ggtcatatat actatgggca tgagaggtct cggcgacacg  1020
gcatcgccca cgatcaacgc cacaactctg gcgcaaatcg tcgccgcgga ggagcagatc  1080
ctctccgagg ttttcaacac gacgaacatc tcttggatcc cgcagatgtg gtgtctctac  1140
aaggaagtgg gcggctacta cgaagacggg ctccgtgtgg cggacgatat cacgctcctc  1200
tgggcagacg acaactgggg gaacatcgag agactgccga ttggcaatga gactgcacgg  1260
tctggcggtg ctggcgtcta ttatcacttt gactacgtcg ggaccccca agactacaag  1320 tggatcaaca ctatttcatt gcagaaaacc tgggagcaga tgcatctcgc atacgagcgg  1380
caggcaagga atatttggat cgtgaatgtt ggcgacttga aagcattggt tagcaagcct  1440
cttccgtggg aatatccgtc atatattgac aagatgacta ggaaatcccg actaaccact  1500
tcttcgactt ggcctacgat acacccagct ggtccgatcc ggacagcacc agccggtggc  1560
tcaagctctg ggccactcgt gaattcgggg cagcgggggc cgacaaagtc gcagacatcg  1620 taaccgcta cggccagtac gcagctagac gcaaattcga gatgatcacc ccgagcacgt  1680
tcagcatcat caactacaac gaggctaaca acgtggtgag tcaatgggag agtctggtca  1740
acgatgcccg tgatgtgtac cgcggactca gcgaagctgc ccggccggcg ttcttcgagc  1800
tggtattgca accttgcatg gctggccaca tcatcactca gatccatgtt acggccgcca  1860
agaataatct ctatgcgtcc cagagacgga caagcgcgaa ggcaatggca gacaaggcgt  1920
tgaaactgtt caaagaggac cacgacttga cggtttccta tcacaagatt cttgatggaa  1980
aatggaacca tatcatggac cagacgcatc tgggttacct ttactggtga gtattttttt  2040
ttactaataa ccttgaccga ggttttgctg aaacggattc gtataggcag cagccgatga  2100
gaaacacact ccccctctc caatacactc agctgttaga ggacagtttg gcgggtccaa  2160
tgggtgtttc tgtcgagggc agcaatgcct ctgtccctgg cgacgatcaa taccacgctt  2220
tgtcgagtac cacctgacc ctgccaccca tagatccta cggaccgtcg acgcgctgga  2280
tcgagatcta ctctcgctca actgaaagct tcgagttcca atctccccc aacgtctcct  2340
```

```
gggtcaccgc gacaccgtcc tccggcaccg tccatgttag tggaaacgga acgaccaccg    2400
acgtccgcgt gcagctgtcc gtcgactggg acaaggctcc tatcggctcg agcctcgtct    2460
cgatcaacgt cagcatccca accggccact tcccgacggg ggactacggg aactcggcca    2520
tgccggttgt ccagctcccc gtgaacaaga cggtcgtgcc agcgtccttc cacggcttcg    2580
tcgagtcgga cggcgtcgtc agcatcgagg cgccgcacgc aacgcgcaac acctcgacgg    2640
cgaacgtctc ctacgccgtg atcccggggt acggacgcac actgtcgggc gtcaccttgc    2700
tgccggtgaa cgcgccgtca cagaaagcgc cttcctcccc gcgtctcgag tacgacatgt    2760
acctcttcag ccctgcggcc aacgcagca ccgtcaacat aacgctgtac ctgggaccgt    2820
cactcaacgt caaccctgac cgaccgctgc gatacgcgct ggccttcgac gacgacgaca    2880
atccccaggt agtgcagtac gtcccgagca cggtgctggg cacctaccca ccggactggc    2940
cctcggccgt gtccaacaac gtgtgggcgt cgacgacgtc gtatacaatc aagggcttta    3000
acggaaacag cactagtgca acaggaacgg gatccgcgca cacgctcaag ctgtgggctc    3060
ttgagcctgg cgtggtgttt gagaagattg tcattgatct gggcgggcag agggatagtt    3120
atctcggtcc gccggagagt cggattgtgt ag    3152
```

<210> SEQ ID NO 75  
<211> LENGTH: 3039  
<212> TYPE: DNA  
<213> ORGANISM: Rasamsonia emersonii  
<220> FEATURE:  
<221> NAME/KEY: source  
<222> LOCATION: (1)..(3039)  
<223> OTHER INFORMATION: /organism="Rasamsonia emersonii"  
　　　/mol_type="unassigned DNA"

<400> SEQUENCE: 75

```
atgatcctct ccagtctcct tgtggggtgc gtctccctat ggggagcagc acatgccctt      60
ggacaacagc ctgtcgtcgc cttcacctcc agtccaggat atctgaagct tgcaggccca     120
ggaactcccc ctggaacggt tgttctcgat tcagccgact ggccggcagt cttgagagca     180
gccggtgacc ttgccgtgga cttttgggcgt gttactggaa cgaacctgac caaaacggtg    240
atcaatggca ccacaacgtc gtctgggcta gcagcagtat caaacaaggg ccccgtgatt    300
atcgccggca ccattggcaa ctccagtctc atcaatgctt tggcgcagtc cggcaagatc    360
gacgtctccg cgacagaggg cagatgggag gccttccaga ccgaaatcgt ggacaatcct    420
ttcccgggga tatcgcgggc gttggtcgtc agtggcagcg acaggcgtgg cactgtctac    480
gggctgtacg acatctcaga gcagatcggg gtctcgccgt ggtactggtt cgccgacgtg    540
ccgcccgctc agcacgagga gatatacgct ttggacacga agaaaatcca gggctcgccg    600
tcggtcaaat accgcggatt gttcatcaac gacgaggcac ctgccttgac aaactggatc    660
aatgtgaact acccaccctg caagtatggg cctgggttca cgccgactt ctacgcacac    720 gtgttcgaac tcctcctgag gctgagagcc aactacctgt ggccggcaga atggagcaac    780
atcttcgctc tggacgatcc gcgcaatttc cccacagcag acctgtacgg gattgtgatt    840
ggaaccagcc acacagagcc cctgatgcga tggactctgg agcagagctt gcttctccag    900
ggcccgtgga attggcttac gaacgagaaa acatctacc agttcctgaa agaaggcgtc    960
gagaggtcca agaattacga ggtcatatat actatgggca tgagaggtct cggcgacacg   1020
gcatcgccca cgatcaacgc cacaactctg gcgcaaatcg tcgccgcgga ggagcagatc   1080
ctctccgagg ttttcaacac gacgaacatc tcttggatcc cgcagatgtg gtgtctctac   1140
```

| | |
|---|---|
| aaggaagtgg gcggctacta cgaagacggg ctccgtgtgg cggacgatat cacgctcctc | 1200 |
| tgggcagacg acaactgggg gaacatcgag agactgccga ttggcaatga gactgcacgg | 1260 |
| tctggcggtg ctggcgtcta ttatcacttt gactacgtcg ggaccccca agactacaag | 1320 |
| tggatcaaca ctatttcatt gcagaaaacc tgggagcaga tgcatctcgc atacgagcgg | 1380 |
| caggcaagga atatttggat cgtgaatgtt ggcgacttga aagcattgga aatcccgact | 1440 |
| aaccacttct tcgacttggc ctacgataca cccagctggt ccgatccgga cagcaccagc | 1500 |
| cggtggctca agctctgggc cactcgtgaa ttcggggcag cggggggccga caaagtcgca | 1560 |
| gacatcgtaa accgctacgg ccagtacgca gctagacgca aattcgagat gatcaccccg | 1620 |
| agcacgttca gcatcatcaa ctacaacgag gctaacaacg tggtgagtca atgggagagt | 1680 |
| ctggtcaacg atgcccgtga tgtgtaccgc ggactcagcg aagctgcccg gccggcgttc | 1740 |
| ttcgagctgg tattgcaacc ttgcatggct ggccacatca tcactcagat ccatgttacg | 1800 |
| gccgccaaga taatctcta tgcgtcccag agacggacaa gcgcgaaggc aatggcagac | 1860 |
| aaggcgttga aactgttcaa agaggaccac gacttgacgg tttcctatca caagattctt | 1920 |
| gatggaaaat ggaaccatat catggaccag acgcatctgg gttacctttta ctggcagcag | 1980 |
| ccgatgagaa acacactccc ccctctccaa tacactcagc tgttagagga cagtttggcg | 2040 |
| ggtccaatgg gtgtttctgt cgagggcagc aatgcctctg tccctggcga cgatcaatac | 2100 |
| cacgctttgt cgagtaccac cctgaccctg ccacccatag atccctacgg accgtcgacg | 2160 |
| cgctggatcg agatctactc tcgctcaact gaaagcttcg agttccaaat ctcccccaac | 2220 |
| gtctcctggg tcaccgcgac accgtcctcc ggcaccgtcc atgttagtgg aaacggaacg | 2280 |
| accaccgacg tccgcgtgca gctgtccgtc gactgggaca aggctcctat cggctcgagc | 2340 |
| ctcgtctcga tcaacgtcag catcccaacc ggccacttcc cgacggggga ctacgggaac | 2400 |
| tcggccatgc cggttgtcca gctcccgtg aacaagacgg tcgtgccagc gtccttccac | 2460 |
| ggcttcgtcg agtcggacgg cgtcgtcagc atcgaggcgc cgcacgcaac gcgcaacacc | 2520 |
| tcgacggcga acgtctccta cgccgtgatc ccggggtacg gacgcacact gtcgggcgtc | 2580 |
| accttgctgc cggtgaacgc gccgtcacag aaagcgcctt cctccccgcg tctcgagtac | 2640 |
| gacatgtacc tcttcagccc tgcggccaac ggcagcaccg tcaacataac gctgtacctg | 2700 |
| ggaccgtcac tcaacgtcaa ccctgaccga ccgctgcgat acgcgctggc cttcgacgac | 2760 |
| gacgacaatc cccaggtagt gcagtacgtc ccgagcacgg tgctgggcac ctacccaccg | 2820 |
| gactggcccct cggccgtgtc caacaacgtg tgggcgtcga cgacgtcgta tacaatcaag | 2880 |
| ggctttaacg gaaacagcac tagtgcaaca ggaacgggat ccgcgcacac gctcaagctg | 2940 |
| tgggctcttg agcctggcgt ggtgtttgag aagattgtca ttgatctggg cgggcagagg | 3000 |
| gatagttatc tcggtccgcc ggagagtcgg attgtgtag | 3039 |

<210> SEQ ID NO 76
<211> LENGTH: 6493
<212> TYPE: DNA
<213> ORGANISM: Rasamsonia emersonii
<220> FEATURE:
<221> NAME/KEY: source
<222> LOCATION: (1)..(6493)
<223> OTHER INFORMATION: /organism="Rasamsonia emersonii"
    /mol_type="unassigned DNA"

<400> SEQUENCE: 76

| | |
|---|---|
| ggagttgctt gcccgggcag gatatcggtt ggcggcgtgg ttggacttga ttgcgaagca | 60 |

```
gtagagacag gtattctgct gatagcatgg atttatatta tcaataagca gaggcctaaa    120
gacattcaac cagaagaaac gtccttcatg caacagcaag ctagaacata tacatatgag    180
aacaagcata gtgccaatca agcagaccta tactgtactc tattacaaca aactactatc    240
acggtagtcg tacactggtc aatgaaataa tgtgagtaaa aatgatcatg attctatgac    300
agaacagcta gtacgcttga tttattgggg tataaatttt actttattta ggtggttaag    360
agccagcaga ctagatatat agctcagata taatataatt aatagtcaca gaaaaaaata    420
aataaaaata aaaatagcaa gatccatgat atggtataca caaaaaaata ataatcataa    480
atcacacaat tccatcctct ccaaaaccac ctagccagct cctaccaaac gatacatact    540
cagtccaagc aaatcccccg ttccgtcctc ccgtccgtcc gatcagtccc gaataccgac    600
caaaaaaaaa aagagacaaa atccaaatca cgggttcatt cacatcccca caggataccc    660
atggatcagt cgtcctactt actgtggtac agattagaac agaaaattag gttttttacac   720 aactcagggt ggttgcattg cattgcattg tgctgtggag ttagttaact tagttgtact    780
ccatccagtt catacgcagt acattattgg gcatttgacc ccatcagaca agatatctaa    840
ggataagagt agaaattagg taataatagt caaaagagaa gaagagatac caagggaact    900
agatactaac aaccaatcag gatatgccac agtgtggaac agaatggaag cagacaggat    960
caacataact ggaaataacc ttttctttct ttcttcgtac agcatcttgg caggaagtaa   1020
cttgatattg ttaattaatg tccatgtcca tgtccatgtc tttgttatgt cttgtcttgt   1080
ctttcttgtg tgctacaagt acagtgtaac agattcatat ccgctgaaac agacataaca   1140
ttcgacacat ggaatacgga gataaagaaa taaattatac tatatacgga atgatatcaa   1200
taaatatccg tgttgtactc cttattaaga aagagtggcg cttggcgcgt ctacgtgcat   1260
ggactggtac tacatatttg attacttcga tttttaataa caacaaccta gtagacgtat   1320
gtatgtcatg tgaaactttc gattgcgtgc tttcttgtct acttgtcgac ttgttacaat   1380
cttgtcgaat attaataata ataatccatc gcactgacta cttggcaagt actccgtaca   1440
tcaggttaca tacatactga ttctctaaag ctagataacg aataggattc tcgcacagac   1500
agtatgtgtc tcttgtctgt cagatgataa gcagatgaac aaagaaagta taactgctta   1560
ctacctacat gccgacattt agtcgattcc tttcggagaa tttattatgg attattaata   1620
gcataccccg ggattggcag aaggggtaaa aggtccgact agacaaggat atccatacag   1680
tacataccgt tgatacagat cgaatcacat gcatactgct gatggtgtga tgaatccttg   1740
aattagacaa tcatccagac ctgtctggac agagatcctg gcactgaaca atccactcat   1800
tgctatctat cggtactctg tacctgtttc agctgaagct tgccaatcgc agactgccat   1860
ctgcaactga tcagcgccag gatgcaggtc atgatacccc agcgttgttc ccgaggtgtc   1920
attgcttaaa cgcgttaacc agtgtgctaa acgtgctaaa cgtgctaaat gctaaactgc   1980
tgatgctatg cagctgcatc gccgaatctg gagaatgcag atcacctgcc gacggcgggc   2040
tccgggcacg tgcacggggg accccgtagg acagaaacgt ccatcgagag tacgagtac    2100 ggagtattac aagaccctgt ccatcagacc ctgtccatcg tcattgccaa gatctctcat   2160
tgtttgctgt tcatgctcg gatcaccagt ggacagcaat gccccgtgaa cagcaagccg    2220
catgctggtc cgtgtcttgt ccgtgtgccg atgtagtatt gctaacgaga cccagaatgg   2280
catcaatgac gttgcggatg acagaatgag ggggatcatc agtacgtctg ctatcaggat   2340
gattatccta cggagtattt actcagctga agacaggaac aagatcgtct gatggatgag   2400
gcccacggcc agccagcaca gactccgtac tcttcagtct tctggatttg accgttcgac   2460
```

-continued

```
ggcgcctccg acgtagcatc tcgctagcct gatccttggc tgcgcctatc gtcggctcat    2520 gccctgttg  atgacgggga agtggagcgg cgccgcgata aggttgcctt gctaatttag    2580
cgcctgcacg ctccagccaa aaagaccaat attgaggtcg atcgtctccc ctggctccgt    2640
gctgctggcc tgcgatcgcc ggcgcgatca taccctgcaa tcacgccgcc agcctatcac    2700
agaccatgcg gtccttgcac catctgggag ctcgagctct cctgactgcc gtcggggcgt    2760
caatgcgtcc ggagcctccg acgagggcct ctgctcctcg tctgtcctac tggagcttgt    2820
ccgtcagacg tcgcatcctg agccgtgtgc tgatatcgcc atggctctga cgtgatcgac    2880
tgcgagcggc cggcgaggct ataagaagcc gcaacttgct gctcgaagta ccgtctccca    2940
tccatcgatc agacagtcag cagtcctcac tcagtcagtc ctcagtcgtc cttcaccacc    3000
atgggtctgt ccaaagcctt cgtgtctgca ctctcgctgt gctccgccgt cgccgtggcc    3060 gcccgaccg  ggccagctcc caacgtgcag ttctccctga agcaggtcgc ggtgccccgg    3120
accaagcctc gtgcgccccc agctgccgac tacgcgcgcg ctctggccaa gtatggcgct    3180
ccaattccgt cgtctgtgcg gacggccgcg tccggcacgc agagcggctc tgcggccaac    3240
acgcccgtcg ccggcgacag cttgtatctc acgcccgtta ccatcggcca gagcacgctg    3300
aacctggact ttgacacggg ctctgcggat ctgtaagtgt cccaactctc gcaagaacaa    3360
gaacggagca gctgactcgt ccagctgggt cttctccaac gagacgccct ccagcgagcg    3420
cggcaaccac gccatctaca agcccagctc gacggccaag aagctgaacg gctacacctg    3480
gagcatctcg tacggcgacg gcagctcggc cggcggcgac gtctaccagg acagcgtctc    3540
ggtgggcggc gtcaacgcct ccaaccaggc ggtcgaggcc gccaccaagg tcagctccga    3600
gttcacgcag gagccgggcg acggcttgct gggcctggcc ttcagcagca tcaacaccgt    3660
caagcccaag ccgcagacga ccttcttcga cacggtcaag tcctcgctcg ccaagccgct    3720
gttcgccgtc accctcaagc acaacgagcc cggcagctac gactttggct acatcgacag    3780
ctccaagtac aagggcagca tccagtacac ccaggtcgac aactcgcagg gcttctggca    3840
gttcacggcc gacggctact cgattggcgg cagcagcggc agcggtggct ccatttctgg    3900
cattgctggt aagaactccc cctacatcag agttatctag atgctgattt cgcagacacc    3960
ggcaccaccc tcctcctgct cgacgaccag atcgtcaacg agtactacca gcaggtccag    4020
ggcgcgcaga acgaccagaa cgccggcggc tacaccttcc cgtgcgacgc gcagctgccc    4080
gagctgagct tcaccatcgg ccagtacacc gccaccgtgc cggccgagta cctcaacttc    4140
cagcccgtgt cgcagggcag ccagacctgc ttcggcggtc tgcagtccaa ccagggcatt    4200
ggcttctcca tcttcggcga cgtcttcctc aagagccagt acgtcgtctt tgactcggac    4260
ggtcctcagc tgggctttgc tgctcaggcg tagaccagtc gtcctccagc ccaggttggt    4320
tggtaggaga tgattttcg  atcgatcgat tatcatggtg attgatagga tatgtgcatg    4380
agcagttgcc tgtacataca tacataatga tttattgaat caattagtta tgatcaatct    4440
cgaatatatt ttcagtgaaa tacgtacatg gtcatagcat aacgatatac tccgttttct    4500
tcaggtagct agtaaatata cacaaattca tcgttctccc ggtccgtcag gtccaggaag    4560
gctttgtctc cgatcgtccc gtcgggatca ctctcgctgg tatcgtgata cgctccctc     4620 atcgagtaat caaccacctt ggccggcttt ccattccgca cgcgccgccg ctcctgcatc    4680
cggttcagca cgaccaaatt cgcccactgc gccagcacga cggccaccag cgccacgaag    4740
atggccagac aagcccgcac gccggccga  tacgccggcg cgtccttctt gctgaagagc    4800
```

| | |
|---|---|
| agcgggccga cgatgttgcc cgccgagctg gccgcgttgt acaggctcat cagcgccgat | 4860 |
| ttcttcgttg tgccgcccgt gttgcccacg atccacgtca cgatcagtgg gttgccgccg | 4920 |
| aagagaaacg cgagcaggta gtagcctacc aggagggagg gttcgactga gttttgcttc | 4980 |
| gtgctgttat tactgcgtgg cacggcgtac agaattgcca ggcccgcgac taccggcagc | 5040 |
| atgaagccgg ccagcacgac gcccttcatc cgcgcccgct gcgccagata gctccccgcc | 5100 |
| aggatgacca gcagctgcag cgcgccaaac ggcatgttga gcagactcgt cgtgtacgcg | 5160 |
| tcgtaccccca ggccgttgag gatcagcggg ccgaacgtgt tgctcacgct ggcgccgacg | 5220 |
| ttcagcagca tcgccatgcc gatccagagg taggttttgg gctcgagcgc tgcctcgacg | 5280 |
| acgtgccgga tcttgaactc gcggctccct gtgcccgtct ggttcgcgcg cagccgctcg | 5340 |
| atggcctgcg cttttttccgt ctccgtcagg aaccgcgctg aggggatgtc gttgtctagt | 5400 |
| ttccagtaga tgaacggcac tgagatgatg gtcaggaggc cgacggtgag gaagatactg | 5460 |
| cgccagtcgt cagcagtcag tcagtcagcg ttcggggtag aaggggagta catctgccat | 5520 |
| ggcctcagaa caggcgactc gatatggccc aacccgtacg acaggggccgc cgcgatgaca | 5580 |
| gtcgccgcgc cgttggtact gtaccaggcc gcaatgcgca gcggctgctc ggcgcggcgg | 5640 |
| taccactggc tggtgatgac gctgaacagc ggcagacagg cggcctcgaa caggccgagg | 5700 |
| aagaagcgcg cggccatcag ggaggcgaaa ctgcgacagg cggccatggc ggcctgggcg | 5760 |
| acgcccagc ccagacacag cgcgggcatc aggcggcgat gcggcacgcg cacgatcagc | 5820 |
| cacgacgaga acggctgcca gacgagctgg gcgatgggcg cgatcgaccc cagcagcgag | 5880 |
| tactggttgc ccgtcaggtg cgtgtcggcc tgcaagccga aggtggcccc gtacccgagc | 5940 |
| accgacttgt ccaggatctg caggaagtac acccacacga ggatggccag gatgacgcgg | 6000 |
| tctgtcttgc gccggatgcg cttgctgtcg gcgtccgtga gtgggattct ctgctggccg | 6060 |
| atcaggcgga gcgccgtgtc gccgtggacg gcgggttgct cttcttcatg ggtgacggtc | 6120 |
| ggtttggatg ccatggtagc gattactaga tgtaatcaag ttgtaatggg agacaaacga | 6180 |
| ccaagttctc tctcgacgtt ttataccggc ttatatgtct gttcagcagc attgcaagtc | 6240 |
| aagtaatgac atcggaattc ctccggttcc ccgcattgcg cggcgatcat cggctggcac | 6300 |
| tagcagtata gctagctcag agtccgtatt actggattct attgcattgc gctgattgca | 6360 |
| gacgttgact gacagcagga gctttgactc tattacccccc acgcttcggc aattccccgc | 6420 |
| gtgctcgggc ctctatgcac ccccacgtgg gggaacattc cagagtatgc aggcagtagt | 6480 |
| atgcagcatg gat | 6493 |

<210> SEQ ID NO 77
<211> LENGTH: 1194
<212> TYPE: DNA
<213> ORGANISM: Rasamsonia emersonii
<220> FEATURE:
<221> NAME/KEY: source
<222> LOCATION: (1)..(1194)
<223> OTHER INFORMATION: /organism="Rasamsonia emersonii"
    /mol_type="unassigned DNA"

<400> SEQUENCE: 77

| | |
|---|---|
| atgggtctgt ccaaagcctt cgtgtctgca ctctcgctgt gctccgccgt cgccgtggcc | 60 |
| gccccgaccg ggccagctcc caacgtgcag ttctccctga gcaggtcgc ggtgccccgg | 120 |
| accaagcctc gtcgcccccc agctgccgac tacgcgcgcg ctctggccaa gtatggcgct | 180 |
| ccaattccgt cgtctgtgcg gacggccgcg tccggcacgc agagcggctc tgcggccaac | 240 |

```
acgcccgtcg ccggcgacag cttgtatctc acgcccgtta ccatcggcca gagcacgctg    300
aacctggact ttgacacggg ctctgcggat ctctgggtct tctccaacga dacgccctcc    360
agcgagcgcg gcaaccacgc catctacaag cccagctcga cggccaagaa gctgaacggc    420
tacacctgga gcatctcgta cggcgacggc agctcggccg gcggcgacgt ctaccaggac    480
agcgtctcgg tgggcggcgt caacgcctcc aaccaggcgg tcgaggccgc caccaaggtc    540
agctccgagt tcacgcagga gccgggcgac ggcttgctgg gcctggcctt cagcagcatc    600
aacaccgtca agcccaagcc gcagacgacc ttcttcgaca cggtcaagtc ctcgctcgcc    660
aagccgctgt tcgccgtcac cctcaagcac aacgagcccg gcagctacga ctttggctac    720
atcgacagct ccaagtacaa gggcagcatc cagtacaccc aggtcgacaa ctcgcagggc    780
ttctggcagt tcacggccga cggctactcg attggcggca gcagcggcag cggtggctcc    840
atttctggca ttgctgacac cggcaccacc ctcctcctgc tcgacgacca gatcgtcaac    900
gagtactacc agcaggtcca gggcgcgcag aacgaccaga cgccggcgg ctacaccttc    960
ccgtgcgacg cgcagctgcc cgagctgagc ttcaccatcg ccagtacac cgccaccgtg    1020
ccggccgagt acctcaactt ccagcccgtg tcgcagggca gccagacctg cttcggcggt    1080
ctgcagtcca accagggcat tggcttctcc atcttcggcg acgtcttcct caagagccag    1140
tacgtcgtct ttgactcgga cggtcctcag ctgggctttg ctgctcaggc gtag          1194
```

<210> SEQ ID NO 78
<211> LENGTH: 397
<212> TYPE: PRT
<213> ORGANISM: Rasamsonia emersonii

<400> SEQUENCE: 78

```
Met Gly Leu Ser Lys Ala Phe Val Ser Ala Leu Ser Leu Cys Ser Ala
1               5                   10                  15

Val Ala Val Ala Ala Pro Thr Gly Pro Ala Pro Asn Val Gln Phe Ser
            20                  25                  30

Leu Lys Gln Val Ala Val Pro Arg Thr Lys Pro Arg Ala Pro Pro Ala
        35                  40                  45

Ala Asp Tyr Ala Arg Ala Leu Ala Lys Tyr Gly Ala Pro Ile Pro Ser
    50                  55                  60

Ser Val Arg Thr Ala Ala Ser Gly Thr Gln Ser Gly Ser Ala Ala Asn
65                  70                  75                  80

Thr Pro Val Ala Gly Asp Ser Leu Tyr Leu Thr Pro Val Thr Ile Gly
                85                  90                  95

Gln Ser Thr Leu Asn Leu Asp Phe Asp Thr Gly Ser Ala Asp Leu Trp
            100                 105                 110

Val Phe Ser Asn Glu Thr Pro Ser Ser Glu Arg Gly Asn His Ala Ile
        115                 120                 125

Tyr Lys Pro Ser Ser Thr Ala Lys Lys Leu Asn Gly Tyr Thr Trp Ser
    130                 135                 140

Ile Ser Tyr Gly Asp Gly Ser Ser Ala Gly Gly Asp Val Tyr Gln Asp
145                 150                 155                 160

Ser Val Ser Val Gly Gly Val Asn Ala Ser Asn Gln Ala Val Glu Ala
                165                 170                 175

Ala Thr Lys Val Ser Ser Glu Phe Thr Gln Glu Pro Gly Asp Gly Leu
            180                 185                 190

Leu Gly Leu Ala Phe Ser Ser Ile Asn Thr Val Lys Pro Lys Pro Gln
        195                 200                 205
```

```
Thr Thr Phe Phe Asp Thr Val Lys Ser Ser Leu Ala Lys Pro Leu Phe
    210                 215                 220

Ala Val Thr Leu Lys His Asn Glu Pro Gly Ser Tyr Asp Phe Gly Tyr
225                 230                 235                 240

Ile Asp Ser Ser Lys Tyr Lys Gly Ser Ile Gln Tyr Thr Gln Val Asp
                245                 250                 255

Asn Ser Gln Gly Phe Trp Gln Phe Thr Ala Asp Gly Tyr Ser Ile Gly
            260                 265                 270

Gly Ser Ser Gly Ser Gly Gly Ser Ile Ser Gly Ile Ala Asp Thr Gly
        275                 280                 285

Thr Thr Leu Leu Leu Leu Asp Asp Gln Ile Val Asn Glu Tyr Tyr Gln
    290                 295                 300

Gln Val Gln Gly Ala Gln Asn Asp Gln Asn Ala Gly Gly Tyr Thr Phe
305                 310                 315                 320

Pro Cys Asp Ala Gln Leu Pro Glu Leu Ser Phe Thr Ile Gly Gln Tyr
                325                 330                 335

Thr Ala Thr Val Pro Ala Glu Tyr Leu Asn Phe Gln Pro Val Ser Gln
            340                 345                 350

Gly Ser Gln Thr Cys Phe Gly Gly Leu Gln Ser Asn Gln Gly Ile Gly
        355                 360                 365

Phe Ser Ile Phe Gly Asp Val Phe Leu Lys Ser Gln Tyr Val Val Phe
370                 375                 380

Asp Ser Asp Gly Pro Gln Leu Gly Phe Ala Ala Gln Ala
385                 390                 395
```

<210> SEQ ID NO 79
<211> LENGTH: 1066
<212> TYPE: DNA
<213> ORGANISM: Aspergillus nidulans
<220> FEATURE:
<221> NAME/KEY: source
<222> LOCATION: (1)..(1066)
<223> OTHER INFORMATION: /organism="Aspergillus nidulans"
      /mol_type="unassigned DNA"

<400> SEQUENCE: 79

```
agacagctct ggcggctctg aggtgcagtg gatgattatt aatccgggac cggccgcccc      60
tccgccccga agtggaaagg ctggtgtgcc cctcgttgac caagaatcta ttgcatcatc     120
ggagaatatg gagcttcatc gaatcaccgg cagtaagcga aggagaatgt gaagccaggg     180
gtgtatagcc gtcggcgaaa tagcatgcca ttaacctagg tacagaagtc caattgcttc     240
cgatctggta aaagattcac gagatagtac cttctccgaa gtaggtagag cgagtacccg     300
gcgcgtaagc tccctaattg gcccatccgg catctgtagg gcgtccaaat atcgtgcctc     360
tcctgctttg cccggtgtat gaaaccggaa aggccgctca ggagctggcc agcggcgcag     420
accgggaaca caagctggca gtcgacccat ccggtgctct gcactcgacc tgctgaggtc     480
cctcagtccc tggtaggcag cttttgcccg tctgtccgcc cggtgtgtcg gcggggttga     540
caaggtcgtt gcgtcagtcc aacatttgtt gccatatttt cctgctctcc ccaccagctg     600
ctctttctt ttctctttct tttcccatct tcagtatatt catcttccca tccaagaacc     660
tttatttccc ctaagtaagt actttgctac atccatactc catccttccc atcccttatt     720
cctttgaacc tttcagttcg agctttccca cttcatcgca gcttgactaa cagctacccc     780
gcttgagcag acatcaccat ggccaagttg accagtgccg ttccggtgct caccgcgcgc     840
gacgtcgccg gagcggtcga gttctggacc gaccggctcg ggttctcccg ggacttcgtg     900
```

```
gaggacgact tcgccggtgt ggtccgggac gacgtgaccc tgttcatcag cgcggtccag    960
gaccaggtgg tgccggacaa caccctggcc tgggtgtggg tgcgcggcct ggacgagctg   1020
tacgccgagt ggtcggaggt cgtgtccacg aacttccggg acgcct                 1066
```

<210> SEQ ID NO 80
<211> LENGTH: 1062
<212> TYPE: DNA
<213> ORGANISM: Aspergillus nidulans
<220> FEATURE:
<221> NAME/KEY: source
<222> LOCATION: (1)..(1062)
<223> OTHER INFORMATION: /organism="Aspergillus nidulans"
    /mol_type="unassigned DNA"

<400> SEQUENCE: 80

```
accagtgccg ttccggtgct caccgcgcgc gacgtcgccg agcggtcga gttctggacc     60 gaccggctcg ggttctcccg ggacttcgtg gaggacgact tcgccggtgt ggtccgggac   120
gacgtgaccc tgttcatcag cgcggtccag gaccaggtgg tgccggacaa caccctggcc   180
tgggtgtggg tgcgcggcct ggacgagctg tacgccgagt ggtcggaggt cgtgtccacg   240
aacttccggg acgcctccgg gccggccatg accgagatcg gcgagcagcc gtgggggcgg   300
gagttcgccc tgcgcgaccc ggccggcaac tgcgtgcact tcgtggccga ggagcaggac   360
tgaccgacgc cgaccaacac cgccggtccg acggcggccc acgggtccca ggagcttgag   420
atccacttaa cgttactgaa atcatcaaac agcttgacga atctggatat aagatcgttg   480
gtgtcgatgt cagctccgga gttgagacaa atggtgttca ggatctcgat aagatacgtt   540
catttgtcca agcagcaaag agtgccttct agtgatttaa tagctccatg tcaacaagaa   600
taaaacgcgt tttcgggttt acctcttcca gatacagctc atctgcaatg cattaatgca   660
ttgactgcaa cctagtaacg ccttcaggct ccggcgaaga gaagaatagc ttagcagagc   720 tatttcatt ttcgggagac gagatcaagc agatcaacgg tcgtcaagag acctacgaga    780
ctgaggaatc cgctcttggc tccacgcgac tatatattg tctctaattg tactttgaca   840
tgctcctctt ctttactctg atagcttgac tatgaaaatt ccgtcaccag ccctgggttc   900
gcaaagataa ttgcatgttt cttccttgaa ctctcaagcc tacaggacac acattcatcg   960
taggtataaa cctcgaaatc attcctacta agatggtata caatagtaac catgcatggt  1020
tgcctagtga atgctccgta acacccaata cgccggccgg cc                    1062
```

<210> SEQ ID NO 81
<211> LENGTH: 1501
<212> TYPE: DNA
<213> ORGANISM: Rasamsonia emersonii
<220> FEATURE:
<221> NAME/KEY: source
<222> LOCATION: (1)..(1501)
<223> OTHER INFORMATION: /organism="Rasamsonia emersonii"
    /mol_type="unassigned DNA"

<400> SEQUENCE: 81

```
ccaattattc aaatcttcaa cctgggtcct ttgcgactag actcggcact atacccacct    60
gagtcgaatc tccgctggac gattttttt cttagaagaa aaaagcttc agaggctaag    120 gattaggctt ccgtacggac tccatgccct atcagacaga gactccgcaa ctcatctgat   180
ctcttcgatg gagggaaaat ctgctgtttt tcgcaaattt ccaacccacc agaaacaccc   240
agaactgtca cgactcacac gtcctacggt cttttgtgtga gtaaactga ttatattcac    300 agatgggtta ctcaatgcag gtacaaactt tgatcgcgct ctttttggga ccgtctatca   360
```

```
accggcttcg aaaaatggct cgactagcca atctgacagg aaattgcgat gttgcaaccg    420
tgtatacgga gtcctctgta caacctctgc caacctctgc cacctcggta catgtacgga    480
gtagctcccc gcagccgcga ttggatgcat taaagtgggt caaccgcagt ggcttgcagt    540
ccgctgcacg agtccgtatg caataattct tgacacacac gagtgcacat aataatagga    600
aagcagacaa actttgagct gaaggctgtc gagcttggca aattgcagga tctggctagt    660
ttcgaagtcg acttcgcgcg cgcagcagta ttgcattatt gagtgtgacc tgctgcgtgg    720
gattagcgtc gcaccggccg aaagctagtc tcatccaagg ctgagcctga gcgctaatta    780
ccccggatca gccaagccct aatggatcta atgaggtgcc tcctccagca ttcggcctgc    840
atggtgcggc gaccctctc tccacgtcca ataattgctg ttgcgcctgt cgaaccctgc    900
caccgcatct ttgccgtttt actccgagat ctgaaaagcc tgctgtggat ggcagttcgc    960
aatatgcact ctcaatcagg tctgtagcat cttttaacta ttattctatt actaattgct   1020
tctggaaggc ttgtggggtg tggtttgtca tcaagttggc tccctgagcg ccgcgttgca   1080
atctccacgc gcggttgtac ggagtatatt catgcggatc cccggggcag agccgtagtg   1140 catgtgcacac taatcgatca tccgctcaat tggatcctgg atttcgaccc tggcttgaac   1200
atatccaatg atcttccagg gacgaaccga cccggtcatg ctttgttacc tacgtacgga   1260
gtagcggcct gggtgatggt tccggaaggt ctgctaaaag gagatcgagt ataccccccg   1320
gggtccgtct gagacttata aagggctctc tgcaactctc cggccgactt ttttcttcat   1380
tcgacagcca tcactcgttt atctggtcga ttctgcagac ttgcccaagg agcaaagagc   1440
atcttcatac gcgcatcatc catctccagc tttctctctc caaacataca ccgtcaaaat   1500
g                                                                  1501

<210> SEQ ID NO 82
<211> LENGTH: 301
<212> TYPE: DNA
<213> ORGANISM: Aspergillus nidulans
<220> FEATURE:
<221> NAME/KEY: source
<222> LOCATION: (1)..(301)
<223> OTHER INFORMATION: /organism="Aspergillus nidulans"
     /mol_type="unassigned DNA"

<400> SEQUENCE: 82
ctaataagtg tcagatagca atttgcacaa gaaatcaata ccagcaactg taaataagcg    60
ctgaagtgac catgccatgc tacgaaagag cagaaaaaaa cctgccgtag aaccgaagag   120
atatgacacg cttccatctc tcaaaggaag aatcccttca gggttgcgtt tccagtctag   180
acacgtataa cggcacaagt gtctctcacc aaatggggtta tatctcaaat gtgatctaag   240
gatggaaagc ccagaatatt ggctggggttg atggctgctt cgagtgcagt ctcatgctgc   300
c                                                                   301
```

CARBOHYDRATE DEGRADING POLYPEPTIDE AND USES THEREOF

CROSS REFERENCE TO RELATED APPLICATIONS

This application is a Continuation of U.S. application Ser. No. 14/763,263, now U.S. Pat. No. 9,988,615 filed on 24 Jul. 2016, which is a § 371 National Stage Application of PCT/EP2014/051998, filed 3 Feb. 2014, which claims priority to EP 13153824.1, filed 4 Feb. 2013, EP 13156678.8, filed 26 Feb. 2013, EP13153829.0, filed 4 Feb. 2013, EP13156679.6, filed 26 Feb. 2013, EP13153831.6, filed 4 Feb. 2013, EP13156682.0, filed 26 Feb. 2013, EP13153833.2, filed 4 Feb. 2013, EP13156684.6, filed 26 Feb. 2013, EP13153834.0, filed 4 Feb. 2013, EP13156685.3, filed 26 Feb. 2013, EP13153835.7, filed 4 Feb. 2013, EP13156688.7, filed 26 Feb. 2013, EP13153836.5, filed 4 Feb. 2013, EP13156690.3, filed 26 Feb. 2013, EP13153837.3, filed 4 Feb. 2013, EP13156692.9, filed 26 Feb. 2013, EP13153839.9, filed 4 Feb. 2013, EP13156693.7, filed 26 Feb. 2013, EP13153840.7, filed 4 Feb. 2013, EP13156694.5, filed 26 Feb. 2013, EP13153841.5, filed 4 Feb. 2013, EP13156696.0, filed 26 Feb. 2013, EP13153828.2, filed 4 Feb. 2013, EP13156698.6, filed 26 Feb. 2013, EP13153825.8, filed 4 Feb. 2013, EP13156701.8, filed 26 Feb. 2013, EP13153823.3, filed 4 Feb. 2013, EP13156702.6, filed 26 Feb. 2013 EP13153821.7, filed 4 Feb. 2013, and EP13156703.4, filed 26 Feb. 2013. The contents of each of these applications is hereby incorporated by reference.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "Sequence_Listing_2919208-341001_ST25.txt" created on Apr. 17, 2018, and 213,843 bytes in size) is submitted concurrently with the instant application, and the entire contents of the Sequence Listing are incorporated herein by reference.

The invention relates to sequences comprising genes that encode polypeptides having lignocellulosic material degrading activity. The invention features the full-length coding sequence of the novel gene as well as the amino acid sequence of the full-length functional protein, and variants and fragments of the gene or the amino acid sequence. The invention also relates to methods for using these proteins in industrial processes. Also included in the invention are cells transformed with a polynucleotide according to the invention suitable for producing these proteins. Also the invention relates to the successful expression of the genes that encode polypeptides having lignocellulosic material degrading activity in a host organism such as *Aspergillus niger* and/or *Rasamsonia emersonii*.

DESCRIPTION OF RELATED ART

Carbohydrates constitute the most abundant organic compounds on earth. However, much of this carbohydrate is sequestered in complex polymers including starch (the principle storage carbohydrate in seeds and grain), and a collection of carbohydrates and lignin known as lignocellulose. The main carbohydrate components of lignocellulose are cellulose, hemicellulose, and pectins. These complex polymers are often referred to collectively as lignocellulose.

Bioconversion of renewable lignocellulosic biomass to a fermentable sugar that is subsequently fermented to produce alcohol (e.g., ethanol) as an alternative to liquid fuels has attracted an intensive attention of researchers since 1970s, when the oil crisis broke out because of decreasing the output of petroleum by OPEC. Ethanol has been widely used as a 10% blend to gasoline in the USA or as a neat fuel for vehicles in Brazil in the last two decades. More recently, the use of E85, an 85% ethanol blend has been implemented especially for clean city applications. The importance of fuel bioethanol will increase in parallel with increases in prices for oil and the gradual depletion of its sources. Additionally, fermentable sugars are being used to produce plastics, polymers and other bio-based products and this industry is expected to grow substantially therefore increasing the demand for abundant low cost fermentable sugars which can be used as a feed stock in lieu of petroleum based feedstocks.

The sequestration of such large amounts of carbohydrates in plant biomass provides a plentiful source of potential energy in the form of sugars, both five carbon and six carbon sugars that could be utilized for numerous industrial and agricultural processes. However, the enormous energy potential of these carbohydrates is currently under-utilized because the sugars are locked in complex polymers, and hence are not readily accessible for fermentation. Methods that generate sugars from plant biomass would provide plentiful, economically-competitive feedstocks for fermentation into chemicals, plastics, such as for instance succinic acid and (bio) fuels, including ethanol, methanol, butanol synthetic liquid fuels and biogas.

Regardless of the type of cellulosic feedstock, the cost and hydrolytic efficiency of enzymes are major factors that restrict the commercialization of the biomass bioconversion processes. The production costs of microbially produced enzymes are tightly connected with a productivity of the enzyme-producing strain and the final activity yield in the fermentation broth.

In spite of the continued research of the last few decades to understand enzymatic lignocellulosic biomass degradation and cellulase production, it remains desirable to discover or to engineer new highly active cellulases and hemicellulases. It would also be highly desirable to construct highly efficient enzyme compositions capable of performing rapid and efficient biodegradation of lignocellulosic materials, in particular such cellulases and hemicellulases that have increased thermostability.

Such enzymes may be used to produce sugars for fermentation into chemicals, plastics, such as for instance succinic acid and (bio) fuels, including ethanol, methanol, butanol, synthetic liquid fuels and biogas, for ensiling, and also as enzyme in other industrial processes, for example in the food or feed, textile, pulp or paper or detergent industries and other industries.

SUMMARY

The present invention provides a polypeptide having hemicellulase activity or an activity according to Table 1 which comprises the amino acid sequence set out in SEQ ID NO: 2, 7, 12, 17, 22, 27, 32, 37, 42, 47, 52, 57, 62, 67 or 72 or an amino acid sequence encoded by the nucleotide sequence of SEQ ID NO: 1, 6, 11, 16, 21, 26, 31, 36, 41, 46, 51, 56, 61, 66 or 71, SEQ ID NO: 4, 9, 14, 19, 24, 29, 34, 39, 44, 49, 54, 59, 64, 69 or 74, or a variant polypeptide or variant polynucleotide thereof, wherein the variant polypeptide has at least 75% sequence identity with the sequence set out in SEQ ID NO: 2, 7, 12, 17, 22, 27, 32, 37, 42, 47, 52, 57, 62, 67 or 72 or the variant polynucleotide encodes a polypeptide that has at least 75% sequence identity with the sequence set out in SEQ ID NO: 2, 7, 12, 17, 22, 27, 32, 37, 42, 47, 52, 57, 62, 67 or 72.

TABLE 1

Temer numbers of the proteins of the invention and their activity

| | Temer number | activity | activity |
|---|---|---|---|
| 1 | Temer00088 | beta-xylosidase | GH3 |
| 2 | Temer09484 | beta-xylosidase | GH3 |
| 3 | Temer08028 | alpha-galactosidase | GH27 |
| 4 | Temer02362 | alpha-galactosidase | GH27 |
| 5 | Temer08862 | alpha-galactosidase | GH27 |
| 6 | Temer04790 | xyloglucanase | GH12 |
| 7 | Temer05249 | alpha-arabinofuranosidase | GH51 |
| 8 | Temer06848 | alpha-arabinofuranosidase | GH51 |
| 9 | Temer02056 | alpha-arabinofuranosidase | GH51 |
| 10 | Temer03124 | endo-xylanase | GH43 |
| 11 | Temer09491 | mannosidase/xylosidase | GH31 |
| 12 | Temer06400 | feruloyl esterase | CE1 |
| 13 | Temer08570 | endo-xylanase | GH39 |
| 14 | Temer08163 | endo-exo-xylanase | GH30 |
| 15 | Temer07305 | alpha-glucuronidase | GH115 |

The polypeptide of the invention has preferably beta-xylosidase, alpha-galactosidase, xyloglucanase, alpha-arabinofuranosidase, endo-xylanase, mannosidase/xylosidase, feruloyl esterase, xylosidase, endo-exo-xylanase or alpha-glucuronidase activity.

Furthermore the invention provides a nucleic acid sequence coding for an hemicellulase, whereby the nucleic acid sequence is selected from the group consisting of:

(a) a nucleic acid sequence having at least 70% identity with the nucleic acid sequence of SEQ ID NO: 1, 6, 11, 16, 21, 26, 31, 36, 41, 46, 51, 56, 61, 66 or 71, SEQ ID NO: 4, 9, 14, 19, 24, 29, 34, 39, 44, 49, 54, 59, 64, 69 or 74 or SEQ ID NO: 5, 10, 15, 20, 25, 30, 35, 40, 45, 50, 55, 60, 65, 70 or 75;

(b) a nucleic acid sequence hybridizing with the complement of the nucleic acid sequence of SEQ ID NO: 1, 6, 11, 16, 21, 26, 31, 36, 41, 46, 51, 56, 61, 66 or 71, SEQ ID NO: 4, 9, 14, 19, 24, 29, 34, 39, 44, 49, 54, 59, 64, 69 or 74 or SEQ ID NO: 5, 10, 15, 20, 25, 30, 35, 40, 45, 50, 55, 60, 65, 70 or 75;

(c) a nucleic acid sequence encoding (i) the amino acid sequence of SEQ ID NO: 2, 7, 12, 17, 22, 27, 32, 37, 42, 47, 52, 57, 62, 67 or 72, (ii) an amino acid sequence having at least 70% identity with the amino acid sequence of SEQ ID NO: 2, 7, 12, 17, 22, 27, 32, 37, 42, 47, 52, 57, 62, 67 or 72, or (iii) an amino acid sequence that differs in 1, 2, 3, 4, 5, 6, 7, 8, 9, 10, 11 or 12 amino acids from the amino acid sequence of SEQ ID NO: 2, 7, 12, 17, 22, 27, 32, 37, 42, 47, 52, 57, 62, 67 or 72; or (d) a nucleotide sequence which is the reverse complement of a nucleotide sequence as defined in (a), (b) or (c).

The invention also provides a nucleic acid construct or vector comprising the polynucleotide of the invention and a cell comprising a polypeptide of the invention or a nucleic acid construct or vector of the invention.

According to an aspect of the invention the cell is a fungal cell, preferably a fungal cell selected from the group consisting of the genera *Acremonium*, *Agaricus*, *Aspergillus*, *Aureobasidium*, *Chrysosporium*, *Coprinus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Piromyces*, *Panerochaete*, *Pleurotus*, *Schizophyllum*, *Talaromyces*, *Rasamsonia*, *Thermoascus*, *Thielavia*, *Tolypocladium*, and *Trichoderma*. According to another aspect of the invention one or more gene of the cell of the invention is deleted, knocked-out or disrupted in full or in part, wherein optionally the gene encodes for a protease.

The invention also provides a method for the preparation of a polypeptide according to the invention having hemicellulase or an activity according to Table 1, which method comprises cultivating a cell of the invention under conditions which allow for expression of said polypeptide and, optionally, recovering the expressed polypeptide. Furthermore the invention provides a composition comprising: (i) a polypeptide of the invention and; (ii) a cellulase and/or an additional hemicellulase and/or a pectinase, preferably the cellulase is a GH61, cellobiohydrolase, cellobiohydrolase I, cellobiohydrolase II, endo-β-1,4-glucanase, β-glucosidase or β-(1,3)(1,4)-glucanase and/or the hemicellulase is an endoxylanase, β-xylosidase, α-L-arabinofuranosidase, α-D-glucuronidase feruloyl esterase, coumaroyl esterase, α-galactosidase, β-galactosidase, β-mannanase or β-mannosidase.

Additionally the invention provides a method for the treatment of a substrate comprising hemicellulose, optionally a plant material, which method comprises contacting the substrate with a polypeptide of the invention and/or a composition of the invention.

Another aspect of the invention relates to the use of a polypeptide of the invention and/or a composition of the invention to produce sugar from a lignocellulosic material.

The invention also provides:

a method for the preparation of a polypeptide having carbohydrate material degrading or carbohydrate hydrolysing activity, which method comprises cultivating a cell of the invention under conditions which allow for expression of said polypeptide and, optionally, recovering the expressed polypeptide;

a polypeptide obtainable by such a method; and a composition comprising: (i) a polypeptide of the invention and; (ii) a cellulase and/or a hemicellulase and/or a pectinase;

The polypeptides of the invention having carbohydrate material degrading or carbohydrate hydrolysing activity may be used in industrial processes. Thus, the invention provides a method for the treatment of a substrate comprising carbohydrate material which method comprises contacting the substrate with a polypeptide or a composition of the invention.

In particular, the invention provides a method for producing a sugar or sugars from lignocellulosic material which method comprises contacting the lignocellulosic material with a polypeptide or a composition of the invention.

Sugars produced in this way may be used in a fermentation process. Accordingly, the invention provides a method for producing a fermentation product, which method comprises: producing a fermentable sugar using the described above; and fermenting the resulting fermentable sugar, thereby to produce a fermentation product.

A polypeptide or a composition of the invention may also be used, for example, in the preparation of a food product, in the preparation of a detergent, in the preparation of an animal feed, in the treatment of pulp or in the manufacture of a paper or in the preparation of a fabric or textile or in the cleaning thereof.

The invention also provides:

a processed material obtainable by contacting a plant material or lignocellulosic material with a polypeptide or a composition of the invention;

a food or feed comprising a polypeptide or a composition of the invention; and a plant or a part thereof which comprises a polynucleotide, a polypeptide, a vector or a cell according to the invention.

BRIEF DESCRIPTION OF THE SEQUENCE LISTING

Figure 1:
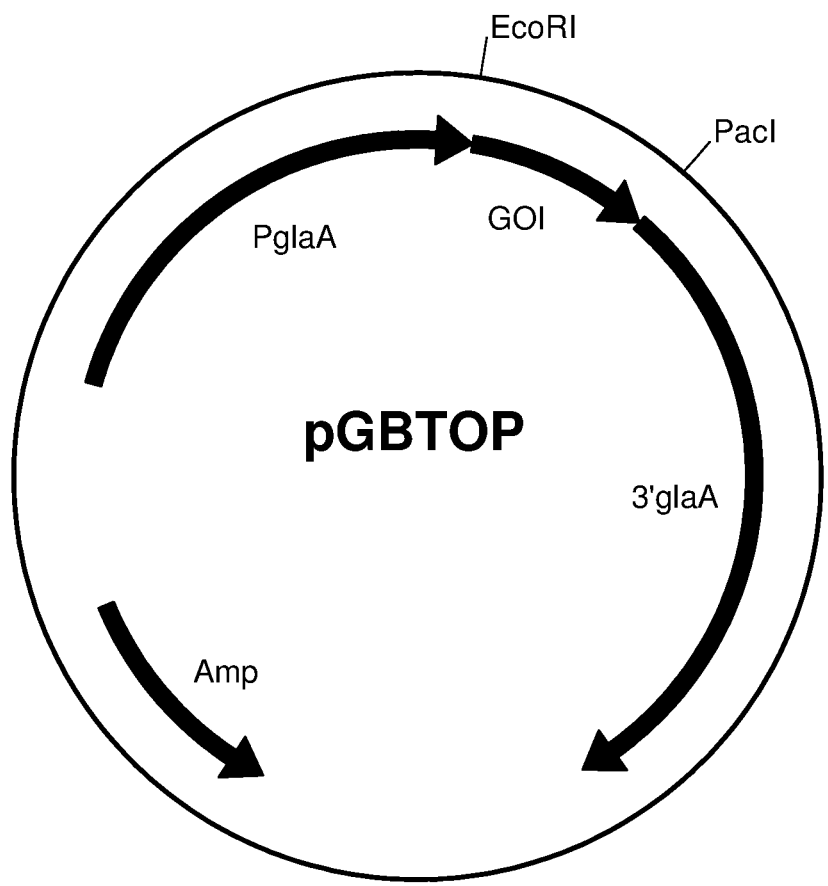
FIG. 1: Map of pGBTOP for expression of genes in *A. niger*. Depicted are the gene of interest (GOI) expressed from the glucoamylase promoter (PglaA). In addition, the glucoamylase flank (3'glaA) of the expression cassette is depicted. In this application a gene of interest is the coding sequence of Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 as defined hereinafter.

TABLE 2 shows codon-pair optimised coding sequence SEQ ID NO's, amino acid sequence SEQ ID NO's, signal sequence SEQ ID NO's, genomic DNA sequence SEQ ID NO's and wild-type coding sequence SEQ ID NO's of the the present invention

| | Temer number | Codon-pair optimized coding sequence SEQ ID NO: | Amino acid sequence SEQ ID NO: | Signal sequence SEQ ID NO: | Genomic DNA sequence SEQ ID NO: | Wild-type coding sequence SEQ ID NO: |
|---|---|---|---|---|---|---|
| 1 | Temer00088 | 1 | 2 | 3 | 4 | 5 |
| 2 | Temer09484 | 6 | 7 | 8 | 9 | 10 |
| 3 | Temer08028 | 11 | 12 | 13 | 14 | 15 |
| 4 | Temer02362 | 16 | 17 | 18 | 19 | 20 |
| 5 | Temer08862 | 21 | 22 | 23 | 24 | 25 |
| 6 | Temer04790 | 26 | 27 | 28 | 29 | 30 |
| 7 | Temer05249 | 31 | 32 | 33 | 34 | 35 |
| 8 | Temer06848 | 36 | 37 | 38 | 39 | 40 |
| 9 | Temer02056 | 41 | 42 | 43 | 44 | 45 |
| 10 | Temer03124 | 46 | 47 | 48 | 49 | 50 |
| 11 | Temer09491 | 51 | 52 | 53 | 54 | 55 |
| 12 | Temer06400 | 56 | 57 | 58 | 59 | 60 |

TABLE 2-continued shows codon-pair optimised coding sequence SEQ ID NO's, amino acid
sequence SEQ ID NO's, signal sequence SEQ ID NO's, genomic DNA sequence SEQ
ID NO's and wild-type coding sequence SEQ ID NO's of the the present invention

| | Temer number | Codon-pair optimized coding sequence SEQ ID NO: | Amino acid sequence SEQ ID NO: | Signal sequence SEQ ID NO: | Genomic DNA sequence SEQ ID NO: | Wild-type coding sequence SEQ ID NO: |
|---|---|---|---|---|---|---|
| 13 | Temer08570 | 61 | 62 | 63 | 64 | 65 |
| 14 | Temer08163 | 66 | 67 | 68 | 69 | 70 |
| 15 | Temer07305 | 71 | 72 | 73 | 74 | 75 |

SEQ ID NO: 76 *R. emersonii* RePepA (genomic sequence including flanks)
SEQ ID NO: 77 *R. emersonii* RePepA (cDNA)
SEQ ID NO: 78 *R. emersonii* RePepA (protein)
SEQ ID NO: 79 *A. nidulans* gpdA promoter and 5' part of the ble coding region
SEQ ID NO: 80 3' part of the ble coding region and *A. nidulans* TrpC terminator
SEQ ID NO: 81 *R. emersonii* promoter 2
SEQ ID NO: 82 *A. nidulans* AmdS terminator Detailed Description of a Preferred Embodiment Throughout the present specification and the accompanying claims, the words "comprise" and "include" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

The present invention provides polynucleotides encoding polypeptides, e.g. enzymes which have the ability to modify, for example degrade, a carbohydrate material. A carbohydrate material is a material which comprises, consists of or substantially consists of one or more carbohydrates. Enzymes are herein a subclass of polypeptides.

Substrate (also called feedstock) herein is used to refer to a substance that comprises carbohydrate material, which may be treated with enzymes according to the invention, so that the carbohydrate material therein is modified. In addition to the carbohydrate material the substrate may contain any other component, including but not limited to non-carbohydrate material and starch.

The present invention provides polynucleotides encoding polypeptides, e.g. enzymes which have the ability to modify, for example degrade, a carbohydrate material. A carbohydrate material is a material which comprises, consists of or substantially consists of one or more carbohydrates. Enzymes are herein a subclass of polypeptides.

TEMER09484

Typically, a polypeptide of the invention encodes a polypeptide having at least beta-xylosidase activity, tentatively called TEMER09484, having an amino acid sequence according to SEQ ID NO: 2, or a sequence which is a variant thereof, typically functionally equivalent to the polypeptide having the sequence of SEQ ID NO: 2, or a sequence which is a fragment of either thereof.

A β-xylosidase (EC 3.2.1.37) is any polypeptide which is capable of catalyzing the hydrolysis of 1,4-β-D-xylans, to remove successive D-xylose residues from the non-reducing termini. Such enzymes may also hydrolyze xylobiose. This enzyme may also be referred to as xylan 1,4-β-xylosidase, 1,4-β-D-xylan xylohydrolase, exo-1,4-β-xylosidase or xylobiase.

A polypeptide of the invention may have one or more alternative and/or additional carbohydrate degrading and/or carbohydrate hydrolysing activities other than that of beta-xylosidase activity, for example one of the other carbohydrate degrading and/or carbohydrate hydrolysing activities mentioned herein.

TEMER00088

Typically, a polypeptide of the invention encodes a polypeptide having at least beta-xylosidase activity, tentatively called TEMER00088, having an amino acid sequence according to SEQ ID NO: 7, or a sequence which is a variant thereof, typically functionally equivalent to the polypeptide having the sequence of SEQ ID NO: 7, or a sequence which is a fragment of either thereof.

A β-xylosidase (EC 3.2.1.37) is any polypeptide which is capable of catalyzing the hydrolysis of 1,4-β-D-xylans, to remove successive D-xylose residues from the non-reducing termini. Such enzymes may also hydrolyze xylobiose. This enzyme may also be referred to as xylan 1,4-β-xylosidase, 1,4-β-D-xylan xylohydrolase, exo-1,4-β-xylosidase or xylobiase.

A polypeptide of the invention may have one or more alternative and/or additional carbohydrate degrading and/or carbohydrate hydrolysing activities other than that of beta-xylosidase activity, for example one of the other carbohydrate degrading and/or carbohydrate hydrolysing activities mentioned herein.

TEMER08028

Typically, a polypeptide of the invention encodes a polypeptide having at least alpha-galactosidase activity, tentatively called TEMER08028, having an amino acid sequence according to SEQ ID NO: 12, or a sequence which is a variant thereof, typically functionally equivalent to the polypeptide having the sequence of SEQ ID NO: 12, or a sequence which is a fragment of either thereof.

Herein, an α-galactosidase (EC 3.2.1.22; GH27) is any polypeptide which is capable of catalyzing the hydrolysis of terminal, non-reducing α-D-galactose residues in α-D-galactosides, including galactose oligosaccharides, galactomannans, galactans and arabinogalactans. Such a polypeptide may also be capable of hydrolyzing α-D-fucosides. This enzyme may also be referred to as melibiase.

A polypeptide of the invention may have one or more alternative and/or additional carbohydrate degrading and/or carbohydrate hydrolysing activities other than that of alpha-galactosidase activity, for example one of the other carbohydrate degrading and/or carbohydrate hydrolysing activities mentioned herein.

TEMER02362

Typically, a polypeptide of the invention encodes a polypeptide having at least alpha-galactosidase activity, tentatively called TEMER02362, having an amino acid sequence according to SEQ ID NO: 17, or a sequence which is a variant thereof, typically functionally equivalent to the polypeptide having the sequence of SEQ ID NO: 17, or a sequence which is a fragment of either thereof.

Herein, an α-galactosidase (EC 3.2.1.22; GH27) is any polypeptide which is capable of catalyzing the hydrolysis of terminal, non-reducing α-D-galactose residues in α-D-galactosides, including galactose oligosaccharides, galactomannans, galactans and arabinogalactans. Such a polypeptide may also be capable of hydrolyzing α-D-fucosides. This enzyme may also be referred to as melibiase.

A polypeptide of the invention may have one or more alternative and/or additional carbohydrate degrading and/or carbohydrate hydrolysing activities other than that of alpha-galactosidase activity, for example one of the other carbohydrate degrading and/or carbohydrate hydrolysing activities mentioned herein.

TEMER08862

Typically, a polypeptide of the invention encodes a polypeptide having at least alpha-galactosidase activity, tentatively called TEMER08862, having an amino acid sequence according to SEQ ID NO: 22, or a sequence which is a variant thereof, typically functionally equivalent to the polypeptide having the sequence of SEQ ID NO: 22, or a sequence which is a fragment of either thereof.

Herein, an α-galactosidase (EC 3.2.1.22; GH27) is any polypeptide which is capable of catalyzing the hydrolysis of terminal, non-reducing α-D-galactose residues in α-D-galactosides, including galactose oligosaccharides, galactomannans, galactans and arabinogalactans. Such a polypeptide may also be capable of hydrolyzing α-D-fucosides. This enzyme may also be referred to as melibiase.

A polypeptide of the invention may have one or more alternative and/or additional carbohydrate degrading and/or carbohydrate hydrolysing activities other than that of alpha-galactosidase activity, for example one of the other carbohydrate degrading and/or carbohydrate hydrolysing activities mentioned herein.

TEMER04790

Typically, a polypeptide of the invention encodes a polypeptide having at least xyloglucanase activity, tentatively called TEMER04790, having an amino acid sequence according to SEQ ID NO: 27, or a sequence which is a variant thereof, typically functionally equivalent to the polypeptide having the sequence of SEQ ID NO: 27, or a sequence which is a fragment of either thereof.

Herein, a xyloglucanase is an xyloglucan-specific endo-β-1,4-glucanase, which catalyzes the cleavage of xyloglucan, a backbone of β1→4-linked glucose residues, most of which substituted with 1-6 linked xylose side chains.

A polypeptide of the invention may have one or more alternative and/or additional carbohydrate degrading and/or carbohydrate hydrolysing activities other than that of xyloglucanase activity, for example one of the other carbohydrate degrading and/or carbohydrate hydrolysing activities mentioned herein.

TEMER05249

Typically, a polypeptide of the invention encodes a polypeptide having at least alpha-arabinofuranosidase activity, tentatively called TEMER05249, having an amino acid sequence according to SEQ ID NO: 32, or a sequence which is a variant thereof, typically functionally equivalent to the polypeptide having the sequence of SEQ ID NO: 32, or a sequence which is a fragment of either thereof.

Herein, an α-L-arabinofuranosidase (EC 3.2.1.55) is any polypeptide which is capable of acting on α-L-arabinofuranosides, α-L-arabinans containing (1,2) and/or (1,3)- and/or (1,5)-linkages, arabinoxylans and arabinogalactans. This enzyme may also be referred to as α-N-arabinofuranosidase, arabinofuranosidase or arabinosidase.

A polypeptide of the invention may have one or more alternative and/or additional carbohydrate degrading and/or carbohydrate hydrolysing activities other than that of alpha-arabinofuranosidase activity, for example one of the other carbohydrate degrading and/or carbohydrate hydrolysing activities mentioned herein.

TEMER06848

Typically, a polypeptide of the invention encodes a polypeptide having at least alpha-arabinofuranosidase activity, tentatively called TEMER06848, having an amino acid sequence according to SEQ ID NO: 37, or a sequence which is a variant thereof, typically functionally equivalent to the polypeptide having the sequence of SEQ ID NO: 37, or a sequence which is a fragment of either thereof.

Herein, an α-L-arabinofuranosidase (EC 3.2.1.55) is any polypeptide which is capable of acting on α-L-arabinofuranosides, α-L-arabinans containing (1,2) and/or (1,3)- and/or (1,5)-linkages, arabinoxylans and arabinogalactans. This enzyme may also be referred to as α-N-arabinofuranosidase, arabinofuranosidase or arabinosidase.

A polypeptide of the invention may have one or more alternative and/or additional carbohydrate degrading and/or carbohydrate hydrolysing activities other than that of alpha-arabinofuranosidase activity, for example one of the other carbohydrate degrading and/or carbohydrate hydrolysing activities mentioned herein.

TEMER02056

Typically, a polypeptide of the invention encodes a polypeptide having at least alpha-arabinofuranosidase activity, tentatively called TEMER02056, having an amino acid sequence according to SEQ ID NO: 42, or a sequence which is a variant thereof, typically functionally equivalent to the polypeptide having the sequence of SEQ ID NO: 42, or a sequence which is a fragment of either thereof.

Herein, an α-L-arabinofuranosidase (EC 3.2.1.55) is any polypeptide which is capable of acting on α-L-arabinofuranosides, α-L-arabinans containing (1,2) and/or (1,3)- and/or (1,5)-linkages, arabinoxylans and arabinogalactans. This enzyme may also be referred to as α-N-arabinofuranosidase, arabinofuranosidase or arabinosidase.

A polypeptide of the invention may have one or more alternative and/or additional carbohydrate degrading and/or carbohydrate hydrolysing activities other than that of alpha-arabinofuranosidase activity, for example one of the other carbohydrate degrading and/or carbohydrate hydrolysing activities mentioned herein.

TEMER03124

Typically, a polypeptide of the invention encodes a polypeptide having at least endo-xylanase activity, tentatively called TEMER03124, having an amino acid sequence according to SEQ ID NO: 47, or a sequence which is a variant thereof, typically functionally equivalent to the polypeptide having the sequence of SEQ ID NO: 47, or a sequence which is a fragment of either thereof.

Herein, an endoxylanase (EC 3.2.1.8) is any polypeptide which is capable of catalyzing the endo-hydrolysis of 1,4-β-D-xylosidic linkages in xylans. This enzyme may also be referred to as endo-1,4-β-xylanase or 1,4-β-D-xylan xylanohydrolase. An alternative is EC 3.2.1.136, a glucuronoarabinoxylan endoxylanase, an enzyme that is able to hydrolyze 1,4 xylosidic linkages in glucuronoarabinoxylans.

A polypeptide of the invention may have one or more alternative and/or additional carbohydrate degrading and/or carbohydrate hydrolysing activities other than that of endoxylanase activity, for example one of the other carbohydrate degrading and/or carbohydrate hydrolysing activities mentioned herein.

TEMER09491

Typically, a polypeptide of the invention encodes a polypeptide having at least mannosidase and/or xylosidase activity, tentatively called TEMER09491, having an amino acid sequence according to SEQ ID NO: 52, or a sequence which is a variant thereof, typically functionally equivalent to the polypeptide having the sequence of SEQ ID NO: 52, or a sequence which is a fragment of either thereof.

Herein, a β-xylosidase (EC 3.2.1.37) is any polypeptide which is capable of catalyzing the hydrolysis of 1,4-β-D-xylans, to remove successive D-xylose residues from the non-reducing termini. Such enzymes may also hydrolyze xylobiose. This enzyme may also be referred to as xylan 1,4-β-xylosidase, 1,4-β-D-xylan xylohydrolase, exo-1,4-β-xylosidase or xylobiase.

Herein, a β-mannosidase (EC 3.2.1.25) is any polypeptide which is capable of catalyzing the hydrolysis of terminal, non-reducing β-D-mannose residues in β-D-mannosides. This enzyme may also be referred to as mannanase or mannase.

A polypeptide of the invention may have one or more alternative and/or additional carbohydrate degrading and/or carbohydrate hydrolysing activities other than that of mannosidase and/or xylosidase activity, for example one of the other carbohydrate degrading and/or carbohydrate hydrolysing activities mentioned herein.

TEMER06400

Typically, a polypeptide of the invention encodes a polypeptide having at least feruloyl esterase activity, tentatively called TEMER06400, having an amino acid sequence according to SEQ ID NO: 57, or a sequence which is a variant thereof, typically functionally equivalent to the polypeptide having the sequence of SEQ ID NO: 57, or a sequence which is a fragment of either thereof.

Herein, a feruloyl esterase (EC 3.1.1.73; CE1) is any polypeptide which is capable of catalyzing a reaction of the form: feruloyl-saccharide+H(2)O=ferulate+saccharide. The saccharide may be, for example, an oligosaccharide or a polysaccharide. It may typically catalyze the hydrolysis of the 4-hydroxy-3-methoxycinnamoyl (feruloyl) group from an esterified sugar, which is usually arabinose in 'natural' substrates. p-nitrophenol acetate and methyl ferulate are typically poorer substrates. This enzyme may also be referred to as cinnamoyl ester hydrolase, ferulic acid esterase or hydroxycinnamoyl esterase. It may also be referred to as a hemicellulase accessory enzyme, since it may help xylanases and pectinases to break down plant cell wall hemicellulose and pectin.

A polypeptide of the invention may have one or more alternative and/or additional carbohydrate degrading and/or carbohydrate hydrolysing activities other than that of feruloyl esterase activity, for example one of the other carbohydrate degrading and/or carbohydrate hydrolysing activities mentioned herein.

TEMER08570

Typically, a polypeptide of the invention encodes a polypeptide having at least endo-xylanase activity, tentatively called TEMER08570, having an amino acid sequence according to SEQ ID NO: 62, or a sequence which is a variant thereof, typically functionally equivalent to the polypeptide having the sequence of SEQ ID NO: 62, or a sequence which is a fragment of either thereof.

Herein, a β-xylosidase (EC 3.2.1.37; GH39) is any polypeptide which is capable of catalyzing the hydrolysis of 1,4-β-D-xylans, to remove successive D-xylose residues from the non-reducing termini. Such enzymes may also hydrolyze xylobiose. This enzyme may also be referred to as xylan 1,4-β-xylosidase, 1,4-β-D-xylan xylohydrolase, exo-1,4-β-xylosidase or xylobiase.

A polypeptide of the invention may have one or more alternative and/or additional carbohydrate degrading and/or carbohydrate hydrolysing activities other than that of xylosidase activity, for example one of the other carbohydrate degrading and/or carbohydrate hydrolysing activities mentioned herein.

TEMER08163

Typically, a polypeptide of the invention encodes a polypeptide having at least endo- and/or exo-xylanase activity, tentatively called TEMER08163, having an amino acid sequence according to SEQ ID NO: 67, or a sequence which is a variant thereof, typically functionally equivalent to the polypeptide having the sequence of SEQ ID NO: 67, or a sequence which is a fragment of either thereof. TEMER08163 advantageously produces xylobiose as main product.

Herein, an endoxylanase (EC 3.2.1.8) is any polypeptide which is capable of catalyzing the endo-hydrolysis of 1,4-β-D-xylosidic linkages in xylans. This enzyme may also be referred to as endo-1,4-β-xylanase or 1,4-β-D-xylan xylanohydrolase. An alternative is EC 3.2.1.136, a glucuronoarabinoxylan endoxylanase, an enzyme that is able to hydrolyze 1,4 xylosidic linkages in glucuronoarabinoxylans.

A polypeptide of the invention may have one or more alternative and/or additional carbohydrate degrading and/or carbohydrate hydrolysing activities other than that of endo- and/or exo-xylanase activity, for example one of the other carbohydrate degrading and/or carbohydrate hydrolysing activities mentioned herein.

TEMER07305

Typically, a polypeptide of the invention encodes a polypeptide having at least alpha-glucuronidase activity, tentatively called TEMER07305, having an amino acid sequence according to SEQ ID NO: 72, or a sequence which is a variant thereof, typically functionally equivalent to the polypeptide having the sequence of SEQ ID NO: 72, or a sequence which is a fragment of either thereof.

Herein, an α-D-glucuronidase (EC 3.2.1.139; GH115) is any polypeptide which is capable of catalyzing a reaction of the following form: alpha-D-glucuronoside+H(2)O=an alcohol+D-glucuronate. This enzyme may also be referred to as alpha-glucuronidase or alpha-glucosiduronase. These enzymes may also hydrolyze 4-O-methylated glucoronic acid, which can also be present as a substituent in xylans. Alternative is EC 3.2.1.131: xylan alpha-1,2-glucuronosidase, which catalyses the hydrolysis of alpha-1,2-(4-O-methyl)glucuronosyl links.

A polypeptide of the invention may have one or more alternative and/or additional carbohydrate degrading and/or carbohydrate hydrolysing activities other than that of alpha-glucuronidase activity, for example one of the other carbohydrate degrading and/or carbohydrate hydrolysing activities mentioned herein.

Carbohydrate in this context includes all saccharides, for example polysaccharides, oligosaccharides, disaccharides or monosaccharides.

A polypeptide according to the invention may modify a carbohydrate material by chemically degrading or physically degrading such material or hydrolysing the carbohydrate. Chemical modification of the carbohydrate material may result in the degradation of such material, for example by hydrolysis, oxidation or other chemical modification such as by the action of a lyase. Physical modification may or may not be accompanied by chemical modification.

Suitable Carbohydrate Materials

Lignocellulolytic or lignocellulosic materials or biomass are abundant in nature and have great value as alternative energy source. Second generation biofuels, also known as advanced biofuels, are fuels that can be manufactured from various types of biomass. Biomass is a wide-ranging term meaning any source of organic carbon that is renewed rapidly as part of the carbon cycle. Biomass is derived from plant materials but can also include animal materials. The composition of lignocellulosic biomass varies, the major component is cellulose (35-50%), followed by xylan (20-35%, a type of hemicellulose) and lignin (10-25%), in addition to minor components such as proteins, oils and ash that make up the remaining fraction of lignocellulosic biomass. Lignocellulosic biomass contains a variety of carbohydrates. The term carbohydrate is most common in biochemistry, where it is a synonym of saccharide. Carbohydrates (saccharides) are divided into four chemical groupings: monosaccharides, disaccharides, oligosaccharides, and polysaccharides. In general, monosaccharides and disaccharides, which are smaller (lower molecular weight) carbohydrates, are commonly referred to as sugars.

A non-starch carbohydrate suitable for modification by a polypeptide of the invention is lignocellulose. The major polysaccharides comprising different lignocellulosic residues, which may be considered as a potential renewable feedstock, are cellulose (glucans), hemicelluloses (xylans, heteroxylans and xyloglucans). In addition, some hemicellulose may be present as glucomannans, for example in wood-derived feedstocks. The enzymatic hydrolysis of these polysaccharides to soluble sugars, for example glucose, xylose, arabinose, galactose, fructose, mannose, rhamnose, ribose, D-galacturonic acid and other hexoses and pentoses occurs under the action of different enzymes acting in concert.

Lignin fills the spaces in the cell wall between cellulose, hemicellulose, and pectin components, especially in xylem tracheids, vessel elements and sclereid cells. It is covalently linked to hemicellulose and, therefore, crosslinks different plant polysaccharides, conferring mechanical strength to the cell wall and by extension the plant as a whole. Lignin is a highly hydrophobic crosslinked aromatic polymeric material that is formed by different monolignol monomers, which can be methoxylated to various degrees. There are three monolignol monomers, methoxylated to various degrees: p-coumaryl alcohol, coniferyl alcohol, and sinapyl alcohol. These lignols are incorporated into lignin in the form of the phenylpropanoids p-hydroxyphenyl (H), guaiacyl (G), and syringyl (S), respectively. Biodegradation of lignin is a prerequisite for processing biofuel from plant raw materials. Lignin can be degraded by applying different pretreatment methods, or by using ligninases or lignin-modifying enzymes (LME's). The improving of lignin degradation would drive the output from biofuel processing to better gain or better efficiency factor, for example by improving the accessibility to the (hemi)cellulosic components or by removing lignin-(hemi)cellulose linkages in oligosaccharides released by the action of (hemi)cellulases.

In addition, pectins and other pectic substances such as arabinans may make up considerably proportion of the dry mass of typically cell walls from non-woody plant tissues (about a quarter to half of dry mass may be pectins).

Cellulose is a linear polysaccharide composed of glucose residues linked by β-1,4 bonds. The linear nature of the cellulose fibers, as well as the stoichiometry of the β-linked glucose (relative to α) generates structures more prone to interstrand hydrogen bonding than the highly branched α-linked structures of starch. Thus, cellulose polymers are generally less soluble, and form more tightly bound fibers than the fibers found in starch.

Hemicellulose is a complex polymer, and its composition often varies widely from organism to organism and from one tissue type to another. In general, a main component of hemicellulose is β-1,4-linked xylose, a five carbon sugar. However, this xylose is often branched at O-3 and/or O-2 and can be substituted with linkages to arabinose, galactose, mannose, glucuronic acid, galacturonic acid or by esterification to acetic acid (and esterification of ferulic acid to arabinose). Hemicellulose can also contain glucan, which is a general term for β-linked six carbon sugars (such as the β-(1,3)(1,4) glucans and heteroglucans mentioned previously) and additionally glucomannans (in which both glucose and mannose are present in the linear backbone, linked to each other by β-linkages).

The composition, nature of substitution, and degree of branching of hemicellulose is very different in dicotyledonous plants (dicots, i.e., plant whose seeds have two cotyledons or seed leaves such as lima beans, peanuts, almonds, peas, kidney beans) as compared to monocotyledonous plants (monocots; i.e., plants having a single cotyledon or seed leaf such as corn, wheat, rice, grasses, barley). In dicots, hemicellulose is comprised mainly of xyloglucans that are 1,4-β-linked glucose chains with 1,6-β-linked xylosyl side chains. In monocots, including most grain crops, the principal components of hemicellulose are heteroxylans. These are primarily comprised of 1,4-β-linked xylose backbone polymers with 1,3-α linkages to arabinose, galactose, mannose and glucuronic acid or 4-O-methyl-glucuronic acid as well as xylose modified by ester-linked acetic acids. Also present are β glucans comprised of 1,3- and 1,4-β-linked glucosyl chains. In monocots, cellulose, heteroxylans and β-glucans may be present in roughly equal amounts, each comprising about 15-25% of the dry matter of cell walls. Also, different plants may comprise different amounts of, and different compositions of, pectic substances. For example, sugar beet contains about 19% pectin and about 21% arabinan on a dry weight basis.

Accordingly, a composition of the invention may be tailored in view of the particular feedstock (also called substrate) which is to be used. That is to say, the spectrum of activities in a composition of the invention may vary depending on the feedstock in question.

Enzyme combinations or physical treatments can be administered concomitantly or sequentially. The enzymes can be produced either exogenously in microorganisms, yeasts, fungi, bacteria or plants, then isolated and added to the lignocellulosic feedstock. Alternatively, the enzymes are produced, but not isolated, and crude cell mass fermentation broth, or plant material (such as corn stover), and the like are added to the feedstock. Alternatively, the crude cell mass or enzyme production medium or plant material may be treated to prevent further microbial growth (for example, by heating or addition of antimicrobial agents), then added to the feedstock. These crude enzyme mixtures may include the organism producing the enzyme. Alternatively, the enzyme may be produced in a fermentation that uses feedstock (such as corn stover) to provide nutrition to an organism that produces an enzyme(s). In this manner, plants that produce the enzymes may serve as the lignocellulosic feedstock and be added into lignocellulosic feedstock.

Enzymatic Activity

Endo-1,4-β-glucanases (EG) and exo-cellobiohydrolases (CBH) catalyze the hydrolysis of insoluble cellulose to cellooligosaccharides (cellobiose as a main product), while β-glucosidases (BGL) convert the oligosaccharides, mainly cellobiose and cellotriose to glucose.

Xylanases together with other accessory enzymes, for example α-L-arabinofuranosidases, feruloyl and acetylxylan esterases, glucuronidases, and β-xylosidases) catalyze the hydrolysis of part of the hemicelluloses.

Pectic substances include pectins, arabinans, galactans and arabinogalactans. Pectins are the most complex polysaccharides in the plant cell wall. They are built up around a core chain of α(1,4)-linked D-galacturonic acid units interspersed to some degree with L-rhamnose. In any one cell wall there are a number of structural units that fit this description and it has generally been considered that in a single pectic molecule, the core chains of different structural units are continuous with one another.

Pectinases include, for example an endo-polygalacturonase, a pectin methyl esterase, an endo-galactanase, a β-galactosidase, a pectin acetyl esterase, an endo-pectin lyase, pectate lyase, α-rhamnosidase, an exo-galacturonase, an exo-polygalacturonate lyase, a rhamnogalacturonan hydrolase, a rhamnogalacturonan lyase, a rhamnogalacturonan acetyl esterase, a rhamnogalacturonan galacturonohydrolase, a xylogalacturonase, an α-arabinofuranosidase.

The principal types of structural unit are: galacturonan (homogalacturonan), which may be substituted with methanol on the carboxyl group and acetate on O-2 and O-3; rhamnogalacturonan I (RGI), in which galacturonic acid units alternate with rhamnose units carrying (1,4)-linked galactan and (1,5)-linked arabinan side-chains. The arabinan side-chains may be attached directly to rhamnose or indirectly through the galactan chains; xylogalacturonan, with single xylosyl units on O-3 of galacturonic acid (closely associated with RGI); and rhamnogalacturonan II (RGII), a particularly complex minor unit containing unusual sugars, for example apiose. An RGII unit may contain two apiosyl residues which, under suitable ionic conditions, can reversibly form esters with borate.

As set out above, a polypeptide of the invention will typically have an activity according to Table 1. However, a polypeptide of the invention may have one or more of the activities set out above in addition to or alternative to that activity. Also, a composition of the invention as described herein may have one or more of the activities mentioned above in addition to that provided by a polypeptide of the invention having an activity according to Table 1.

Polynucleotide Sequence

The invention provides genomic polynucleotide sequences comprising the gene encoding the Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 as well as its coding sequence. Accordingly, the invention relates to an isolated polynucleotide comprising the genomic nucleotide sequence according to the coding nucleotide sequence according to SEQ ID NO: 1, 6, 11, 16, 21, 26, 31, 36, 41, 46, 51, 56, 61, 66 or 71 or SEQ ID NO: 4, 9, 14, 19, 24, 29, 34, 39, 44, 49, 54, 59, 64, 69 or 74 or SEQ ID NO: 5, 10, 15, 20, 25, 30, 35, 40, 45, 50, 55, 60, 65, 70 or 75 and to variants, such as functional equivalents, of either thereof.

In particular, the invention relates to an isolated polynucleotide which is capable of hybridizing selectively, for example under stringent conditions, preferably under highly stringent conditions, with the reverse complement of a polynucleotide comprising the sequence set out in SEQ ID NO: 1, 6, 11, 16, 21, 26, 31, 36, 41, 46, 51, 56, 61, 66 or 71 or in SEQ ID NO: 4, 9, 14, 19, 24, 29, 34, 39, 44, 49, 54, 59, 64, 69 or 74 or in SEQ ID NO: 5, 10, 15, 20, 25, 30, 35, 40, 45, 50, 55, 60, 65, 70 or 75.

More specifically, the invention relates to a polynucleotide comprising or consisting essentially of a nucleotide sequence according to SEQ ID NO: 1, 6, 11, 16, 21, 26, 31, 36, 41, 46, 51, 56, 61, 66 or 71 or SEQ ID NO: 4, 9, 14, 19, 24, 29, 34, 39, 44, 49, 54, 59, 64, 69 or 74 or SEQ ID NO: 5, 10, 15, 20, 25, 30, 35, 40, 45, 50, 55, 60, 65, 70 or 75.

The invention also relates to an isolated polynucleotide comprising or consisting essentially of a sequence which encodes at least one functional domain of a polypeptide according to SEQ ID NO: 2, 7, 12, 17, 22, 27, 32, 37, 42, 47, 52, 57, 62, 67, 72 or a variant thereof, such as a functional equivalent, or a fragment of either thereof.

As used herein, the terms "gene" and "recombinant gene" refer to nucleic acid molecules which may be isolated from chromosomal DNA, which include an open reading frame encoding a protein, e.g. the activity according to the present invention.

A gene may include coding sequences, non-coding sequences, introns and/or regulatory sequences. Moreover, the term "gene" may refer to an isolated nucleic acid molecule as defined herein.

A nucleic acid molecule of the present invention, such as a nucleic acid molecule having the nucleotide sequence of SEQ ID NO: 1, 6, 11, 16, 21, 26, 31, 36, 41, 46, 51, 56, 61, 66 or 71 or SEQ ID NO: 4, 9, 14, 19, 24, 29, 34, 39, 44, 49, 54, 59, 64, 69 or 74 or SEQ ID NO: 5, 10, 15, 20, 25, 30, 35, 40, 45, 50, 55, 60, 65, 70 or 75 or a variant thereof, such as a functional equivalent, can be isolated using standard molecular biology techniques and the sequence information provided herein. For example, using all or a portion of the nucleic acid sequence of SEQ ID NO: 1, 6, 11, 16, 21, 26, 31, 36, 41,46, 51, 56, 61, 66 or 71 as a hybridization probe, nucleic acid molecules according to the invention can be isolated using standard hybridization and cloning techniques (e. g., as described in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989).

Moreover, a nucleic acid molecule encompassing all or a portion of SEQ ID NO: 1,6, 11, 16, 21, 26, 31, 36, 41, 46, 51, 56, 61, 66 or 71 or SEQ ID NO: 4, 9, 14, 19, 24, 29, 34, 39, 44, 49, 54, 59, 64, 69 or 74 or SEQ ID NO: 5, 10, 15, 20, 25, 30, 35, 40, 45, 50, 55, 60, 65, 70 or 75 may be isolated by the polymerase chain reaction (PCR) using synthetic oligonucleotide primers designed based upon the sequence information contained in SEQ ID NO: 1, 6, 11, 16, 21, 26, 31, 36, 41, 46, 51, 56, 61, 66 or 71 or in SEQ ID NO:

4, 9, 14, 19, 24, 29, 34, 39, 44, 49, 54, 59, 64, 69 or 74 or in SEQ ID NO: 5, 10, 15, 20, 25, 30, 35, 40, 45, 50, 55, 60, 65, 70 or 75.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis.

Furthermore, oligonucleotides corresponding to or hybridizable to a nucleotide sequence according to the invention can be prepared by standard synthetic techniques, e.g., using an automated DNA synthesizer.

In a preferred embodiment, an isolated nucleic acid molecule of the invention comprises the nucleotide sequence shown in SEQ ID NO: 1, 6, 11, 16, 21, 26, 31, 36, 41, 46, 51, 56, 61, 66 or 71 or in SEQ ID NO: 4, 9, 14, 19, 24, 29, 34, 39, 44, 49, 54, 59, 64, 69 or 74 or in SEQ ID NO: 5, 10, 15, 20, 25, 30, 35, 40, 45, 50, 55, 60, 65, 70 or 75.

In another preferred embodiment, an isolated nucleic acid molecule of the invention comprises a nucleic acid molecule which is the reverse complement of the nucleotide sequence shown in SEQ ID NO: 1, 6, 11, 16, 21, 26, 31, 36, 41, 46, 51, 56, 61, 66 or 71 or in SEQ ID NO: 4, 9, 14, 19, 24, 29, 34, 39, 44, 49, 54, 59, 64, 69 or 74 or in SEQ ID NO: 5, 10, 15, 20, 25, 30, 35, 40, 45, 50, 55, 60, 65, 70 or 75 or a variant, such as a functional equivalent, of either such nucleotide sequence.

A nucleic acid molecule which is complementary to another nucleotide sequence is one which is sufficiently complementary to the other nucleotide sequence such that it can hybridize to the other nucleotide sequence thereby forming a stable duplex.

One aspect of the invention pertains to isolated nucleic acid molecules that encode a polypeptide of the invention or a variant, such as a functional equivalent thereof, for example a biologically active fragment or domain, as well as nucleic acid molecules sufficient for use as hybridization probes to identify nucleic acid molecules encoding a polypeptide of the invention and fragments of such nucleic acid molecules suitable for use as PCR primers for the amplification or mutation of nucleic acid molecules.

A polynucleotide according to the invention may be "isolated". In the context of this invention, an "isolated polynucleotide" or "isolated nucleic acid" is a DNA or RNA that is not immediately contiguous with one or both of the coding sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g. promotor) sequences that are immediately contiguous to the coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA that is part of a hybrid gene encoding an additional polypeptide that is substantially free of cellular material, viral material, or culture medium (when produced by recombinant DNA techniques), or chemical precursors or other chemicals (when chemically synthesized). Moreover, an "isolated nucleic acid fragment" is a nucleic acid fragment that is not naturally occurring as a fragment and would not be found in the natural state.

As used herein, the terms "polynucleotide" or "nucleic acid molecule" are intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. The nucleic acid may be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

Another embodiment of the invention provides an isolated nucleic acid molecule which is antisense to a Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 nucleic acid molecule, e.g., the coding strand of a Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 nucleic acid molecule. Also included within the scope of the invention are the complementary strands of the nucleic acid molecules described herein.

Unless otherwise indicated, all nucleotide sequences determined by sequencing a DNA molecule herein were determined using an automated DNA sequencer and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule.

The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

The person skilled in the art is capable of identifying such erroneously identified bases and knows how to correct for such errors.

A nucleic acid molecule according to the invention may comprise only a portion or a fragment of the nucleic acid sequence shown in SEQ ID NO: 1, 6, 11, 16, 21, 26, 31, 36, 41, 46, 51, 56, 61, 66 or 71 or in SEQ ID NO: 4, 9, 14, 19, 24, 29, 34, 39, 44, 49, 54, 59, 64, 69 or 74 or in SEQ ID NO: 5, 10, 15, 20, 25, 30, 35, 40, 45, 50, 55, 60, 65, 70 or 75 (or of a variant of either thereof), for example a fragment which can be used as a probe or primer or a fragment encoding a portion of a Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 protein.

The nucleotide sequence determined from the cloning of the Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 gene and cDNA allows for the generation of probes and primers designed for use in identifying and/or cloning other Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 family members, as well as Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 homologues from other species.

The probe/primer typically comprises a substantially purified oligonucleotide which typically comprises a region of nucleotide sequence that hybridizes preferably under highly stringent conditions to at least from about 12 to about 15, preferably from about 18 to about 20, preferably from about 22 to about 25, more preferably about 30, about 35, about 40, about 45, about 50, about 55, about 60, about 65, or about 75 or more consecutive nucleotides of a nucleotide sequence shown in SEQ ID NO: 1, 6, 11, 16, 21, 26, 31, 36, 41, 46, 51, 56, 61, 66 or 71 or in SEQ ID NO: 4, 9, 14, 19, 24, 29, 34, 39, 44, 49, 54, 59, 64, 69 or 74 or in SEQ ID NO: 5, 10, 15, 20, 25, 30, 35, 40, 45, 50, 55, 60, 65, 70 or 75 or of a variant, such as a functional equivalent, of either thereof.

Probes based on the Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 nucleotide sequences can be used to detect transcripts or genomic Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 sequences encoding the same or homologous proteins for instance in other organisms. In preferred embodiments, the probe further comprises a label group attached thereto, e.g., the label group can be a radioisotope, a fluorescent compound, an enzyme, or an enzyme cofactor. Such probes can also be used as part of a diagnostic test kit for identifying cells which express a TEMER09484 protein.

The polynucleotides herein may be synthetic polynucleotides. The synthetic polynucleotides may be optimized in codon use, preferably according to the methods described in WO2006/077258 and/or PCT/EP2007/055943, which are herein incorporated by reference. PCT/EP2007/055943 addresses codon-pair optimization. Codon-pair optimization is a method wherein the nucleotide sequences encoding a polypeptide have been modified with respect to their codon-usage, in particular the codon-pairs that are used, to obtain improved expression of the nucleotide sequence encoding the polypeptide and/or improved production of the encoded polypeptide. Codon pairs are defined as a set of two subsequent triplets (codons) in a coding sequence.

The invention further relates to a nucleic acid construct comprising the polynucleotide as described before. "Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term "expression cassette" when the nucleic acid construct contains all the control sequences required for expression of a coding sequence. The term "coding sequence" as defined herein is a sequence, which is transcribed into mRNA and translated into a transcriptional activator of a protease promoter of the invention. The boundaries of the coding sequence are generally determined by the ATG start codon at the 5'end of the mRNA and a translation stop codon sequence terminating the open reading frame at the 3' end of the mRNA. A coding sequence can include, but is not limited to, DNA, cDNA, and recombinant nucleic acid sequences. Preferably, the nucleic acid has high GC content. The GC content herein indicates the number of G and C nucleotides in the construct, divided by the total number of nucleotides, expressed in %. The GC content is preferably 56% or more, 57% or more, 58% or more, 59% or more, 60% or more, or in the range of 56-70% or the range of 58-65%. Preferably, the DNA construct comprises a promoter DNA sequence, a coding sequence in operative association with said promoter DNA sequence and control sequences such as:

- one translational termination sequence orientated in 5' towards 3' direction selected from the following list of sequences: TAAG, TAGA and TAAA, preferably TAAA, and/or
- one translational initiator coding sequence orientated in 5' towards 3' direction selected from the following list of sequences: GCTACCCCC; GCTACCTCC; GCTAC-CCTC; GCTACCTTC; GCTCCCCCC; GCTC-CCTCC; GCTCCCCTC; GCTCCCTTC; GCTGC-CCCC; GCTGCCTCC; GCTGCCCTC; GCTGCCTTC; GCTTCCCCC; GCTTCCTCC; GCT-TCCCTC; and GCTTCCTTC, preferably GCT TCC TTC, and/or
- one translational initiator sequence selected from the following list of sequences: 5'-mwChkyCAAA-3'; 5'-mwChkyCACA-3' or 5'-mwChkyCAAG-3', using ambiguity codes for nucleotides: m (A/C); w (A/T); y (C/T); k (G/T); h (A/C/T), preferably 5'-CACCGT-CAAA-3' or 5'-CGCAGTCAAG-3'.

In the context of this invention, the term "translational initiator coding sequence" is defined as the nine nucleotides immediately downstream of the initiator or start codon of the open reading frame of a DNA coding sequence. The initiator or start codon encodes for the AA methionine. The initiator codon is typically ATG, but may also be any functional start codon such as GTG.

In the context of this invention, the term "translational termination sequence" is defined as the four nucleotides starting from the translational stop codon at the 3' end of the open reading frame or nucleotide coding sequence and oriented in 5' towards 3' direction.

In the context of this invention, the term "translational initiator sequence" is defined as the ten nucleotides immediately upstream of the initiator or start codon of the open reading frame of a DNA sequence coding for a polypeptide. The initiator or start codon encodes for the AA methionine. The initiator codon is typically ATG, but may also be any functional start codon such as GTG. It is well known in the art that uracil, U, replaces the deoxynucleotide thymine, T, in RNA.

Homology and Identity

Amino acid or nucleotide sequences are said to be homologous when exhibiting a certain level of similarity. Two sequences being homologous indicate a common evolutionary origin. Whether two homologous sequences are closely related or more distantly related is indicated by "percent identity" or "percent similarity", which is high or low respectively. Although disputed, to indicate "percent identity" or "percent similarity", "level of homology" or "percent homology" are frequently used interchangeably.

The terms "homology", "percent homology", "percent identity" or "percent similarity" are used interchangeably herein. For the purpose of this invention, it is defined here that in order to determine the percent identity of two amino acid sequences or of two nucleic acid sequences, the complete sequences are aligned for optimal comparison purposes. In order to optimize the alignment between the two sequences gaps may be introduced in any of the two sequences that are compared. Such alignment is carried out over the full length of the sequences being compared. Alternatively, the alignment may be carried out over a shorter length, for example over about 20, about 50, about 100 or more nucleic acids/based or amino acids. The identity is the percentage of identical matches between the two sequences over the reported aligned region.

A comparison of sequences and determination of percent identity between two sequences can be accomplished using a mathematical algorithm. The skilled person will be aware of the fact that several different computer programs are available to align two sequences and determine the homology between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent identity between two amino acid sequences can be determined using the Needleman and Wunsch algorithm for the alignment of two sequences. (Needleman, S. B. and Wunsch, C. D. (1970) J. Mol. Biol. 48, 443-453). The algorithm aligns amino acid sequences as well as nucleotide sequences. The Needleman-Wunsch algorithm has been implemented in the computer program NEEDLE. For the purpose of this invention the NEEDLE program from the EMBOSS package was used (version 2.8.0 or higher, *EMBOSS: The European Molecular Biology Open Software Suite* (2000) Rice, P. Longden, I. and Bleasby, A. Trends in Genetics 16, (6) pp 276-277, http://emboss.bioinformatics.nl/). For protein sequences, EBLOSUM62 is used for the substitution matrix. For nucleotide sequences, EDNAFULL is used. Other matrices can be specified. The optional parameters used for alignment of amino acid sequences are a gap-open penalty of 10 and a gap extension penalty of 0.5. The skilled person will appreciate that all these different parameters will yield slightly different results but that the overall percentage identity of two sequences is not significantly altered when using different algorithms.

Global Homology Definition

The homology or identity is the percentage of identical matches between the two full sequences over the total aligned region including any gaps or extensions. The homology or identity between the two aligned sequences is calculated as follows: Number of corresponding positions in the alignment showing an identical amino acid in both sequences divided by the total length of the alignment including the gaps. The identity defined as herein can be obtained from NEEDLE and is labelled in the output of the program as "IDENTITY".

Longest Identity Definition

The homology or identity between the two aligned sequences is calculated as follows: Number of corresponding positions in the alignment showing an identical amino acid in both sequences divided by the total length of the alignment after subtraction of the total number of gaps in the alignment. The identity defined as herein can be obtained from NEEDLE by using the NOBRIEF option and is labelled in the output of the program as "longest-identity". For purposes of the invention the level of identity (homology) between two sequences (amino acid or nucleotide) is calculated according to the definition of "longest-identity" as can be carried out by using the program NEEDLE.

The protein sequences of the present invention can further be used as a "query sequence" to perform a search against sequence databases, for example to identify other family members or related sequences. Such searches can be performed using the BLAST programs. Software for performing BLAST analyses is publicly available through the National Center for Biotechnology Information (http://www.ncbi.nlm.nih.gov). BLASTP is used for amino acid sequences and BLASTN for nucleotide sequences. The BLAST program uses as defaults:

Cost to open gap: default=5 for nucleotides/11 for proteins

Cost to extend gap: default=2 for nucleotides/1 for proteins

Penalty for nucleotide mismatch: default=−3

Reward for nucleotide match: default=1

Expect value: default=10

Wordsize: default=11 for nucleotides/28 for megablast/3 for proteins

Furthermore the degree of local identity (homology) between the amino acid sequence query or nucleic acid sequence query and the retrieved homologous sequences is determined by the BLAST program. However only those sequence segments are compared that give a match above a certain threshold. Accordingly the program calculates the identity only for these matching segments. Therefore the identity calculated in this way is referred to as local identity.

Vectors

Another aspect of the invention pertains to vectors, including cloning and expression vectors, comprising a polynucleotide of the invention encoding a TEMER09484 protein or a functional equivalent thereof and methods of growing, transforming or transfecting such vectors in a suitable host cell, for example under conditions in which expression of a polypeptide of the invention occurs. As used herein, the term "vector" refers to a nucleic acid molecule capable of transporting another nucleic acid to which it has been linked.

Polynucleotides of the invention can be incorporated into a recombinant replicable vector, for example a cloning or expression vector. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells are described below.

The vector into which the expression cassette or polynucleotide of the invention is inserted may be any vector which may conveniently be subjected to recombinant DNA procedures, and the choice of the vector will often depend on the host cell into which it is to be introduced.

A vector according to the invention may be an autonomously replicating vector, i. e. a vector which exists as an extra-chromosomal entity, the replication of which is independent of chromosomal replication, e. g. a plasmid. Alternatively, the vector may be one which, when introduced into a host cell, is integrated into the host cell genome and replicated together with the chromosome (s) into which it has been integrated.

One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. The terms "plasmid" and "vector" can be used interchangeably herein as the plasmid is the most commonly used form of vector. However, the invention is intended to include such other forms of expression vectors, such as cosmid, viral vectors (e.g., replication defective retroviruses, adenoviruses and adeno-associated viruses) and phage vectors which serve equivalent functions.

Vectors according to the invention may be used in vitro, for example for the production of RNA or used to transfect or transform a host cell.

A vector of the invention may comprise two or more, for example three, four or five, polynucleotides of the invention, for example for overexpression.

The recombinant expression vectors of the invention comprise a nucleic acid of the invention in a form suitable for expression of the nucleic acid in a host cell, which means that the recombinant expression vector includes one or more regulatory sequences, selected on the basis of the host cells to be used for expression, which is operably linked to the nucleic acid sequence to be expressed.

Within a vector, such as an expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell), i.e. the term "operably linked" refers to a juxtaposition wherein the components described are in a relationship permitting them to function in their intended manner. A regulatory sequence such as a promoter, enhancer or other expression regulation signal "operably linked" to a coding sequence is positioned in such a way that expression of the coding sequence is achieved under condition compatible with the control sequences or the sequences are arranged so that they function in concert for their intended purpose, for example transcription initiates at a promoter and proceeds through the DNA sequence encoding the polypeptide.

A vector or expression construct for a given host cell may thus comprise the following elements operably linked to each other in a consecutive order from the 5'-end to 3'-end relative to the coding strand of the sequence encoding the polypeptide of the first invention: (1) a promoter sequence capable of directing transcription of the nucleotide sequence encoding the polypeptide in the given host cell; (2) optionally, a signal sequence capable of directing secretion of the polypeptide from the given host cell into a culture medium; (3) a DNA sequence of the invention encoding a mature and preferably active form of a polypeptide having cellobiohydrolase activity; and preferably also (4) a transcription termination region (terminator) capable of terminating transcription downstream of the nucleotide sequence encoding the polypeptide.

Downstream of the nucleotide sequence according to the invention there may be a 3' untranslated region containing one or more transcription termination sites (e. g. a terminator). The origin of the terminator is less critical. The terminator can, for example, be native to the DNA sequence encoding the polypeptide. However, preferably a yeast terminator is used in yeast host cells and a filamentous fungal terminator is used in filamentous fungal host cells. More preferably, the terminator is endogenous to the host cell (in which the nucleotide sequence encoding the polypeptide is to be expressed). In the transcribed region, a ribosome binding site for translation may be present. The coding portion of the mature transcripts expressed by the constructs will include a translation initiating AUG at the beginning and a termination codon appropriately positioned at the end of the polypeptide to be translated.

Enhanced expression of the polynucleotide of the invention may also be achieved by the selection of heterologous regulatory regions, e. g. promoter, secretion leader and/or terminator regions, which may serve to increase expression and, if desired, secretion levels of the protein of interest from the expression host and/or to provide for the inducible control of the expression of a polypeptide of the invention.

It will be appreciated by those skilled in the art that the design of the expression vector can depend on such factors as the choice of the host cell to be transformed, the level of expression of protein desired, etc. The vectors, such as expression vectors, of the invention can be introduced into host cells to thereby produce proteins or peptides, encoded by nucleic acids as described herein (e.g. TEMER09484 proteins, mutant forms of TEMER09484 proteins, fragments, variants or functional equivalents thereof. The vectors, such as recombinant expression vectors, of the invention can be designed for expression of TEMER09484 proteins in prokaryotic or eukaryotic cells.

For example, TEMER09484 proteins can be expressed in bacterial cells such as *E. coli*, insect cells (using baculovirus expression vectors), filamentous fungi, yeast cells or mammalian cells. Suitable host cells are discussed further in Goeddel, Gene Expression Technology: Methods in Enzymology 185, Academic Press, San Diego, Calif. (1990). Representative examples of appropriate hosts are described hereafter.

Appropriate culture mediums and conditions for the above-described host cells are known in the art.

The recombinant expression vector can be transcribed and translated in vitro, for example using T7 promoter regulatory sequences and T7 polymerase.

For most filamentous fungi and yeast, the vector or expression construct is preferably integrated in the genome of the host cell in order to obtain stable transformants.

However, for certain yeasts also suitable episomal vectors are available into which the expression construct can be incorporated for stable and high level expression, examples thereof include vectors derived from the 2p and pKD1 plasmids of *Saccharomyces* and *Kluyveromyces*, respectively, or vectors containing an AMA sequence (e.g. AMA1 from *Aspergillus*). In case the expression constructs are integrated in the host cells genome, the constructs are either integrated at random loci in the genome, or at predetermined target loci using homologous recombination, in which case the target loci preferably comprise a highly expressed gene.

Accordingly, expression vectors useful in the present invention include chromosomal-, episomal- and virus-derived vectors e.g., vectors derived from bacterial plasmids, bacteriophage, yeast episome, yeast chromosomal elements, viruses such as baculoviruses, papova viruses, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids.

The term "control sequences" or "regulatory sequences" is defined herein to include at least any component which may be necessary and/or advantageous for the expression of a polypeptide. Any control sequence may be native or foreign to the nucleic acid sequence of the invention encoding a polypeptide. Such control sequences may include, but are not limited to, a promoter, a leader, optimal translation initiation sequences (as described in Kozak, 1991, J. Biol. Chem. 266:19867-19870), a secretion signal sequence, a pro-peptide sequence, a polyadenylation sequence, a transcription terminator. At a minimum, the control sequences typically include a promoter, and transcriptional and translational stop signals. As set out above, the term "operably linked" is defined herein as a configuration in which a control sequence is appropriately placed at a position relative to the coding sequence of the DNA sequence such that the control sequence directs the production of a polypeptide.

The control sequences may be provided with linkers for the purpose of introducing specific restriction sites facilitating ligation of the control sequences with the coding region of the nucleic acid sequence encoding a polypeptide. The term "operably linked" is defined herein as a configuration in which a control sequence is appropriately placed at a position relative to the coding sequence of the DNA sequence such that the control sequence directs the production of a polypeptide.

The control sequence may be an appropriate promoter sequence, a nucleic acid sequence, which is recognized by a host cell for expression of the nucleic acid sequence. The promoter sequence contains transcriptional control sequences, which mediate the expression of the polypeptide. The promoter may be any nucleic acid sequence, which shows transcriptional activity in the cell including mutant, truncated, and hybrid promoters, and may be obtained from genes encoding extracellular or intracellular polypeptides either homologous or heterologous to the cell.

The term "promoter" is defined herein as a DNA sequence that binds RNA polymerase and directs the polymerase to the correct downstream transcriptional start site of a nucleic acid sequence encoding a biological compound to initiate transcription. RNA polymerase effectively catalyzes the assembly of messenger RNA complementary to the appropriate DNA strand of a coding region. The term "promoter" will also be understood to include the 5'-non-coding region (between promoter and translation start) for translation after transcription into mRNA, cis-acting transcription control elements such as enhancers, and other nucleotide sequences capable of interacting with transcription factors. The promoter may be any appropriate promoter sequence suitable for a eukaryotic or prokaryotic host cell, which shows transcriptional activity, including mutant, truncated, and hybrid promoters, and may be obtained from polynucleotides encoding extra-cellular or intracellular polypeptides either homologous (native) or heterologous (foreign) to the cell. The promoter may be a constitutive or inducible promoter.

Preferably the promoter is an inducible promoter. More preferably the promoter is a carbohydrate inducible promoter. Carbohydrate inducible promoters that are preferably used are selected from a starch-inducible promoter (i.e. a promoter inducible by starch, a monomer, a dimer, a oligomer thereof, such as for example a maltose-inducible promoter, an isomaltose-inducible promoter), a cellulose-inducible promoter (i.e. a promoter inducible by cellulose, a monomer, a dimer and/or oligomer thereof, such as for example a cellobiose-inducible promoter, a sophorose-inducible promoter), a hemicellulose inducible promoter (i.e. a promoter inducible by hemicellulose, a monomer, a dimer, and/or a oligomer thereof, such as e.g. a xylan-inducible promoter, an arabinose-inducible promoter, a xylose-inducible promoter), a pectin-inducible promoter (i.e. a promoter inducible by pectin, a monomer, a dimer and/or an oligomer thereof such as for example a galacturonic acid-inducible promoter, a rhamnose-inducible promoter), an arabinan-inducible promoter (i.e. a promoter inducible by arabinan, a monomer, a dimer, and/or an oligomer thereof such as for example an arabinose-inducible promoter), a glucose-inducible promoter, a lactose-inducible promoter, a galactose-inducible promoter. Other inducible promoters are copper-, oleic acid-inducible promoters.

Promoters suitable in filamentous fungi are promoters which may be selected from the group, which includes but is not limited to promoters obtained from the polynucleotides encoding *A. oryzae* TAKA amylase, *Rhizomucor miehei* aspartic proteinase, *Aspergillus* gpdA promoter, *A. niger* neutral alpha-amylase, *A. niger* acid stable alpha-amylase, *A. niger* or *A. awamori* glucoamylase (glaA), *A. niger* or *A. awamori* endoxylanase (xlnA) or beta-xylosidase (xlnD), *T. reesei* cellobiohydrolase I (CBHI), *R. miehei* lipase, *A. oryzae* alkaline protease, *A. oryzae* triose phosphate isomerase, *A. nidulans* acetamidase, *Fusarium venenatum* amyloglucosidase (WO 00/56900), *Fusarium venenatum* Dania (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the polynucleotides encoding *A. niger* neutral alpha-amylase and *A. oryzae* triose phosphate isomerase), and mutant, truncated, and hybrid promoters thereof. Other examples of promoters are the promoters described in WO2006/092396 and WO2005/100573, which are herein incorporated by reference. An even other example of the use of promoters is described in WO2008/098933. Preferred carbohydrate inducible promoters which can be used in filamentous fungi are the *A. oryzae* TAKA amylase, *A. niger* neutral alpha-amylase, *A. niger* acid stable alpha-amylase, *A. niger* or *A. awamori* glucoamylase (glaA), *A. niger* or *A. awamori* endoxylanase (xlnA) or beta-xylosidase (xlnD), T., *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the polynucleotides encoding

*A. niger* neutral alpha-amylase and *A. oryzae* triose phosphate isomerase) as defined above.

Examples of such promoters from Gram-positive microorganisms include, but are not limited to, gnt (gluconate operon promoter); penP from *Bacillus licheniformis*; glnA (glutamine synthetase); xylAB (xylose operon); araABD (L-arabinose operon) and Pspac promoter, a hybrid SPO1/lac promoter that can be controlled by inducers such as isopropyl-β-D-thiogalactopyranoside [IPTG] ((Yansura D. G., Henner D. J. Proc Natl Acad Sci USA. 1984 81(2):439-443). Activators are also sequence-specific DNA binding proteins that induce promoter activity. Examples of such promoters from Gram-positive microorganisms include, but are not limited to, two-component systems (PhoP-PhoR, DegU-DegS, SpoOA-Phosphorelay), LevR, Mry and GltC. (ii) Production of secondary sigma factors can be primarily responsible for the transcription from specific promoters. Examples from Gram-positive microorganisms include, but are not limited to, the promoters activated by sporulation specific sigma factors: σF, σE, σG and σK and general stress sigma factor, σB. The σB-mediated response is induced by energy limitation and environmental stresses (Hecker M, Völker U. Mol Microbiol. 1998; 29(5):1129-1136.). (iii) Attenuation and antitermination also regulates transcription. Examples from Gram-positive microorganisms include, but are not limited to, trp operon and sacB gene. (iv) Other regulated promoters in expression vectors are based the sacR regulatory system conferring sucrose inducibility (Klier A F, Rapoport G. Annu Rev Microbiol. 1988; 42:65-95).

Suitable inducible promoters useful in bacteria, such as Bacilli, include: promoters from Gram-positive microorganisms such as, but are not limited to, SP01-26, SP01-15, veg, pyc (pyruvate carboxylase promoter), and amyE. Examples of promoters from Gram-negative microorganisms include, but are not limited to, tac, tet, trp-tet, lpp, lac, lpp-lac, laclq, T7, T5, T3, gal, trc, ara, SP6, λ-PR, and λ-PL.

Additional examples of promoters useful in bacterial cells, such as Bacilli, include the α-amylase and SPo2 promoters as well as promoters from extracellular protease genes.

Another example of a suitable promoter is the promoter obtained from the *E. coli* lac operon. Another example is the promoter of the *Streptomyces coelicolor* agarase gene (dagA). Another example is the promoter of the *Bacillus lentus* alkaline protease gene (aprH). Another example is the promoter of the *Bacillus licheniformis* alkaline protease gene (subtilisin Carlsberg gene). Another example is the promoter of the *Bacillus subtilis* levansucrase gene (sacB). Another example is the promoter of the *Bacillus subtilis* alphaamylase gene (amyF). Another example is the promoter of the *Bacillus licheniformis* alphaamylase gene (amyL). Another example is the promoter of the *Bacillus stearothermophilus* maltogenic amylase gene (amyM). Another example is the promoter of the *Bacillus amyloliquefaciens* alpha-amylase gene (amyQ). Another example is a "consensus" promoter having the sequence TTGACA for the "−35" region and TATAAT for the "−10" region. Another example is the promoter of the *Bacillus licheniformis* penicillinase gene (penP). Another example are the promoters of the *Bacillus subtilis* xylA and xylB genes.

Preferably the promoter sequence is from a highly expressed gene. Examples of preferred highly expressed genes from which promoters may be selected and/or which are comprised in preferred predetermined target loci for integration of expression constructs, include but are not limited to genes encoding glycolytic enzymes such as triose-phosphate isomerases (TPI), glyceraldehyde-phosphate dehydrogenases (GAPDH), phosphoglycerate kinases (PGK), pyruvate kinases (PYK or PKI), alcohol dehydrogenases (ADH), as well as genes encoding amylases, glucoamylases, proteases, xylanases, cellobiohydrolases, β-galactosidases, alcohol (methanol) oxidases, elongation factors and ribosomal proteins. Specific examples of suitable highly expressed genes include e. g. the LAC4 gene from *Kluyveromyces* sp., the methanol oxidase genes (AOX and MOX) from *Hansenula* and *Pichia*, respectively, the glucoamylase (glaA) genes from *A. niger* and *A. awamori*, the *A. oryzae* TAKA-amylase gene, the *A. nidulans* gpdA gene and the *T. reesei* cellobiohydrolase genes.

Promoters which can be used in yeast include e.g. promoters from glycolytic genes, such as the phosphofructokinase (PFK), triose phosphate isomerase (TPI), glyceraldehyde-3-phosphate dehydrogenase (GPD, TDH3 or GAPDH), pyruvate kinase (PYK), phosphoglycerate kinase (PGK) promoters from yeasts or filamentous fungi; more details about such promoters from yeast may be found in (WO 93/03159). Other useful promoters are ribosomal protein encoding gene promoters, the lactase gene promoter (LAC4), alcohol dehydrogenase promoters (ADHI, ADH4, and the like), and the enolase promoter (ENO). Other promoters, both constitutive and inducible, and enhancers or upstream activating sequences will be known to those of skill in the art. The promoters used in the host cells of the invention may be modified, if desired, to affect their control characteristics. Suitable promoters in this context include both constitutive and inducible natural promoters as well as engineered promoters, which are well known to the person skilled in the art. Suitable promoters in eukaryotic host cells may be GAL7, GAL10, or GAL1, CYC1, HIS3, ADH1, PGL, PH05, GAPDH, ADC1, TRP1, URA3, LEU2, ENO1, TPI1, and AOX1. Other suitable promoters include PDC1, GPD1, PGK1, TEF1, and TDH3. Examples of carbohydrate inducible promoters which can be used are GAL promoters, such as GAL1 or GAL10 promoters.

All of the above-mentioned promoters are readily available in the art.

Transcription of the DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

The control sequence may also be a suitable transcription terminator sequence, a sequence recognized by a filamentous fungal cell to terminate transcription. The terminator sequence is operably linked to the 3' terminus of the nucleic acid sequence encoding the polypeptide. Any terminator, which is functional in the cell, may be used in the present invention.

The control sequence may also be a terminator. Preferred terminators for filamentous fungal cells are obtained from the genes encoding *A. oryzae* TAKA amylase, *A. niger* glucoamylase (glaA), *A. nidulans* anthranilate synthase, *A. niger* alpha-glucosidase, trpC gene and *Fusarium oxysporum* trypsin-like protease.

The control sequence may also include a suitable leader sequence, a non-translated region of a mRNA which is important for translation by the filamentous fungal cell. The leader sequence is operably linked to the 5' terminus of the nucleic acid sequence encoding the polypeptide. Any leader sequence, which is functional in the cell, may be used in the present invention. Preferred leaders for filamentous fungal cells are obtained from the genes encoding *A. oryzae* TAKA amylase and *A. nidulans* triose phosphate isomerase and *A. niger* glaA. Other preferred sequences are isolated and/or disclosed in WO2006/077258.

Other control sequences may be isolated from the *Penicillium* IPNS gene, or pcbC gene, the beta tubulin gene. All the control sequences cited in WO 01/21779 are herewith incorporated by reference.

The control sequence may also be a polyadenylation sequence, a sequence which is operably linked to the 3' terminus of the nucleic acid sequence and which, when transcribed, is recognized by the filamentous fungal cell as a signal to add polyadenosine residues to transcribed mRNA. Any polyadenylation sequence, which is functional in the cell, may be used in the present invention. Preferred polyadenylation sequences for filamentous fungal cells are obtained from the genes encoding *A. oryzae* TAKA amylase, *A. niger* glucoamylase, *A. nidulans* anthranilate synthase, *Fusarium oxysporum* trypsin-like protease and *A. niger* alpha-glucosidase.

When the polypeptide according to the invention is to be secreted from the host cell into the cultivation medium, an appropriate signal sequence can be added to the polypeptide in order to direct the de novo synthesized polypeptide to the secretion route of the host cell. The person skilled in the art knows to select an appropriate signal sequence for a specific host. The signal sequence may be native to the host cell, or may be foreign to the host cell. As an example, a signal sequence from a protein native to the host cell can be used. Preferably, said native protein is a highly secreted protein, i.e. a protein that is secreted in amounts higher than 10% of the total amount of protein being secreted. The signal sequences preferably used according to the invention are for example: pmeA.

As an alternative for a signal sequence, the polypeptide of the invention can be fused to a secreted carrier protein, or part thereof. Such chimeric construct is directed to the secretion route by means of the signal sequence of the carrier protein, or part thereof. In addition, the carrier protein will provide a stabilizing effect to the polypeptide according to the invention and or may enhance solubility. Such carrier protein may be any protein. Preferably, a highly secreted protein is used as a carrier protein. The carrier protein may be native or foreign to the polypeptide according to the invention. The carrier protein may be native of may be foreign to the host cell. Examples of such carrier proteins are glucoamylase, prepro sequence of alpha-Mating factor, cellulose binding domain of *Clostridium cellulovorans* cellulose binding protein A, glutathione S-transferase, chitin binding domain of *Bacillus circulans* chitinase A1, maltose binding domain encoded by the malE gene of *E. coli* K12, beta-galactosidase, and alkaline phosphatase. A preferred carrier protein for expression of such chimeric construct in *Aspergillus* cells is glucoamylase. The carrier protein and polypeptide according to the invention may contain a specific amino acid motif to facilitate isolation of the polypeptide; the polypeptide according to the invention may be released by a special releasing agent. The releasing agent may be a proteolytic enzyme or a chemical agent. An example of such amino acid motif is the KEX protease cleavage site, which is well-known to the person skilled in the art.

A signal sequence can be used to facilitate secretion and isolation of a protein or polypeptide of the invention. Signal sequences are typically characterized by a core of hydrophobic amino acids, which are generally cleaved from the mature protein during secretion in one or more cleavage events. Such signal peptides contain processing sites that allow cleavage of the signal sequence from the mature proteins as they pass through the secretory pathway. The signal sequence directs secretion of the protein, such as from a eukaryotic host into which the expression vector is transformed, and the signal sequence is subsequently or concurrently cleaved. The protein can then be readily purified from the extracellular medium by known methods. Alternatively, the signal sequence can be linked to the protein of interest using a sequence, which facilitates purification, such as with a GST domain. Thus, for instance, the sequence encoding the polypeptide may be fused to a marker sequence, such as a sequence encoding a peptide, which facilitates purification of the fused polypeptide. In certain preferred embodiments of this aspect of the invention, the marker sequence is a hexa-histidine peptide, such as the tag provided in a pQE vector (Qiagen, Inc.), among others, many of which are commercially available. As described in Gentz et al, Proc. Natl. Acad. Sci. USA 86:821-824 (1989), for instance, hexa-histidine provides for convenient purification of the fusion protein. The HA tag is another peptide useful for purification which corresponds to an epitope derived of influenza hemaglutinin protein, which has been described by Wilson et al., Cell 37:767 (1984), for instance.

Preferably, a TEMER09484 fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers, which give rise to complementary overhangs between two consecutive gene fragments which can subsequently be annealed and reamplified to generate a chimeric gene sequence (see, for example, Current Protocols in Molecular Biology, eds. Ausubel et al. John Wiley & Sons: 1992). Moreover, many expression vectors are commercially available that already encode a fusion moiety (e.g., a GST polypeptide). A TEMER09484-encoding nucleic acid can be cloned into such an expression vector such that the fusion moiety is linked in-frame to the TEMER09484 protein.

(Over)Expression

In a preferred embodiment, the polynucleotides of the present invention as described herein may be over-expressed in a microbial strain of the invention compared to the parent microbial strain in which said gene is not over-expressed. Over-expression of a polynucleotide sequence is defined herein as the expression of the said sequence gene which results in an activity of the enzyme encoded by the said sequence in a microbial strain being at least about 1.5-fold the activity of the enzyme in the parent microbial; preferably the activity of said enzyme is at least about 2-fold, more preferably at least about 3-fold, more preferably at least about 4-fold, more preferably at least about 5-fold, even more preferably at least about 10-fold and most preferably at least about 20-fold the activity of the enzyme in the parent microbial.

The vector may further include sequences flanking the polynucleotide giving rise to RNA which comprise sequences homologous to eukaryotic genomic sequences or viral genomic sequences. This will allow the introduction of the polynucleotides of the invention into the genome of a host cell.

An integrative cloning vector may integrate at random or at a predetermined target locus in the chromosome(s) of the host cell into which it is to be integrated. In a preferred embodiment of the invention, an integrative cloning vector may comprise a DNA fragment which is homologous to a DNA sequence in a predetermined target locus in the genome of host cell for targeting the integration of the cloning vector to this predetermined locus. In order to promote targeted integration, the cloning vector may be preferably linearized prior to transformation of the host cell. Linearization may preferably be performed such that at least one but preferably either end of the cloning vector is flanked by sequences homologous to the target locus. The length of the homologous sequences flanking the target locus is preferably at least about 0.1 kb, such as about at least 0.2 kb, more preferably at least about 0.5 kb, even more preferably at least about 1 kb, most preferably at least about 2 kb. Preferably, the parent host strains may be modified for improved frequency of targeted DNA integration as described in WO05/095624 and/or WO2007/115886.

The deletion example provided in the present invention, uses the promoter of the gene as 5'-flank and the gene as the 3'-flank to insert a selection marker between the promoter and gene, thereby disturbing (i.e. functionally inactivating) gene transcription. The gene sequences given above can be used to make similar functionally inactivated genes. The genes may be split in two, yielding a 5'-flank and a 3'-flank, but the gene may also be used to clone a larger piece of genomic DNA containing the promoter and terminator regions of the gene, which than can function as 5'-flank and a 3'-flanks.

The vector system may be a single vector, such as a single plasmid, or two or more vectors, such as two or more plasmids, which together contain the total DNA to be introduced into the genome of the host cell.

The vector may contain a polynucleotide of the invention oriented in an antisense direction to provide for the production of antisense RNA.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, transduction, infection, lipofection, cationic lipid-mediated transfection or electroporation. Suitable methods for transforming or transfecting host cells can be found in Sambrook, et al. (Molecular Cloning: A Laboratory Manual, $2^{nd}$, ed. Cold Spring Harbor Laboratory, Cold Spring Harbor Laboratory Press, Cold Spring Harbor, N.Y., 1989), Davis et al., Basic Methods in Molecular Biology (1986) and other laboratory manuals.

The person skilled in the art knows how to transform cells with the one or more expression cassettes and the selectable marker. For example, the skilled person may use one or more expression vectors, wherein the one or more cloning vectors comprise the expression cassettes and the selectable marker.

Transformation of the mutant microbial host cell may be conducted by any suitable known methods, including e.g. electroporation methods, particle bombardment or microprojectile bombardment, protoplast methods and *Agrobacterium* mediated transformation (AMT). Preferably the protoplast method is used. Procedures for transformation are described by J. R. S. Fincham, Transformation in fungi. 1989, Microbiological reviews. 53, 148-170.

Transformation may involve a process consisting of protoplast formation, transformation of the protoplasts, and regeneration of the cell wall in a manner known perse. Suitable procedures for transformation of *Aspergillus* cells are described in EP 238 023 and Yelton et al., 1984, Proceedings of the National Academy of Sciences USA 81:1470-1474. Suitable procedures for transformation of *Aspergillus* and other filamentous fungal host cells using *Agrobacterium tumefaciens* are described in e.g. De Groot et al., *Agrobacterium tumefaciens*-mediated transformation of filamentous fungi. Nat Biotechnol. 1998, 16:839-842. Erratum in: Nat Biotechnol 1998 16:1074. A suitable method of transforming *Fusarium* species is described by Malardier et al., 1989, Gene 78:147156 or in WO 96/00787. Other methods can be applied such as a method using biolistic transformation as described in: Christiansen et al., *Biolistic transformation of the obligate plant pathogenic fungus, Erysiphe graminis* f. sp. *hordei*. 1995, Curr Genet. 29:100-102. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, Journal of Bacteriology 153: 163; and Hinnen et al., 1978, Proceedings of the National Academy of Sciences USA 75: 1920.

In order to enhance the amount of copies of the polynucleotide coding for the compound of interest or coding for a compound involved in the production by the cell of the compound of interest (the gene) in the mutated microbial host cell, multiple transformations of the host cell may be required. In this way, the ratios of the different enzymes produced by the host cell may be influenced. Also, an expression vector may comprise multiple expression cassettes to increase the amount of copies of the polynucleotide(s) to be transformed.

Another way could be to choose different control sequences for the different polynucleotides, which—depending on the choice—may cause a higher or a lower production of the desired polypeptide(s).

The cells transformed with the selectable marker can be selected based on the presence of the selectable marker. In case of transformation of (*Aspergillus*) cells, usually when the cell is transformed with all nucleic acid material at the same time, when the selectable marker is present also the polynucleotide(s) encoding the desired polypeptide(s) are present.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include, but are not limited to, those which confer resistance to drugs or which complement a defect in the host cell. They include e. g. versatile marker genes that can be used for transformation of most filamentous fungi and yeasts such as acetamidase genes or cDNAs (the amdS, niaD, facA genes or cDNAs from *A. nidulans, A. oryzae* or *A. niger*), or genes providing resistance to antibiotics like G418, hygromycin, bleomycin, kanamycin, methotrexate, phleomycin orbenomyl resistance (benA). Alternatively, specific selection markers can be used such as auxotrophic markers which require corresponding mutant host strains: e. g. URA3 (from *S. cerevisiae* or analogous genes from other yeasts), pyrG or pyrA (from *A. nidulans* or *A. niger*), argB (from *A. nidulans* or *A. niger*) or trpC. In a preferred embodiment the selection marker is deleted from the transformed host cell after introduction of the expression construct so as to obtain transformed host cells capable of producing the polypeptide which are free of selection marker genes.

Other markers include ATP synthetase, subunit 9 (oliC), orotidine-5'-phosphate decarboxylase (pvrA), the bacterial G418 resistance gene (this may also be used in yeast, but not in fungi), the ampicillin resistance gene (*E. coli*), the neomycin resistance gene (*Bacillus*) and the *E. coli* uidA gene, coding for β-glucuronidase (GUS). Vectors may be used in vitro, for example for the production of RNA or used to transfect or transform a host cell.

Expression of proteins in prokaryotes is often carried out in *E. coli* with vectors containing constitutive or inducible promoters directing the expression of either fusion or non-fusion proteins. Fusion vectors add a number of amino acids to a protein encoded therein, e.g. to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein.

As indicated, the expression vectors will preferably contain selectable markers. Such markers include dihydrofolate reductase or neomycin resistance for eukaryotic cell culture and tetracyline or ampicillin resistance for culturing in *E. coli* and other bacteria.

Vectors preferred for use in bacteria are for example disclosed in WO-A1-2004/074468, which are hereby enclosed by reference. Other suitable vectors will be readily apparent to the skilled artisan.

For secretion of the translated protein into the lumen of the endoplasmic reticulum, into the periplasmic space or into the extracellular environment, appropriate secretion signal may be incorporated into the expressed polypeptide. The signals may be endogenous to the polypeptide or they may be heterologous signals.

The TEMER09484 polypeptide may be expressed in a modified form, such as a fusion protein, and may include not only secretion signals but also additional heterologous functional regions. Thus, for instance, a region of additional amino acids, particularly charged amino acids, may be added to the N-terminus of the polypeptide to improve stability and persistence in the host cell, during purification or during subsequent handling and storage. Also, peptide moieties may be added to the polypeptide to facilitate purification The invention provides an isolated polypeptide having the amino acid sequence according to SEQ ID NO: 2, 7, 12, 17, 22, 27, 32, 37, 42, 47, 52, 57, 62, 67 or 72, and an amino acid sequence obtainable by expressing the polynucleotide of SEQ ID NO: 1, 6, 11, 16, 21, 26, 31,36, 41, 46, 51, 56, 61, 66 or 71 or SEQ ID NO: 4, 9, 14, 19, 24, 29, 34, 39, 44, 49, 54, 59, 64, 69 or 74 or SEQ ID NO: 5, 10, 15, 20, 25, 30, 35, 40, 45, 50, 55, 60, 65, 70 or 75 in an appropriate host. Also, a peptide or polypeptide comprising a variant of the above polypeptides, such as a functional equivalent, is comprised within the present invention. The above polypeptides are collectively comprised in the term "polypeptides according to the invention"

The term "variant peptide" or "variant polypeptide" is defined herein as a peptide or polypeptide, respectively, comprising one or more alterations, such as substitutions, insertions, deletions and/or truncations of one or more specific amino acid residues at one or more specific positions in the peptide or polypeptide, respectively. Accordingly, a variant signal peptide is a signal peptide comprising one or more alterations, such as substitutions, insertions, deletions and/or truncations of one or more specific amino acid residues at one or more specific positions in the signal peptide.

The term "polynucleotide" is identical to the term "nucleic acid molecule" and can herein be read interchangeably. The term refers to a polynucleotide molecule, which is a ribonucleic acid (RNA) or deoxyribonucleic acid (DNA) molecule, either single stranded or double stranded. A polynucleotide may either be present in isolated form, or be comprised in recombinant nucleic acid molecules or vectors, or be comprised in a host cell.

The term "variant polynucleotide" is defined herein as a polynucleotide comprising one or more alterations, such as substitutions, insertions, deletions and/or truncations of one or more nucleotides at one or more specific positions in the polynucleotide.

The terms "peptide" and "oligopeptide" are considered synonymous (as is commonly recognized) and each term can be used interchangeably, as the context requires, to indicate a chain of at least two amino acids coupled by peptidyl linkages. The word "polypeptide" is used herein for chains containing more than seven amino acid residues. All oligopeptide and polypeptide formulas or sequences herein are written from left to right and in the direction from amino terminus to carboxy terminus. The one-letter code of amino acids used herein is commonly known in the art and can be found in Sambrook, et al. (Molecular Cloning: A Laboratory Manual, $2^{nd}$, ed. Cold Spring Harbor Laboratory, Cold Spring Harbor Laboratory Press, Cold Spring Harbor, N.Y., 1989)

By "isolated" polypeptide or protein is intended a polypeptide or protein removed from its native environment. For example, recombinantly produced polypeptides and proteins expressed in host cells are considered isolated for the purpose of the invention as are native or recombinant polypeptides which have been substantially purified by any suitable technique such as, for example, the single-step purification method disclosed in Smith and Johnson, Gene 67:31-40 (1988).

The Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 protein according to the invention can be recovered and purified from recombinant cell cultures by methods known in the art. Most preferably, high performance liquid chromatography ("HPLC") is employed for purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

The invention also features biologically active fragments of the polypeptides according to the invention.

Biologically active fragments of a polypeptide of the invention include polypeptides comprising amino acid sequences sufficiently identical to or derived from the amino acid sequence of the Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 protein (e.g., the amino acid sequence of SEQ ID NO: 2, 7, 12, 17, 22, 27, 32, 37, 42, 47, 52, 57, 62, 67 or 72), which include fewer amino acids than the full length protein but which exhibit at least one biological activity of the corresponding full-length protein. Typically, biologically active fragments comprise a domain or motif with at least one activity of the Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 protein.

A biologically active fragment of a protein of the invention can be a polypeptide which is, for example, about 10, about 25, about 50, about 100 or more amino acids in length or at least about 100 amino acids, at least 150, 200, 250, 300, 350, 400 amino acids in length, or of a length up the total number of amino acids of polypeptide of the invention.

Moreover, other biologically active portions, in which other regions of the protein are deleted, can be prepared by recombinant techniques and evaluated for one or more of the biological activities of the native form of a polypeptide of the invention. The invention also features nucleic acid fragments which encode the above biologically active fragments of the Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 protein.

Proteins

In another aspect of the invention, improved Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 proteins are provided. Improved Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 proteins are proteins wherein at least one biological activity is improved. Such proteins may be obtained by randomly introducing mutations along all or part of the Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 coding sequence, such as by saturation mutagenesis, and the resulting mutants can be expressed recombinantly and screened for biological activity. For instance, the art provides for standard assays for measuring the enzymatic activity of the protein of the invention and thus improved proteins may easily be selected.

Improved variants of the amino acid sequences of the present invention leading to an improved cellobiohydrolase function may be obtained by the corresponding genes of the present invention. Among such modifications are included:
1. Error prone PCR to introduce random mutations, followed by a screening of obtained variants and isolating of variants with improved kinetic properties
2. Family shuffling of related variants of the genes encoding the cellobiohydrolase, followed by a screening of obtained variants and isolating of variants with improved kinetic properties Variants of the genes of the present invention leading to an increased level of mRNA and/or protein, resulting in more an activity according to Table 1 may be obtained by the polynucleotide sequences of said genes. Among such modifications are included:
1. Improving the codon usage in such a way that the codons are (optimally) adapted to the parent microbial host.
2. Improving the codon pair usage in such a way that the codons are (optimally)adapted to the parent microbial host
3. Addition of stabilizing sequences to the genomic information encoding the cellobiohydrolase resulting in mRNA molecules with an increased half life Preferred methods to isolate variants with improved catalytic properties or increased levels of mRNA or protein are described in WO03/010183 and WO03/01311. Preferred methods to optimize the codon usage in parent microbial strains are described in PCT/EP2007/05594. Preferred methods for the addition of stabilizing elements to the genes encoding the cellobiohydrolase of the invention are described in WO2005/059149.

In a preferred embodiment the protein of the invention has an amino acid sequence according to SEQ ID NO: 2, 7, 12, 17, 22, 27, 32, 37, 42, 47, 52, 57, 62, 67 or 72. In another embodiment, the polypeptide of the invention is substantially homologous to the amino acid sequence according to SEQ ID NO: 2, 7, 12, 17, 22, 27, 32, 37, 42, 47, 52, 57, 62, 67 or 72 and retains at least one biological activity of a polypeptide according to SEQ ID NO: 2, 7, 12, 17, 22, 27, 32, 37, 42, 47, 52, 57, 62, 67 or 72, yet differs in amino acid sequence due to natural variation or mutagenesis as described.

In a further preferred embodiment, the protein of the invention has an amino acid sequence encoded by an isolated nucleic acid fragment capable of hybridizing to a nucleic acid according to SEQ ID NO: 1, 6, 11, 16, 21, 26, 31, 36, 41, 46, 51, 56, 61, 66 or 71 or SEQ ID NO: 4, 9, 14, 19, 24, 29, 34, 39, 44, 49, 54, 59, 64, 69 or 74 or SEQ ID NO: 5, 10, 15, 20, 25, 30, 35, 40, 45, 50, 55, 60, 65, 70 or 75, preferably under highly stringent hybridization conditions.

Accordingly, the Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 protein or the protein of the invention is preferably a protein which comprises an amino acid sequence at least 50%, at least 60%, at least 65%, at least 70%, at least 75%, at least 80%, at least 85%, at least 90%, at least 91%, 92%, 93%, 94%, 95%, 96%, 95%, 96%, 97%, 98%, 97%, 98%, 99%, 99.8%, 99.9% or more homologous to the amino acid sequence shown in SEQ ID NO: 2, 7, 12, 17, 22, 27, 32, 37, 42, 47, 52, 57, 62, 67 or 72 and, typically, retains at least one functional activity of the polypeptide according to SEQ ID NO: 2, 7, 12, 17, 22, 27, 32, 37, 42, 47, 52, 57, 62, 67 or 72.

According to one aspect of the invention the polypeptide of the invention may comprise the amino acid sequence set out in SEQ ID NO: 2, 7, 12, 17, 22, 27, 32, 37, 42, 47, 52, 57, 62, 67 or 72 or an amino acid sequence that differs in 1, 2, 3, 4, 5, 6, 7, 8, 9, 10, 11 or 12 amino acids from the amino acid sequence set out in SEQ ID NO: 2, 7, 12, 17, 22, 27, 32, 37, 42, 47, 52, 57, 62, 67 or 72 and whereby the polypeptide still has the activity or function of the polypeptide of the invention. The skilled person will appreciate that these minor amino acid changes in the polypeptide of the invention may be present (for example naturally occurring mutations) or made (for example using r-DNA technology) without loss of the protein function or activity. In case these mutations are present in a binding domain, active site, or other functional domain of the polypeptide a property of the polypeptide may change (for example its thermostability) but the polypeptide may keep its hemicellulase activity. In case a mutation is present which is not close to the active site, binding domain, or other functional domain, less effect may be expected.

Functional equivalents of a protein according to the invention can also be identified e.g. by screening combinatorial libraries of mutants, e.g. truncation mutants, of the protein of the invention for an activity according to Table 1. In one embodiment, a variegated library of variants is generated by combinatorial mutagenesis at the nucleic acid level. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g. for phage display). There are a variety of methods that can be used to produce libraries of potential variants of the polypeptides of the invention from a degenerate oligonucleotide sequence. Methods for synthesizing degenerate oligonucleotides are known in the art (see, e.g., Narang (1983) Tetrahedron 39:3; Itakura et al. (1984) Annu. Rev. Biochem. 53:323; Itakura et al. (1984) Science 198: 1056; Ike et al. (1983) Nucleic Acid Res. 11:477).

In addition, libraries of fragments of the coding sequence of a polypeptide of the invention can be used to generate a variegated population of polypeptides for screening a subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the protein of interest.

Several techniques are known in the art for screening gene products of combinatorial libraries made by point mutations of truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan (1992) Proc. Natl. Acad. Sci. USA 89:7811-7815; Delgrave et al. (1993) Protein Engineering 6(3): 327-331).

In addition to the Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 gene sequence shown in SEQ ID NO: 1, 6, 11, 16, 21, 26, 31, 36, 41, 46, 51, 56, 61, 66 or 71 or in SEQ ID NO: 4, 9, 14, 19, 24, 29, 34, 39, 44, 49, 54, 59, 64, 69 or 74 or in SEQ ID NO: 5, 10, 15, 20, 25, 30, 35, 40, 45, 50, 55, 60, 65, 70 or 75, it will be apparent for the person skilled in the art that DNA sequence polymorphisms may exist within a given population, which may lead to changes in the amino acid sequence of the Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 protein. Such genetic polymorphisms may exist in cells from different populations or within a population due to natural allelic variation. Allelic variants may also include functional equivalents.

Fragments of a polynucleotide according to the invention may also comprise polynucleotides not encoding functional polypeptides. Such polynucleotides may function as probes or primers for a PCR reaction.

Nucleic acids according to the invention irrespective of whether they encode functional or non-functional polypeptides can be used as hybridization probes or polymerase chain reaction (PCR) primers. Uses of the nucleic acid molecules of the present invention that do not encode a polypeptide having a Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 activity include, inter alia, (1) isolating the gene encoding the Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 protein, or allelic variants thereof from a cDNA library e.g. from suitable microorganisms; (2) in situ hybridization (e.g. FISH) to metaphase chromosomal spreads to provide precise chromosomal location of the Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 gene as described in Verma et al., Human Chromosomes: a Manual of Basic Techniques, Pergamon Press, New York (1988); (3) Northern blot analysis for detecting expression of Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 mRNA in specific tissues and/or cells and 4) probes and primers that can be used as a diagnostic tool to analyse the presence of a nucleic acid hybridizable to the Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 probe in a given biological (e.g. tissue) sample.

Also encompassed by the invention is a method of obtaining a functional equivalent of a Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 gene. Such a method entails obtaining a labelled probe that includes an isolated nucleic acid which encodes all or a portion of the protein sequence according to SEQ ID NO: 2, 7, 12, 17, 22, 27, 32, 37, 42, 47, 52, 57, 62, 67 or 72 or a variant thereof; screening a nucleic acid fragment library with the labelled probe under conditions that allow hybridization of the probe to nucleic acid fragments in the library, thereby forming nucleic acid duplexes, and preparing a full-length gene sequence from the nucleic acid fragments in any labelled duplex to obtain a gene related to the Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 gene.

In one embodiment, a Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 nucleic acid of the invention is at least 50%, at least 60%, at least 65%, at least 70%, at least 75%, at least 80%, at least 85%, at least 90%, at least 91%, 92%, 93%, 94%, 95%, 96%, 97%, 98%, 99%, or more homologous to a nucleic acid sequence shown in SEQ ID NO: 1, 6, 11, 16, 21, 26, 31, 36, 41, 46, 51, 56, 61, 66 or 71 or in SEQ ID NO: 4, 9, 14, 19, 24, 29, 34, 39, 44, 49, 54, 59, 64, 69 or 74 or in SEQ ID NO: 5, 10, 15, 20, 25, 30, 35, 40, 45, 50, 55, 60, 65, 70 or 75 or the complement thereof.

Provided also are host cells comprising a polynucleotide or vector of the invention. The polynucleotide may be heterologous to the genome of the host cell. The term "heterologous", usually with respect to the host cell, means that the polynucleotide does not naturally occur in the genome of the host cell or that the polypeptide is not naturally produced by that cell.

In another embodiment, the invention features cells, e.g., transformed host cells or recombinant host cells that contain a nucleic acid encompassed by the invention. A "transformed cell" or "recombinant cell" is a cell into which (or into an ancestor of which) has been introduced, by means of recombinant DNA techniques, a nucleic acid according to the invention. Both prokaryotic and eukaryotic cells are included, e.g., bacteria, fungi, yeast, and the like, especially preferred are cells from filamentous fungi, such as *Aspergillus niger*.

A host cell can be chosen that modulates the expression of the inserted sequences, or modifies and processes the gene product in a specific, desired fashion. Such modifications (e.g., glycosylation) and processing (e.g., cleavage) of protein products may facilitate optimal functioning of the protein.

Various host cells have characteristic and specific mechanisms for post-translational processing and modification of proteins and gene products. Appropriate cell lines or host systems familiar to those of skill in the art of molecular biology and/or microbiology can be chosen to ensure the desired and correct modification and processing of the foreign protein expressed. To this end, eukaryotic host cells that possess the cellular machinery for proper processing of the primary transcript, glycosylation, and phosphorylation of the gene product can be used. Such host cells are well known in the art.

If desired, a cell as described above may be used to in the preparation of a polypeptide according to the invention. Such a method typically comprises cultivating a host cell (e. g. transformed or transfected with an expression vector as described above) under conditions to provide for expression (by the vector) of a coding sequence encoding the polypeptide, and optionally recovering the expressed polypeptide. Polynucleotides of the invention can be incorporated into a recombinant replicable vector, e. g. an expression vector. The vector may be used to replicate the nucleic acid in a compatible host cell. Thus in a further embodiment, the invention provides a method of making a polynucleotide of the invention by introducing a polynucleotide of the invention into a replicable vector, introducing the vector into a compatible host cell, and growing the host cell under conditions which bring about the replication of the vector. The vector may be recovered from the host cell.

Preferably the polypeptide is produced as a secreted protein in which case the nucleotide sequence encoding a mature form of the polypeptide in the expression construct is operably linked to a nucleotide sequence encoding a signal sequence. Preferably the signal sequence is native (homologous) to the nucleotide sequence encoding the polypeptide. Alternatively the signal sequence is foreign (heterologous) to the nucleotide sequence encoding the polypeptide, in which case the signal sequence is preferably endogenous to the host cell in which the nucleotide sequence according to the invention is expressed. Examples of suitable signal sequences for yeast host cells are the signal sequences derived from yeast a-factor genes. Similarly, a suitable signal sequence for filamentous fungal host cells is e. g. a signal sequence derived from a filamentous fungal amyloglucosidase (AG) gene, e. g. the *A. niger* glaA gene. This may be used in combination with the amyloglucosidase (also called (gluco) amylase) promoter itself, as well as in combination with other promoters. Hybrid signal sequences may also be used with the context of the present invention.

Preferred heterologous secretion leader sequences are those originating from the fungal amyloglucosidase (AG) gene (glaA-both 18 and 24 amino acid versions e. g. from *Aspergillus*), the α-factor gene (yeasts e. g. *Saccharomyces* and *Kluyveromyces*) or the α-amylase gene (*Bacillus*).

The vectors may be transformed or transfected into a suitable host cell as described above to provide for expression of a polypeptide of the invention. This process may comprise culturing a host cell transformed with an expression vector as described above under conditions to provide for expression by the vector of a coding sequence encoding the polypeptide.

Host Cells

The invention thus provides host cells transformed or transfected with or comprising a polynucleotide or vector of the invention. Preferably the polynucleotide is carried in a vector for the replication and expression of the polynucleotide. The cells will be chosen to be compatible with the said vector and may for example be prokaryotic (for example bacterial), fungal, yeast or plant cells.

A heterologous host may also be chosen wherein the polypeptide of the invention is produced in a form which is substantially free from other cellulose-degrading or hemicellulose degrading enzymes. This may be achieved by choosing a host which does not normally produce such enzymes.

The invention encompasses processes for the production of the polypeptide of the invention by means of recombinant expression of a DNA sequence encoding the polypeptide. For this purpose the DNA sequence of the invention can be used for gene amplification and/or exchange of expression signals, such as promoters, secretion signal sequences, in order to allow economic production of the polypeptide in a suitable homologous or heterologous host cell. A homologous host cell is a host cell which is of the same species or which is a variant within the same species as the species from which the DNA sequence is derived.

Suitable host cells are preferably prokaryotic microorganisms such as bacteria, or more preferably eukaryotic organisms, for example fungi, such as yeasts or filamentous fungi, or plant cells. In general, yeast cells are preferred over fungal cells because they are easier to manipulate. However, some proteins are either poorly secreted from yeasts, or in some cases are not processed properly (e. g. hyperglycosylation in yeast). In these instances, a fungal host organism should be selected.

The host cell may over-express the polypeptide, and techniques for engineering over-expression are well known. The host may thus have two or more copies of the encoding polynucleotide (and the vector may thus have two or more copies accordingly).

In the context of the present invention the "parent microbial host cell" and the "mutant microbial host cell" may be any type of host cell. The specific embodiments of the mutant microbial host cell are hereafter described. It will be clear to those skilled in the art that embodiments applicable to the mutant microbial host cell are as well applicable to the parent microbial host cell unless otherwise indicated.

The mutant microbial host cell according to the present invention may be a prokaryotic cell. Preferably, the prokaryotic host cell is bacterial cell. The term "bacterial cell" includes both Gram-negative and Gram-positive microorganisms. Suitable bacteria may be selected from e.g. *Escherichia, Anabaena, Caulobactert, Gluconobacter, Rhodobacter, Pseudomonas, Paracoccus, Bacillus, Brevibacterium, Corynebacterium, Rhizobium (Sinorhizobium), Flavobacterium, Klebsiella, Enterobacter, Lactobacillus, Lactococcus, Methylobacterium, Staphylococcus* or *Streptomyces*. Preferably, the bacterial cell is selected from the group consisting of *B. subtilis, B. amyloliquefaciens, B. licheniformis, B. puntis, B. megaterium, B. halodurans, B. pumilus, G. oxydans, Caulobactert crescentus* CB 15, *Methylobacterium extorquens, Rhodobacter sphaeroides, Pseudomonas zeaxanthinifaciens, Paracoccus denitrificans, E. coli, C. glutamicum, Staphylococcus carnosus, Streptomyces lividans, Sinorhizobium melioti* and *Rhizobium radiobacter*.

According to an embodiment, the mutant microbial host cell according to the invention is a eukaryotic host cell. Preferably, the eukaryotic cell is a mammalian, insect, plant, fungal, or algal cell. Preferred mammalian cells include e.g. Chinese hamster ovary (CHO) cells, COS cells, 293 cells, PerC6 cells, and hybridomas. Preferred insect cells include e.g. Sf9 and Sf21 cells and derivatives thereof. More preferably, the eukaryotic cell is a fungal cell, i.e. a yeast cell, such as *Candida, Hansenula, Kluyveromyces, Pichia, Saccharomyces, Schizosaccharomyces,* or *Yarrowia* strain. More preferably the eukaryotic host cell is a *Kluyveromyces lactis, S. cerevisiae, Hansenula polymorpha, Yarrowia lipolytica* or *Pichia pastoris*, or a filamentous fungal cell. Most preferably, the eukaryotic cell is a filamentous fungal cell.

Filamentous fungi include all filamentous forms of the subdivision *Eumycota* and *Oomycota* (as defined by Hawksworth et al., In, Ainsworth and Bisby's Dictionary of The Fungi, 8th edition, 1995, CAB International, University Press, Cambridge, UK). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. Filamentous fungal strains include, but are not limited to, strains of *Acremonium, Agaricus, Aspergillus, Aureobasidium, Chrysosporium, Coprinus, Cryptococcus, Filibasidium, Fusarium, Humicola, Magnaporthe, Mucor, Myceliophthora, Neocallimastix, Neurospora, Paecilomyces, Penicillium, Piromyces, Panerochaete, Pleurotus, Schizophyllum, Talaromyces, Rasamsonia, Thermoascus, Thielavia, Tolypocladium,* and *Trichoderma*.

Preferred filamentous fungal cells belong to a species of an *Acremonium, Aspergillus, Chrysosporium, Myceliophthora, Penicillium, Talaromyces, Rasamsonia, Thielavia, Fusarium* or *Trichoderma* genus, and most preferably a species of *Aspergillus niger, Acremonium alabamense, Aspergillus awamori, Aspergillus foetidus, Aspergillus sojae, Aspergillus fumigatus, Talaromyces emersonii, Rasamsonia emersonii, Aspergillus oryzae, Chrysosporium lucknowense, Fusarium oxysporum, Myceliophthora thermophila, Trichoderma reesei, Thielavia terrestris* or *Penicillium chrysogenum*. A more preferred host cell belongs to the genus *Aspergillus* or *Rasamsonia*, more preferably the host cell belongs to the species *Aspergillus niger* or *Rasamsonia emersonii*. When the host cell according to the invention is an *Aspergillus niger* host cell, the host cell preferably is CBS 513.88, CBS124.903 or a derivative thereof.

Several strains of filamentous fungi are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), Agricultural Research Service Patent Culture Collection, Northern Regional Research Center (NRRL), and All-Russian Collection of Microorganisms of Russian Academy of Sciences, (abbreviation in Russian—VKM, abbreviation in English—RCM), Moscow, Russia. Useful strains in the context of the present invention may be *Aspergillus niger* CBS 513.88, CBS124.903, *Aspergillus oryzae* ATCC 20423, IFO 4177, ATCC 1011, CBS205.89, ATCC 9576, ATCC14488-14491, ATCC 11601, ATCC12892, *P. chrysogenum* CBS 455.95, *P. chrysogenum* Wisconsin 54-1255 (ATCC28089), *Penicillium citrinum* ATCC 38065, *Penicillium chrysogenum* P2, *Thielavia terrestris* NRRL8126, *Talaromyces emersonii* CBS 124.902, *Acremonium chrysogenum* ATCC 36225 or ATCC 48272, *Trichoderma reesei* ATCC 26921 or ATCC 56765 or ATCC 26921, *Aspergillus sojae* ATCC11906, *Myceliophthora thermophila* C1, Garg 27K, VKM-F 3500 D, *Chrysosporium lucknowense* C1, Garg 27K, VKM-F 3500 D, ATCC44006 and derivatives thereof.

According to one embodiment of the invention, when the mutant microbial host cell according to the invention is a filamentous fungal host cell, the mutant microbial host cell may comprise one or more modifications in its genome such that the mutant microbial host cell is deficient in the production of at least one product selected from glucoamylase (glaA), acid stable alpha-amylase (amyA), neutral alphaamylase (amyBI and amyBII), oxalic acid hydrolase (oahA), a toxin, preferably ochratoxin and/or fumonisin, a protease transcriptional regulator prtT, PepA, a product encoded by the gene hdfA and/or hdfB, a non-ribosomal peptide synthase npsE if compared to a parent host cell and measured under the same conditions.

Therefore, when the mutant microbial host cell according to the invention is a filamentous fungal host cell the host cell may comprise one or more modifications in its genome to result in a deficiency in the production of the major extracellular aspartic protease PepA. For example the host cell according to the invention may further comprise a disruption of the pepA gene encoding the major extracellular aspartic protease PepA.

When the mutant microbial host cell according to the invention is a filamentous fungal host cell the host cell according to the invention may additionally comprises one or more modifications in its genome to result in a deficiency in the production of the product encoded by the hdfA and/or hdfB gene. For example the host cell according to the invention may further comprise a disruption of the hdfA and/or hdfB gene. Filamentous fungal host cells which are deficient in a product encoded by the hdfA and/or hdfB gene have been described in WO 2005/095624.

When the mutant microbial host cell according to the invention is a filamentous fungal host cell the host cell according to the invention may additionally comprise a modification in its genome which results in the deficiency in the production of the non-ribosomal peptide synthase npsE. Such host cells deficient in the production of non-ribosomal peptide synthase npsE have been described in WO2012/001169 (npsE has a genomic sequence as depicted in SEQ ID NO: 35, a coding sequence depicted in SEQ ID NO: 36, the mRNA depicted in SEQ ID NO: 37 and the nrps protein depicted in SEQ ID NO: 38 of WO2012/001169).

When the mutant microbial host cell according to the invention is a filamentous fungal host cell the host cell may additionally comprise at least two substantially homologous DNA domains suitable for integration of one or more copies of a polynucleotide encoding a compound of interest wherein at least one of the at least two substantially homologous DNA domains is adapted to have enhanced integration preference for the polynucleotide encoding a compound of interest compared to the substantially homologous DNA domain it originates from, and wherein the substantially homologous DNA domain where the adapted substantially homologous DNA domain originates from has a gene conversion frequency that is at least 10% higher than one of the other of the at least two substantially homologous DNA domains. These cells have been described in WO2011/009700. Strains containing two or more copies of these substantially homologous DNA domains are also referred hereafter as strain containing two or more amplicons. Examples of host cells comprising such amplicons are e.g. described in van Dijck et al, 2003, Regulatory Toxicology and Pharmacology 28; 27-35: On the safety of a new generation of DSM *Aspergillus niger* enzyme production strains. In van Dijck et al, an *Aspergillus niger* strain is described that comprises 7 amplified glucoamylase gene loci, i.e. 7 amplicons. Preferred host cells within this context are filamentous fungus host cells, preferably *A. niger* host cells, comprising two or more amplicons, preferably two or more ΔglaA amplicons (preferably comprising 3, 4, 5, 6, 7 ΔglaA amplicons) wherein the amplicon which has the highest frequency of gene conversion, has been adapted to have enhanced integration preference for the polynucleotide encoding a compound of interest compared to the amplicon it originates from. Adaptation of the amplicon can be performed according to any one of the methods described in WO2011/009700 (which is here fully incorporated by reference). An example of these host cells, described in WO2011/009700, are host cells comprising three ΔglaA amplicons being a BamHI truncated amplicon, a SalI truncated amplicon and a BglII truncated amplicon and wherein the BamHI amplicon has been adapted to have enhanced integration preference for a polynucleotide encoding a compound of interest compared to the BamHI amplicon it originates from. Host cells comprising two or more amplicons wherein one amplicon has been adapted to have enhanced integration preference for a polynucleotide encoding a compound of interest compared to the amplicon it originates from are hereafter referred as host cells comprising an adapted amplicon.

When the mutant microbial host cell according to the invention is a filamentous fungal host cell the host cell according to the invention may additionally comprises a modification of Sec61. A preferred SEC61 modification is a modification which results in a one-way mutant of SEC61; i.e. a mutant wherein the de novo synthesized protein can enter the ER via SEC61, but the protein cannot leave the ER via SEC61. Such modifications are extensively described in WO2005/123763. Most preferably, the SEC 61 modification is the S376W mutation in which Serine 376 is replaced by Tryptophan.

Host cells according to the invention include plant cells, and the invention therefore extends to transgenic organisms, such as plants and parts thereof, which contain one or more cells of the invention. The cells may heterologously express the polypeptide of the invention or may heterologously contain one or more of the polynucleotides of the invention. The transgenic (or genetically modified) plant may therefore have inserted (e. g. stably) into its genome a sequence encoding one or more of the polypeptides of the invention. The transformation of plant cells can be performed using known techniques, for example using a Ti or a Ri plasmid from *Agrobacterium tumefaciens*. The plasmid (or vector) may thus contain sequences necessary to infect a plant, and derivatives of the Ti and/or Ri plasmids may be employed.

Alternatively direct infection of a part of a plant, such as a leaf, root or stem can be effected. In this technique the plant to be infected can be wounded, for example by cutting the plant with a razor or puncturing the plant with a needle or rubbing the plant with an abrasive. The wound is then inoculated with the *Agrobacterium*. The plant or plant part can then be grown on a suitable culture medium and allowed to develop into a mature plant. Regeneration of transformed cells into genetically modified plants can be achieved by using known techniques, for example by selecting transformed shoots using an antibiotic and by sub-culturing the shoots on a medium containing the appropriate nutrients, plant hormones and the like.

The invention also includes cells that have been modified to express the cellobiohydrolase of the invention or a variant thereof. Such cells include transient, or preferably stable higher eukaryotic cell lines, such as mammalian cells or insect cells, lower eukaryotic cells, such as yeast and (e. g. filamentous) fungal cells or prokaryotic cells such as bacterial cells.

It is also possible for the proteins of the invention to be transiently expressed in a cell line or on a membrane, such as for example in a baculovirus expression system. Such systems, which are adapted to express the proteins according to the invention, are also included within the scope of the present invention.

According to the present invention, the production of the polypeptide of the invention can be effected by the culturing of microbial expression hosts, which have been transformed with one or more polynucleotides of the present invention, in a conventional nutrient fermentation medium.

Polypeptide/Enzyme Production

The recombinant host cells according to the invention may be cultured using procedures known in the art. For each combination of a promoter and a host cell, culture conditions are available which are conducive to the expression the DNA sequence encoding the polypeptide. After reaching the desired cell density or titer of the polypeptide the culture is stopped and the polypeptide is recovered using known procedures.

The fermentation medium can comprise a known culture medium containing a carbon source (e.g. glucose, maltose, molasses, starch, cellulose, xylan, pectin, lignocellolytic biomass hydrolysate, etc.), a nitrogen source (e.g. ammonium sulphate, ammonium nitrate, ammonium chloride, etc.), an organic nitrogen source (e.g. yeast extract, malt extract, peptone, etc.) and inorganic nutrient sources (e.g. phosphate, magnesium, potassium, zinc, iron, etc.). Optionally, an inducer (e.g. cellulose, pectin, xylan, maltose, maltodextrin or xylogalacturonan) may be included.

The selection of the appropriate medium may be based on the choice of expression host and/or based on the regulatory requirements of the expression construct. Such media are known to those skilled in the art. The medium may, if desired, contain additional components favoring the transformed expression hosts over other potentially contaminating microorganisms.

The fermentation can be performed over a period of from about 0.5 to about 30 days. It may be a batch, continuous or fed-batch process, suitably at a temperature in the range of 0-100° C. or 0-80° C., for example, from about 0 to about 50° C. and/or at a pH, for example, from about 2 to about 10. Preferred fermentation conditions are a temperature in the range of from about 20 to about 45° C. and/or at a pH of from about 3 to about 9. The appropriate conditions are usually selected based on the choice of the expression host and the protein to be expressed.

After fermentation, if necessary, the cells can be removed from the fermentation broth by means of centrifugation or filtration. After fermentation has stopped or after removal of the cells, the polypeptide of the invention may then be recovered and, if desired, purified and isolated by conventional means.

Polypeptide/Enzyme Compositions

The invention provides a composition comprising a polypeptide of the invention and a cellulase and/or a hemicellulase and/or a pectinase and/or ligninase or a lignin-modifying enzyme.

When the polypeptide of the invention is a cellulase, a composition of the invention will typically comprise a hemicellulase and/or a pectinase and/or ligninase or a lignin-modifying enzyme in addition to the polypeptide of the invention.

When the polypeptide of the invention is a hemicellulase, a composition of the invention will typically comprise a cellulase and/or a pectinase and/or ligninase or a lignin-modifying enzyme in addition to the polypeptide of the invention.

When the polypeptide of the invention is a pectinase, a composition of the invention will typically comprise a cellulase and/or a hemicellulase and/or ligninase or a lignin-modifying enzyme in addition to the polypeptide of the invention.

When the polypeptide of the invention is a ligninase or a lignin-modifying enzyme, a composition of the invention will typically comprise a cellulase and/or a hemicellulase and/or a pectinase in addition to the polypeptide of the invention.

A composition of the invention may comprise one, two or three or more classes of cellulase, for example one, two or all of a GH61, an endo-1,4-β-glucanase (EG), an exo-cellobiohydrolase (CBH) and a β-glucosidase (BGL).

A composition of the invention may comprise a polypeptide which has the same enzymatic activity, for example the same type of cellulase, hemicellulase and/or pectinase activity as that provided by a polypeptide of the invention.

A composition of the invention may comprise a polypeptide which has a different type of cellulase activity and/or hemicellulase activity and/or pectinase activity than that provided by a polypeptide of the invention. For example, a composition of the invention may comprise one type of cellulase and/or hemicellulase activity and/or pectinase activity provided by a polypeptide of the invention and a second type of cellulase and/or hemicellulase activity and/or pectinase activity provided by an additional hemicellulase/pectinase.

Herein, a cellulase is any polypeptide which is capable of degrading or cellulose. A polypeptide which is capable of degrading cellulose is one which is capable of catalysing the process of breaking down cellulose into smaller units, either partially, for example into cellodextrins, or completely into glucose monomers. A cellulase according to the invention may give rise to a mixed population of cellodextrins and glucose monomers when contacted with the cellulase. Such degradation will typically take place by way of a hydrolysis reaction.

Herein, a hemicellulase is any polypeptide which is capable of degrading or hemicellulose. That is to say, a hemicellulase may be capable of degrading or one or more of xylan, glucuronoxylan, arabinoxylan, glucomannan and xyloglucan. A polypeptide which is capable of degrading a hemicellulose is one which is capable of catalysing the process of breaking down the hemicellulose into smaller polysaccharides, either partially, for example into oligosaccharides, or completely into sugar monomers, for example hexose or pentose sugar monomers. A hemicellulase according to the invention may give rise to a mixed population of oligosaccharides and sugar monomers when contacted with the hemicellulase. Such degradation will typically take place by way of a hydrolysis reaction.

Herein, a pectinase is any polypeptide which is capable of degrading or pectin. A polypeptide which is capable of degrading pectin is one which is capable of catalysing the process of breaking down pectin into smaller units, either partially, for example into oligosaccharides, or completely into sugar monomers. A pectinase according to the invention may give rise to a mixed population of oligosaccharides and sugar monomers when contacted with the pectinase. Such degradation will typically take place by way of a hydrolysis reaction.

Herein, a ligninase or a lignin-modifying enzyme is any polypeptide which is capable of degrading or modifying lignin or degradation components thereof. A polypeptide which is capable of degrading or modifying lignin is one which is capable of catalysing the process of breaking down lignin into smaller units, either partially, for example into monophenolic compounds. A ligninase or a lignin-modifying enzyme according to the invention may give rise to a mixed population of phenolic compounds when contacted with the lignin. Such degradation will typically take place by way of an oxidation reaction. Herein, a ligninase or a lignin-modifying enzyme may also be any polypeptide which is capable of degrading phenolic degradation products of lignin. A polypeptide which is capable of degrading phenolic degradation products of lignin is one which is capable of catalysing the process of breaking down phenolic degradation products of lignin into even smaller units, for example by catalysing a ring opening reaction of the phenolic ring. A ligninase or a lignin-modifying enzyme according to the invention may give rise to a mixed population of ring-opened degradation products of phenolic compounds when contacted with the phenolic degradation products of lignin. Such degradation will typically take place by way of an oxidation reaction. The a ligninase or a lignin-modifying enzyme may further be capable of breaking linkages between cellulose or hemicellulose and the lignin or degradation products thereof. Enzymes that can break down lignin include lignin peroxidases, manganese peroxidases, laccases and feruloyl esterases, and other enzymes described in the art known to depolymerize or otherwise break lignin polymers. Also included are enzymes capable of hydrolyzing bonds formed between hemicellulosic sugars (notably arabinose) and lignin. Ligninases include but are not limited to the following group of enzymes: lignin peroxidases (EC 1.11.14), manganese peroxidases (EC 1.11.1.13), laccases (EC 1.10.3.2) and feruloyl esterases (EC 3.1.1.73).

Accordingly, a composition of the invention may comprise any cellulase, for example, a GH61, a cellobiohydrolase, an endo-β-1,4-glucanase, a β-glucosidase or a β-(1,3)(1,4)-glucanase.

GH61 (glycoside hydrolase family 61 or sometimes referred to EGIV) proteins are oxygen-dependent polysaccharide monooxygenases (PMO's) according to the latest literature. Often in literature these proteins are mentioned to enhance the action of cellulases on lignocellulose substrates. GH61 was originally classified as endogluconase based on measurement of very weak endo-1,4-β-d-glucanase activity in one family member. The term "GH61" as used herein, is to be understood as a family of enzymes, which share common conserved sequence portions and foldings to be classified in family 61 of the well-established CAZY GH classification system (http://www.cazy.org/GH61.html). The glycoside hydrolase family 61 is a member of the family of glycoside hydrolases EC 3.2.1. GH61 is used herein as being part of the cellulases.

Herein, a cellobiohydrolase (EC 3.2.1.91) is any polypeptide which is capable of catalysing the hydrolysis of 1,4-β-D-glucosidic linkages in cellulose or cellotetraose, releasing cellobiose from the non-reducing ends of the chains. This enzyme may also be referred to as cellulase 1,4-β-cellobiosidase, 1,4-β-cellobiohydrolase, 1,4-β-D-glucan cellobiohydrolase, avicelase, exo-1,4-β-D-glucanase, exocellobiohydrolase or exoglucanase. It may be a have the EC code EC 3.2.1.91.

Herein, an endo-β-1,4-glucanase (EC 3.2.1.4) is any polypeptide which is capable of catalysing the endohydrolysis of 1,4-β-D-glucosidic linkages in cellulose, lichenin or cereal β-D-glucans. Such a polypeptide may also be capable of hydrolyzing 1,4-linkages in β-D-glucans also containing 1,3-linkages. This enzyme may be referred to as cellulase, avicelase, β-1,4-endoglucan hydrolase, β-1,4-glucanase, carboxymethyl cellulase, cellude xtrinase, endo-1,4-β-D-glucanase, endo-1,4-β-D-glucanohydrolase, endo-1,4-β-glucanase or endoglucanase. The endo-glucanase may also catalyze the cleavage of xyloglucan, a backbone of β1→4-linked glucose residues, most of which substituted with 1-6 linked xylose side chains, and the enzyme is then referred to as a xyloglucan-specific endo-β-1,4-glucanase or a xyloglucanase.

Herein, a β-glucosidase (EC 3.2.1.21) is any polypeptide which is capable of catalysing the hydrolysis of terminal, non-reducing β-D-glucose residues with release of β-D-glucose. Such a polypeptide may have a wide specificity for β-D-glucosides and may also hydrolyze one or more of the following: a β-D-galactoside, an α-L-arabinoside, a β-D-xyloside or a β-D-fucoside. This enzyme may also be referred to as amygdalase, β-D-glucoside glucohydrolase, cellobiase or gentobiase.

Herein a β-(1,3)(1,4)-glucanase (EC 3.2.1.73) is any polypeptide which is capable of catalyzing the hydrolysis of 1,4-β-D-glucosidic linkages in β-D-glucans containing 1,3- and 1,4-bonds. Such a polypeptide may act on lichenin and cereal β-D-glucans, but not on β-D-glucans containing only 1,3- or 1,4-bonds. This enzyme may also be referred to as licheninase, 1,3-1,4-β-D-glucan 4-glucanohydrolase, β-glucanase, endo-1-1,3-1,4 glucanase, lichenase or mixed linkage β-glucanase. An alternative for this type of enzyme is EC 3.2.1.6, which is described as endo-1,3(4)-beta-glucanase. This type of enzyme hydrolyses 1,3- or 1,4-linkages in beta-D-glucans when the glucose residue whose reducing group is involved in the linkage to be hydrolyzed is itself substituted at C-3. Alternative names include endo-1,3-beta-glucanase, laminarinase, 1,3-(1,3; 1,4)-beta-D-glucan 3 (4) glucanohydrolase; substrates include laminarin, lichenin and cereal beta-D-glucans.

A composition of the invention may comprise any hemicellulase, for example, an endo-xylanase, a β-xylosidase, a α-L-arabionofuranosidase, an α-D-glucuronidase, an cellobiohydrolase, a feruloyl esterase, a coumaroyl esterase, an α-galactosidase, a β-galactosidase, a β-mannanase or a β-mannosidase.

Herein, an endoxylanase (EC 3.2.1.8) is any polypeptide which is capable of catalyzing the endo-hydrolysis of 1,4-β-D-xylosidic linkages in xylans. This enzyme may also be referred to as endo-1,4-β-xylanase or 1,4-β-D-xylan xylanohydrolase. An alternative is EC 3.2.1.136, a glucuronoarabinoxylan endoxylanase, an enzyme that is able to hydrolyze 1,4 xylosidic linkages in glucuronoarabinoxylans.

Herein, a β-xylosidase (EC 3.2.1.37; GH3) is any polypeptide which is capable of catalyzing the hydrolysis of 1,4-β-D-xylans, to remove successive D-xylose residues from the non-reducing termini. Such enzymes may also hydrolyze xylobiose. This enzyme may also be referred to as xylan 1,4-β-xylosidase, 1,4-β-D-xylan xylohydrolase, exo-1,4-β-xylosidase or xylobiase.

Herein, an α-L-arabinofuranosidase (EC 3.2.1.55) is any polypeptide which is capable of acting on α-L-arabinofuranosides, α-L-arabinans containing (1,2) and/or (1,3)- and/or (1,5)-linkages, arabinoxylans and arabinogalactans. This enzyme may also be referred to as α-N-arabinofuranosidase, arabinofuranosidase or arabinosidase.

Herein, an α-D-glucuronidase (EC 3.2.1.139) is any polypeptide which is capable of catalyzing a reaction of the following form: alpha-D-glucuronoside+H(2)O=an alcohol+D-glucuronate. This enzyme may also be referred to as alpha-glucuronidase or alpha-glucosiduronase. These enzymes may also hydrolyze 4-O-methylated glucoronic acid, which can also be present as a substituent in xylans.

Alternative is EC 3.2.1.131: xylan alpha-1,2-glucuronosidase, which catalyses the hydrolysis of alpha-1,2-(4-O-methyl)glucuronosyl links.

Herein, an acetyl xylan esterase (EC 3.1.1.72) is any polypeptide which is capable of catalyzing the deacetylation of xylans and xylo-oligosaccharides. Such a polypeptide may catalyze the hydrolysis of acetyl groups from polymeric xylan, acetylated xylose, acetylated glucose, alpha-napthyl acetate or p-nitrophenyl acetate but, typically, not from triacetylglycerol. Such a polypeptide typically does not act on acetylated mannan or pectin.

Herein, a feruloyl esterase (EC 3.1.1.73) is any polypeptide which is capable of catalyzing a reaction of the form: feruloyl-saccharide+H(2)O=ferulate+saccharide. The saccharide may be, for example, an oligosaccharide or a polysaccharide. It may typically catalyze the hydrolysis of the 4-hydroxy-3-methoxycinnamoyl (feruloyl) group from an esterified sugar, which is usually arabinose in 'natural' substrates. p-nitrophenol acetate and methyl ferulate are typically poorer substrates. This enzyme may also be referred to as cinnamoyl ester hydrolase, ferulic acid esterase or hydroxycinnamoyl esterase. It may also be referred to as a hemicellulase accessory enzyme, since it may help xylanases and pectinases to break down plant cell wall hemicellulose and pectin.

Herein, a coumaroyl esterase (EC 3.1.1.73) is any polypeptide which is capable of catalyzing a reaction of the form: coumaroyl-saccharide+H(2)O=coumarate+saccharide. The saccharide may be, for example, an oligosaccharide or a polysaccharide. This enzyme may also be referred to as trans-4-coumaroyl esterase, trans-p-coumaroyl esterase, p-coumaroyl esterase or p-coumaric acid esterase. This enzyme also falls within EC 3.1.1.73 so may also be referred to as a feruloyl esterase.

Herein, an α-galactosidase (EC 3.2.1.22) is any polypeptide which is capable of catalyzing the hydrolysis of terminal, non-reducing α-D-galactose residues in α-D-galactosides, including galactose oligosaccharides, galactomannans, galactans and arabinogalactans. Such a polypeptide may also be capable of hydrolyzing α-D-fucosides. This enzyme may also be referred to as melibiase.

Herein, a β-galactosidase (EC 3.2.1.23) is any polypeptide which is capable of catalyzing the hydrolysis of terminal non-reducing β-D-galactose residues in β-D-galactosides. Such a polypeptide may also be capable of hydrolyzing α-L-arabinosides. This enzyme may also be referred to as exo-(1->4)-β-D-galactanase or lactase.

Herein, a β-mannanase (EC 3.2.1.78) is any polypeptide which is capable of catalyzing the random hydrolysis of 1,4-β-D-mannosidic linkages in mannans, galactomannans and glucomannans. This enzyme may also be referred to as mannan endo-1,4-β-mannosidase or endo-1,4-mannanase.

Herein, a β-mannosidase (EC 3.2.1.25) is any polypeptide which is capable of catalyzing the hydrolysis of terminal, non-reducing β-D-mannose residues in β-D-mannosides. This enzyme may also be referred to as mannanase or mannase.

A composition of the invention may comprise any pectinase, for example an endo polygalacturonase, a pectin methyl esterase, an endo-galactanase, a beta galactosidase, a pectin acetyl esterase, an endo-pectin lyase, pectate lyase, alpha rhamnosidase, an exo-galacturonase, an exo-polygalacturonate lyase, a rhamnogalacturonan hydrolase, a rhamnogalacturonan lyase, a rhamnogalacturonan acetyl esterase, a rhamnogalacturonan galacturonohydrolase or a xylogalacturonase.

Herein, an endo-polygalacturonase (EC 3.2.1.15) is any polypeptide which is capable of catalyzing the random hydrolysis of 1,4-α-D-galactosiduronic linkages in pectate and other galacturonans. This enzyme may also be referred to as polygalacturonase pectin depolymerase, pectinase, endopolygalacturonase, pectolase, pectin hydrolase, pectin polygalacturonase, poly-α-1,4-galacturonide glycanohydrolase, endogalacturonase; endo-D-galacturonase or poly(1,4-α-D-galacturonide) glycanohydrolase.

Herein, a pectin methyl esterase (EC 3.1.1.11) is any enzyme which is capable of catalyzing the reaction: pectin+n H$_2$O=n methanol+pectate. The enzyme may also been known as pectinesterase, pectin demethoxylase, pectin methoxylase, pectin methylesterase, pectase, pectinoesterase or pectin pectylhydrolase.

Herein, an endo-galactanase (EC 3.2.1.89) is any enzyme capable of catalyzing the endohydrolysis of 1,4-β-D-galactosidic linkages in arabinogalactans. The enzyme may also be known as arabinogalactan endo-1,4-β-galactosidase, endo-1,4-β-galactanase, galactanase, arabinogalactanase or arabinogalactan 4-β-D-galactanohydrolase.

Herein, a pectin acetyl esterase is defined herein as any enzyme which has an acetyl esterase activity which catalyzes the deacetylation of the acetyl groups at the hydroxyl groups of GalUA residues of pectin Herein, an endo-pectin lyase (EC 4.2.2.10) is any enzyme capable of catalyzing the eliminative cleavage of (1→4)-α-D-galacturonan methyl ester to give oligosaccharides with 4-deoxy-6-O-methyl-α-D-galact-4-enuronosyl groups at their non-reducing ends. The enzyme may also be known as pectin lyase, pectin trans-eliminase; endo-pectin lyase, polymethylgalacturonic transeliminase, pectin methyltranseliminase, pectolyase, PL, PNL or PMGL or (1→4)-6-O-methyl-α-D-galacturonan lyase.

Herein, a pectate lyase (EC 4.2.2.2) is any enzyme capable of catalyzing the eliminative cleavage of (1→4)-α-D-galacturonan to give oligosaccharides with 4-deoxy-α-D-galact-4-enuronosyl groups at their non-reducing ends. The enzyme may also be known polygalacturonic transeliminase, pectic acid transeliminase, polygalacturonate lyase, endopectin methyltranseliminase, pectate transeliminase, endogalacturonate transeliminase, pectic acid lyase, pectic lyase, α-1,4-D-endopolygalacturonic acid lyase, PGA lyase, PPase-N, endo-α-1,4-polygalacturonic acid lyase, polygalacturonic acid lyase, pectin trans-eliminase, polygalacturonic acid trans-eliminase or (1→4)-α-D-galacturonan lyase.

Herein, an alpha rhamnosidase (EC 3.2.1.40) is any polypeptide which is capable of catalyzing the hydrolysis of terminal non-reducing α-L-rhamnose residues in α-L-rhamnosides or alternatively in rhamnogalacturonan. This enzyme may also be known as α-L-rhamnosidase T, α-L-rhamnosidase N or α-L-rhamnoside rhamnohydrolase.

Herein, exo-galacturonase (EC 3.2.1.82) is any polypeptide capable of hydrolysis of pectic acid from the non-reducing end, releasing digalacturonate. The enzyme may also be known as exo-poly-α-galacturonosidase, exopolygalacturonosidase or exopolygalacturanosidase.

Herein, exo-galacturonase (EC 3.2.1.67) is any polypeptide capable of catalyzing: (1,4-α-D-galacturonide)$_n$+H$_2$O= (1,4-α-D-galacturonide)$_{n-1}$+D-galacturonate. The enzyme may also be known as galacturan 1,4-α-galacturonidase, exopolygalacturonase, poly(galacturonate) hydrolase, exo-D-galacturonase, exo-D-galacturonanase, exo-poly-D-galacturonase or poly(1,4-α-D-galacturonide) galacturonohydrolase.

Herein, exo-polygalacturonate lyase (EC 4.2.2.9) is any polypeptide capable of catalyzing eliminative cleavage of 4-(4-deoxy-α-D-galact-4-enuronosyl)-D-galacturonate from the reducing end of pectate, i.e. de-esterified pectin. This enzyme may be known as pectate disaccharide-lyase, pectate exo-lyase, exopectic acid transeliminase, exo-pectate lyase, exopolygalacturonic acid-trans-eliminase, PATE, exo-PATE, exo-PGL or (1→4)-α-D-galacturonan reducing-end-disaccharide-lyase.

Herein, rhamnogalacturonan hydrolase is any polypeptide which is capable of hydrolyzing the linkage between galactosyluronic acid and rhamnopyranosyl in an endo-fashion in strictly alternating rhamnogalacturonan structures, consisting of the disaccharide [(1,2-alpha-L-rhamnoyl-(1,4)-alpha-galactosyluronic acid].

Herein, rhamnogalacturonan lyase is any polypeptide which is any polypeptide which is capable of cleaving α-L-Rhap-(1→4)-α-D-GalpA linkages in an endo-fashion in rhamnogalacturonan by beta-elimination.

Herein, rhamnogalacturonan acetyl esterase is any polypeptide which catalyzes the deacetylation of the backbone of alternating rhamnose and galacturonic acid residues in rhamnogalacturonan.

Herein, rhamnogalacturonan galacturonohydrolase is any polypeptide which is capable of hydrolyzing galacturonic acid from the non-reducing end of strictly alternating rhamnogalacturonan structures in an exo-fashion.

Herein, xylogalacturonase is any polypeptide which acts on xylogalacturonan by cleaving the β-xylose substituted galacturonic acid backbone in an endo-manner. This enzyme may also be known as xylogalacturonan hydrolase.

Herein, an α-L-arabinofuranosidase (EC 3.2.1.55) is any polypeptide which is capable of acting on α-L-arabinofuranosides, α-L-arabinans containing (1,2) and/or (1,3)- and/or (1,5)-linkages, arabinoxylans and arabinogalactans. This enzyme may also be referred to as α-N-arabinofuranosidase, arabinofuranosidase or arabinosidase.

Herein, endo-arabinanase (EC 3.2.1.99) is any polypeptide which is capable of catalyzing endohydrolysis of 1,5-α-arabinofuranosidic linkages in 1,5-arabinans. The enzyme may also be know as endo-arabinase, arabinan endo-1,5-α-L-arabinosidase, endo-1,5-α-L-arabinanase, endo-α-1,5-arabanase; endo-arabanase or 1,5-α-L-arabinan 1,5-α-L-arabinanohydrolase.

A composition of the invention will typically comprise at least one cellulase and/or at least one hemicellulase and/or at least one pectinase (one of which is a polypeptide according to the invention). A composition of the invention may comprise a cellobiohydrolase, an endoglucanase and/or a β-glucosidase. Such a composition may also comprise one or more hemicellulases and/or one or more pectinases.

One or more (for example two, three, four or all) of an amylase, a protease, a lipase, a ligninase, a hexosyltransferase or a glucuronidase may be present in a composition of the invention.

"Protease" includes enzymes that hydrolyze peptide bonds (peptidases), as well as enzymes that hydrolyze bonds between peptides and other moieties, such as sugars (glycopeptidases). Many proteases are characterized under EC 3.4, and are suitable for use in the invention incorporated herein by reference. Some specific types of proteases include, cysteine proteases including pepsin, papain and serine proteases including chymotrypsins, carboxypeptidases and metalloendopeptidases.

"Lipase" includes enzymes that hydrolyze lipids, fatty acids, and acylglycerides, including phospoglycerides, lipoproteins, diacylglycerols, and the like. In plants, lipids are used as structural components to limit water loss and pathogen infection. These lipids include waxes derived from fatty acids, as well as cutin and suberin.

"Hexosyltransferase" (2.4.1-) includes enzymes which are capable of transferring glycosyl groups, more specifically hexosyl groups. In addition to transfer of a glycosyl-group from a glycosyl-containing donor to another glycosyl-containing compound, the acceptor, the enzymes can also transfer the glycosyl-group to water as an acceptor. This reaction is also known as a hydrolysis reaction, instead of a transfer reaction. An example of a hexosyltransferase which may be used in the invention is a β-glucanosyltransferase. Such an enzyme may be able to catalyze degradation of (1,3)(1,4)glucan and/or cellulose and/or a cellulose degradation product.

"Glucuronidase" includes enzymes that catalyze the hydrolysis of a glucoronoside, for example β-glucuronoside to yield an alcohol. Many glucuronidases have been characterized and may be suitable for use in the invention, for example β-glucuronidase (EC 3.2.1.31), hyalurono-glucuronidase (EC 3.2.1.36), glucuronosyl-disulfoglucosamine glucuronidase (3.2.1.56), glycyrrhizinate β-glucuronidase (3.2.1.128) or α-D-glucuronidase (EC 3.2.1.139).

A composition of the invention may comprise an expansin or expansin-like protein, such as a swollenin (see Salheimo et al., Eur. J. Biochem. 269, 4202-4211, 2002) or a swollenin-like protein.

Expansins are implicated in loosening of the cell wall structure during plant cell growth. Expansins have been proposed to disrupt hydrogen bonding between cellulose and other cell wall polysaccharides without having hydrolytic activity. In this way, they are thought to allow the sliding of cellulose fibers and enlargement of the cell wall. Swollenin, an expansin-like protein contains an N-terminal Carbohydrate Binding Module Family 1 domain (CBD) and a C-terminal expansin-like domain. For the purposes of this invention, an expansin-like protein or swollenin-like protein may comprise one or both of such domains and/or may disrupt the structure of cell walls (such as disrupting cellulose structure), optionally without producing detectable amounts of reducing sugars.

A composition of the invention may comprise the polypeptide product of a cellulose integrating protein, scaffoldin or a scaffoldin-like protein, for example CipA or CipC from *Clostridium thermocellum* or *Clostridium cellulolyticum* respectively.

Scaffoldins and cellulose integrating proteins are multi-functional integrating subunits which may organize cellulolytic subunits into a multi-enzyme complex. This is accomplished by the interaction of two complementary classes of domain, i.e. a cohesion domain on scaffoldin and a dockerin domain on each enzymatic unit. The scaffoldin subunit also bears a cellulose-binding module (CBM) that mediates attachment of the cellulosome to its substrate. A scaffoldin or cellulose integrating protein for the purposes of this invention may comprise one or both of such domains.

A composition of the invention may comprise a cellulose induced protein or modulating protein, for example as encoded by cip1 or cip2 gene or similar genes from *Trichoderma reesei/Hypocrea jacorina* (see Foreman et al., J. Biol. Chem. 278(34), 31988-31997, 2003). The polypeptide product of these genes are bimodular proteins, which contain a cellulose binding module and a domain which function or activity can not be related to known glycosyl hydrolase families. Yet, the presence of a cellulose binding module and the co-regulation of the expression of these genes with cellulases components indicates previously unrecognized activities with potential role in biomass degradation.

A composition of the invention may be composed of a member of each of the classes of the polypeptides mentioned above, several members of one polypeptide class, or any combination of these polypeptide classes.

A composition of the invention may be composed of polypeptides, for example enzymes, from (1) commercial suppliers; (2) cloned genes expressing polypeptides, for example enzymes; (3) complex broth (such as that resulting from growth of a microbial strain in media, wherein the strains secrete proteins and enzymes into the media; (4) cell lysates of strains grown as in (3); and/or (5) plant material expressing polypeptides, for example enzymes. Different polypeptides, for example enzymes in a composition of the invention may be obtained from different sources.

Use of the Polypeptides

The polypeptides and polypeptide compositions according to the invention may be used in many different applications. For instance they may be used to produce fermentable sugars. The fermentable sugars can then, as part of a biofuel process, be converted into biogas or ethanol, butanol, isobutanol, 2 butanol or other suitable substances. Alternatively the polypeptides and their compositions may be used as enzyme, for instance in production of food products, in detergent compositions, in the paper and pulp industry and in antibacterial formulations, in pharmaceutical products such as throat lozenges, toothpastes, and mouthwash. Some of the uses will be illustrated in more detail below.

In the uses and methods described below, the components of the compositions described above may be provided concomitantly (i.e. as a single composition per se) or separately or sequentially.

The invention also relates to the use of the cellobiohydrolase according to the invention and compositions comprising such an enzyme in industrial processes.

Despite the long term experience obtained with these processes, the cellobiohydrolase according to the invention may feature a number of significant advantages over enzymes currently used. Depending on the specific application, these advantages may include aspects such as lower production costs, higher specificity towards the substrate, reduced antigenicity, fewer undesirable side activities, higher yields when produced in a suitable microorganism, more suitable pH and temperature ranges, non-inhibition by hydrophobic, lignin-derived products or less product inhibition or, in the case of the food industry a better taste or texture of a final product as well as food grade and kosher aspects.

In principle, a cellobiohydrolase or composition of the invention may be used in any process which requires the treatment of a material which comprises polysaccharide. Thus, a polypeptide or composition of the invention may be used in the treatment of polysaccharide material. Herein, polysaccharide material is a material which comprises or consists essential of one or, more typically, more than one polysaccharide.

Typically, plants and material derived therefrom comprise significant quantities of non-starch polysaccharide material. Accordingly, a polypeptide of the invention may be used in the treatment of a plant or fungal material or a material derived therefrom.

Lignocellulose

An important component of plant non-starch polysaccharide material is lignocellulose (also referred to herein as lignocellulolytic biomass). Lignocellulose is plant material that comprises cellulose and hemicellulose and lignin. The carbohydrate polymers (cellulose and hemicelluloses) are tightly bound to the lignin by hydrogen and covalent bonds. Accordingly, a polypeptide of the invention may be used in the treatment of lignocellulolytic material. Herein, lignocellulolytic material is a material which comprises or consists essential of lignocellulose. Thus, in a method of the invention for the treatment of a non-starch polysaccharide, the non-starch polysaccharide may be a lignocellulosic material/biomass.

Accordingly, the invention provides a method of treating a substrate comprising non-starch polysaccharide in which the treatment comprises the degradation and/or hydrolysis and/or modification of cellulose and/or hemicellulose and/or a pectic substance.

Degradation in this context indicates that the treatment results in the generation of hydrolysis products of cellulose and/or hemicellulose and/or a pectic substance, i.e. saccharides of shorter length are present as result of the treatment than are present in a similar untreated non-starch polysaccharide. Thus, degradation in this context may result in the liberation of oligosaccharides and/or sugar monomers.

All plants contain non-starch polysaccharide as do virtually all plant-derived polysaccharide materials. Accordingly, in a method of the invention for the treatment of substrate comprising a non-starch polysaccharide, said substrate may be provided in the form of a plant or a plant derived material or a material comprising a plant or plant derived material, for example a plant pulp, a plant extract, a foodstuff or ingredient therefore, a fabric, a textile or an item of clothing.

Lignocellulolytic biomass suitable for use in the invention includes biomass and can include virgin biomass and/or non-virgin biomass such as agricultural biomass, commercial organics, construction and demolition debris, municipal solid waste, waste paper and yard waste. Common forms of biomass include trees, shrubs and grasses, wheat, wheat straw, sugar cane bagasse, corn, corn husks, corn cobs, corn kernel including fiber from kernels, products and by-products from milling of grains such as corn, wheat and barley (including wet milling and dry milling) often called "bran or fiber" as well as municipal solid waste, waste paper and yard waste. The biomass can also be, but is not limited to, herbaceous material, agricultural residues, forestry residues, municipal solid wastes, waste paper, and pulp and paper mill residues. "Agricultural biomass" includes branches, bushes, canes, corn and corn husks, energy crops, forests, fruits, flowers, grains, grasses, herbaceous crops, leaves, bark, needles, logs, roots, saplings, short rotation woody crops, shrubs, switch grasses, trees, vegetables, fruit peels, vines, sugar beet pulp, wheat middlings, oat hulls, and hard and soft woods (not including woods with deleterious materials). In addition, agricultural biomass includes organic waste materials generated from agricultural processes including farming and forestry activities, specifically including forestry wood waste. Agricultural biomass may be any of the aforestated singularly or in any combination or mixture thereof. Further examples of suitable biomass are orchard primings, chaparral, mill waste, urban wood waste, municipal waste, logging waste, forest thinnings, short-rotation woody crops, industrial waste, wheat straw, oat straw, rice straw, barley straw, rye straw, flax straw, soy hulls, rice hulls, rice straw, corn gluten feed, oat hulls, sugar cane, corn stover, corn stalks, corn cobs, corn husks, prairie grass, gamagrass, foxtail; sugar beet pulp, citrus fruit pulp, seed hulls, cellulosic animal wastes, lawn clippings, cotton, seaweed, trees, shrubs, grasses, wheat, wheat straw, sugar cane bagasse, corn, corn husks, corn hobs, corn kernel, fiber from kernels, products and by-products from wet or dry milling of grains, municipal solid waste, waste paper, yard waste, herbaceous material, agricultural residues, forestry residues, municipal solid waste, waste paper, pulp, paper mill residues, branches, bushes, canes, corn, corn husks, an energy crop, forest, a fruit, a flower, a grain, a grass, a herbaceous crop, a leaf, bark, a needle, a log, a root, a sapling, a shrub, switch grass, a tree, a vegetable, fruit peel, a vine, sugar beet pulp, wheat middlings, oat hulls, hard or soft wood, organic waste material generated from an agricultural process, forestry wood waste, or a combination of any two or more thereof.

Apart from virgin biomass or feedstocks already processed in food and feed or paper and pulping industries, the biomass/feedstock may additionally be pretreated with heat, mechanical and/or chemical modification or any combination of such methods in order to enhance enzymatic degradation.

Pretreatment

Before enzymatic treatment, the feedstock may optionally be pre-treated with heat, mechanical and/or chemical modification or any combination of such methods in order to to enhance the accessibility of the substrate to enzymatic hydrolysis and/or hydrolyse the hemicellulose and/or solubilize the hemicellulose and/or cellulose and/or lignin, in any way known in the art. The pretreatment may comprise exposing the lignocellulosic material to (hot) water, steam (steam explosion), an acid, a base, a solvent, heat, a peroxide, ozone, mechanical shredding, grinding, milling or rapid depressurization, or a combination of any two or more thereof. This chemical pretreatment is often combined with heat-pretreatment, e.g. between 150-220° C. for 1 to 30 minutes.

Presaccharifation

After the pretreatment step, a liquefaction/hydrolysis or presaccharification step involving incubation with an enzyme or enzyme mixture can be utilized. The pre-saccharification step can be performed at many different temperatures but it is preferred that the presaccharification step occur at the temperature best suited to the enzyme mix being tested, or the predicted enzyme optimum of the enzymes to be tested. The temperature of the presaccharification step may range from about 10° C. to about 95° C., about 20° C. to about 85° C., about 30° C. to about 70° C., about 40° C. to about 60° C., about 37° C. to about 50° C., preferably about 37° C. to about 80° C., more preferably about 60-70° C. even more preferably around 65° C. The pH of the presaccharification mixture may range from about 2.0 to about 10.0, but is preferably about 3.0 to about 7.0, more preferably about 4.0 to about 6.0, even more preferably about 4.0 to about 5.0. Again, the pH may be adjusted to maximize enzyme activity and may be adjusted with the addition of the enzyme. Comparison of the results of the assay results from this test will allow one to modify the method to best suit the enzymes being tested.

The liquefaction/hydrolysis or presaccharification step reaction may occur from several minutes to several hours, such as from about 1 hour to about 120 hours, preferably from about 2 hours to about 48 hours, more preferably from about 2 to about 24 hours, most preferably for from about 2 to about 6 hours. The cellulase treatment may occur from several minutes to several hours, such as from about 6 hours to about 120 hours, preferably about 12 hours to about 72 hours, more preferably about 24 to 48 hours.

Saccharification

The invention provides a method for producing a sugar from a lignocellulosic material which method comprises contacting a polypeptide of the invention to a composition of the invention with the lignocellulosic material.

Such a method allows free sugars (monomers) and/or oligosaccharides to be generated from lignocellulosic biomass. These methods involve converting lignocellulosic biomass to free sugars and small oligosaccharides with a polypeptide or composition of the invention.

The process of converting a complex carbohydrate such as lignocellulose into sugars preferably allows conversion into fermentable sugars. Such a process may be referred to as "saccharification." Accordingly, a method of the invention may result in the liberation of one or more hexose and/or pentose sugars, such as one or more of glucose, xylose, arabinose, galactose, galacturonic acid, glucuronic acid, mannose, rhamnose, ribose and fructose.

Accordingly, another aspect of the invention includes methods that utilize the polypeptide of composition of the invention described above together with further enzymes or physical treatments such as temperature and pH to convert the lignocellulosic plant biomass to sugars and oligosaccharides.

While the composition has been discussed as a single mixture it is recognized that the enzymes may be added sequentially where the temperature, pH, and other conditions may be altered to increase the activity of each individual enzyme. Alternatively, an optimum pH and temperature can be determined for the enzyme mixture.

The enzymes are reacted with substrate under any appropriate conditions. For example, enzymes can be incubated at about 25° C., about 30° C., about 35° C., about 37° C., about 40° C., about 45° C., about 50° C., about 55° C., about 60° C., about 65° C., about 70° C., about 75° C., about 80° C., about 85° C., about 90° C. or higher. That is, they can be incubated at a temperature of from about 20° C. to about 95° C., for example in buffers of low to medium ionic strength and/or from low to neutral pH. By "medium ionic strength" is intended that the buffer has an ion concentration of about 200 millimolar (mM) or less for any single ion component. The pH may range from about pH 2.5, about pH 3.0, about pH 3.5, about pH 4.0, about pH 4.5, about pH 5, about pH 5.5, about pH 6, about pH 6.5, about pH 7, about pH 7.5, about pH 8.0, to about pH 8.5. Generally, the pH range will be from about pH 3.0 to about pH 7. For the production of ethanol an acidic medium is preferred, e.g. pH=4, whereas for the production of biogas neutral pH, e.g. pH=7 is desirable. Incubation of enzyme combinations under these conditions results in release or liberation of substantial amounts of the sugar from the lignocellulose. By substantial amount is intended at least 20%, 30%, 40%, 50%, 60%, 70%, 80%, 90%, 95% or more of available sugar.

The polypeptides, such as enzymes, can be produced either exogenously in microorganisms, yeasts, fungi, bacteria or plants, then isolated and added, for example, to lignocellulosic feedstock. Alternatively, the enzymes are produced, but not isolated, and crude cell mass fermentation broth, or plant material (such as corn stover), and the like may be added to, for example, the feedstock. Alternatively, the crude cell mass or enzyme production medium or plant material may be treated to prevent further microbial growth (for example, by heating or addition of antimicrobial agents), then added to, for example, a feedstock. These crude enzyme mixtures may include the organism producing the enzyme. Alternatively, the enzyme may be produced in a fermentation that uses feedstock (such as corn stover) to provide nutrition to an organism that produces an enzyme(s). In this manner, plants that produce the enzymes may themselves serve as a lignocellulosic feedstock and be added into lignocellulosic feedstock.

Fermentation of Sugars

The fermentable sugars can be converted to useful value-added fermentation products, non-limiting examples of which include amino acids, vitamins, pharmaceuticals, animal feed supplements, specialty chemicals, chemical feedstocks, plastics, solvents, fuels, or other organic polymers, lactic acid, and ethanol, including fuel ethanol. In particular the sugars may be used as feedstocks for fermentation into chemicals, plastics, such as for instance succinic acid and (bio) fuels, including ethanol, methanol, butanol synthetic liquid fuels and biogas.

For instance, in the method of the invention, an enzyme or combination of enzymes acts on a lignocellulosic substrate or plant biomass, serving as the feedstock, so as to convert this complex substrate to simple sugars and oligosaccharides for the production of ethanol or other useful fermentation products.

Sugars released from biomass can be converted to useful fermentation products such a one of those including, but not limited to, amino acids, vitamins, pharmaceuticals, animal feed supplements, specialty chemicals, chemical feedstocks, plastics, and ethanol, including fuel ethanol.

Accordingly, the invention provides a method for the preparation of a fermentation product, which method comprises:
  a. degrading lignocellulose using a method as described herein; and
  b. fermentation of the resulting material,
thereby to prepare a fermentation product.

The fermentation may be carried out under aerobic or anaerobic conditions. Preferably, the process is carried out under micro-aerophilic or oxygen limited conditions.

An anaerobic fermentation process is herein defined as a fermentation process run in the absence of oxygen or in which substantially no oxygen is consumed, preferably about 5 or less, about 2.5 or less or about 1 mmol/L/h or less, and wherein organic molecules serve as both electron donor and electron acceptors.

An oxygen-limited fermentation process is a process in which the oxygen consumption is limited by the oxygen transfer from the gas to the liquid. The degree of oxygen limitation is determined by the amount and composition of the ingoing gas flow as well as the actual mixing/mass transfer properties of the fermentation equipment used. Preferably, in a process under oxygen-limited conditions, the rate of oxygen consumption is at least about 5.5, more preferably at least about 6 and even more preferably at least about 7 mmol/L/h.

A method for the preparation of a fermentation product may optionally comprise recovery of the fermentation product.

SSF

Fermentation and Saccharification may also be executed in Simultaneous Saccharification and Fermentation (SSF) mode. One of the advantages of this mode is reduction of the sugar inhibition on enzymatic hydrolysis (Sugar inhibition on cellulases is described by Caminal B&B Vol XXVII Pp 1282-1290).

Fermentation Products

Fermentation products which may be produced according to the invention include amino acids, vitamins, pharmaceuticals, animal feed supplements, specialty chemicals, chemical feedstocks, plastics, solvents, fuels, or other organic polymers, lactic acid, and ethanol, including fuel ethanol (the term "ethanol" being understood to include ethyl alcohol or mixtures of ethyl alcohol and water).

Specific value-added products that may be produced by the methods of the invention include, but not limited to, biofuels (including ethanol and butanol and a biogas); lactic acid; a plastic; a specialty chemical; an organic acid, including citric acid, succinic acid, fumaric acid, itaconic acid and maleic acid; 3-hydroxy-propionic acid, acrylic acid; acetic acid; 1,3-propane-diol; ethylene, glycerol; a solvent; an animal feed supplement; a pharmaceutical, such as a β-lactam antibiotic or a cephalosporin; vitamins; an amino acid, such as lysine, methionine, tryptophan, threonine, and aspartic acid; an industrial enzyme, such as a protease, a cellulase, an amylase, a glucanase, a lactase, a lipase, a lyase, an oxidoreductases, a transferase or a xylanase; and a chemical feedstock.

Biogas

The invention also provides use of a polypeptide or composition a described herein in a method for the preparation of biogas. Biogas typically refers to a gas produced by the biological breakdown of organic matter, for example non-starch carbohydrate containing material, in the absence of oxygen. Biogas originates from biogenic material and is a type of biofuel. One type of biogas is produced by anaerobic digestion or fermentation of biodegradable materials such as biomass, manure or sewage, municipal waste, and energy crops. This type of biogas is comprised primarily of methane and carbon dioxide. The gas methane can be combusted or oxidized with oxygen. Air contains 21% oxygen. This energy release allows biogas to be used as a fuel. Biogas can be used as a low-cost fuel in any country for any heating purpose, such as cooking. It can also be utilized in modern waste management facilities where it can be used to run any type of heat engine, to generate either mechanical or electrical power.

The first step in microbial biogas production consists in the enzymatic degradation of polymers and complex substrates (for example non-starch carbohydrate). Accordingly, the invention provides a method for preparation of a biogas in which a substrate comprising non-starch carbohydrate is contacted with a polypeptide or composition of the invention, thereby to yield fermentable material which may be converted into a biogas by an organism such as a microorganism. In such a method, a polypeptide of the invention may be provided by way of an organism, for example a microorganism which expresses such a polypeptide.

Use of Enzymes in Food Products

The polypeptides and compositions of the invention may be used in a method of processing plant material to degrade or modify the cellulose or hemicellulose or pectic substance constituents of the cell walls of the plant or fungal material.

Such methods may be useful in the preparation of food product. Accordingly, the invention provides a method for preparing a food product which method comprises incorporating a polypeptide or composition of the invention during preparation of the food product.

The invention also provides a method of processing a plant material which method comprises contacting the plant material with a polypeptide or composition of the invention to degrade or modify the cellulose in the (plant) material. Preferably, the plant material is a plant pulp or plant extract, such as juices.

The present invention also provides a method for reducing the viscosity, clarity and/or filterability of a plant extract which method comprises contacting the plant extract with a polypeptide or composition of the invention in an amount effective in degrading cellulose or hemicellulose or pectic substances contained in the plant extract.

Plant and cellulose/hemicellulose/pectic substance-containing materials include plant pulp, parts of plants and plant extracts. In the context of this invention an extract from a plant material is any substance which can be derived from plant material by extraction (mechanical and/or chemical), processing or by other separation techniques. The extract may be juice, nectar, base, or concentrates made thereof. The plant material may comprise or be derived from vegetables, e. g., carrots, celery, onions, legumes or leguminous plants (soy, soybean, peas) or fruit, e. g., pome or seed fruit (apples, pears, quince etc.), grapes, tomatoes, citrus (orange, lemon, lime, mandarin), melons, prunes, cherries, black currants, redcurrants, raspberries, strawberries, cranberries, pineapple and other tropical fruits, trees and parts thereof (e. g. pollen, from pine trees), or cereal (oats, barley, wheat, maize, rice). The material (to be hydrolysed) may also be agricultural residues, such as sugar beet pulp, com cobs, wheat straw, (ground) nutshells, or recyclable materials, e. g. (waste) paper.

The polypeptides of the invention can thus be used to treat plant material including plant pulp and plant extracts. They may also be used to treat liquid or solid foodstuffs or edible foodstuff ingredients, or be used in the extraction of coffee, plant oils, starch or as a thickener in foods.

Typically, the polypeptides of the invention are used as a composition/enzyme preparation as described above. The composition will generally be added to plant pulp obtainable by, for example mechanical processing such as crushing or milling plant material. Incubation of the composition with the plant will typically be carried out for at time of from 10 minutes to 5 hours, such as 30 minutes to 2 hours, preferably for about 1 hour. The processing temperature is preferably from about 1000° C. to about 55° C., e. g. from about 15° C. to about 25° C., optimally about 20° C. and one can use from about 10 g to about 300 g, preferably from about 30 g to about 70 g, optimally about 50 g of enzyme per ton of material to be treated.

All of the enzyme(s) or their compositions used may be added sequentially or at the same time to the plant pulp. Depending on the composition of the enzyme preparation the plant material may first be macerated (e. g. to a pure) or liquefied. Using the polypeptides of the invention processing parameters such as the yield of the extraction, viscosity of the extract and/or quality of the extract can be improved.

Alternatively, or in addition to the above, a polypeptide of the invention may be added to the raw juice obtained from pressing or liquefying the plant pulp. Treatment of the raw juice will be carried out in a similar manner to the plant pulp in respect of dosage, temperature and holding time. Again, other enzymes such as those discussed previously may be included. Typical incubation conditions are as described in the previous paragraph.

Once the raw juice has been incubated with the polypeptides of the invention, the juice is then centrifuged or (ultra) filtered to produce the final product.

After treatment with the polypeptide of the invention the (end) product can be heat treated, e.g. at about 100° C. for a time of from about 1 minute to about 1 hour, under conditions to partially or fully inactivate the polypeptide(s) of the invention.

A composition containing a polypeptide of the invention may also be used during the preparation of fruit or vegetable purees.

The polypeptide of the invention may also be used in brewing, wine making, distilling or baking. It may therefore be used in the preparation of alcoholic beverages such as wine and beer. For example it may improve the filterability or clarity, for example of beers, wort (e.g. containing barley and/or sorghum malt) or wine.

Furthermore, a polypeptide or composition of the invention may be used for treatment of brewers spent grain, i.e. residuals from beer wort production containing barley or malted barley or other cereals, so as to improve the utilization of the residuals for, e.g., animal feed.

The protein may assist in the removal of dissolved organic substances from broth or culture media, for example where distillery waste from organic origin is bioconverted into microbial biomass. The polypeptide of the invention may improve filterability and/or reduce viscosity in glucose syrups, such as from cereals produced by liquefaction (e.g. with α-amylase).

In baking the polypeptide may improve the dough structure, modify its stickiness or suppleness, improve the loaf volume and/or crumb structure or impart better textural characteristics such as break, shred or crumb quality.

The present invention thus relates to methods for preparing a dough or a cereal-based food product comprising incorporating into the dough a polypeptide or composition of the present invention. This may improve one or more properties of the dough or the cereal-based food product obtained from the dough relative to a dough or a cereal-based food product in which the polypeptide is not incorporated.

The preparation of the cereal-based food product according to the invention further can comprise steps known in the art such as boiling, drying, frying, steaming or baking of the obtained dough.

Products that are made from a dough that is boiled are for example boiled noodles, dumplings, products that are made from fried dough are for example doughnuts, beignets, fried noodles, products that are made for steamed dough are for example steamed buns and steamed noodles, examples of products made from dried dough are pasta and dried noodles and examples of products made from baked dough are bread, cookies and cake.

The term "improved property" is defined herein as any property of a dough and/or a product obtained from the dough, particularly a cereal-based food product, which is improved by the action of the polypeptide according to the invention relative to a dough or product in which the polypeptide according to the invention is not incorporated. The improved property may include, but is not limited to, increased strength of the dough, increased elasticity of the dough, increased stability of the dough, improved machinability of the dough, improved proofing resistance of the dough, reduced stickiness of the dough, improved extensibility of the dough, increased volume of the cereal-based food product, reduced blistering of the cereal-based food product, improved crumb structure of the baked product, improved softness of the cereal-based food product, improved flavour of the cereal-based food product, improved anti-staling of the cereal-based food product. Improved properties related to pasta and noodle type of cereal-based products are for example improved firmness, reduced stickiness, improved cohesiveness and reduced cooking loss.

The improved property may be determined by comparison of a dough and/or a cereal-based food product prepared with and without addition of a polypeptide of the present invention. Organoleptic qualities may be evaluated using procedures well established in the baking industry, and may include, for example, the use of a panel of trained taste-testers.

The term "dough" is defined herein as a mixture of cereal flour and other ingredients firm enough to knead or roll. Examples of cereals are wheat, rye, corn, maize, barley, rice, groats, buckwheat and oat. Wheat is I here and hereafter intended to encompass all known species of Triticum genus, for example aestivum, durum and/or spelt. Examples of suitable other ingredients are: the cellobiohydrolase according to the present invention, additional enzymes, chemical additives and/or processing aids. The dough may be fresh, frozen, pre-pared, or pre-baked. The preparation of a dough from the ingredients described above is well known in the art and comprises mixing of said ingredients and processing aids and one or more moulding and optionally fermentation steps. The preparation of frozen dough is described by Kulp and Lorenz in Frozen and Refrigerated Doughs and Batters.

The term "cereal-based food product" is defined herein as any product prepared from a dough, either of a soft or a crisp character. Examples of cereal-based food products, whether of a white, light or dark type, which may be advantageously produced by the present invention are bread (in particular white, whole-meal or rye bread), typically in the form of loaves or rolls, French baguette-type bread, pasta, noodles, doughnuts, bagels, cake, pita bread, tortillas, tacos, cakes, pancakes, biscuits, cookies, pie crusts, steamed bread, and crisp bread, and the like.

The term "baked product" is defined herein as any cereal-based food product prepared by baking the dough.

Non-starch polysaccharides (NSP) can increase the viscosity of the digesta which can, in turn, decrease nutrient availability and animal performance. The use of the cellobiohydrolase of the present invention can improve phosphorus utilization as well as cation minerals and protein during animal digesta.

Adding specific nutrients to feed improves animal digestion and thereby reduces feed costs. A lot of feed additives are being currently used and new concepts are continuously developed. Use of specific enzymes like non-starch carbohydrate degrading enzymes could breakdown the fibre releasing energy as well as increasing the protein digestibility due to better accessibility of the protein when the fibre gets broken down. In this way the feed cost could come down as well as the protein levels in the feed also could be reduced.

Non-starch polysaccharides (NSPs) are also present in virtually all feed ingredients of plant origin. NSPs are poorly utilized and can, when solubilized, exert adverse effects on digestion. Exogenous enzymes can contribute to a better utilization of these NSPs and as a consequence reduce any anti-nutritional effects. Non-starch carbohydrate degrading enzymes of the present invention can be used for this purpose in cereal-based diets for poultry and, to a lesser extent, for pigs and other species.

A non-starch carbohydrate degrading polypeptide/enzyme of the invention (of a composition comprising the polypeptide/enzyme of the invention) may be used in the detergent industry, for example for removal from laundry of carbohydrate-based stains. A detergent composition may comprise a polypeptide/enzyme of the invention and, in addition, one or more of a cellulase, a hemicellulase, a pectinase, a protease, a lipase, a cutinase, an amylase or a carbohydrase.

Use of Enzymes in Detergent Compositions

A detergent composition comprising an a polypeptide or composition of the invention may be in any convenient form, for example a paste, a gel, a powder or a liquid. A liquid detergent may be aqueous, typically containing up to about 70% water and from about 0 to about 30% organic solvent or non-aqueous material.

Such a detergent composition may, for example, be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dish washing operations.

In general, the properties of the enzyme should be compatible with the aselected detergent (for example, pH-optimum, compatibility with other enzymatic and/or non-enzymatic ingredients, etc.) and the enzyme(s) should be present in an effective amount.

A detergent composition may comprise a surfactant, for example an anionic or non-ionic surfactant, a detergent builder or complexing agent, one or more polymers, a bleaching system (for example an $H_2O_2$ source) or an enzyme stabilizer. A detergent composition may also comprise any other conventional detergent ingredient such as, for example, a conditioner including a clay, a foam booster, a sud suppressor, an anti-corrosion agent, a soil-suspending agent, an an-soil redeposition agent, a dye, a bactericide, an optical brightener, a hydrotropes, a tarnish inhibitor or a perfume.

Use of Enzymes in Paper and Pulp Processing

A polypeptide or composition of the present invention may be used in the paper and pulp industry, inter alia in the bleaching process to enhance the brightness of bleached pulps whereby the amount of chlorine used in the bleaching stages may be reduced, and to increase the freeness of pulps in the recycled paper process (Eriksson, K. E. L., Wood Science and Technology 24 (1990):79-101; Paice, et al., Biotechnol. and Bioeng. 32 (1988):235-239 and Pommier et al., Tappi Journal (1989):187-191). Furthermore, a polypeptide or composition of the invention may be used for treatment of lignocellulosic pulp so as to improve the bleachability thereof. Thereby the amount of chlorine need to obtain a satisfactory bleaching of the pulp may be reduced.

A polypeptide or composition of the invention may be used in a method of reducing the rate at which cellulose-containing fabrics become harsh or of reducing the harshness of cellulose-containing fabrics, the method comprising treating cellulose-containing fabrics with a polypeptide or composition as described above. The present invention further relates to a method providing colour clarification of coloured cellulose-containing fabrics, the method comprising treating coloured cellulose-containing fabrics with a polypeptide or composition as described above, and a method of providing a localized variation in colour of coloured cellulose-containing fabrics, the method comprising treating coloured cellulose-containing fabrics with a polypeptide or composition as described above. The methods of the invention may be carried out by treating cellulose-containing fabrics during washing. However, if desired, treatment of the fabrics may also be carried out during soaking or rinsing or simply by adding the polypeptide or composition as described above to water in which the fabrics are or will be immersed.

Other Enzyme Uses

In addition, a polypeptide or composition of the present invention can also be used in antibacterial formulation as well as in pharmaceutical products such as throat lozenges, toothpastes, and mouthwash.

The following Examples illustrate the invention:

EXPERIMENTAL INFORMATION

Strains and Enzyme Compositions

*Aspergillus niger* strain is deposited at the CBS Institute under the deposit number CBS 513.88.

*Rasamsonia* (*Talaromyces*) *emersonii* strain TEC-142 is deposited at CENTRAAL BUREAU VOOR SCHIMMEL-CULTURES, Uppsalalaan 8, P.O. Box 85167, NL-3508 AD Utrecht, The Netherlands on 1 Jul. 2009 having the Accession Number CBS 124902. TEC-142S is a single isolate of TEC-142.

*Rasamsonia* (*Talaromyces*) *emersonii* strain was deposited at CENTRAAL BUREAU VOOR SCHIMMELCULTURES, Uppsalalaan 8, P.O. Box 85167, NL-3508 AD Utrecht, The Netherlands in December 1964 having the Accession Number CBS 393.64. Other suitable strains can be equally used in the present examples to show the effect and advantages of the invention. For example TEC-101, TEC-147, TEC-192, TEC-201 or TEC-210 are suitable *Rasamsonia* strains which are described in WO2011/000949.

TEC-210 cellulase-containing composition was produced according to the procedures such as inoculation and fermentation as described in WO2011/000949.

Beta-glucosidase (BG) is produced by overexpression of EBA4 in *Aspergillus niger* as described in WO2011/098577 followed by fermentation of the *Aspergillus niger* transformant. EBA4 is a *Rasamsonia emersonii* (*Talaromyces emersonii*) BG and is identified in WO2011/098577 as *T. emersonii* beta-glucosidase (BG) and represented by SEQ ID NO: 5 in WO2011/098577.

Celluclast (*Trichoderma* cellulase) was obtained from Sigma

Molecular Biology Techniques

In these strains, using molecular biology techniques known to the skilled person (see: Sambrook & Russell, *Molecular Cloning: A Laboratory Manual*, 3rd Ed., CSHL Press, Cold Spring Harbor, N.Y., 2001), several genes were over expressed and others were down regulated as described below. Examples of the general design of expression vectors for gene over expression and disruption vectors for down-regulation, transformation, use of markers and selective media can be found in WO199846772, WO199932617, WO2001121779, WO2005095624, WO2006040312, EP 635574B, WO2005100573, WO2011009700, WO2012001169 and WO2011054899. All gene replacement vectors comprise approximately 1-2 kb flanking regions of the respective ORF sequences, to target for homologous recombination at the predestined genomic loci. In addition, *A. niger* vectors contain the *A. nidulans* bi-directional amdS selection marker for transformation, in-between direct repeats. The method applied for gene deletion in all examples herein uses linear DNA, which integrates into the genome at the homologous locus of the flanking sequences by a double cross-over, thus substituting the gene to be deleted by the amdS gene. After transformation, the direct repeats allow for the removal of the selection marker by a (second) homologous recombination event. The removal of the amdS marker can be done by plating on fluoro-acetamide media, resulting in the selection of marker-gene-free strains. Using this strategy of transformation and subsequent counter-selection, which is also described as the "MARKER-GENE FREE" approach in EP 0 635 574, the amdS marker can be used indefinitely in strain modification programs.

Media and Solutions:

Potato dextrose agar, PDA, (Fluka, Cat. No. 70139): per liter: Potato extrac 4 g; Dextrose 20 g; Bacto agar 15 g; pH 5.4; Sterilize 20 min at 120° C.

*Rasamsonia* agar medium: per liter: Salt fraction no. 3 15 g; Cellulose 30 g; Bacto peptone 7.5 g; Grain flour 15 g; KH2PO4 5 g; CaCl2.2aq 1 g; Bacto agar 20 g; pH 6.0; Sterilize 20 min at 120° C.

Salt fraction composition: The "salt fraction no. 3" was fitting the disclosure of WO98/37179, Table 1. Deviations from the composition of this table were CaCl2.2aq 1.0 g/l, KCl 1.8 g/L, citric acid 1 aq 0.45 g/L (chelating agent).

Shake Flask Media for *Rasamsonia*

*Rasamsonia* medium 1: per liter: Glucose 20 g; Yeast extract (Difco) 20 g; Clerol FBA3107 (AF) 4 drops; pH 6.0; Sterilize 20 min at 120° C.

*Rasamsonia* medium 2: per liter: Salt fraction no. 3 15 g; Cellulose 20 g; Bacto peptone 4 g; Grain flour 7.5 g; KH2PO4 10 g; CaCl2.2H20 0.5 g; Clerol FBA3107 (AF) 0.4 ml; pH 5; Sterilize 20 min at 120° C.

*Rasamsonia* medium 3: per liter: Salt fraction no. 3 15 g; glucose 50 g; Bacto peptone 7.5 g; KH2PO4 10 g; CaCl2.2H20 0.5 g; Clerol FBA3107 (AF) 0.4 ml; pH 5; Sterilize 20 min at 120° C.

Spore Batch Preparation for *Rasamsonia*

Strains were grown from stocks on *Rasamsonia* agar medium in 10 cm diameter Petri dishes for 5-7 days at 40° C. For MTP fermentations, strains were grown in 96-well plates containing *Rasamsonia* agar medium. Strain stocks were stored at −80° C. in 10% glycerol.

Chromosomal DNA Isolation

Strains were grown in YGG medium (per liter: 8 g KCl, 16 g glucose.H2O, 20 ml of 10% yeast extract, 10 ml of 100× pen/strep, 6.66 g YNB+amino acids, 1.5 g citric acid, and 6 g K2HPO4). for 16 hours at 42° C., 250 rpm, and chromosomal DNA was isolated using the DNeasy plant mini kit (Qiagen, Hilden, Germany).

MTP Fermentation of *Rasamsonia*

96 wells microtiter plates (MTP) with sporulated *R. emersonii* strains were used to harvest spores for MTP fermentations. To do this, 200 µl of 10 times diluted *Rasamsonia* medium 1 was added to each well and after resuspending the mixture, 100 µl of spore suspension was incubated in humidity shakers (Infors) for 44° C. at 550 rpm, and 80% humidity for 16 hours. Subsequently, 50 µl of pre-culture was used to inoculate 250 µl of *Rasamsonia* medium 2 in MTP plates. The 96-well plates were incubated in humidity shakers (Infors) for 44° C. at 550 rpm, and 80% humidity for 6 days. Plates were centrifuged and supernatants were harvested.

Shake Flask Growth Protocol of *Rasamsonia*

Spores were directly inoculated into 500 ml shake flasks containing 100 ml of either *Rasamsonia* medium 2 or 3 and incubated at 45° C. at 250 rpm in an incubator shaker for 3-4 days. Alternatively, spores were inoculated in 100 ml shake flasks containing *Rasamsonia* medium 1 and incubated at 45° C. at 250 rpm in an incubator shaker for 1 day (preculture) and, subsequently, 5 or 10 ml of biomass from the pre-culture was transferred to 500 ml shake flasks containing 100 ml of *Rasamsonia* medium 2 or 3 and grown under conditions as described above.

Protein Analysis

Protein samples were separated under reducing conditions on NuPAGE 4-12% Bis-Tris gel (Invitrogen, Breda, The Netherlands) and stained. Gels were stained with either InstantBlue (Expedeon, Cambridge, United Kingdom), SimplyBlue safestain (Invitrogen, Breda, The Netherlands) or Sypro Ruby (Invitrogen, Breda, The Netherlands) according to manufacturer's instructions.

Total Protein Content

Protein content of the recovered supernatant was determined according to Bradford method. The amount of protein in the enzyme samples was determined with Bradford Protein assay, using Coomassie protein reagent. 25 µl of appropriately diluted enzyme sample was mixed with 1.2 ml Coomassie reagent. After 10 minutes at room temperature the absorbance of the mixture at 595 nm was determined using a spectrophotometer (Uvikon XL). Protein content was calculated in comparison to BSA standard.

Sugar-release Activity Assay from Acid Pretreated Corn Stover Feedstock

For each (hemi-)cellulase assay condition, the enzyme culture supernatant was analysed in duplicate according to the following procedure: 5 mg protein/g dry matter feedstock of the enzyme culture supernatant was transferred to a suitable vial containing 800 µL 2.5% (w/w) dry matter of a mildly acid pre-treated corn stover substrate in a 50 mM citrate buffer, buffered at pH 3.5 or pH 4.5 or 5.0. Additionally, as a blank sample the same amount of enzyme culture supernatant was added to another vial, where the 800 µL 2.5% (w/w) dry matter of a mildly acid pre-treated corn stover substrate in a 50 mM citrate buffer was replaced by 800 µL 50 mM citrate buffer, buffered at pH 4.5. The assay samples buffered at pH 3.5 were incubated at 65° C. for 72 hours. The assay samples buffered at pH 5.0 were incubated at 50° C. for 72 hours. The assay samples buffered at pH 4.5, and blank samples for correction of the monomeric sugar content in the enzyme supernatants were incubated at 65° C. for 72 hours. Also, assay samples buffered at pH 4.5 were incubated at 75° C. for 72 hours.

In addition to the individual incubations as described above, the enzyme culture supernatant was also tested in combination with two different hemicellulase mixtures; TEC-210 (*Rasamsonia emersonii*) to which additional beta-glucosidase (BG) (*Aspergillus niger* strain expressing a BG from *Rasamsonia emersonii*) was added (0.08 mg/g dry matter) and Celluclast (*Trichoderma reesei*) to which additional BG (Novozym-188) was added (0.08 mg/g dry matter). The mixtures were added to a concentration of 1 mg protein/g dry matter of the feedstock. These incubations were performed at the same conditions as described above.

For each procedure, an assay was performed where the enzyme supernatant was replaced by demineralized water, in order to correct for possible monomeric sugars present in the feedstock after incubation.

After incubation of the assay samples, a fixed volume of an internal standard, maleic acid (20 g/L), EDTA (40 g/L) and DSS (2,2-Dimethyl-2-silapentane-5-sulfonate) (0.5 g/L), was added to each vial. After centrifugation, 650 µL of the supernatant was transferred to a new vial.

The supernatant of the samples is lyophilized overnight, subsequently 50 µL D2O is added to the dried residue and lyophilized once more. The dried residue is dissolved in 600 µL of D2O. 1D 1H NMR spectra are recorded on a Bruker Avance III HD 400 MHz, equipped with a N2 cooled cryo-probe, using a pulse program without water suppression at a temperature of 17° C. with a 90 degrees excitation pulse, acquisition time of 2.0 s and relaxation delay of 10 s. The analyte concentrations are calculated based on the following signals (δ relative to DSS (4,4-dimethyl-4-silapentane-1-sulfonic acid)): ½ of β-glucose peak at 4.63 ppm (d, 0.31H, J=8 Hz), ½ of β-xylose peak at 4.56 ppm (d, 0.315H, J=8 Hz), Xylo-oligo peak at 4.45 ppm (d, 1H, J=8 Hz), ½ of β anomer of the reducing end of cellobiose peak at 4.66 ppm (d, 0.31H, J=8 Hz). The signal user for the standard:Maleic acid peak at 6.26 ppm (s, 2H)

The (hemi-)cellulase enzyme solution may contain residual sugars. Therefore, the results of the assay are corrected for the sugar content measured after incubation of the enzyme solution.

β-xylosidase Activity Measurement

This assay measures the release of p-nitrophenol by the action of β-xylosidase on p-nitrophenyl-β-D-xylopyranoside (PNPX). One β-xylosidase unit of activity is the amount of enzyme that liberates 1 micromole of p-nitrophenol in one minute at 60° C. and pH 4.5. Acetate buffer (0.1 M, pH 4.5) is prepared as follows: 8.2 g of anhydrous sodium acetate is dissolved in distilled water so that the final volume of the solution is 1000 ml (Solution A). In a separate flask, 6.0 g (5.72 ml) of glacial acetic acid is mixed with distilled water to make the total volume of 1000 ml (Solution B). The final 0.1 M acetate buffer, pH 4.5 is prepared by mixing Solution A with Solution B until the pH of the resulting solution is equal to 4.5. A drop (~25 µL) Triton X-100 is added/L buffer solution. PNPX (Sigma) is used as the assay substrate.

100 mg of PNPX is dissolved in 84 mL of 0.1 M acetate buffer to obtain a 4.4 mM stock solution. The stop reagent (1 M sodium carbonate solution) is prepared as follows: 10.6 g of anhydrous sodium carbonate is dissolved in 50 ml of distilled water, and the solution volume is adjusted to 100 ml. This reagent is used to terminate the enzymatic reaction.

For the incubation with enzyme, 0.1 mL of 4.4 mM PNPX stock solution is mixed with 0.1 mL of the appropriate diluted enzyme sample and incubated at 60° C. for 60 minutes. After 60 minutes of incubation, 0.1 mL of the reaction mixture is mixed with 0.1 mL of 1 M sodium carbonate solution and the absorbance is measured at 405 nm in microtiter plates as $A_S$ For the substrate blank, 0.1 mL of 4.4 mM PNPX stock solution is mixed with 0.1 mL of 0.1 M acetate buffer, pH 4.5 and treated the same as the samples: incubated at 60° C. for 60 minutes after which 0.1 mL of the reaction mixture is mixed with 0.1 mL of 1 M sodium carbonate solution and the absorbance at 405 nm is measured in microtiter plates as $A_{SB}$.

Enzyme blanks (without addition of substrate) are measured to correct for background color originating from the enzymes. 0.1 mL of the appropriate diluted enzyme sample is mixed with 0.1 mL 0.1 M acetate buffer, pH 4.5 and incubated at 60° C. for 60 minutes. After 60 minutes of incubation, 0.1 mL of the reaction mixture is mixed with 0.1 mL of 1 M sodium carbonate solution and the absorbance is measured at 405 nm in microtiter plates as $A_{EB}$.

A calibration curve of p-nitrophenol (appropriate diluted in 0.1 M acetate buffer, pH 4.5) mixed in a ratio of 1:1 with 1 M sodium carbonate solution is used to quantify its release from PNPX by the action of the enzyme.

After the incubation of enzyme with substrate the corrected absorbance ($=A_S-A_{EB}-A_{SB}$), is used to calculate the amount of p-nitrophenol released by the enzyme.

The activity is expressed as the amount of enzyme required to release 1 µM p-nitrophenol/min under the assay conditions.

This assay can be used to test the activity of enzymes such as, but not limited to, GH3, GH30, GH39, GH43, GH52, and GH54 enzymes.

β-xylosidase Activity Assay 2

This assay measures the release of xylose by the action of β-xylosidase on xylobiose.

Sodium acetate buffer (0.05 M, pH 4.5) was prepared as follows. 4.1 g of anhydrous sodium acetate or 6.8 g of sodium acetate*3H$_2$O was dissolved in distilled water to a final volume of 1000 mL (Solution A). In a separate flask, 3.0 g (2.86 mL) of glacial acetic acid was mixed with distilled water to make the total volume of 1000 mL (Solution B). The final 0.05 M sodium acetate buffer, pH 4.5, was prepared by mixing Solution A with Solution B until the pH of the resulting solution was equal to 4.5. Xylobiose was purchased from Sigma and dissolved in sodium acetate buffer pH 4.5 to a concentration of 100 ug/mL The Assay was Performed as Detailed Below.

The enzyme culture supernatant was added to the substrate in a dosage of 1 and 5 mg protein/g substrate which was then incubated at 62° C. for 24 hours. The reaction was stopped by heating the samples for 10 minutes at 100° C. The release of xylose was analyzed by High Performance Anion Exchange Chromatography.

Substrate Blank

Instead of enzyme culture supernatant the same amount of buffer was added to the substrate solution which was then incubated at 62° C. for 24 hours. The reaction was stopped by heating the samples for 10 minutes at 100° C. The sample was analyzed by High Performance Anion Exchange Chromatography. The analysis was performed using a Dionex HPLC system equipped with a Dionex CarboPac PA-1 (2 mm ID×250 mm) column in combination with a CarboPac PA guard column (2 mm ID×50 mm) and a Dionex PAD-detector (Dionex Co. Sunnyvale). A flow rate of 0.3 mL/min was used with the following gradient of sodium acetate in 0.1 M NaOH: 0-20 min, 0-180 mM. Each elution was followed by a washing step of 5 min 1000 mM sodium acetate in 0.1 M NaOH and an equilibration step of 15 min 0.1 M NaOH.

In case interfering compounds were present that complicate xylose identification the analysis was performed by running isocratic on H$_2$O for 30 min a gradient (0.5M NaOH was added post-column at 0.1 mL/min for detection) followed by a washing step of 5 min 1000 mM sodium acetate in 0.1 M NaOH and an equilibration step of 15 min H$_2$O.

Standards of xylose and xylobiose (Sigma) were used for identification of the substrate and product formed by the enzyme.

This assay can be used to test the activity of enzymes such as, but not limited to, GH3, GH30, GH39, GH43, GH52, and GH54 enzymes.

β-xylosidase Activity Assay 3

The same assay as described above was performed with xylan substrates like Oat arabinoxylan, Beech wood xylan and Birch wood xylan (Sigma) instead of xylobiose to measure xylosidase activity on polymeric substrates.

Assay conditions were the same with the exception that all substrates were solved to a concentration of 2 mg/mL.

The incubation was performed at 60° C. for 24 h at a dosage of 10 mg/g. Next to xylose and xylobiose also xylotriose and xylotetraose were quantified.

α-galactosidase Activity Measurement

This assay measures the release of p-nitrophenol by the action of α-galactosidase on p-nitrophenyl-α-D-galactopyranoside (PNPG). One α-galactosidase unit of activity is the amount of enzyme that liberates 1 micromole of p-nitrophenol in one minute at 60° C. and pH 4.5. Acetate buffer (0.1 M, pH 4.5) is prepared as follows: 8.2 g of anhydrous sodium acetate is dissolved in distilled water so that the final volume of the solution is 1000 ml (Solution A). In a separate flask, 6.0 g (5.72 ml) of glacial acetic acid is mixed with distilled water to make the total volume of 1000 ml (Solution B). The final 0.1 M acetate buffer, pH 4.5 is prepared by mixing Solution A with Solution B until the pH of the resulting solution is equal to 4.5. A drop (~25 µL) Triton X-100 is added/L buffer solution. PNPG (Sigma) is used as the assay substrate.

A stock solution of 4.4 mM PNPG is made in 0.1 M acetate buffer. The stop reagent (1 M sodium carbonate solution) is prepared as follows: 10.6 g of anhydrous sodium carbonate is dissolved in 50 ml of distilled water, and the solution volume is adjusted to 100 ml. This reagent is used to terminate the enzymatic reaction.

For the incubation with enzyme, 0.1 mL of 4.4 mM PNPG stock solution is mixed with 0.1 mL of the appropriate diluted enzyme sample and incubated at 60° C. for 60 minutes. After 60 minutes of incubation, 0.1 mL of the reaction mixture is mixed with 0.1 mL of 1 M sodium carbonate solution and the absorbance is measured at 405 nm in microtiter plates as $A_S$ For the substrate blank, 0.1 mL of 4.4 mM PNPG stock solution is mixed with 0.1 mL of 0.1 M acetate buffer, pH 4.5 and treated the same as the samples: incubated at 60° C. for 60 minutes after which 0.1 mL of the reaction mixture is mixed with 0.1 mL of 1 M sodium carbonate solution and the absorbance at 405 nm is measured in microtiter plates as $A_{SB}$.

Enzyme blanks (without addition of substrate) are measured to correct for background color originating from the enzymes. 0.1 mL of the appropriate diluted enzyme sample is mixed with 0.1 mL 0.1 M acetate buffer, pH 4.5 and incubated at 60° C. for 60 minutes. After 60 minutes of incubation, 0.1 mL of the reaction mixture is mixed with 0.1 mL of 1 M sodium carbonate solution and the absorbance is measured at 405 nm in microtiter plates as $A_{EB}$.

A calibration curve of p-nitrophenol (appropriate diluted in 0.1 M acetate buffer, pH 4.5) mixed in a ratio of 1:1 with 1 M sodium carbonate solution is used to quantify its release from PNPG by the action of the enzyme.

After the incubation of enzyme with substrate the corrected absorbance ($=A_S-A_{EB}-A_{SB}$), is used to calculate the amount of p-nitrophenol released by the enzyme.

The activity is expressed as the amount of enzyme required to release 1 µM p-nitrophenol/min under the assay conditions.

This assay can be used to test the activity of enzymes such as, but not limited to, GH4, GH27 and GH36 enzymes.

Xyloglucanase Activity Assay 1

Sodium acetate buffer (0.05 M, pH 4.5) was prepared as follows. 4.1 g of anhydrous sodium acetate was dissolved in distilled water to a final volume of 1000 mL (Solution A). In a separate flask, 3.0 g (2.86 mL) of glacial acetic acid was mixed with distilled water to make the total volume of 1000 mL (Solution B). The final 0.05 M sodium acetate buffer, pH 4.5, was prepared by mixing Solution A with Solution B until the pH of the resulting solution is 4.5.

Tamarind xyloglucan was solved in sodium acetate buffer to obtain 2.0 mg/mL. The enzyme culture supernatant was added to the substrate in a dosage of 10 mg protein/g substrate which was then incubated at 60° C. for 24 hours. The reaction was stopped by heating the samples for 10 minutes at 100° C. The release of oligosaccharides was analyzed by High Performance Anion Exchange Chromatography As a blank sample the substrate was treated and incubated in the same way but then without the addition of enzyme.

As a reference the substrate was also incubated under the same conditions with a commercial cellulase preparation from *Trichoderma Reesei*(Celluclast; Sigma) which was diluted 50 times after which 20 μL was added to the incubation.

The analysis was performed using a Dionex HPLC system equipped with a Dionex CarboPac PA-1 (2 mm ID×250 mm) column in combination with a CarboPac PA guard column (2 mm ID×50 mm) and a Dionex PAD-detector (Dionex Co. Sunnyvale). A flow rate of 0.3 mL/min was used with the following gradient of sodium acetate in 0.1 M NaOH: 0-40 min, 0-150 mM. Each elution was followed by a washing step of 5 min 1000 mM sodium acetate in 0.1 M NaOH and an equilibration step of 15 min 0.1 M NaOH.

This assay can be used to test the activity of enzymes such as, but not limited to, GH5, GH12, GH16, GH44, and GH74 enzymes.

Xyloglucanase Activity Assay 2

The following example illustrates the assay to measure xyloglucanase activity. Such activity was demonstrated by using xyloglucan as substrate and a reducing sugars assay (PAHBAH) as detection method. The values were compared to a standard, which was prepared using a commercial cellulase preparation from *Trichoderma Reesei* (Celluclast; Sigma).

Reagent A: 5 g of p-Hydroxybenzoic acid hydrazide (PAHBAH) was suspended in 60 mL water, 4.1 mL of concentrated hydrochloric acid was added and the volume was adjusted to 100 ml. Reagent B: 24.9 g of trisodium citrate was dissolved in 500 ml of water. To this solution 2.2 g of calcium chloride and 40 g sodium hydroxide was added. The volume was adjusted to 2 L with water. Both reagents were stored at room temperature. Working Reagent: 10 ml of Reagent A was added to 40 ml of Reagent B. This solution was prepared freshly every day, and was stored on ice between uses. Using the above reagents, the assay was performed as detailed below Next to xyloglucan also carboxymethylcellulose was used as a substrate to determine the specificity of the enzyme.

After incubation 10 μl of each well was mixed with 200 μl working reagent. These solutions were heated at 70° C. for 30. After cooling down, the samples were analyzed by measuring the absorbance at 405 nm. Glucose was used as a standard to quantify reducing ends formed as glucose equivalents.

As controls the substrates were also incubated without addition of enzyme culture supernatant and the enzyme culture supernatants were incubated without substrate.

This assay can be used to test the activity of enzymes such as, but not limited to, GH5, GH12, GH16, GH44, and GH74 enzymes.

Xyloglucanase Activity Assay 3

Sodium acetate buffer (0.05 M, pH 4.5) is prepared as follows. 4.1 g of anhydrous sodium acetate is dissolved in distilled water to a final volume of 1000 mL (Solution A). In a separate flask, 3.0 g (2.86 mL) of glacial acetic acid is mixed with distilled water to make the total volume of 1000 mL (Solution B). The final 0.05 M sodium acetate buffer, pH 4.5, is prepared by mixing Solution A with Solution B until the pH of the resulting solution is 4.5.

Tamarind xyloglucanan is solved in sodium acetate buffer to obtain 2.0 mg/mL. The enzyme is added to the substrate in a dosage of 10 mg protein/g substrate which is then incubated at 60° C. for 24 hours. The reaction is stopped by heating the samples for 10 minutes at 100° C. The formation of lower molecular weight oligosaccharides is analyzed by High Performance size-exclusion Chromatography As a blank sample the substrate is treated and incubated in the same way but then without the addition of enzyme.

As a reference the substrate is also incubated under the same conditions with a commercial cellulase preparation from e.g. *Aspergillus niger* or *Trichoderma Reesei* (the cellulase standard at its own optimal temperature in case of inactivity at 60° C.).

The analysis is performed using High-performance size-exclusion chromatography (HPSEC) performed on three TSK-gel columns (6.0 mm×15.0 cm per column) in series SuperAW4000, SuperAW3000, SuperAW2500; Tosoh Bioscience), in combination with a PWXguard column (Tosoh Bioscience). Elution is performed at 55 C with 0.2 M sodium nitrate at 0.6 mL/min. The eluate was monitored using a Shodex RI-101 (Kawasaki) refractive index (RI) detector. Calibration was performed by using pullulans (Associated Polymer Labs Inc., New York, USA) with a molecular weight in the range of 0.18-788 kDa.

This assay can be used to test the activity of enzymes such as, but not limited to, GH5, GH12, GH16, GH44, and GH74 enzymes.

α-arabinofuranosidase Activity Assay

The following example illustrates an assay to measure the ability of α-arabinofuranosidases to remove the α-L-arabinofuranosyl residues from substituted xylose residues.

For the complete degradation of arabinoxylans to arabinose and xylose, several enzyme activities are needed, including endo-xylanases and arabinofuranosidases. The arabinoxylan molecule from wheat is highly substituted with arabinosyl residues. These can be substituted either to the C2 or the C3 position of the xylosyl residue (single substitution), or both to the C2 and C3 position of the xylose (double substitution).

Single and double substituted oligosaccharides were prepared by incubating wheat arabinoxylan (WAX; 10 mg/mL; Megazyme, Bray, Ireland) in 50 mM acetate buffer pH 4.5 with an appropriate amount of endo-xylanase (from *Aspergillus awamori*, Kormelink F. et al; Journal of Biotechnology (1993) 27: 249-265) 48 hours at 40° C. to produce an sufficient amount of arabinoxylo-oligosaccharides. The reaction was stopped by heating the samples at 100° C. for 10 minutes. The samples were centrifuged for 5 minutes at 10.000×g. The supernatant was used for further experiments. Degradation of the arabinoxylan was followed by analysis of the formed reducing sugars and High Performance Anion Exchange Chromatography (HPAEC).

The enzyme culture supernatant was added to the single and double substituted arabinoxylo-oligosaccharides (endo-xylanase treated WAX; 2 mg/mL) in a dosage of 10 mg protein/g substrate in 50 mM sodium acetate buffer which was then incubated at 65° C. for 24 hours. The reaction was stopped by heating the samples at 100° C. for 10 minutes. The samples were centrifuged for 5 minutes at 10.000×g. The release of arabinose was followed by HPAEC analysis.

The analysis was performed using a Dionex HPLC system equipped with a Dionex CarboPac PA-1 (2 mm ID×250 mm) column in combination with a CarboPac PA guard column (2 mm ID×50 mm) and a Dionex PAD-detector (Dionex Co. Sunnyvale). A flow rate of 0.3 mL/min was used with the following gradient of sodium acetate in 0.1 M NaOH: 0-40 min, 0-400 mM. Each elution was followed by a washing step of 5 min 1000 mM sodium acetate in 0.1 M NaOH and an equilibration step of 15 min 0.1 M NaOH. Arabinose release was identified and quantified by a standard (Sigma).

This assay can be used to test the activity of enzymes such as, but not limited to, GH3, GH43, GH51, GH54, and GH62 enzymes.

Endo-xylanase Activity Assay

Endo-xylanases are enzyme able to hydrolyze β-1,4 bond in the xylan backbone, producing short xylooligosaccharides. This assay measures the release of xylose and xylo-oligosaccharides by the action of xylanases on wheat arabinoxylan (WAX) (Megazyme, Medium viscosity 29 cSt), Oat arabinoxylan, Beech wood xylan and Birch wood xylan (Sigma).

Sodium acetate buffer (0.05 M, pH 4.5) was prepared as follows; 4.1 g of anhydrous sodium acetate was dissolved in distilled water to a final volume of 1000 mL (Solution A). In a separate flask, 3.0 g (2.86 mL) of glacial acetic acid was mixed with distilled water to make the total volume of 1000 mL (Solution B). The final 0.05 M sodium acetate buffer, pH 4.5, was prepared by mixing Solution A with Solution B until the pH of the resulting solution was 4.5. Each substrate was solved in sodium acetate buffer to obtain 2.0 mg/mL. The enzyme culture supernatant was added to the substrate in a dosage of 10 mg protein/g substrate which was then incubated at 60° C. for 20 hours. The reaction was stopped by heating the samples for 10 minutes at 100° C. The release of xylose and xylooligosaccharides was analyzed by High Performance Anion Exchange Chromatography.

As a blank sample the substrate was treated and incubated in the same way but then without the addition of enzyme.

The analysis was performed using a Dionex HPLC system equipped with a Dionex CarboPac PA-1 (2 mm ID×250 mm) column in combination with a CarboPac PA guard column (2 mm ID×50 mm) and a Dionex PAD-detector (Dionex Co. Sunnyvale). A flow rate of 0.3 mL/min was used with the following gradient of sodium acetate in 0.1 M NaOH: 0-40 min, 0-400 mM. Each elution was followed by a washing step of 5 min 1000 mM sodium acetate in 0.1 M NaOH and an equilibration step of 15 min 0.1 M NaOH. Standards of xylose, xylobiose and xylotriose (Sigma) were used to identify these oligomers released by the action of the enzyme.

This assay can be used to test the activity of enzymes such as, but not limited to, GH5, GH8, GH10, and GH11.

α/β-xylosidase Activity Measurement

This assay measures the release of p-nitrophenol by the action of α/β-xylosidase on p-nitrophenyl-α/β-D-xylopyranoside (PNPX). One β-xylosidase unit of activity is the amount of enzyme that liberates 1 micromole of p-nitrophenol in one minute at 60° C. and pH 4.5. Acetate buffer (0.1 M, pH 4.5) is prepared as follows: 8.2 g of anhydrous sodium acetate is dissolved in distilled water so that the final volume of the solution is 1000 ml (Solution A). In a separate flask, 6.0 g (5.72 ml) of glacial acetic acid is mixed with distilled water to make the total volume of 1000 ml (Solution B). The final 0.1 M acetate buffer, pH 4.5 is prepared by mixing Solution A with Solution B until the pH of the resulting solution is equal to 4.5. A drop (~25 μL) Triton X-100 is added/L buffer solution. PNPX (Sigma) is used as the assay substrate.

100 mg of PNPX is dissolved in 84 mL of 0.1 M acetate buffer to obtain a 4.4 mM stock solution. The stop reagent (1 M sodium carbonate solution) is prepared as follows: 10.6 g of anhydrous sodium carbonate is dissolved in 50 ml of distilled water, and the solution volume is adjusted to 100 ml. This reagent is used to terminate the enzymatic reaction.

For the incubation with enzyme, 0.1 mL of 4.4 mM PNPX stock solution is mixed with 0.1 mL of the appropriate diluted enzyme sample and incubated at 60° C. for 60 minutes. After 60 minutes of incubation, 0.1 mL of the reaction mixture is mixed with 0.1 mL of 1 M sodium carbonate solution and the absorbance is measured at 405 nm in microtiter plates as $A_S$.

For the substrate blank, 0.1 mL of 4.4 mM PNPX stock solution is mixed with 0.1 mL of 0.1 M acetate buffer, pH 4.5 and treated the same as the samples: incubated at 60° C. for 60 minutes after which 0.1 mL of the reaction mixture is mixed with 0.1 mL of 1 M sodium carbonate solution and the absorbance at 405 nm is measured in microtiter plates as $A_{SB}$.

Enzyme blanks (without addition of substrate) are measured to correct for background color originating from the enzymes. 0.1 mL of the appropriate diluted enzyme sample is mixed with 0.1 mL 0.1 M acetate buffer, pH 4.5 and incubated at 60° C. for 60 minutes. After 60 minutes of incubation, 0.1 mL of the reaction mixture is mixed with 0.1 mL of 1 M sodium carbonate solution and the absorbance is measured at 405 nm in microtiter plates as $A_{EB}$.

A calibration curve of p-nitrophenol (appropriate diluted in 0.1 M acetate buffer, pH 4.5) mixed in a ratio of 1:1 with 1 M sodium carbonate solution is used to quantify its release from PNPX by the action of the enzyme.

After the incubation of enzyme with substrate the corrected absorbance ($=A_S-A_{EB}-A_{SB}$), is used to calculate the amount of p-nitrophenol released by the enzyme.

The activity is expressed as the amount of enzyme required to release 1 μM p-nitrophenol/min under the assay conditions.

This assay can be used to test the activity of enzymes such as, but not limited to, GH3, GH30, GH31, GH39, GH43, GH52, and GH54 enzymes.

α/β-mannosidase Activity Measurement

This assay measures the release of p-nitrophenol by the action of α/β-mannosidase on p-nitrophenyl-α/β-D-mannopyranoside (PNPM). One α/β-mannosidase unit of activity is the amount of enzyme that liberates 1 micromole of p-nitrophenol in one minute at 60° C. and pH 4.5. Acetate buffer (0.1 M, pH 4.5) is prepared as follows: 8.2 g of anhydrous sodium acetate is dissolved in distilled water so that the final volume of the solution is 1000 ml (Solution A). In a separate flask, 6.0 g (5.72 ml) of glacial acetic acid is mixed with distilled water to make the total volume of 1000 ml (Solution B). The final 0.1 M acetate buffer, pH 4.5 is prepared by mixing Solution A with Solution B until the pH of the resulting solution is equal to 4.5. A drop (~25 μL) Triton X-100 is added/L buffer solution. PNPM (Sigma) is used as the assay substrate.

A stock solution of 4.4 mM PNPM is made in 0.1 M acetate buffer. The stop reagent (1 M sodium carbonate solution) is prepared as follows: 10.6 g of anhydrous sodium carbonate is dissolved in 50 ml of distilled water, and the solution volume is adjusted to 100 ml. This reagent is used to terminate the enzymatic reaction.

For the incubation with enzyme, 0.1 mL of 4.4 mM PNPM stock solution is mixed with 0.1 mL of the appropriate diluted enzyme sample and incubated at 60° C. for 60 minutes. After 60 minutes of incubation, 0.1 mL of the reaction mixture is mixed with 0.1 mL of 1 M sodium carbonate solution and the absorbance is measured at 405 nm in microtiter plates as $A_S$ For the substrate blank, 0.1 mL of 4.4 mM PNPM stock solution is mixed with 0.1 mL of 0.1 M acetate buffer, pH 4.5 and treated the same as the samples: incubated at 60° C. for 60 minutes after which 0.1 mL of the reaction mixture is mixed with 0.1 mL of 1 M sodium carbonate solution and the absorbance at 405 nm is measured in microtiter plates as $A_{SB}$.

Enzyme blanks (without addition of substrate) are measured to correct for background color originating from the enzymes. 0.1 mL of the appropriate diluted enzyme sample is mixed with 0.1 mL 0.1 M acetate buffer, pH 4.5 and incubated at 60° C. for 60 minutes. After 60 minutes of incubation, 0.1 mL of the reaction mixture is mixed with 0.1 mL of 1 M sodium carbonate solution and the absorbance is measured at 405 nm in microtiter plates as $A_{EB}$.

A calibration curve of p-nitrophenol (appropriate diluted in 0.1 M acetate buffer, pH 4.5) mixed in a ratio of 1:1 with 1 M sodium carbonate solution is used to quantify its release from PNPM by the action of the enzyme.

After the incubation of enzyme with substrate the corrected absorbance ($=A_S-A_{EB}-A_{SB}$), is used to calculate the amount of p-nitrophenol released by the enzyme.

The activity is expressed as the amount of enzyme required to release 1 µM p-nitrophenol/min under the assay conditions.

This assay can be used to test the activity of enzymes such as, but not limited to, GH1, GH2, GH5, GH38, GH47, GH92, and GH125 enzymes.

Feruloyl Esterase Activity Measurement

Synthetic substrates: Methyl caffeate, methyl coumarate, methyl sinapinate and methyl ferulate are obtained from Apin Chemicals. Activity towards these synthetic substrates is determined by incubating the enzyme with the substrate at a dosage of about 5 mg/g DM at a pH of 5.0 (50 mM sodium acetate buffer). The reaction will be done at 60° C. for up to 24 h.

At the end of the incubation the samples are boiled for 5 minutes to inactivate the enzymes and centrifuged at room temperature (10 min, 10,000×g). Hydroxycinnamic acid release from the substrate is measured by RP-UHPLC-MS analysis in negative ion mode as described earlier (Appeldoorn et al., 2010) on an Accela UHPLC system (Thermo Scientific) equipped with a Hypersyl GOLD column (2.1 mm×150 mm, 1.9 µm particle size; Thermo Scientific). The mobile phase is composed of (A) H2O+1% (v/v) acetonitrile+0.2% (v/v) acetic acid and (B) acetonitrile+0.2% (v/v) acetic acid. The flow rate is 0.4 mL/min, and the column temperature is 30° C. The elution profile is as follows: first 5 min, isocratic 0% B; 5-23 min, linear from 0 to 50% B; 23-24 min, linear from 50 to 100% B; 24-27 min, isocratic at 100% B; 27-28 min, linear from 100 to 0% B, followed by reconditioning of the column for 7 min. Spectral data are collected from 200 to 600 nm, and quantification is performed at 320 nm. Ferulic, caffeic, sinapic and coumaric acid contents are identified and quantified on the basis of standards.

MS data are collected in the negative mode with an ion spray voltage of 3.5 kV, a capillary voltage of −20 V, and a capillary temperature of 350 C. Full MS scans are made within the range m/z 150-1500, and MS2 data of the most intense ions is obtained.

This assay can be used to test the activity of enzymes such as, but not limited to, CE1 enzymes.

Feruloyl Esterase Activity Measurement

Natural occurring substrate: Arabinoxylan oligomers purified from pretreated corn fibre (CF) (1 mg/ml each) (Appeldoorn et al 2010) are incubated with ferulic acid esterases at a dosage of about 5 mg/g DM at a pH of 5.0 (50 mM sodium acetate buffer). The reaction will be done at 60° C. for up to 24 h.

At the end of the incubation the samples are boiled for 5 minutes to inactivate the enzymes and centrifuged at room temperature (10 min, 10,000×g). Hydroxycinnamic acid release from the substrate is measured by RP-UHPLC-MS analysis in negative ion mode as described earlier (Appeldoorn et al., 2010) on an Accela UHPLC system (Thermo Scientific) equipped with a Hypersyl GOLD column (2.1 mm×150 mm, 1.9 m particle size; Thermo Scientific). The mobile phase is composed of (A) H2O+1% (v/v) acetonitrile+0.2% (v/v) acetic acid and (B) acetonitrile+0.2% (v/v) acetic acid. The flow rate is 0.4 mL/min, and the column temperature is 30° C. The elution profile is as follows: first 5 min, isocratic 0% B; 5-23 min, linear from 0 to 50% B; 23-24 min, linear from 50 to 100% B; 24-27 min, isocratic at 100% B; 27-28 min, linear from 100 to 0% B, followed by reconditioning of the column for 7 min. Spectral data are collected from 200 to 600 nm, and quantification is performed at 320 nm. Ferulic and coumaric acid contents are identified and quantified on the basis of standards.

MS data are collected in the negative mode with an ion spray voltage of 3.5 kV, a capillary voltage of −20 V, and a capillary temperature of 350 C. Full MS scans are made within the range m/z 150-1500, and MS2 data of the most intense ions is obtained.

The total amount of ester-linked ferulic acid in corn oligomers was determined after alkaline hydrolysis and ethylether extraction using the UHPLC method described above.

Reference: MAAIKE M. APPELDOORN et al, J. Agric. Food Chem. 2010, 58, 11294-11301

This assay can be used to test the activity of enzymes such as, but not limited to, CE1 enzymes.

α-glucuronidase Activity Assay

The following example illustrates the assay to measure the α-glucuronidase activity towards aldouronic acids(megazyme). This assay measures the release of xylose and xylooligomers by the action of the α-glucuronidase on the glucuronoxylan oligosaccharides.

Sodium acetate buffer (0.05 M, pH 4.5) was prepared as follows. 4.1 g of anhydrous sodium acetate was dissolved in distilled water to a final volume of 1000 mL (Solution A). In a separate flask, 3.0 g (2.86 mL) of glacial acetic acid was mixed with distilled water to make the total volume of 1000 mL (Solution B). The final 0.05 M sodium acetate buffer, pH 4.5, was prepared by mixing Solution A with Solution B until the pH of the resulting solution was 4.5.

To determine the activity on small oligomers the aldouronic acids are solved in sodium acetate buffer to obtain 1.0 mg/mL. The enzyme culture supernatant was added to the substrate in a dosage of 1 and 10 mg protein/g substrate which was then incubated at 60° C. for 24 hours. The reaction was stopped by heating the samples for 10 minutes at 100° C. The release of xylooligomers as a result of the removal of 4-O-methyl glucuronic is acid were analyzed by High Performance Anion Exchange Chromatography As a blank sample the substrate was treated and incubated in the same way but then without the addition of enzyme.

The analysis was performed using a Dionex HPLC system equipped with a Dionex CarboPac PA-1 (2 mm ID×250 mm) column in combination with a CarboPac PA guard column (2 mm ID×50 mm) and a Dionex PAD-detector (Dionex Co. Sunnyvale). A flow rate of 0.3 mL/min was used with the following gradient of sodium acetate in 0.1 M NaOH: 0-40 min, 0-400 mM. Each elution was followed by a washing step of 5 min 1000 mM sodium acetate in 0.1 M NaOH and an equilibration step of 15 min 0.1 M NaOH.

Standards of xylose, xylobiose and xylotriose (Sigma) were used to identify the xylooligomers released by the action of the enzyme that removes 4-O-methyl-Glucuronic acid from these oligomers.

This assay can be used to test the activity of enzymes such as, but not limited to, GH67 and GH115 enzymes.

Example 1

Construction of *A. niger* Expression Vectors

This Example describes the construction of an expression construct for overexpression of Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 in *A. niger*. Genomic DNA of *Rasamsonia emersonii* strain CBS393.64 was sequenced and analysed. The gene with translated protein annotated as activity according in Table 1 was identified. Sequences of the *R. emersonii* Temer00088, Temer09484, Temer08028, Temer02362, Temer08862, Temer04790, Temer05249, Temer06848, Temer02056, Temer03124, Temer09491, Temer06400, Temer08570, Temer08163 and Temer07305 gene, comprising the codon-pair optimised ORF sequence, protein sequence, signal sequence, genomic sequence and wild-type cDNA sequence are shown in sequence listings SEQ ID NO: 1 to 75.

Construction of Expression Plasmids

The sequence having SEQ ID NO: 1, 6, 11, 16, 21, 26, 31, 36, 41, 46, 51, 56, 61, 66 or 71 is cloned into the pGBTOP vector (FIG. 1) using EcoRI and PacI sites, comprising the glucoamylase promoter and terminator sequence. The *E. coli* part was removed by NotI digestion prior to transformation of *A. niger* CBS 513.88.

Transformation of *A. niger* and Shake Flask Fermentations

*A. niger* strain CBS513.88 is co-transformed with the expression constructs and an appropriate selection marker (amdS or phleomycin) containing plasmid according to method described in the experimental information section. Of recombinant and control *A. niger* strains a large batch of spores is generated by plating spores or mycelia onto PDA plates (Potato Dextrose Agar, Oxoid), prepared according to manufacturer's instructions. After growth for 3-7 days at 30 degrees Celsius, spores are collected after adding 0.01% Triton X-100 to the plates. After washing with sterile water about $10^7$ spores of selected transformants and control strains are inoculated into 100 ml shake flasks with baffles containing 20 ml of liquid pre-culture medium consisting of per liter: 30 g maltose.H$_2$O; 5 g yeast extract; 10 g hydrolyzed casein; 1 g KH$_2$PO$_4$; 0.5 g MgSO$_4$.7H$_2$O; 0.03 g ZnCl$_2$; 0.02 g CaCl$_2$; 0.01 g MnSO$_4$.4H$_2$O; 0.3 g FeSO$_4$.7H$_2$O; 3 g Tween 80; 10 ml penicillin (5000 IU/ml)/ Streptomycin (5000 UG/ml); pH5.5. These cultures are grown at 34 degrees Celsius for 16-24 hours. 10 ml of this culture was inoculated into 500 ml shake flasks with baffles containing 100 ml fermentation medium consisting of per liter: 70 g glucose.H$_2$O; 25 g hydrolyzed casein; 12.5 g yeast extract; 1 g KH$_2$PO$_4$; 2 g K$_2$SO$_4$; 0.5 g MgSO$_4$.7H$_2$O; 0.03 g ZnCl$_2$; 0.02 g CaCl$_2$; 0.01 g MnSO$_4$.4H$_2$O; 0.3 g FeSO$_4$.7H$_2$O; 10 ml penicillin (5000 IU/ml)/Streptomycin (5000 UG/ml); adjusted to pH5.6. These cultures are grown at 34 degrees Celsius until all glucose was depleted (usually after 4-7 days). Samples taken from the fermentation broth are centrifuged (10 min at 5000×g) in a swinging bucket centrifuge and supernatants collected and filtered over a 0.2 µm filter (Nalgene)

Supernatants are analysed for expression of Temer00088, Temer09484, Temer08028, Temer02362, Temer08862, Temer04790, Temer05249, Temer06848, Temer02056, Temer03124, Temer09491, Temer06400, Temer08570, Temer08163 and Temer07305 by SDS-PAGE and total protein measurements.

Example 2

Construction of a *R. emersonii* Expression Vectors

This Example describes the construction of an expression construct for overexpression Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 in *R. emersonii*. The expression cassette was targeted integrated into the RePepA locus.

In order to target the promoter-reporter constructs into the pepA locus, expression vectors were cloned for targeting. The gene with translated protein annotated as protease pepA was identified in the genome. Sequences of *Rasamsonia emersonii* pepA (RePepA), comprising the genomic sequence of the ORF and approximately 3000 bp of the 5' region and 2500 bp of the 3' flanking regions, cDNA and protein sequence, are shown in sequence listings 76, 77 and 78, respectively.

Figure 2:
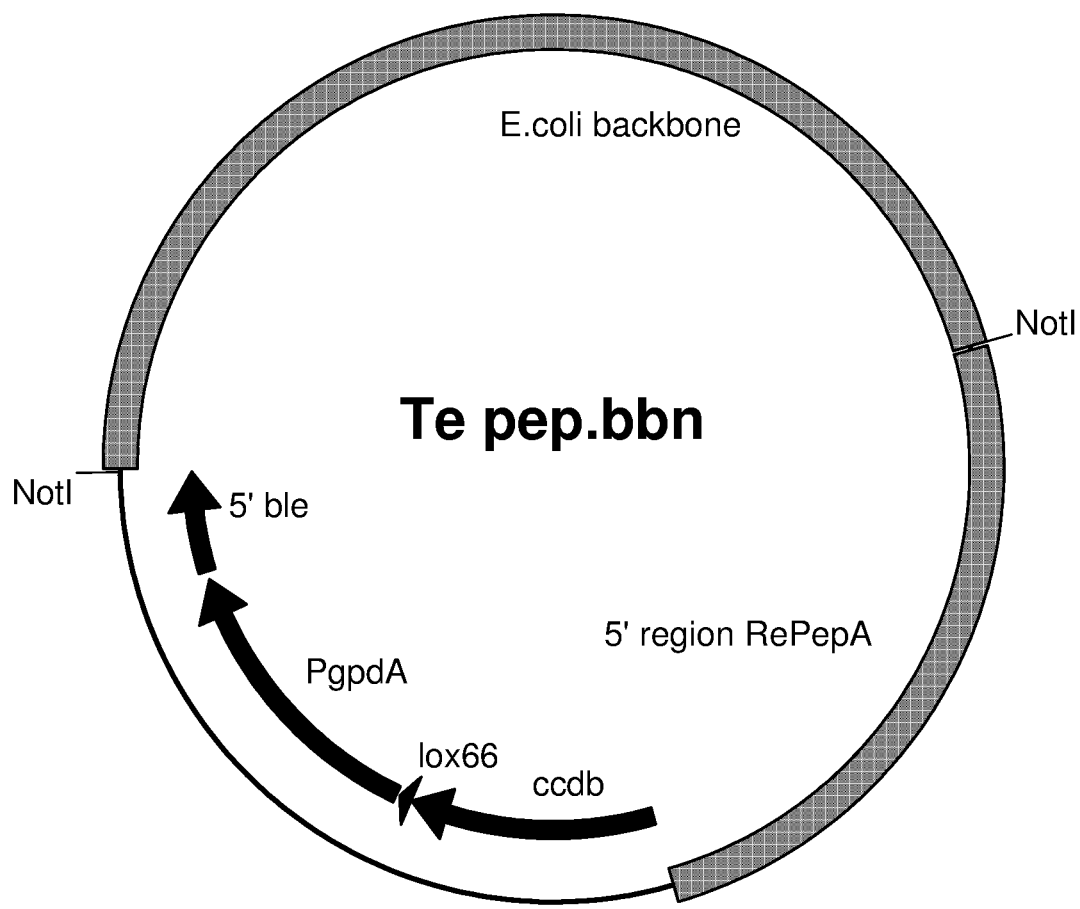
FIG. 2 shows a schematic diagram of plasmid Te pep.bbn, which is the basis for Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 overexpression construct in *R. emersonii* that is targeted to the RePepA locus. The vector comprises a 1500 bp 5' flanking region 1.5 kb upstream of the RePepA ORF for targeting in the RePepA locus, a lox66 site, the non-functional 5' part of the ble coding region (5'ble) driven by the *A. nidulans* gpdA promoter, and a ccdB gene.
Figure 3:
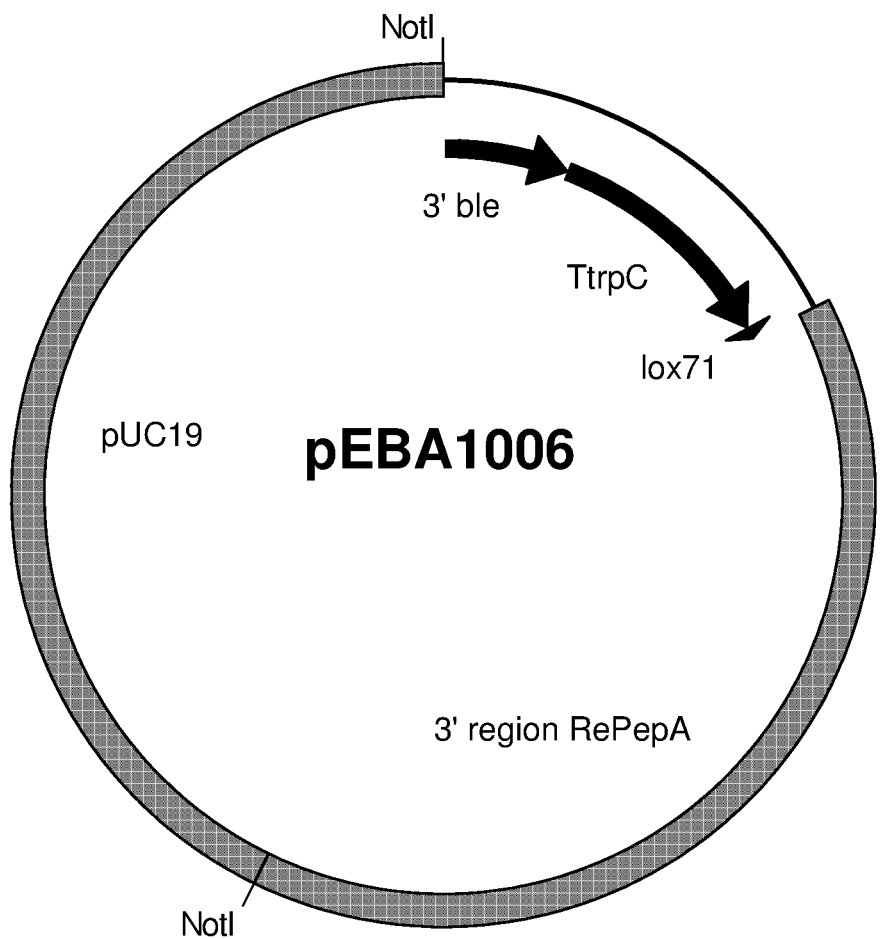
FIG. 3 shows a schematic diagram of plasmid pEBA1006 that was used in bipartite gene-targeting method in combination with the pEBA expression vector containing Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 with the goal to replace the RePepA ORF and approximately 1500 nucleotides upstream of the start ATG codon by the expression cassette of Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 in *Rasamsonia emersonii*. The vector comprises the 3' part of the ble coding region, the *A. nidulans* trpC terminator, a lox71 site, a 2500 bp 3' flanking region of the RePepA ORF, and the backbone of pUC19 (Invitrogen, Breda, The Netherlands). The *E. coli* DNA was removed by digestion with restriction enzyme NotI, prior to transformation of the *R. emersonii* strains.

Two vectors were constructed according to routine cloning procedures for targeting into the RePepA locus. The insert fragments of both vectors together can be applied in the so-called "bipartite gene-targeting" method (Nielsen et al., 2006, 43: 54-64). This method is using two non-functional DNA fragments of a selection marker which are overlapping (see also WO2008113847 for further details of the bipartite method) together with gene-targeting sequences. Upon correct homologous recombination the selection marker becomes functional by integration at a homologous target locus. As also detailed in WO 2008113847, two different deletion vectors, Te pep.bbn and pEBA1006, were designed and constructed to be able to provide the two overlapping DNA molecules for bipartite gene-targeting. The first vector Te pep.bbn (General layout as in FIG. 2) comprises a 1500 bp 5' flanking region approximately 1.5 kb upstream of the RePepA ORF for targeting in the RePepA locus (ORF and approximately 1500 bp of the RePepA promoter), a lox66 site, and the non-functional 5' part of the ble coding region driven by the *A. nidulans* gpdA promoter (PgpdA-ble sequence missing the last 104 bases of the coding sequence at the 3' end of ble, SEQ ID NO: 79). To allow efficient cloning of promoter-reporter cassettes in *E. coli*, a ccdB gene was inserted in between the 5' RePepA flanking region and the lox66 site. The second pEBA1006 vector (General layout as in FIG. 3)

comprises the non-functional 3' part of the ble coding region and the *A. nidulans* trpC terminator (ble-TtrpC sequence missing the first 12 bases of the coding sequence at the 5' end of ble, SEQ ID NO: 80), a lox71 site, and a 2500 bp 3' flanking region of the RePepA ORF for targeting in the RePepA locus. Upon homologous recombination, the first and second non-functional fragments become functional producing a functional ble cassette. Both RePepA upstream and downstream gene flanking regions target for homologous recombination of the bipartite fragments at the predestined RePepA genomic locus.

Figure 4:
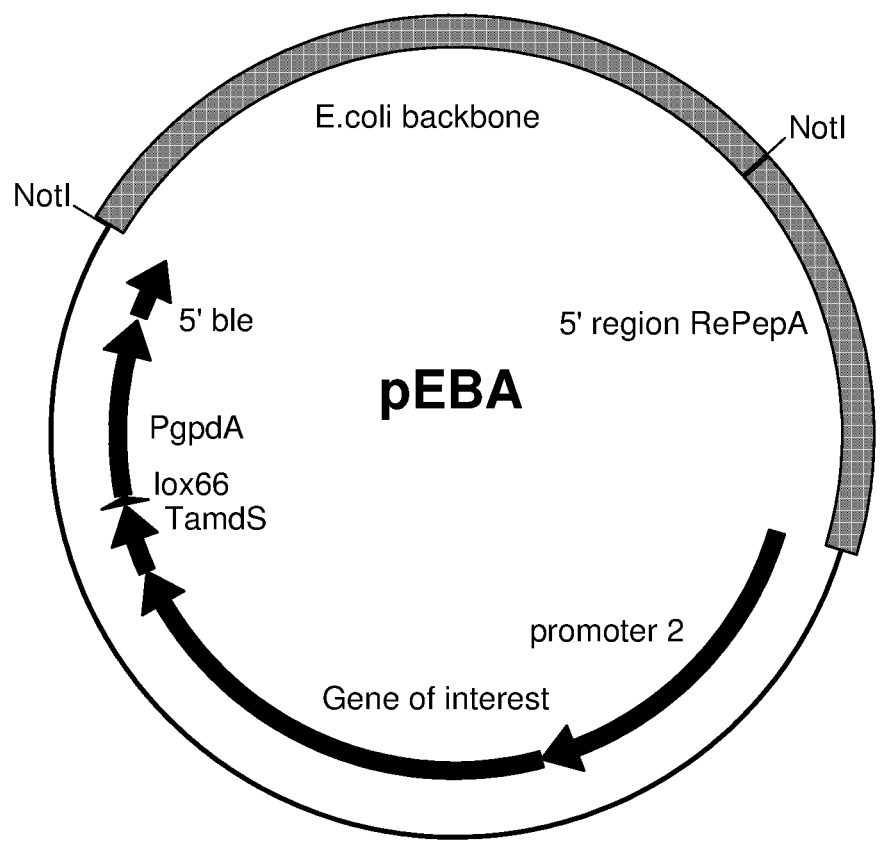
FIG. 4 shows a schematic diagram of pEBA expression plasmid containing Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 that was used in bipartite gene-targeting method in combination with the pEBA1006 vector with the goal to replace the RePepA ORF and approximately 1500 nucleotides upstream of the start ATG codon by the expression cassette of Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 in *Rasamsonia emersonii*. The vector comprises a 1500 bp 5' flanking region 1.5 kb upstream of the RePepA ORF for targeting in the RePepA locus, Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 expression cassette consisting of *R. emersonii* promoter 2, Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 coding region and the *A. nidulans* amdS terminator (TamdS), a lox66 site, the non-functional 5' part of the ble coding region (5' ble) driven by the *A. nidulans* gpdA promoter. The *E. coli* DNA was removed by digestion with restriction enzyme NotI, prior to transformation of the *R. emersonii* strains.
Figure 5:
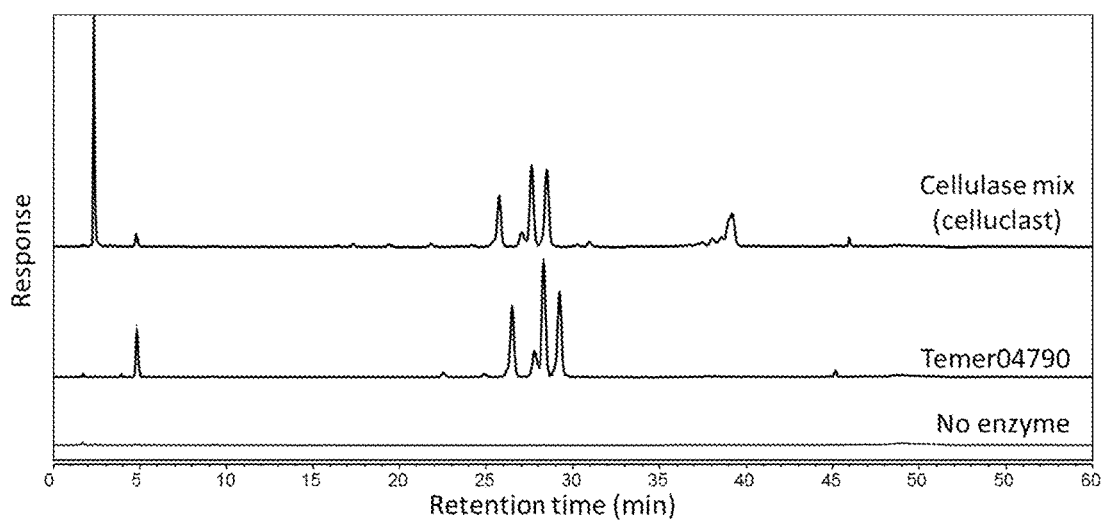
FIG. 5 Chromatogram obtained by High-performance anion exchange chromatography showing oligomer formation by *Rasamsonia emersonii* Temer04790 in comparison with a commercial cellulase mix after incubation on xyloglucan for 24 h incubation at pH 4.5 and 60° C.

The ccdB gene in vector Te pep.bbn is replaced by Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 expression cassettes according to routine cloning procedures. *R. emersonii* promoter 2, represented by SEQ ID NO: 81, is cloned upstream of the *R. emersonii* Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 coding region with *A. nidulans* amdS terminator, generating construct pEBA. The *A. nidulans* amdS terminator sequence is represented by SEQ ID NO: 82. A schematic representation of pEBA for overexpression of the Gene of interest (GOI) being Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 is shown in FIG. 4.

Example 3

Overexpression of Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 Gene in *Rasamsonia emersonii*

Linear DNA of pEBA and pEBA1006 are isolated and used to transform *Rasamsonia emersonii* using method as described earlier in WO2011/054899. The linear DNAs can integrate together into the genome at the RePepA locus, thus substituting the RePepA gene by the Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 and ble gene. Transformants are selected on phleomycin media and colony purified and tested according to procedures as described in WO2011/054899. Growing colonies are diagnosed by PCR for integration at the RePepA locus using a primer in the gpdA promoter of the deletion cassette and a primer directed against the genomic sequence directly upstream of the 5' targeting region. Candidate transformants in which RePepA is replaced by Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305/ble cassettes are obtained.

Example 4

Enzymatic Activity in Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 Overexpressing *Rasamsonia emersonii* Strains Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 overexpressing strains are fermented in shake flask in *Rasamsonia* medium 3 and supernatants are analysed for activity according to Table 1 in a suitable assay. An increase in activity is observed in supernatants of Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 overexpressing strains compared to the wild-type strain, indicating that overexpression of Temer00088, Temer09484, Temer08028, Temer02362, Temer08862, Temer04790, Temer05249, Temer06848, Temer02056, Temer03124, Temer09491, Temer06400, Temer08570, Temer08163 or Temer07305 improves activity in *R. emersonii*.

Example 5

*Aspergillus niger* Shake Flask Fermentation

About $10^7$ spores of selected transformants and control strains were inoculated into 100 ml shake flasks with baffles containing 20 ml of liquid pre-culture medium consisting of per liter: 30 g maltose.$H_2O$; 5 g yeast extract; 10 g hydrolyzed casein; 1 g $KH_2PO_4$; 0.5 g $MgSO_4.7H_2O$; 0.03 g $ZnCl_2$; 0.02 g $CaCl_2$; 0.01 g $MnSO_4.4H_2O$; 0.3 g $FeSO_4.7H_2O$; 3 g Tween 80; 10 ml penicillin (5000 IU/ml)/Streptomycin (5000 UG/ml); pH5.5. These cultures were grown at 34 degrees Celsius for 16-24 hours. 10 ml of this culture was inoculated into 500 ml shake flasks with baffles containing 100 ml fermentation medium consisting of per liter: 70 g glucose.$H_2O$; 25 g hydrolyzed casein; 12.5 g yeast extract; 1 g $KH_2PO_4$; 2 g $K_2SO_4$; 0.5 g $MgSO_4.7H_2O$; 0.03 g $ZnCl_2$; 0.02 g $CaCl_2$; 0.01 g $MnSO_4.4H_2O$; 0.3 g $FeSO_4.7H_2O$; 10 ml penicillin (5000 IU/ml)/Streptomycin (5000 UG/ml); adjusted to pH5.6. These cultures were grown at 34 degrees Celsius until all glucose was depleted (usually after 4-7 days). Samples taken from the fermentation broth were centrifuged (10 min at 5000×g) in a swinging bucket centrifuge and supernatants collected and filtered over a 0.2 μm filter (Nalgene)

Shake Flask Concentration and Protein Concentration Determination with TCA-biuret Method In order to obtain greater amounts of material for further testing the fermentation supernatants obtained as described above (volume between 75 and 100 ml) were concentrated using a 10 kDa spin filter to a volume of approximately 5 ml. Subsequently, the protein concentration in the concentrated supernatant was determined via a TCA-biuret method.

Concentrated protein samples (supernatants) were diluted with water to a concentration between 2 and 8 mg/ml. Bovine serum albumin (BSA) dilutions (0, 1, 2, 5, 8 and 10 mg/ml) were made and included as samples to generate a calibration curve. Of each diluted protein sample 270 μl was transferred into a 10 ml tube containing 830 μl of a 12% (w/v) trichloro acetic acid solution in acetone and mixed thoroughly. Subsequently, the tubes were incubated on ice water for one hour and centrifuged for 30 minutes, at 4° C. and 6000 rpm. The supernatant was discarded and pellets were dried by inverting the tubes on a tissue and letting them stand for 30 minutes at room temperature. Next, 3 ml BioQuant Biuret reagent mix was added to the pellet in the tube and the pellet was solubilized upon mixing followed by addition of 1 ml water. The tube was mixed thoroughly and incubated at room temperature for 30 minutes. The absorption of the mixture was measured at 546 nm with a water sample used as a blank measurement and the protein concentration was calculated via the BSA calibration line.

Example 6

Identification of Thermophilic *Rasamsonia emersonii* Temer09484 Beta-xylosidase Activity on Xylobiose The beta-xylosidase activity of *Rasamsonia emersonii* Temer09484 was analysed as described above. The supernatant of the Temer09484 *A. niger* shake flask fermentation was concentrated and assayed in two dosages for xylose release from xylobiose after incubation for 24 hours at pH 4.5 and 62° C. The enzyme showed significant xylose release from xylobiose as shown in Table 3. This shows that Temer09484 has beta-xylosidase activity.

TABLE 3

Effect of *Rasamsonia emersonii* Temer09484 on release of xylose from xylobiose (100 ug/mL) after 24 h incubation at pH 4.5 and 62° C.

| Protein ID | Dosage (mg/g DM) | Product xylose (ug/mL) |
|---|---|---|
| No enzyme | 0 | 0 |
| Temer09484 | 1 | 100 |
| Temer09484 | 5 | 100 |

Example 7

Identification of Thermophilic *Rasamsonia emersonii* Temer09484 Beta-xylosidase Activity on Polymeric Xylan Substrates As a second experiment the activity of the beta-xylosidase activity of *Rasamsonia emersonii* Temer09484 was also analysed on polymeric xylan substrates. The supernatant of the Temer09484 *A. niger* shake flask was dosed at 10 mg/g to three different polymeric xylan substrates. From all three substrates xylose was released (Table 4) while no xylooligomers were formed. This shows that Temer09484 also has beta-xylosidase activity on polymeric substrates next to small oligomers as shown in Example 6.

TABLE 4

Effect of *Rasamsonia emersonii* Temer09484 on release of xylose from several xylan substrates after incubation for 24 h at pH 4.5 and 60° C. at a dosage of 10 mg/g DM.

| Substrate (2 mg/mL) | ug/mL* xylose |
|---|---|
| Beech wood xylan | 320 |
| Birch wood xylan | 250 |
| Oat arabinoxylan | 334 |

*All substrates contain <3.0 ug/mL xylose when no enzyme was added

Example 8

Improvement of Two Different Cellulose Mixtures by Addition of Temer09484 for the Hydrolysis of Lignocellulosic Feedstocks The supernatant of the Temer09484 *A. niger* shake flask fermentation was concentrated and spiked on a mild acid pretreated corn stover feedstock as described above. The enzyme showed significant xylose release from this feedstock in a wide range of temperatures (50, 65 and 75° C.) and pH values (3.5-4.5-5.0) used during the 72 hours of incubation as shown in Table 5. This shows that Temer09484 is important for the hydrolysis of lignocellulosic feedstocks.

TABLE 5

Effect of *Rasamsonia emersonii* Temer09484 on release of xylose (g/L) from mildly acid pretreated corn stover feedstock after 72 h incubation at different temperature/pH conditions.

| Protein ID | pH 5.0-50° C. | pH 3.5-65° C. | pH 4.5-65° C. | pH 4.5-75° C. |
|---|---|---|---|---|
| Feedstock only-no enzyme | 0.14 | 0.14 | 0.14 | 0.13 |
| Temer09484 | 0.29 | 0.22 | 0.23 | 0.19 |

The supernatant of the Temer09484 *A. niger* shake flask fermentation was also tested in combination with 2 different cellulose mixtures: TEC-210 and Celluclast, both with additional BG added. The xylose release from mildly acid pretreated corn stover was improved for both cellulose mixes by the addition of Temer09484 in a wide range of temperatures (50, 65 and 75° C.) and pH values (3.5-4.5-5.0) used during the 72 hours of incubation as shown in Table 6. This shows that Temer09484 can be used to improve cellulose mixes in a wide range of temperatures and pH values used for the hydrolysis of lignocellulosic feedstocks.

TABLE 6

Effect of *Rasamsonia emersonii* Temer09484 when spiked to two different cellulose mixes on release of xylose (g/L) from mildly acid pretreated corn stover feedstock after 72 h incubation at different temperature/pH conditions.

| Protein ID | pH 5.0-50° C. | pH 3.5-65° C. | pH 4.5-65° C. | pH 4.5-75° C. |
|---|---|---|---|---|
| Feedstock only-no enzyme | 0.14 | 0.14 | 0.14 | 0.13 |
| TEC-210 + 8% BG | 0.51 | 0.45 | 0.57 | 0.22 |
| TEC-210 + 8% BG + Temer09484 | 0.63 | 0.53 | 0.63 | 0.33 |
| Celluclast + 8% BG | 0.49 | 0.23 | 0.27 | 0.19 |
| Celluclast + 8% BG + Temer09484 | 0.61 | 0.24 | 0.32 | 0.24 |

Example 9

Identification of Thermophilic *Rasamsonia emersonii* Temer00088 Beta-xylosidase Activity on Xylobiose The beta-xylosidase activity of *Rasamsonia emersonii* Temer00088 was analysed as described above. The supernatant of the Temer00088 *A. niger* shake flask fermentation was concentrated and assayed in two dosages for xylose release from xylobiose after incubation for 24 hours at pH 4.5 and 62° C. The enzyme showed significant xylose release from xylobiose as shown in Table 7. This shows that Temer00088 has beta-xylosidase activity.

TABLE 7

Effect of *Rasamsonia emersonii* Temer00088 on release of xylose from xylobiose (100 ug/mL) after 24 h incubation at pH 4.5 and 62° C..

| Protein ID | Dosage (mg/g DM) | Product xylose (ug/mL) |
| --- | --- | --- |
| No enzyme | 0 | 0 |
| Temer00088 | 1 | 76 |
| Temer00088 | 5 | 99 |

Example 10

Identification of Thermophilic *Rasamsonia emersonii* Temer00088 Beta-xylosidase Activity on Polymeric Xylan Substrates As a second experiment the activity of the beta-xylosidase activity of *Rasamsonia emersonii* Temer00088 was also analysed on polymeric xylan substrates. The supernatant of the Temer00088 *A. niger* shake flask was dosed at 10 mg/g to three different polymeric xylan substrates. From all three substrates xylose was released (Table 8) while no xylooligomers were formed. This shows that Temer00088 also has beta-xylosidase activity on polymeric substrates next to small oligomers as shown in Example 9.

TABLE 8

Effect of *Rasamsonia emersonii* Terner00088 on release of xylose from several xylan substrates after incubation for 20 h at pH 4.5 and 60° C. at a dosage of 10 mg/g DM.

| Substrate (2 mg/mL) | ug/mL* xylose |
| --- | --- |
| Beech wood xylan | 373 |
| Birch wood xylan | 469 |
| Oat arabinoxylan | 298 |

*All substrates contain <3.0 ug/mL xylose when no enzyme was added

Example 11

Improvement of Two Different Cellulose Mixtures by Addition of Temer00088 for the Hydrolysis of Lignocellulosic Feedstocks The supernatant of the Temer00088 *A. niger* shake flask fermentation was concentrated and spiked on a mild acid pretreated corn stover feedstock as described above. The enzyme showed significant xylose release from this feedstock in a wide range of temperatures (50, 65 and 75° C.) and pH values (3.5-4.5-5.0) used during the 72 hours of incubation as shown in Table 3. This shows that Temer00088 is important for the hydrolysis of lignocellulosic feedstocks.

TABLE 9

Effect of *Rasamsonia emersonii* Temer00088 on release of xylose (g/L) from mildly acid pretreated corn stover feedstock after 72 h incubation at different temperature/pH conditions.

| Protein ID | pH 5.0-50° C. | pH 3.5-65° C. | pH 4.5-65° C. | pH 4.5-75° C. |
| --- | --- | --- | --- | --- |
| Feedstock only-no enzyme | 0.14 | 0.14 | 0.14 | 0.13 |
| Temer00088 | 0.29 | 0.26 | 0.27 | 0.22 |

The supernatant of the Temer00088 *A. niger* shake flask fermentation was also tested in combination with 2 different cellulose mixtures: TEC-210 and Celluclast, both with additional BG added. The xylose release from mildly acid pretreated corn stover was improved for both cellulose mixes by the addition of Temer00088 in a wide range of temperatures (50, 65 and 75° C.) and pH values (3.5-4.5-5.0) used during the 72 hours of incubation as shown in Table 10. This shows that Temer00088 can be used to improve cellulose mixes in a wide range of temperatures and pH values used for the hydrolysis of lignocellulosic feedstocks.

TABLE 10

Effect of *Rasamsonia emersonii* Temer00088 when spiked to two different cellulose mixes on release of xylose (g/L) from mildly acid pretreated corn stover feedstock after 72 h incubation at different temperature/pH conditions.

| Protein ID | pH 5.0-50° C. | pH 3.5-65° C. | pH 4.5-65° C. | pH 4.5-75° C. |
| --- | --- | --- | --- | --- |
| Feedstock only-no enzyme | 0.14 | 0.14 | 0.14 | 0.13 |
| TEC-210 + 8% BG | 0.51 | 0.45 | 0.57 | 0.22 |
| TEC-210 + 8% BG + Temer09484 | 0.62 | 0.59 | 0.67 | 0.39 |
| Celluclast + 8% BG | 0.49 | 0.23 | 0.27 | 0.19 |
| Celluclast + 8% BG + Temer09484 | 0.66 | 0.29 | 0.35 | 0.27 |

Example 12

Identification of Thermophilic *Rasamsonia emersonii* Xyloglucan Specific Endoglucanase The xyloglucanase activity of *Rasamsonia emersonii* Temer04790 was analysed as described above. The supernatant of the Temer04790 *A. niger* shake flask fermentation was concentrated, added to the substrate xyloglucan and incubated for 24 hours at pH 4.5 and 60° C. The enzyme was able to release several oligomers as shown in FIG. 6. This shows that Temer04790 is active on xyloglucan and releases similar oligomers as the commercial cellulase mix Celluclast from *Trichoderma reesei*.

To quantify the amount of oligomers formed reducing ends were measured after incubation of both Temer04790 and the cellulase mix. Carboxymethylcellulose was also used as substrate to determine the specificity of the enzymes and a higher temperature, 75° C. was used next to 60° C. Temer04790 is specific towards xyloglucan as hardly any activity on CMC was seen in contrast to the cellulase mixture (Table 11). Furthermore, Temer04790 was still active at 75° C. while the cellulase mixture was almost inactive on xyloglucan at 75° C.

TABLE 11

Effect of *Rasamsonia emersonii* Temer04790 on the hydrolysis of xyloglucan (tamarind) and carboxymethylcellulose (CMC) (Sigma) measured by the formation of reducing ends expressed as glucose equivalents (ug/mL) after 24 h incubation at pH 4.5 at 60° C. and 75° C..

|  | 60° C. pH 4.5 | | 75° C. pH 4.5 | |
| --- | --- | --- | --- | --- |
|  | xyloglucan | CMC | xyloglucan | CMC |
| no enzyme | −17 | −18 | −18 | −18 |
| Temer04790 | 92 | 8 | 69 | −9 |
| cellulase mix* | 64 | 132 | 5 | 47 |

*Celluclast from *Thrichoderma reesei* (Sigma)

Example 13

Identification of Thermophilic *Rasamsonia emersonii* Arabinofuranosidase Activity The arabinofuranosidase activity of *Rasamsonia emersonii* Temer05249 was analysed as described above. The supernatant of the Temer05249 *A. niger* shake flask fermentation was concentrated and added to arabinoxylooligomers at 10 mg/g followed by incubation for 24 hours at pH 4.5 and 65° C. The enzyme showed significant arabinose release from arabinoxylooligomers as shown in Table 12. This shows that Temer05249 has arabinofuranosidase activity.

TABLE 12

Effect of *Rasamsonia emersonii* Temer05249 on the release of arabinose from wheat arabinoxylan, which was pre-incubated with an endo-xylanase, after incubation for 24 h at pH 4.5 and 65° C. at a dosage of 10 mg/g DM.

| Protein ID | Arabinose (ug/mL) |
| --- | --- |
| No enzyme | 4 |
| Temer05249 | 111 |

Example 14

Identification of Thermophilic *Rasamsonia emersonii* Endo-xylanase Activity

The endo-xylanase activity of *Rasamsonia emersonii* Temer03124 was analysed as described above. The supernatant of the Temer03124 *A. niger* shake flask fermentation was concentrated and added to several xylan substrates at 10 mg/g followed by incubation for 20 hours at pH 4.5 and 60° C. The enzyme showed significant release of xylose and a range of xylooligomers as shown in Table 13. This shows that Temer03124 has endo-xylanase activity.

TABLE 13

Effect of *Rasamsonia emersonii* Temer03124 on release of xylose and xylose oligomers from several xylan substrates after incubation for 20 h at pH 4.5 and 60° C. at a dosage of 10 mg/g DM.

| | ug/mL* | | | |
| --- | --- | --- | --- | --- |
| Substrate (2 mg/mL) | xylose | xylobiose | xylotriose | xylotetraose |
| Beech wood xylan | 34.3 | 12.6 | 10.4 | 11.4 |
| Birch wood xylan | 30.6 | 17.8 | 16.1 | 16.1 |
| Oat arabinoxylan | 27.3 | 17.2 | 12.5 | 10.9 |
| Wheat arabinoxylan | 33.4 | 36.9 | 15.0 | 5.2 |

*All substrates contain <3.5 ug/mL of each product measured if no enzyme is added Example 15

Identification of Thermophilic *Rasamsonia Emersonii* Endo-xylanase Activity

The endo-xylanase activity of *Rasamsonia emersonii* Temer08570 was analysed as described above. The supernatant of the Temer08570 *A. niger* shake flask fermentation was concentrated and added to several xylan substrates at 10 mg/g followed by incubation for 20 hours at pH 4.5 and 60° C. The enzyme showed significant release of xylose and a range of xylooligomers as shown in Table 14. This shows that Temer08570 has endo-xylanase with xylobiose, xylotriose and xylotetraose as main products.

TABLE 14

Effect of *Rasamsonia emersonii* Temer08570 on release of xylose and xylose oligomers from several xylan substrates after incubation for 20 h at pH 4.5 and 60° C. at a dosage of 10 mg/g DM.

| | ug/mL* | | | |
| --- | --- | --- | --- | --- |
| Substrate (2 mg/mL) | xylose | xylobiose | xylotriose | xylotetraose |
| Beech wood xylan | 5 | 19 | 25 | 25 |
| Birch wood xylan | 4 | 14 | 17 | 17 |
| Oat arabinoxylan | 0 | 16 | 18 | 15 |

*All substrates contain <3.5 ug/mL of each product measured if no enzyme is added Example 16

Identification of Thermophilic *Rasamsonia emersonii* Endo-xylanase Activity

The endo-xylanase activity of *Rasamsonia emersonii* Temer08163 was analysed as described above. The supernatant of the Temer08163 *A. niger* shake flask fermentation was concentrated and added to several xylan substrates at 10 mg/g followed by incubation for 20 hours at pH 4.5 and 60° C. The enzyme showed significant release of xylbiose and xylose as shown in Table 15. This shows that Temer08570 has endo-xylanase activity with xylobiose as main product which was 12-25 times higher than the amount of xylose released.

TABLE 15

Effect of *Rasamsonia emersonii* Temer08163 on release of xylose and xylose oligomers from several xylan substrates after incubation for 20 h at pH 4.5 and 60° C. at a dosage of 10 mg/g DM.

| Substrate (2 mg/mL) | ug/mL* | | | |
|---|---|---|---|---|
| | xylose | xylobiose | xylotriose | xylotetraose |
| Beech wood xylan | 22.4 | 581.4 | 0 | 0 |
| Birch wood xylan | 30.9 | 527.3 | 0 | 0 |
| Oat arabinoxylan | 13.6 | 205.1 | 0 | 0 |
| Wheat arabinoxylan | 5.4 | 65.9 | 0 | 0 |

*All substrates contain <3.5 ug/mL of each product measured.

Example 17

Identification of Thermophilic *Rasamsonia Emersonii* Alpha-glucuronidase Activity The alpha-glucuronidase activity of *Rasamsonia emersonii* Temer07305 was analysed as described above. The supernatant of the Temer07305 *A. niger* shake flask fermentation was concentrated and added to aldouronic acids both 1 and 10 mg/g followed by incubation for 24 hours at pH 4.5 and 60° C. The enzyme was able to remove 4-O-methylglucuronic acid from the xyloilogomers resulting in the simultaneous release of xylose, xylobiose, xylotriose and xylotatraose as shown in Table 16. This shows that Temer07305 has alpha-glucuronidase activity.

TABLE 16

The release of xylose and xylose oligomers by *Rasamsonia emersonii* Temer07305 from aldouronic acids as a result of the hydrolysis of 4-O-methylglucuronic acid from these xylooligomers, after incubation for 24 h at pH 4.5 and 60° C. at a dosage of 1 and 10 mg/g DM.

| Protein ID | Dosage (mg/gDM) | Area/ (mg/mL) substrate | | | |
|---|---|---|---|---|---|
| | | xylose | xylobiose | xylotriose | xylotetraose |
| No enzyme | x | 25 | 6 | 0 | 0 |
| Temer07305 | 1 | 45 | 180 | 58 | 19 |
| Temer07305 | 10 | 120 | 180 | 55 | 9 |

The invention claimed is:

1. A method for producing a sugar from a lignocellulosic material, comprising:

(a) pretreatment of the lignocellulosic material; and (b) contacting the pretreated lignocellulosic material with a polypeptide having hemicellulase activity, comprising:

(i) an amino acid sequence having at least 90% sequence identity to SEQ ID NO:32;

(ii) an amino acid sequence encoded by a nucleic acid sequence having at least 90% sequence identity to a sequence selected from the group consisting of SEQ ID NOs: 31, 34, and 35;

(iii) an amino acid sequence encoded by a nucleic acid sequence hybridizing with the complement of a nucleic acid sequence having at least 90% sequence identity with a nucleic acid sequence selected from the group consisting of SEQ ID NOs: 31, 34, and 35; or (iv) an amino acid sequence encoded by a nucleic acid sequence which is the reverse complement of a nucleic acid sequence as defined in (i), (ii) or (iii).

2. The method of claim 1, further comprising contacting the lignocellulosic material with a cellulase and/or an additional hemicellulase and/or a pectinase.

3. The method of claim 2, wherein the cellulase is selected from the group consisting of a GH61, cellobiohydrolase, cellobiohydrolase I, cellobiohydrolase II, endo-β-1,4-glucanase, β-glucosidase, and β-(1,3)(1,4)-glucanase.

4. The method of claim 2, wherein the additional hemicellulase is selected from the group consisting of endoxylanase, β-xylosidase, α-L-arabinofuranosidase, α-D-glucuronidase, cellobiohydrolase, feruloyl esterase, coumaroyl esterase, α-galactosidase, β-galactosidase, β-mannanase, and β-mannosidase.

5. The method of claim 2, wherein the pectinase is selected from the group consisting of endo-polygalacturonase, pectin methyl esterase, endo-galactanase, β-galactosidase, pectin acetyl esterase, endo-pectin lyase, pectate lyase, α-rhamnosidase, exo-galacturonase, exo-polygalacturonate lyase, rhamnogalacturonan hydrolase, rhamnogalacturonan lyase, rhamnogalacturonan acetyl esterase, rhamnogalacturonan galacturonohydrolase, xylogalacturonase, and α-arabinofuranosidase.

6. The method of claim 1, wherein the lignocellulosic material comprises fiber from corn kernels.

7. A method for preparing a fermentation product, comprising:
   (a) performing the method according to claim 1; and
   (b) fermentation of the resulting material, to thereby prepare the fermentation product.

8. The method of claim 1, wherein said polypeptide has alpha-arabinofuranosidase activity.

9. A method for treating a substrate comprising hemicellulose, comprising:
   (a) pretreatment of the substrate; and
   (b) contacting the pretreated substrate with a polypeptide having hemicellulase activity, comprising:
      (i) an amino acid sequence having at least 90% sequence identity to SEQ ID NO:32;
      (ii) an amino acid sequence encoded by a nucleic acid sequence having at least 90% sequence identity to a sequence selected from the group consisting of SEQ ID NOs: 31, 34, and 35;
      (iii) an amino acid sequence encoded by a nucleic acid sequence hybridizing with the complement of a nucleic acid sequence having at least 90% sequence identity with a nucleic acid sequence selected from the group consisting of SEQ ID NOs: 31, 34, and 35; or
      (iv) an amino acid sequence encoded by a nucleic acid sequence which is the reverse complement of a nucleic acid sequence as defined in (i), (ii) or (iii).

10. The method of claim 9, further comprising contacting the lignocellulosic material with a cellulase and/or an additional hemicellulase and/or a pectinase.

11. The method of claim 10, wherein the cellulase is selected from the group consisting of a GH61, cellobiohydrolase, cellobiohydrolase I, cellobiohydrolase II, endo-β-1,4-glucanase, β-glucosidase, and β-(1,3)(1,4)-glucanase.

12. The method of claim 10, wherein the additional hemicellulase is selected from the group consisting of endoxylanase, β-xylosidase, α-L-arabinofuranosidase, α-D-glucuronidase, cellobiohydrolase, feruloyl esterase, coumaroyl esterase, α-galactosidase, β-galactosidase, β-mannanase, and β-mannosidase.

13. The method of claim 10, wherein the pectinase is selected from the group consisting of endo-polygalacturonase, pectin methyl esterase, endo-galactanase, β-galactosidase, pectin acetyl esterase, endo-pectin lyase, pectate lyase, α-rhamnosidase, exo-galacturonase, exo-polygalacturonate lyase, rhamnogalacturonan hydrolase, rhamnogalacturonan lyase, rhamnogalacturonan acetyl esterase, rhamnogalacturonan galacturonohydrolase, xylogalacturonase, and α-arabinofuranosidase.

14. The method of claim 9, wherein said substrate comprises a plant material.

15. The method of claim 9, wherein said substrate comprises fiber from corn kernels.

16. A method for the preparation of a fermentation product, which method comprises:
   (a) performing the method according to claim 9; and
   (b) fermentation of the resulting material, to thereby prepare the fermentation product.

17. A method for preparing a polypeptide having hemicellulase activity, comprising cultivating a cell under conditions which allow for expression of said polypeptide and, optionally, recovering the expressed polypeptide, wherein said polypeptide comprises:
   (i) an amino acid sequence having at least 90% sequence identity to SEQ ID NO:32;
   (ii) an amino acid sequence encoded by a nucleic acid sequence having at least 90% sequence identity to a sequence selected from the group consisting of SEQ ID NOs: 31, 34, and 35;
   (iii) an amino acid sequence encoded by a nucleic acid sequence hybridizing with the complement of a nucleic acid sequence having at least 90% sequence identity with a nucleic acid sequence selected from the group consisting of SEQ ID NOs: 31, 34, and 35; or
   (iv) an amino acid sequence encoded by a nucleic acid sequence which is the reverse complement of a nucleic acid sequence as defined in (i), (ii) or (iii).

* * * * *

UNITED STATES PATENT AND TRADEMARK OFFICE
CERTIFICATE OF CORRECTION

PATENT NO. : 10,316,305 B2
APPLICATION NO. : 15/962058
DATED : June 11, 2019
INVENTOR(S) : Alrik Pieter Los, René Marcel De Jong and Maaike Appeldoorn Page 1 of 1

It is certified that error appears in the above-identified patent and that said Letters Patent is hereby corrected as shown below:

In the Claims

Column 234, Line 2, Claim 10, delete "the lignocellulosic material" and insert --the substrate--, therefor.

Signed and Sealed this
Twenty-eighth Day of July, 2020

Andrei Iancu
*Director of the United States Patent and Trademark Office*